(12) United States Patent
Karancsi et al.

(10) Patent No.: US 11,094,519 B2
(45) Date of Patent: Aug. 17, 2021

(54) COLLISION SURFACE FOR IMPROVED IONISATION

(71) Applicant: Micromass UK Limited, Wilmslow (GB)

(72) Inventors: Tamas Karancsi, Budapest (HU); Daniel Simon, Morichida (HU); Lajos Godorhazy, Erd (HU); Daniel Szalay, Budapest (HU); Steven Derek Pringle, Darwen (GB); Emrys Jones, Manchester (GB); Ian Trivett, Cheadle (GB); Stephen O'Brien, Manchester (GB); Anthony Hesse, Cheshire (GB); Matt Henderson, Stockport (GB); Alvin Chua, Singapore (SG); Zoltan Takáts, Cambridge (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 16/862,039

(22) Filed: Apr. 29, 2020

(65) Prior Publication Data

US 2020/0258729 A1 Aug. 13, 2020

Related U.S. Application Data

(63) Continuation of application No. 15/555,845, filed as application No. PCT/GB2016/050614 on Mar. 7, 2016.

(30) Foreign Application Priority Data

| Mar. 6, 2015 | (GB) | ...................................... 1503863 |
| Mar. 6, 2015 | (GB) | ...................................... 1503864 |

(Continued)

(51) Int. Cl.
*H01J 49/00* (2006.01)
*H01J 49/04* (2006.01)
(Continued)

(52) U.S. Cl.
CPC .......... *H01J 49/049* (2013.01); *A61B 1/2736* (2013.01); *A61B 5/00* (2013.01);
(Continued)

(58) Field of Classification Search
CPC ............. G01N 1/2202; G01N 33/6851; G01N 33/487; G01N 30/724; G01N 27/624;
(Continued)

(56) References Cited

U.S. PATENT DOCUMENTS

| 5,696,352 A | 12/1997 | Kourimsky |
| 6,348,688 B1 * | 2/2002 | Vestal ................... H01J 49/004 250/282 |

(Continued)

FOREIGN PATENT DOCUMENTS

| CA | 2527886 A1 | 12/2004 |
| CA | 2876731 A1 | 12/2013 |

(Continued)

OTHER PUBLICATIONS

Partial European Search Report for EP20181905.9, dated Aug. 27, 2020, 14 pages.

(Continued)

*Primary Examiner* — Michael Maskell
(74) *Attorney, Agent, or Firm* — Kacvinsky Daisak Bluni PLLC

(57) ABSTRACT

An apparatus for performing ambient ionisation mass and/or ion mobility spectrometry is disclosed. The apparatus comprises a substantially cylindrical, tubular, rod-shaped, coil-shaped, helical or spiral-shaped collision assembly; and a first device arranged and adapted to direct analyte, smoke, (Continued)

fumes, liquid, gas, surgical smoke, aerosol or vapour onto said collision assembly.

18 Claims, 90 Drawing Sheets

(30) Foreign Application Priority Data

| Mar. 6, 2015 | (GB) | 1503867 |
|---|---|---|
| Mar. 6, 2015 | (GB) | 1503876 |
| Mar. 6, 2015 | (GB) | 1503877 |
| Mar. 6, 2015 | (GB) | 1503878 |
| Mar. 6, 2015 | (GB) | 1503879 |
| Sep. 9, 2015 | (GB) | 1516003 |
| Oct. 16, 2015 | (GB) | 1518369 |

(51) Int. Cl.

| A61B 10/02 | (2006.01) |
|---|---|
| A61B 17/32 | (2006.01) |
| G01N 3/00 | (2006.01) |
| G01N 9/00 | (2006.01) |
| G01N 33/68 | (2006.01) |
| H01J 49/06 | (2006.01) |
| H01J 49/16 | (2006.01) |
| A61B 5/00 | (2006.01) |
| G01N 27/626 | (2021.01) |
| G16H 20/00 | (2018.01) |
| G16H 10/40 | (2018.01) |
| G16H 50/20 | (2018.01) |
| A61B 1/273 | (2006.01) |
| A61B 5/0507 | (2021.01) |
| A61B 10/00 | (2006.01) |
| A61B 18/04 | (2006.01) |
| A61B 18/18 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 27/622 | (2021.01) |
| G01N 27/624 | (2021.01) |
| G01N 30/72 | (2006.01) |
| A61B 5/145 | (2006.01) |
| A61B 18/00 | (2006.01) |

(52) U.S. Cl.

CPC .......... *A61B 5/0507* (2013.01); *A61B 10/00* (2013.01); *A61B 10/0041* (2013.01); *A61B 10/0233* (2013.01); *A61B 10/0283* (2013.01); *A61B 17/320068* (2013.01); *A61B 18/04* (2013.01); *A61B 18/042* (2013.01); *A61B 18/1815* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 27/626* (2013.01); *G01N 30/724* (2013.01); *G01N 33/6848* (2013.01); *G01N 33/6851* (2013.01); *G16H 10/40* (2018.01); *G16H 20/00* (2018.01); *G16H 50/20* (2018.01); *H01J 49/0027* (2013.01); *H01J 49/0459* (2013.01); *H01J 49/0463* (2013.01); *H01J 49/0468* (2013.01); *H01J 49/068* (2013.01); *H01J 49/16* (2013.01); *A61B 5/14546* (2013.01); *A61B 5/7264* (2013.01); *A61B 2010/0083* (2013.01); *A61B 2017/32007* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *A61B 2505/05* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01)

(58) Field of Classification Search

CPC .. G01N 27/622; G01N 33/6848; G01N 33/92; G01N 9/00; G01N 3/00; G01N 2001/2223; G01N 2405/00; G01N 2333/195; G01N 2800/26; G01N 2570/00; G01N 2405/08; G01N 2405/04; G01N 33/48735; H01J 49/0409; H01J 49/0027; H01J 49/14; H01J 49/24; H01J 49/164; H01J 49/025; H01J 49/0445; H01J 49/0422; H01J 49/10; H01J 49/0468; H01J 49/0463; H01J 49/0004; H01J 49/061; H01J 49/0031; H01J 49/26; H01J 49/068; H01J 49/16; H01J 49/0036; H01J 49/0404; H01J 49/0459; H01J 49/049; A61B 18/04; A61B 1/2736; A61B 18/1445; A61B 90/13; A61B 8/13; A61B 5/015; A61B 5/0507; A61B 5/055; A61B 6/032; A61B 6/037; A61B 5/0066; A61B 1/041; A61B 18/1815; A61B 10/00; A61B 18/042; A61B 5/0075; A61B 18/20; A61B 17/320068; A61B 10/0283; A61B 10/0233; A61B 10/0041; A61B 18/00; A61B 18/14; A61B 17/00; A61B 2018/00589; A61B 2218/002; A61B 2018/00994; A61B 1/00013; A61B 2017/320069; A61B 1/31; A61B 2018/00577; A61B 5/14542; A61B 2010/0083; A61B 2218/008; C12Q 1/18; C12Q 1/025; C12Q 1/04; C12Q 1/24; A61F 13/38; G06F 19/3481; G06F 19/324; G06F 19/18; G16H 50/20

USPC .......................................... 250/281, 282, 288

See application file for complete search history.

(56) References Cited

U.S. PATENT DOCUMENTS

| 2005/0179366 | A1 | 8/2005 | Rose et al. | |
|---|---|---|---|---|
| 2007/0114388 | A1 | 5/2007 | Ogawa et al. | |
| 2008/0042056 | A1* | 2/2008 | Fischer | G01N 33/6851 |
| | | | | 250/288 |
| 2014/0151547 | A1* | 6/2014 | Bajic | G01N 30/724 |
| | | | | 250/282 |
| 2014/0268134 | A1 | 9/2014 | OConnor | |
| 2014/0353489 | A1* | 12/2014 | Szalay | H01J 49/16 |
| | | | | 250/282 |
| 2015/0021469 | A1* | 1/2015 | Bajic | G01N 30/7266 |
| | | | | 250/282 |
| 2015/0048255 | A1* | 2/2015 | Jarrell | H01J 49/16 |
| | | | | 250/424 |
| 2015/0144782 | A1 | 5/2015 | Fogwill et al. | |

FOREIGN PATENT DOCUMENTS

| CN | 101073137 A | 11/2007 |
|---|---|---|
| CN | 101178381 A | 5/2008 |
| CN | 101372502 A | 2/2009 |

(56) References Cited

FOREIGN PATENT DOCUMENTS

| CN | 103748233 A | 4/2014 |
|---|---|---|
| CN | 104062348 A | 9/2014 |
| CN | 104284984 A | 1/2015 |
| EP | 3266035 A1 | 1/2018 |
| GB | 2420008 A | 5/2006 |
| WO | 2008148557 A2 | 12/2008 |

OTHER PUBLICATIONS

Roddy, T., et al., "Imaging of Freeze-Fractured Cells with in Situ Fluorescence and Time-of-Flight Secondary Ion Mass Spectrometry", Analytical Chemistry 74(16):4011-4019(2002).
Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78 (23):7959-7966 (2006).
Ablonczy, Z., et al., "The utilization of fluorescence to identify the components of lipofuscin by imaging mass spectrometry", Proteomics 14(7-8):936-944.
Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).
Extended EP search report for EP Application No. 20172634.6, dated Sep. 14, 2020, 8 pages.
Rath, C.M., et al., "Molecular Analysis of Model Gut Microbiotas by Imaging Mass Spectrometry and Nanodesorption Electrospray Ionization Reveals Dietary Metabolite Tranformations" Analytical Chemistry 84(21):9259-9267 (2012).
Fenselau, C.C., "Rapid Characterization of Microorganisms by Mass Spectrometry—What Can Be Learned and How?" Journal of the American Society for Mass Spectrometry 24(8):1161-1166 (2013).
Uetrecht, C. et al., "Modern Biomolecular Mass Spectrometry and its Role in Studying Virus Structure, Dynamics and Assembly" Angewandte Chemie International Edition 50(36):8248-8262 (2011).
Forbes, T.P. et al., "Chemical imaging of artificial Fingerprints by desorption electro-flow focusing ionization mass spectrometry" Analyst 139(12):2982-2985 (2014).
Cornett, D. S., et al, "A Novel Histology-directed Strategy for MALDI-MS Tissue Profiling That Improves Throughput and Cellular Specificity in Human Breast Cancer", American Society for Biochemistry and Molecular Biology, pp. 1975-1983, Jul. 18, 2006.
Extended European Search Report for Application No. 20210062.4, dated Mar. 9, 2021, 13 pages.
Examination Report under Section 18(3) for Application No. GB1715750.4 dated Mar. 22, 2021, 5 pages.
Examination Report for GB Patent Application No. GB2015580.0, dated Mar. 12, 2021, 4 pages.
Examination Report under Section 18(3) for Application No. GB1714165.6, dated Mar. 22, 2021, 6 pages.
Hrabak, J., et al., "Matrix-Assisted Laser Desorption Ionizataion-Time of Flight (MALDITOF) Mass Spectrometry for Detection of Antibiotic Resistance Mechanisms: from Research to Routine Diagnosis", CMR Journal 26(1): 103-114 (2013).
Hillenkamp, F., et al., "Matrix-Assisted Laser Desorption/Ionization Mass Spectrometry of Biopolymers", Anal Chem 63 (24): 1193A-1203A (1991). Abstract.
CNOA for Application No. 201680026939.2 dated Apr. 27, 2021, original document 10 pages.

\* cited by examiner

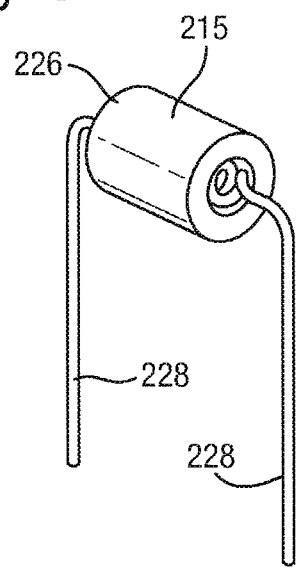
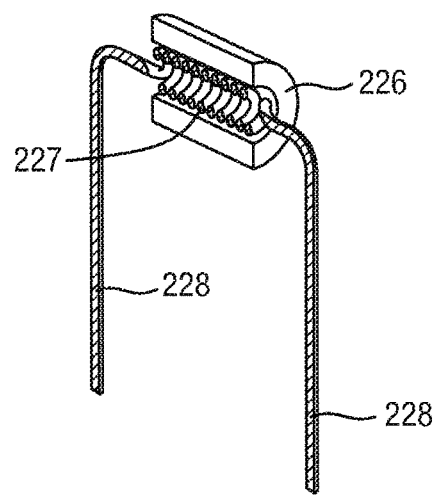
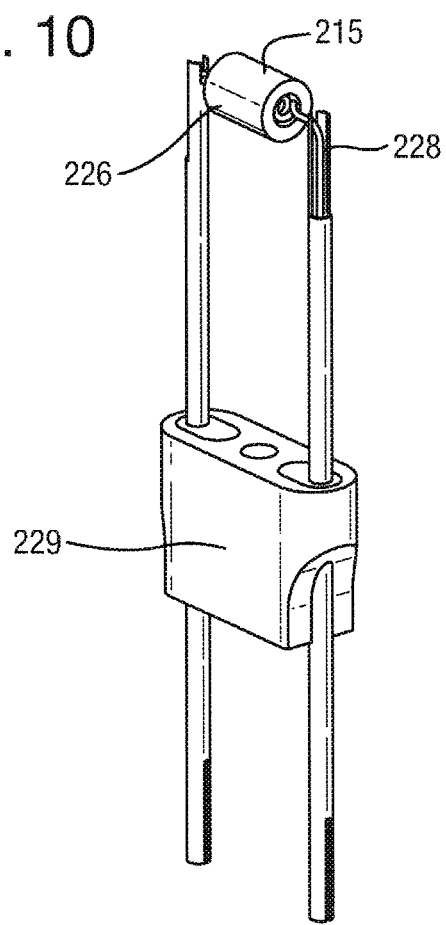

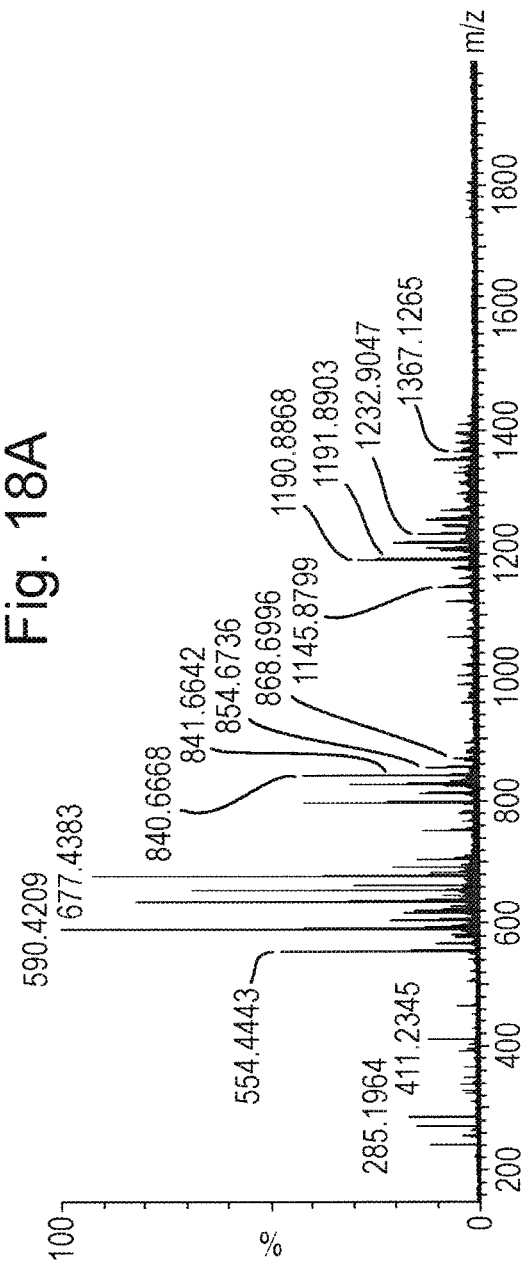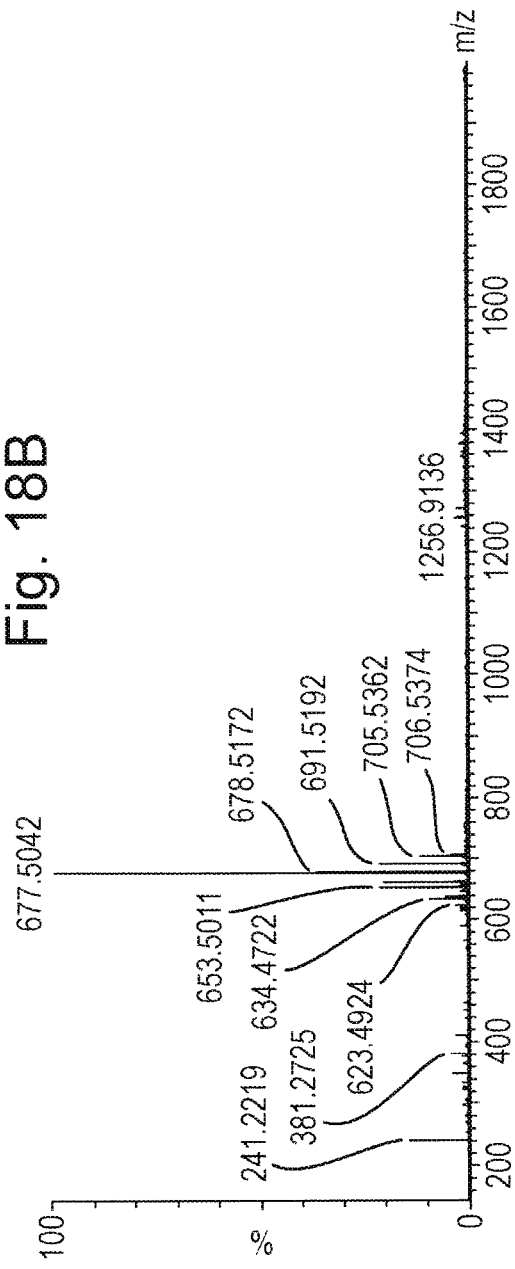

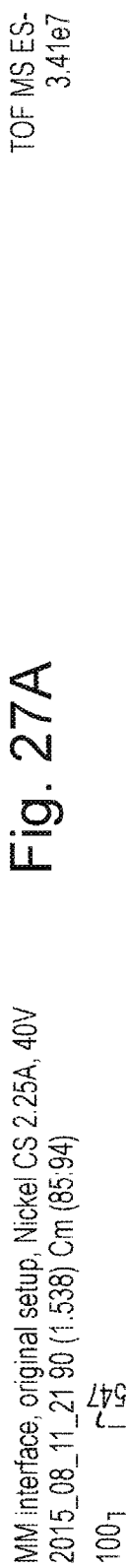
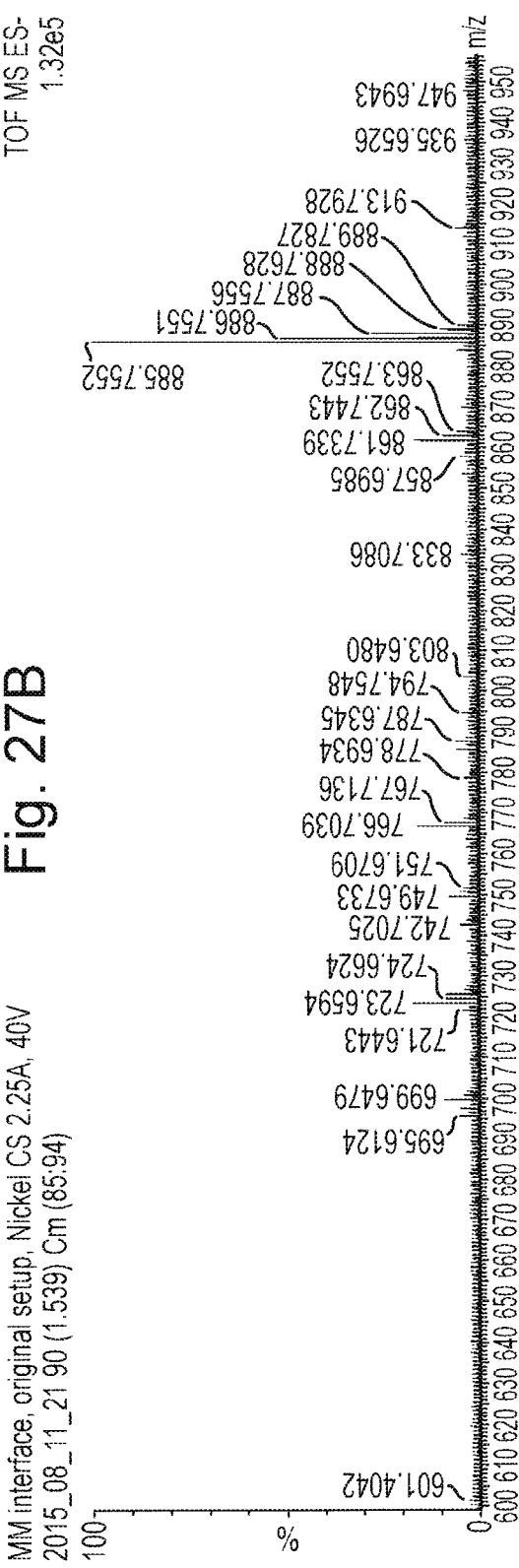
Fig. 27A
Fig. 27B

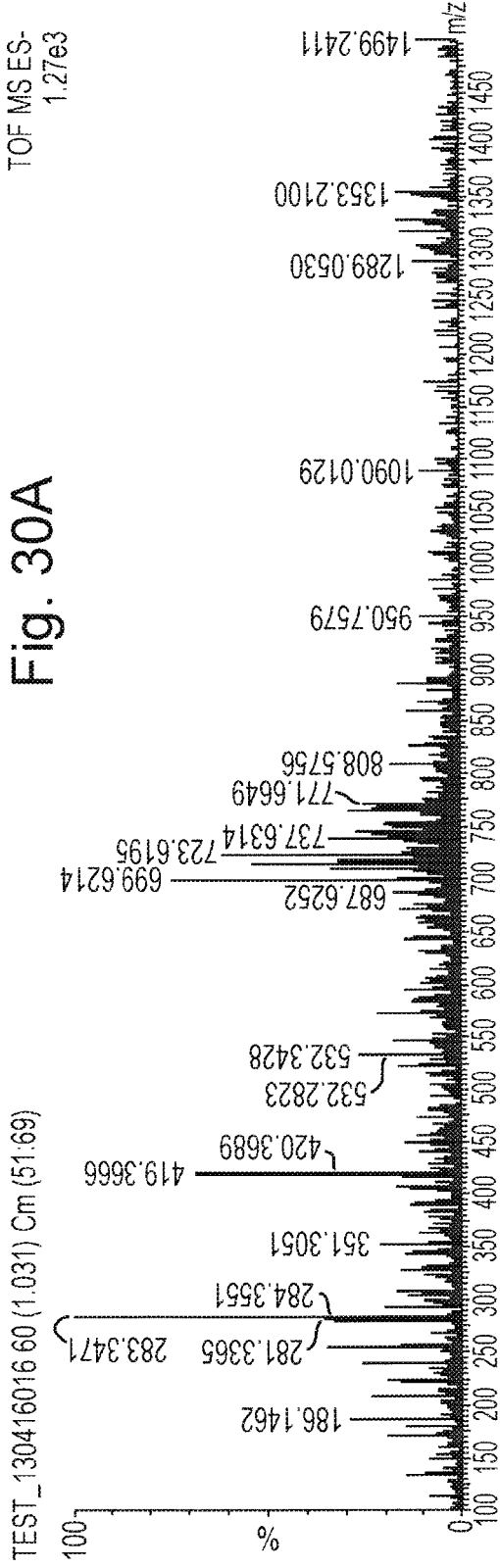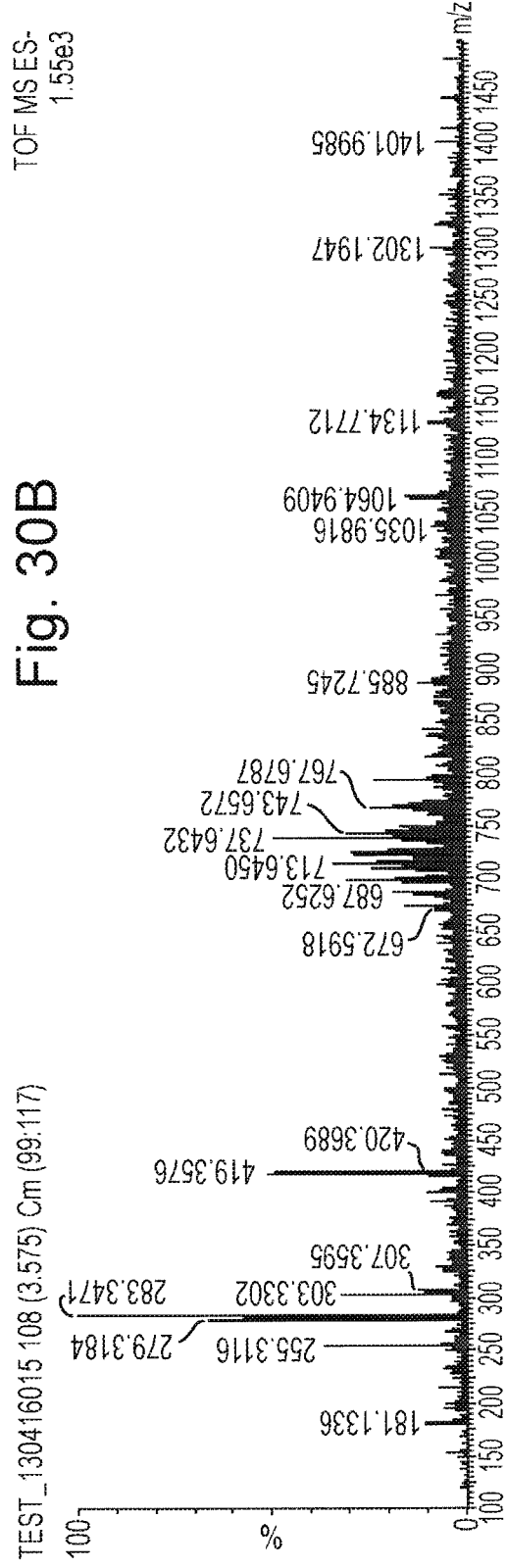

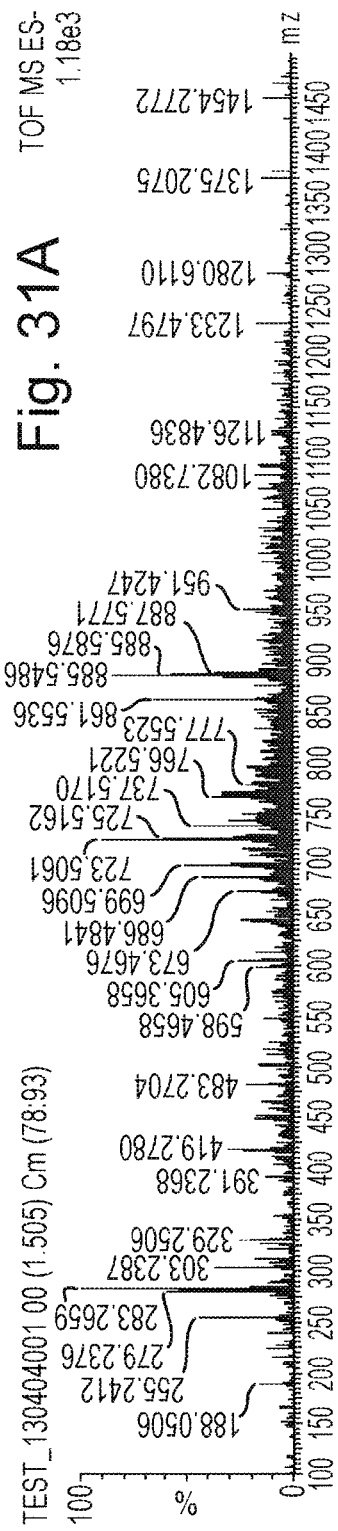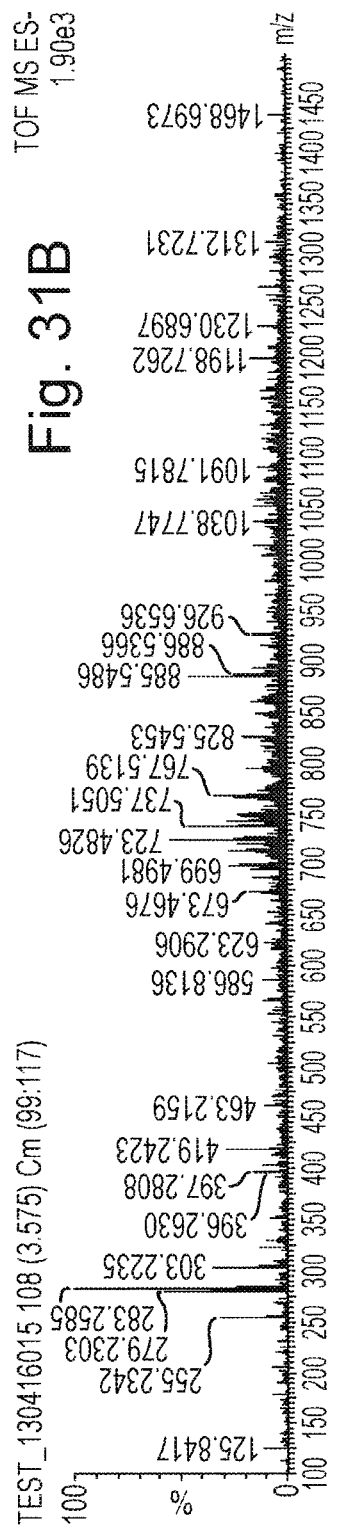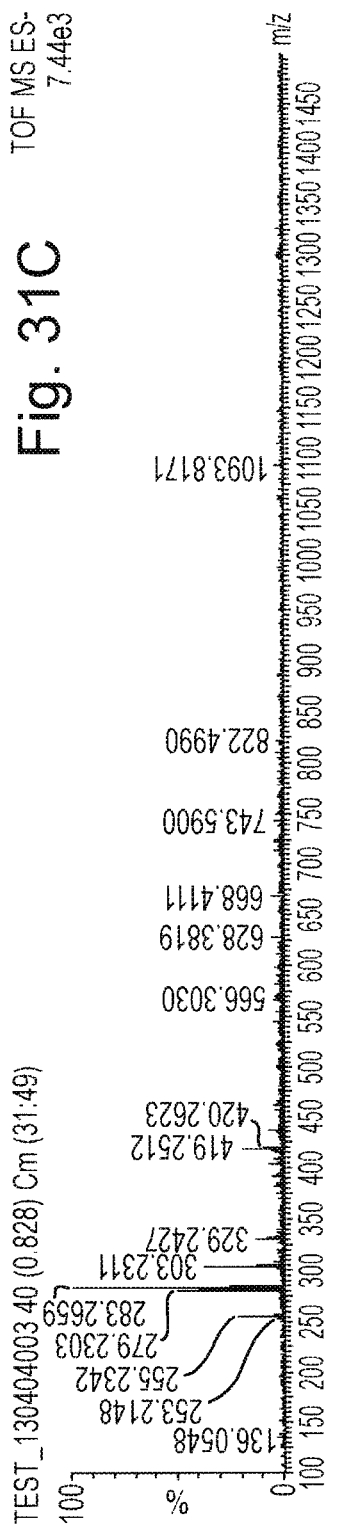

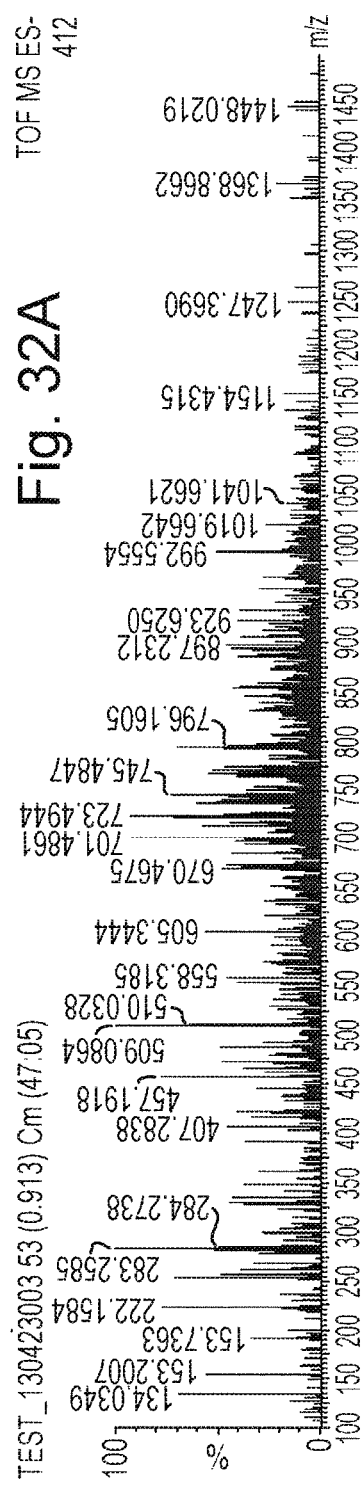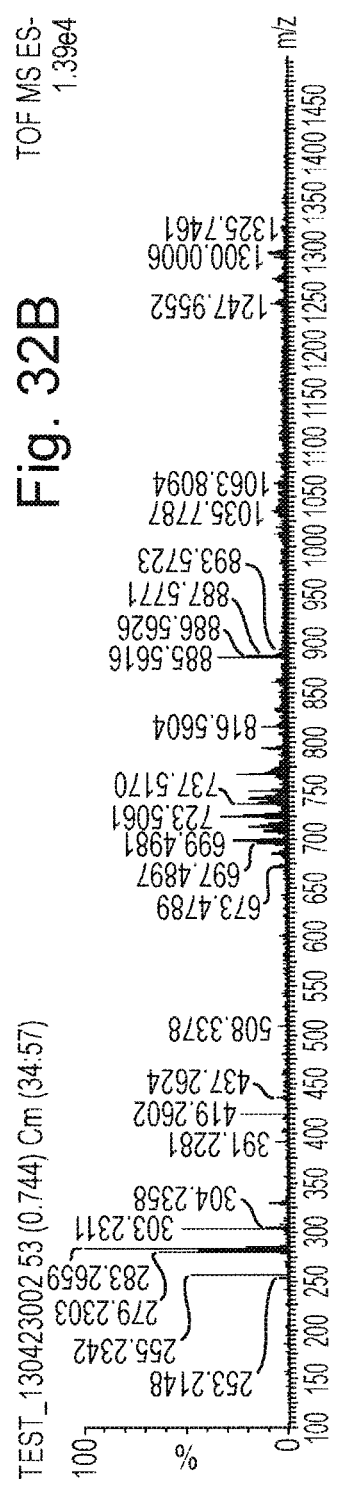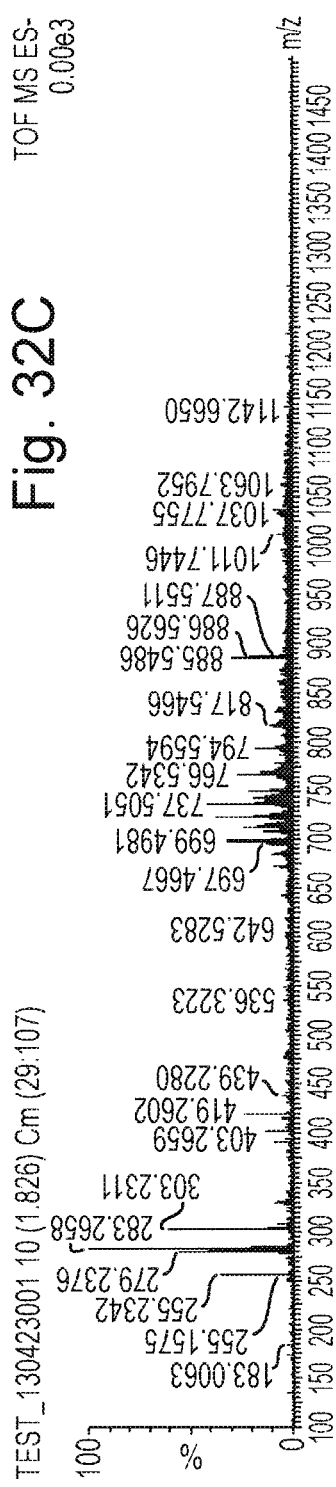

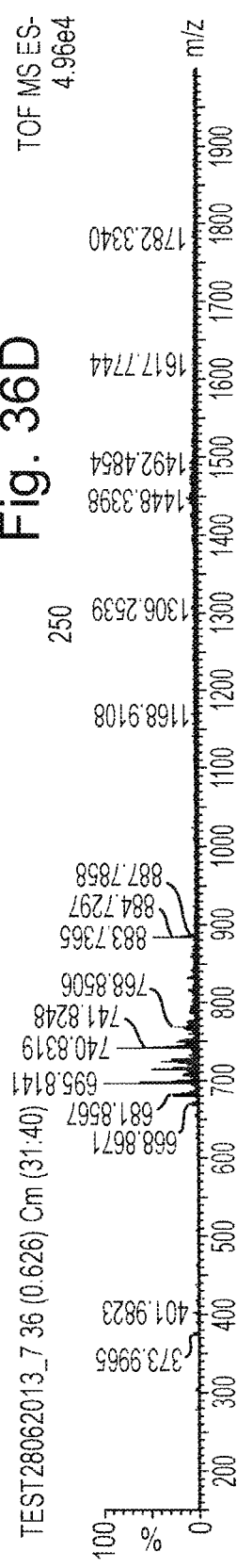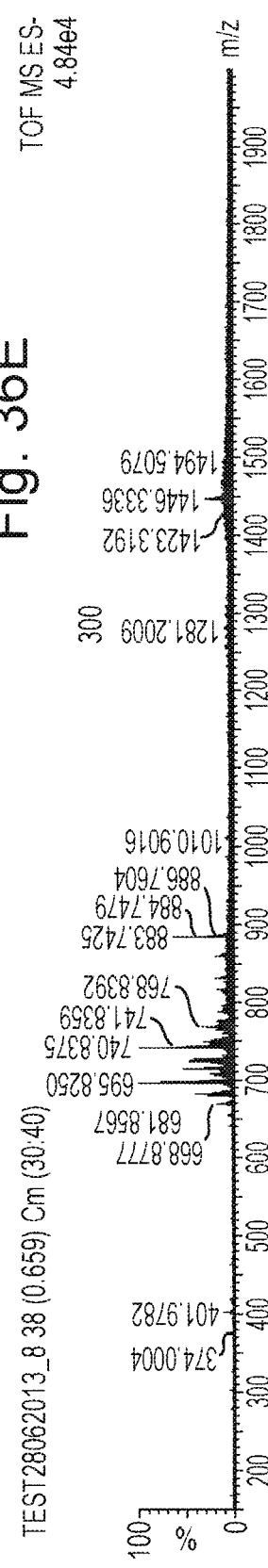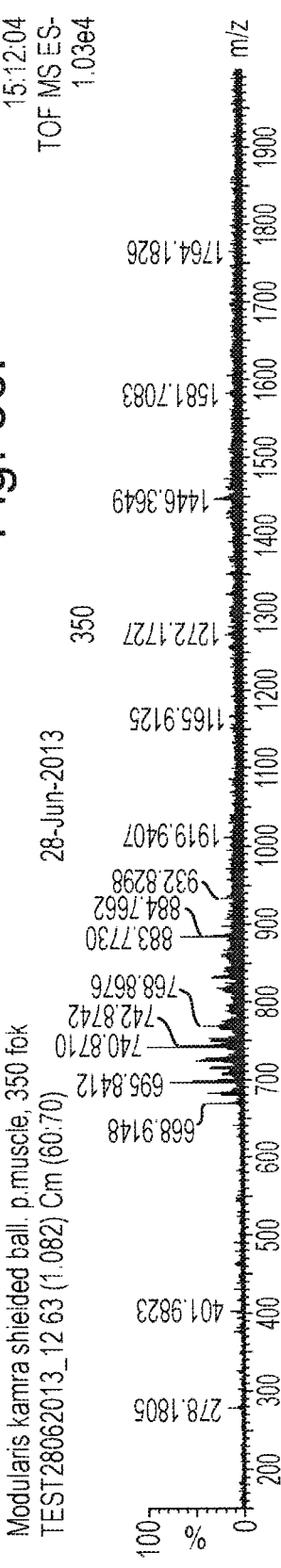

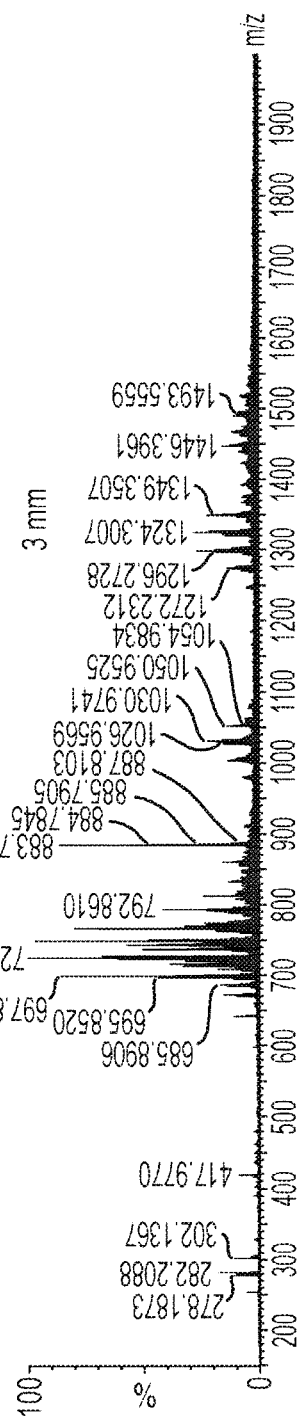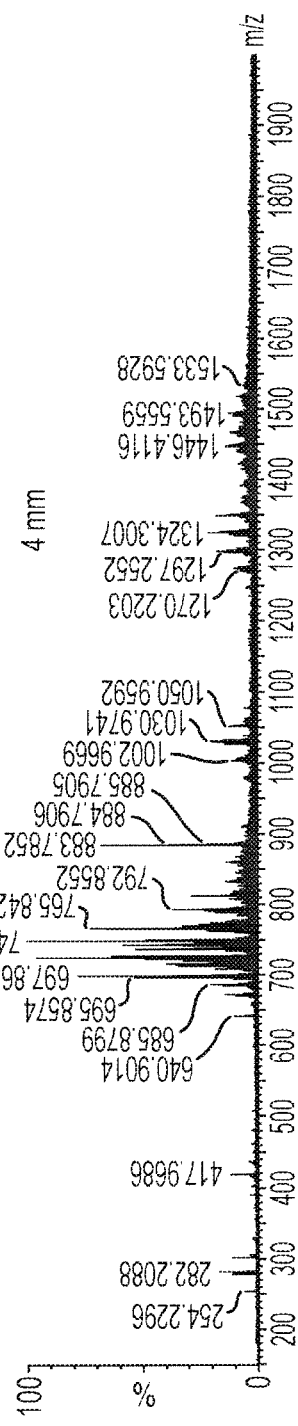

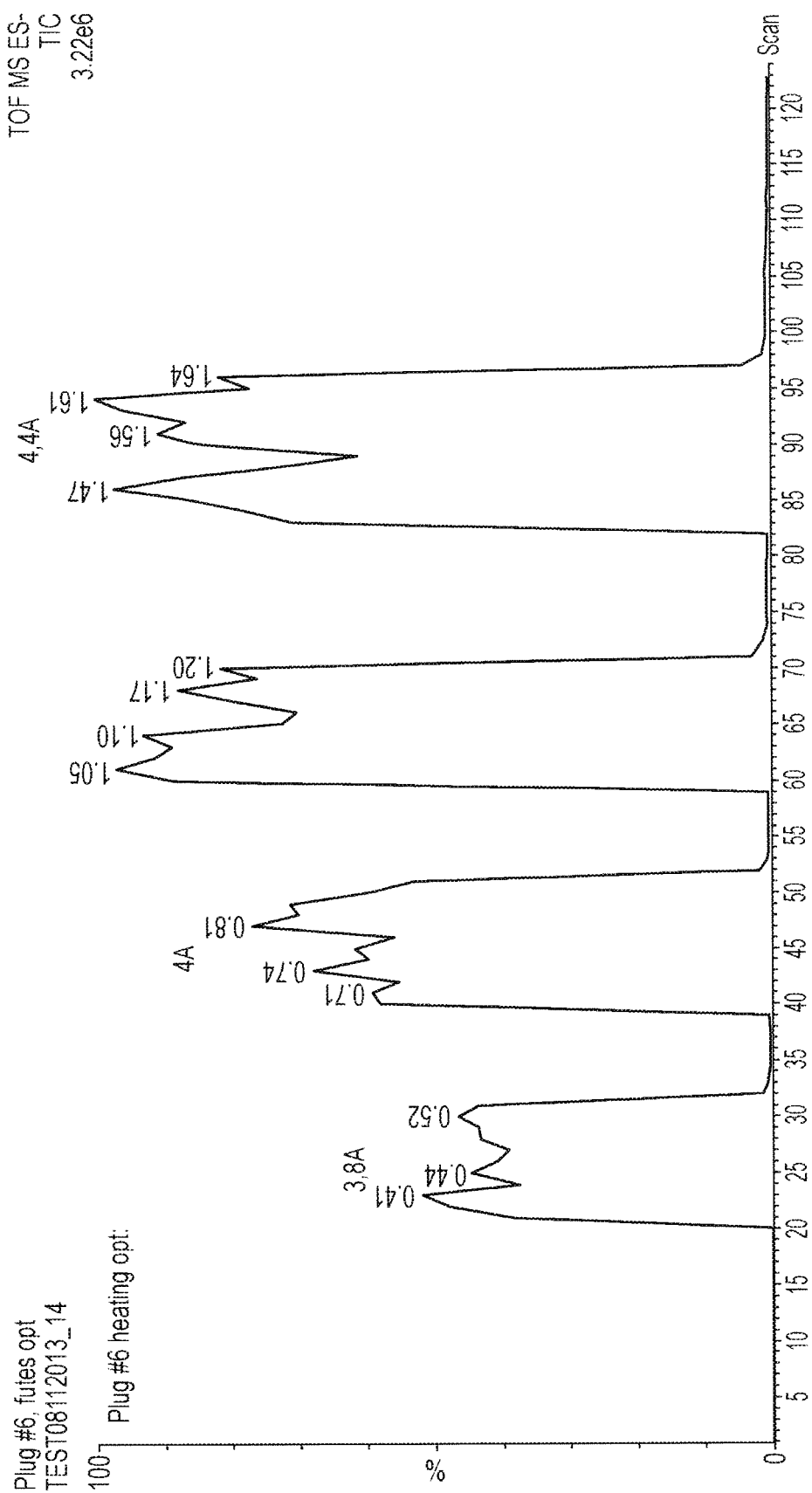

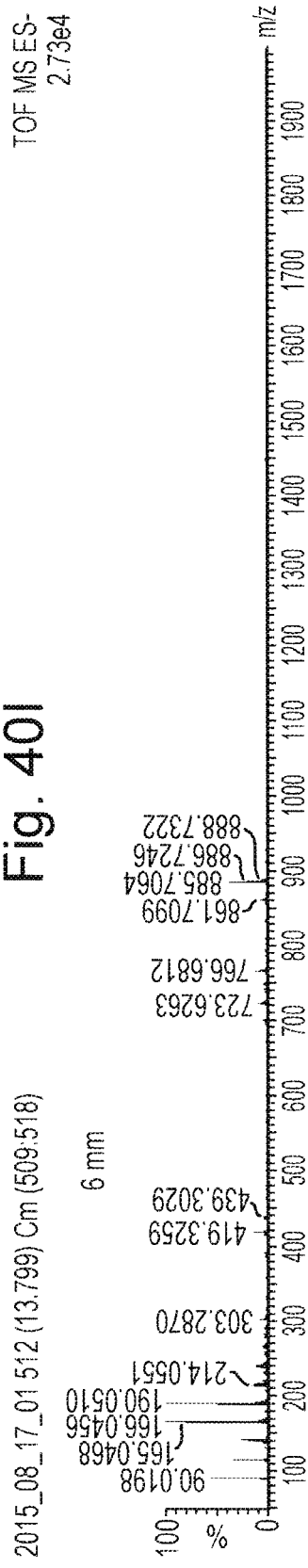
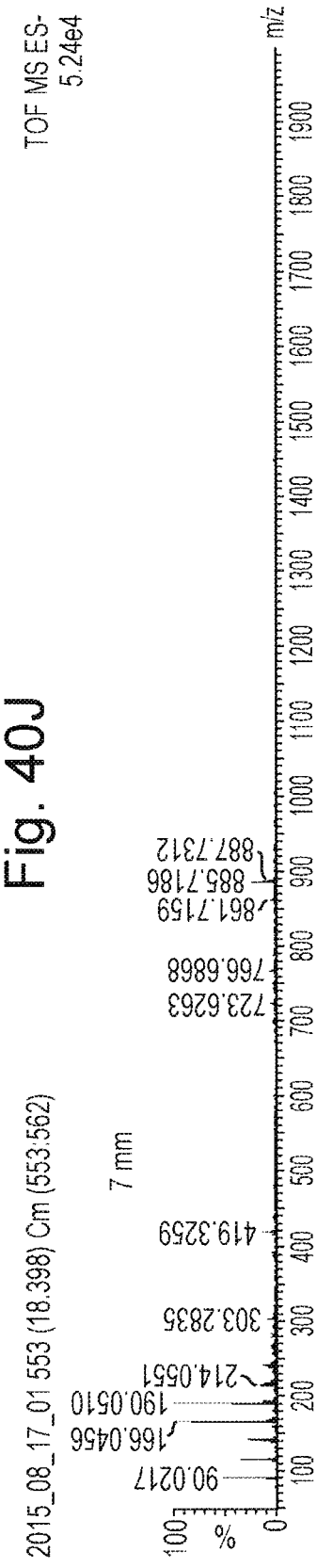
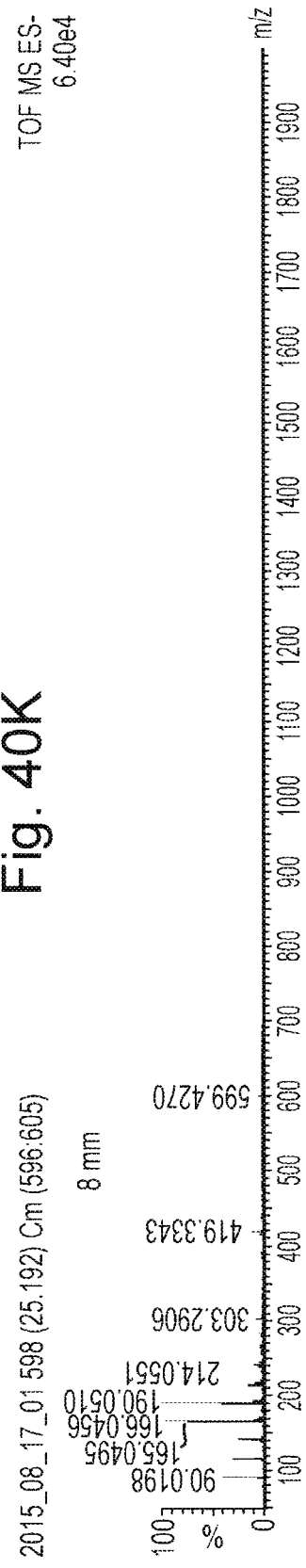

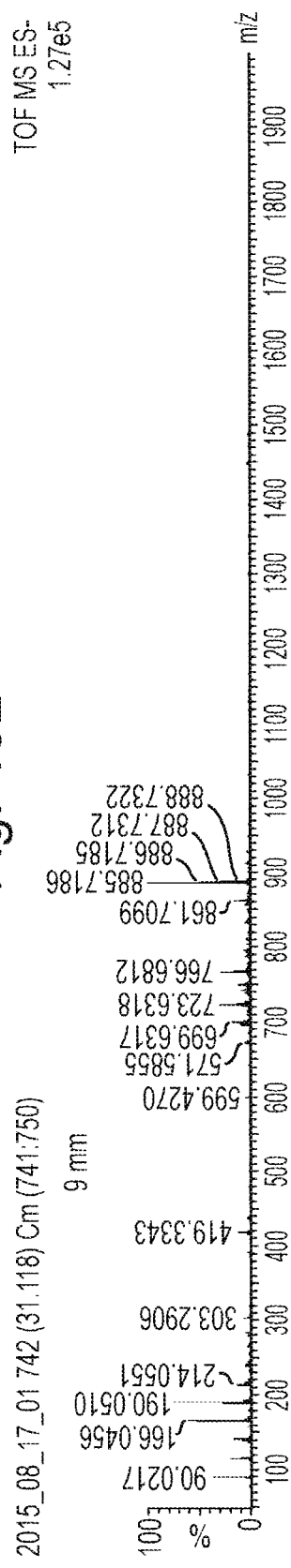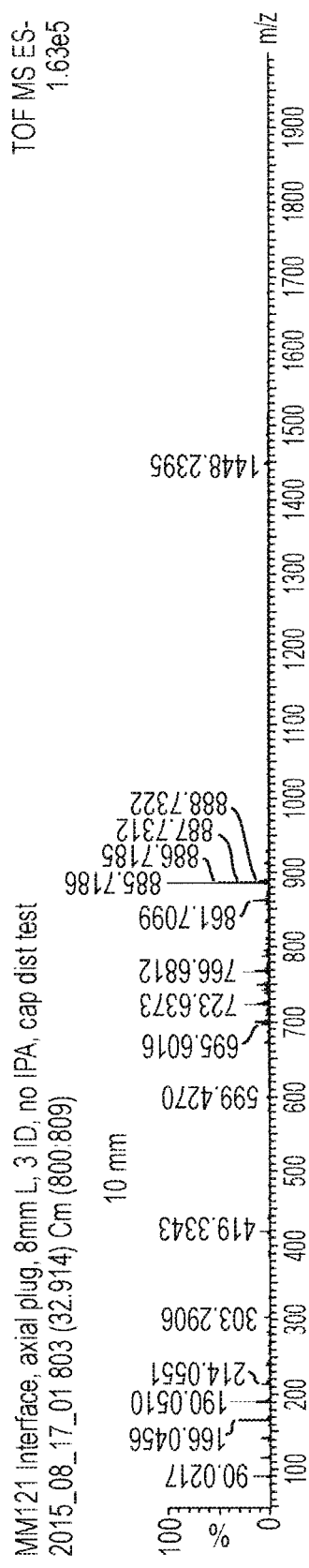

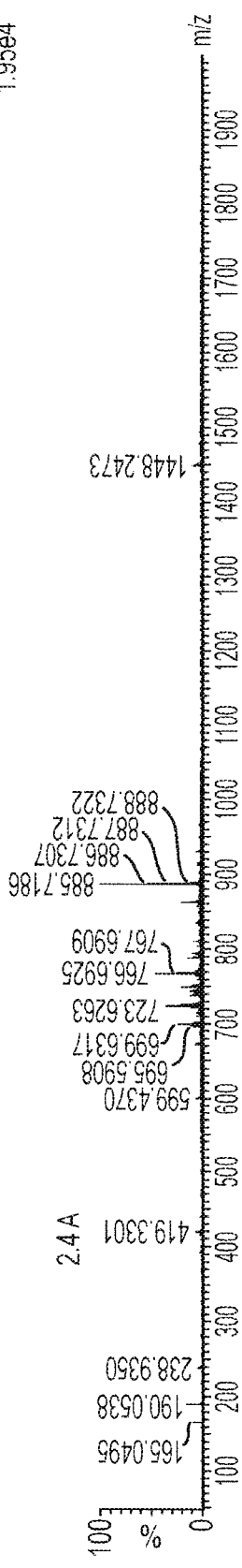
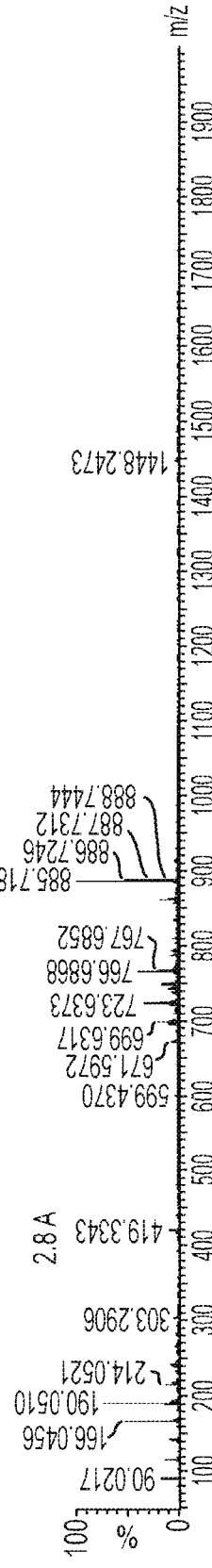
Fig. 41B
Fig. 41C
Fig. 41D

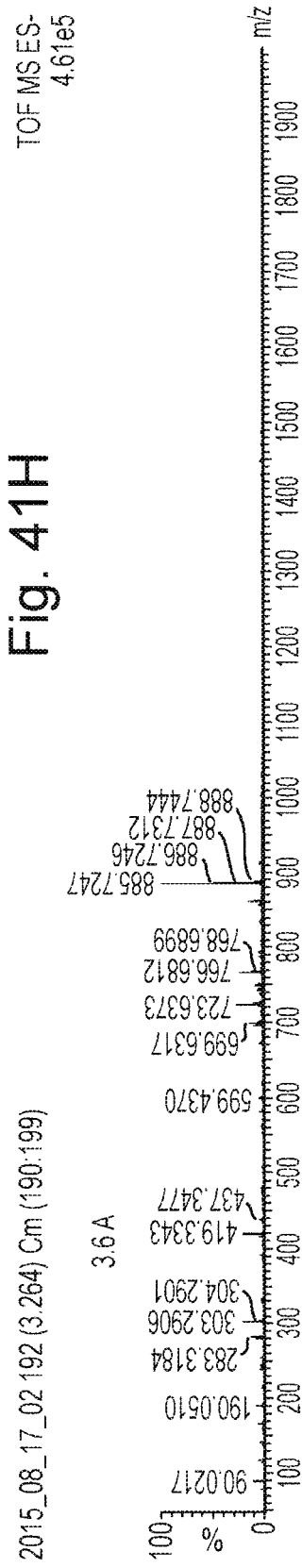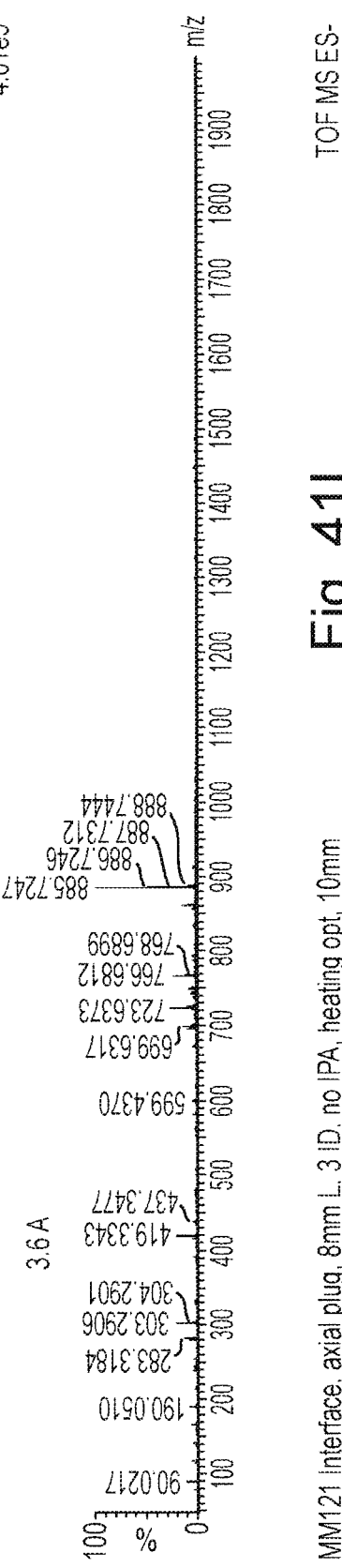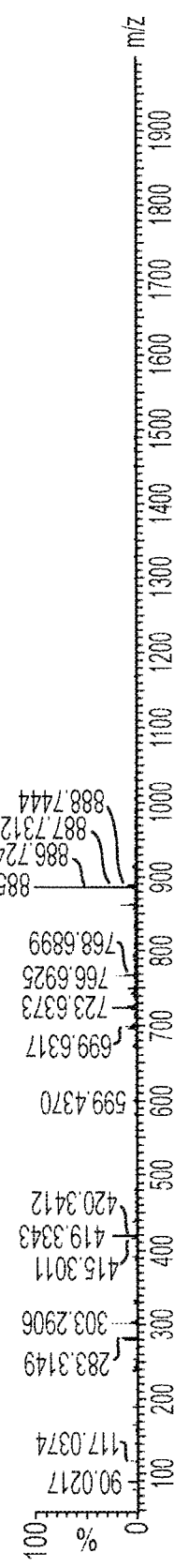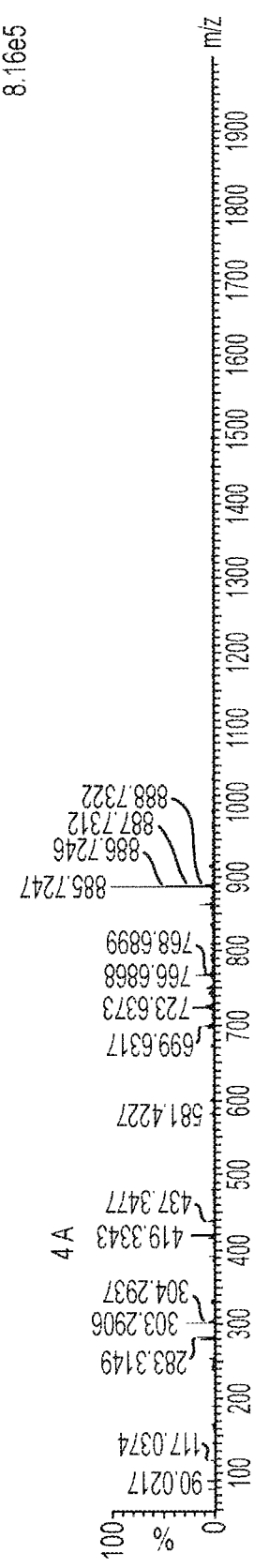
Fig. 41H  Fig. 41I  Fig. 41J

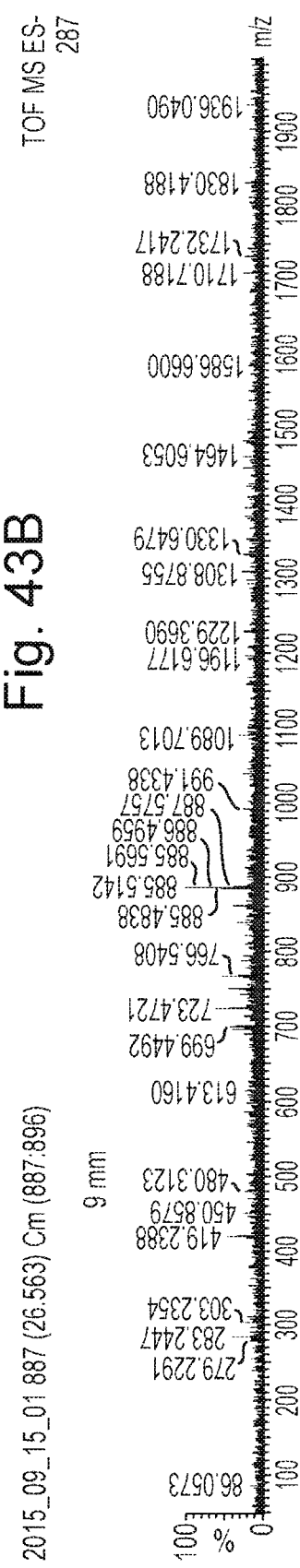
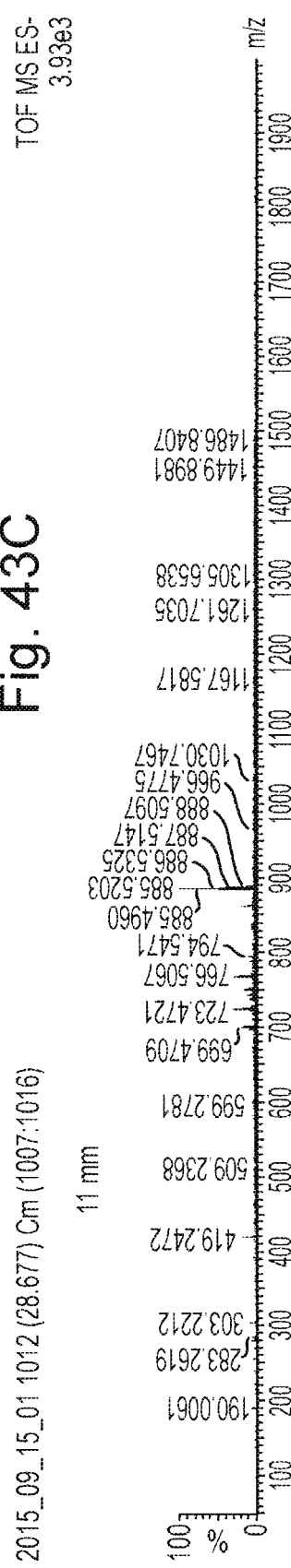
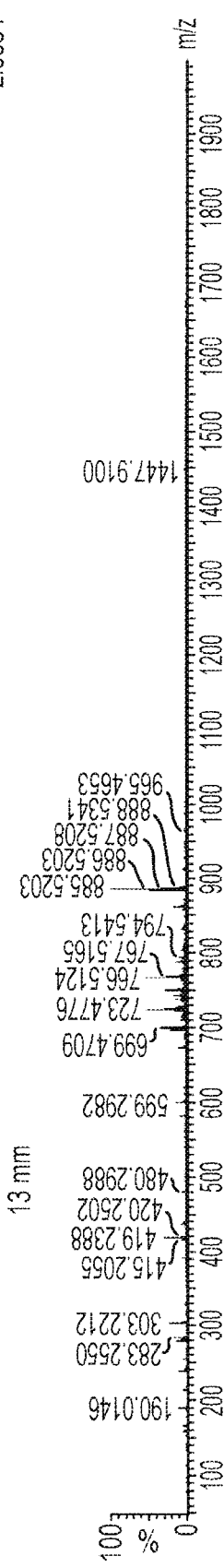
Fig. 43B
Fig. 43C
Fig. 43D

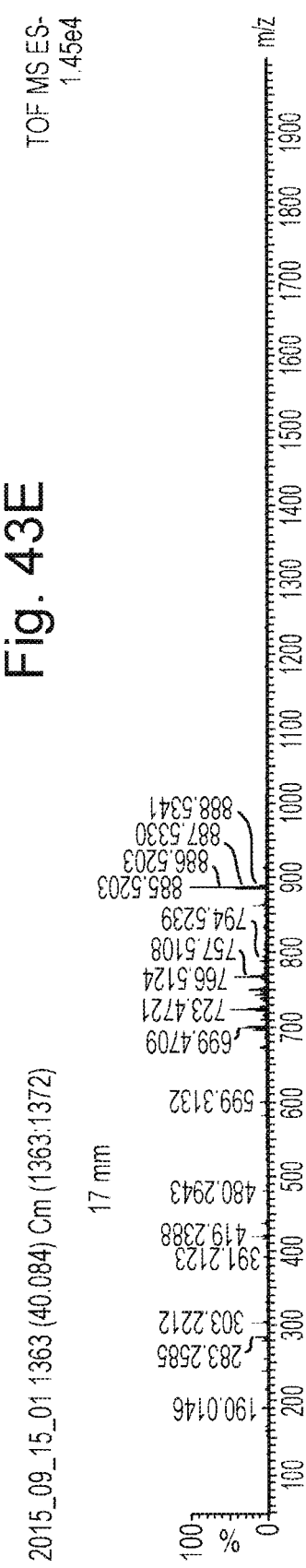
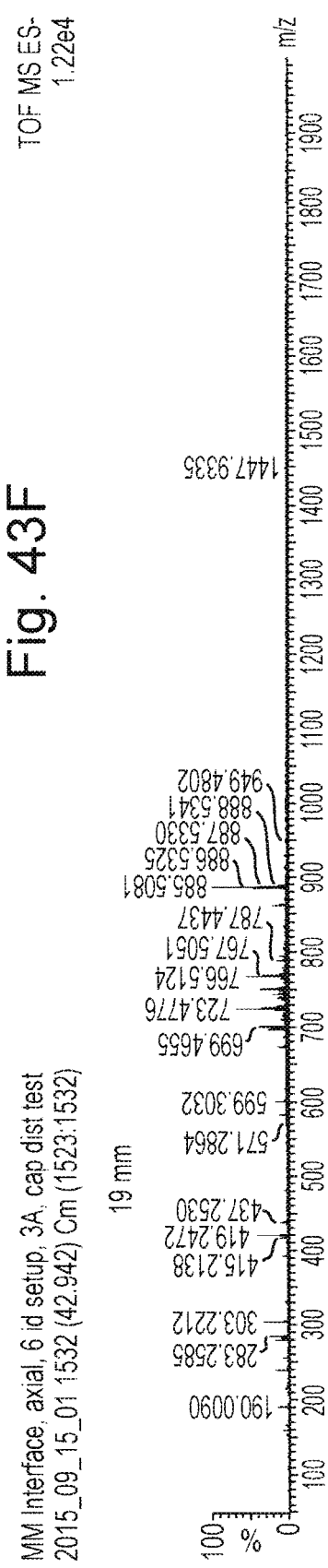

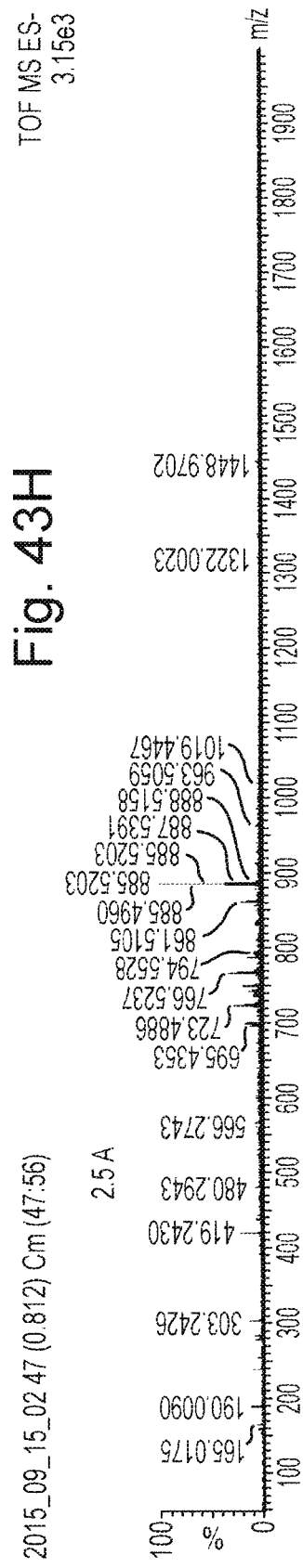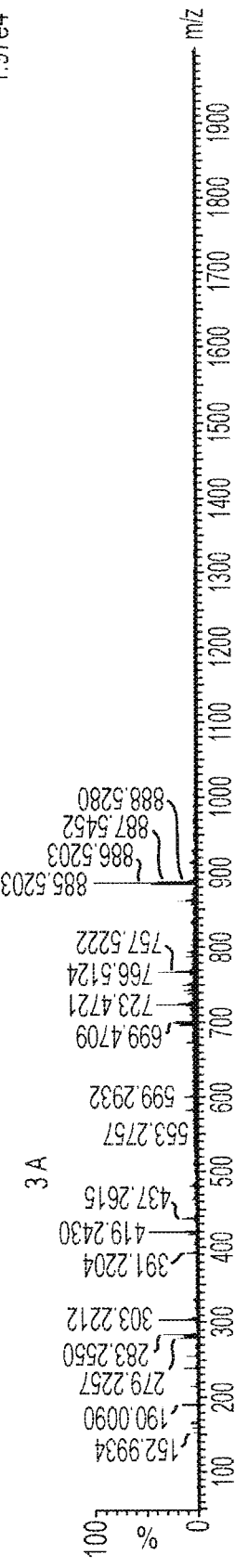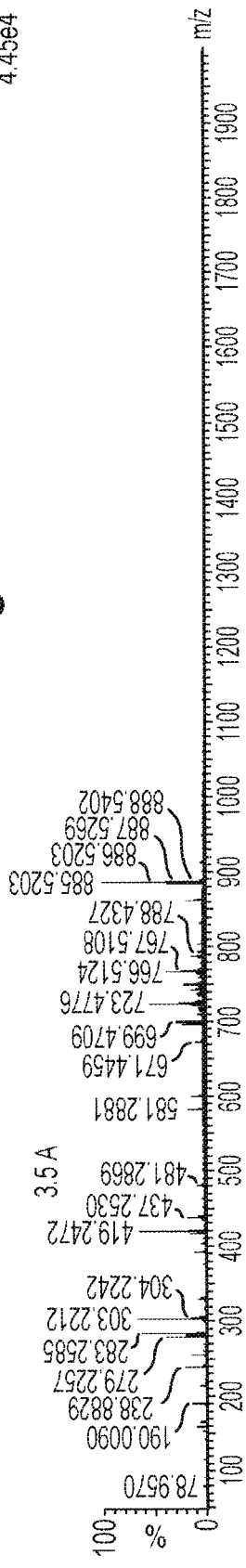

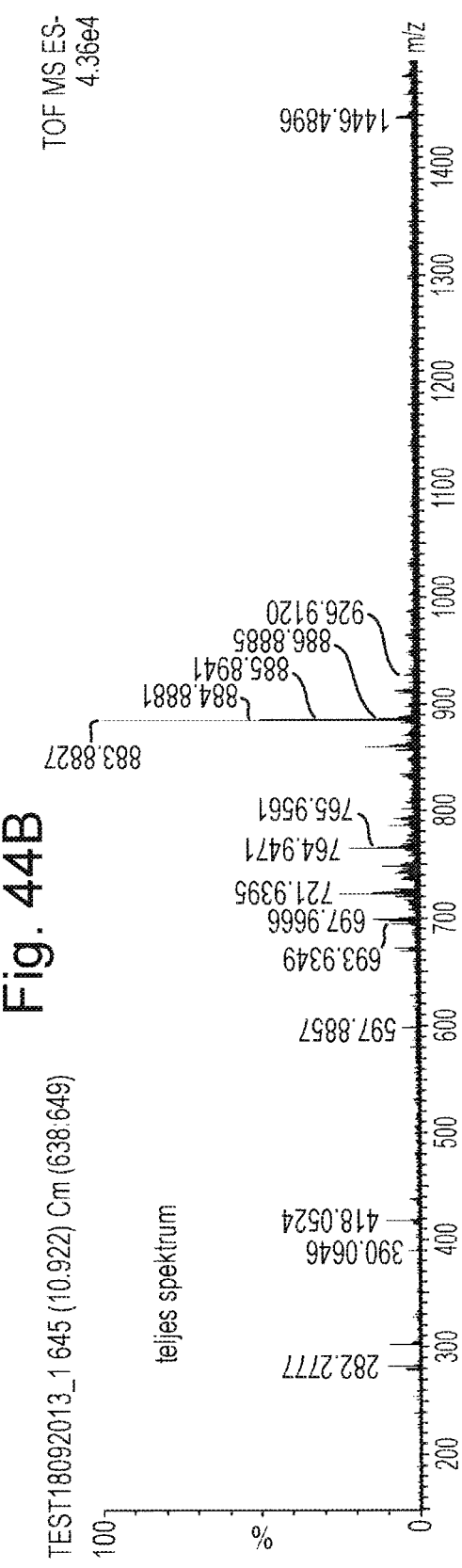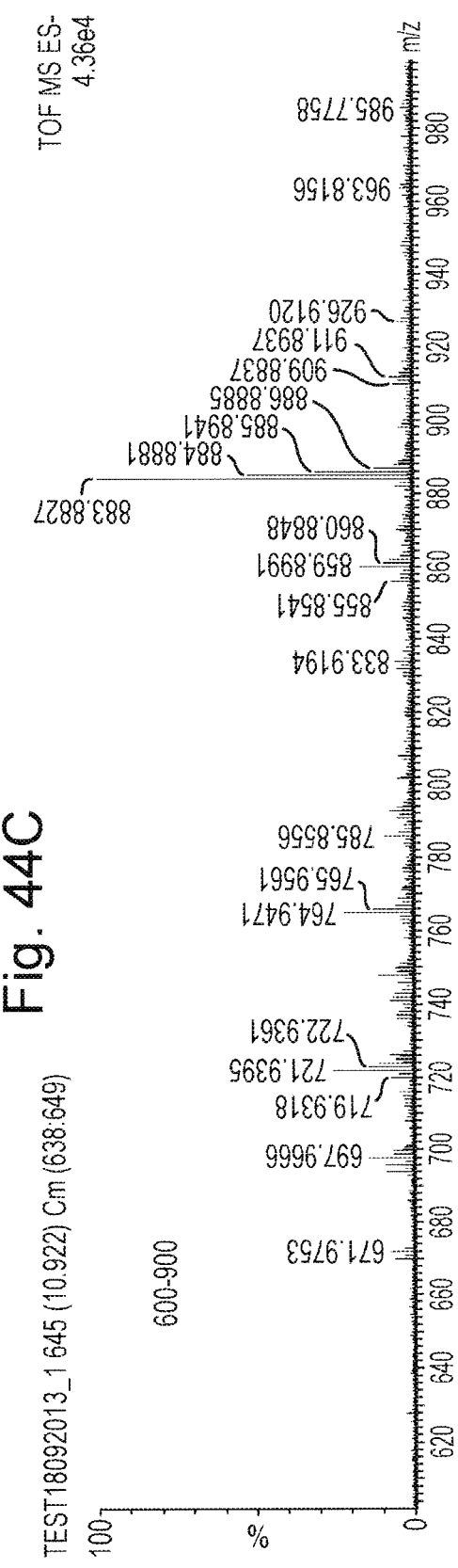

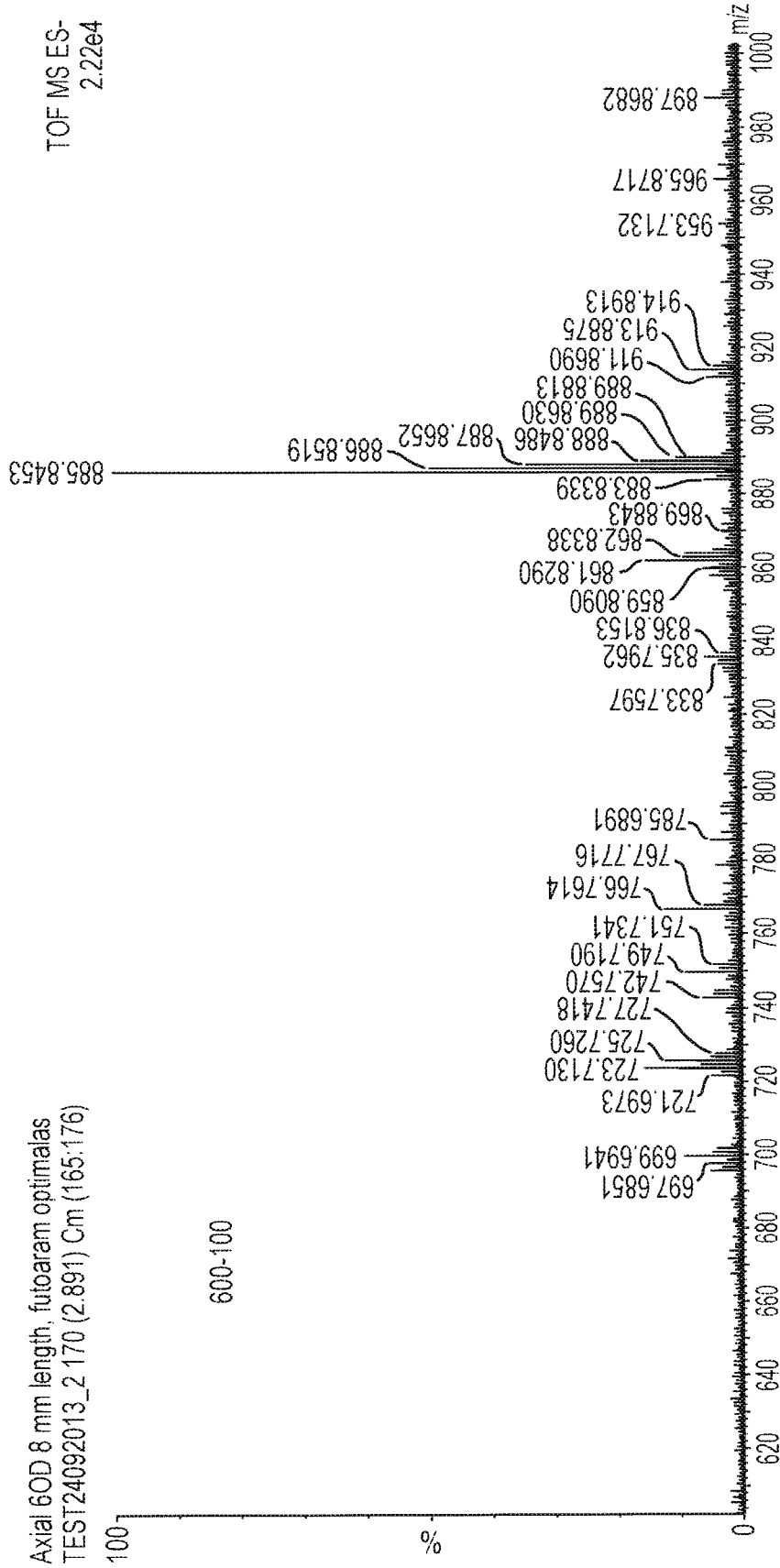

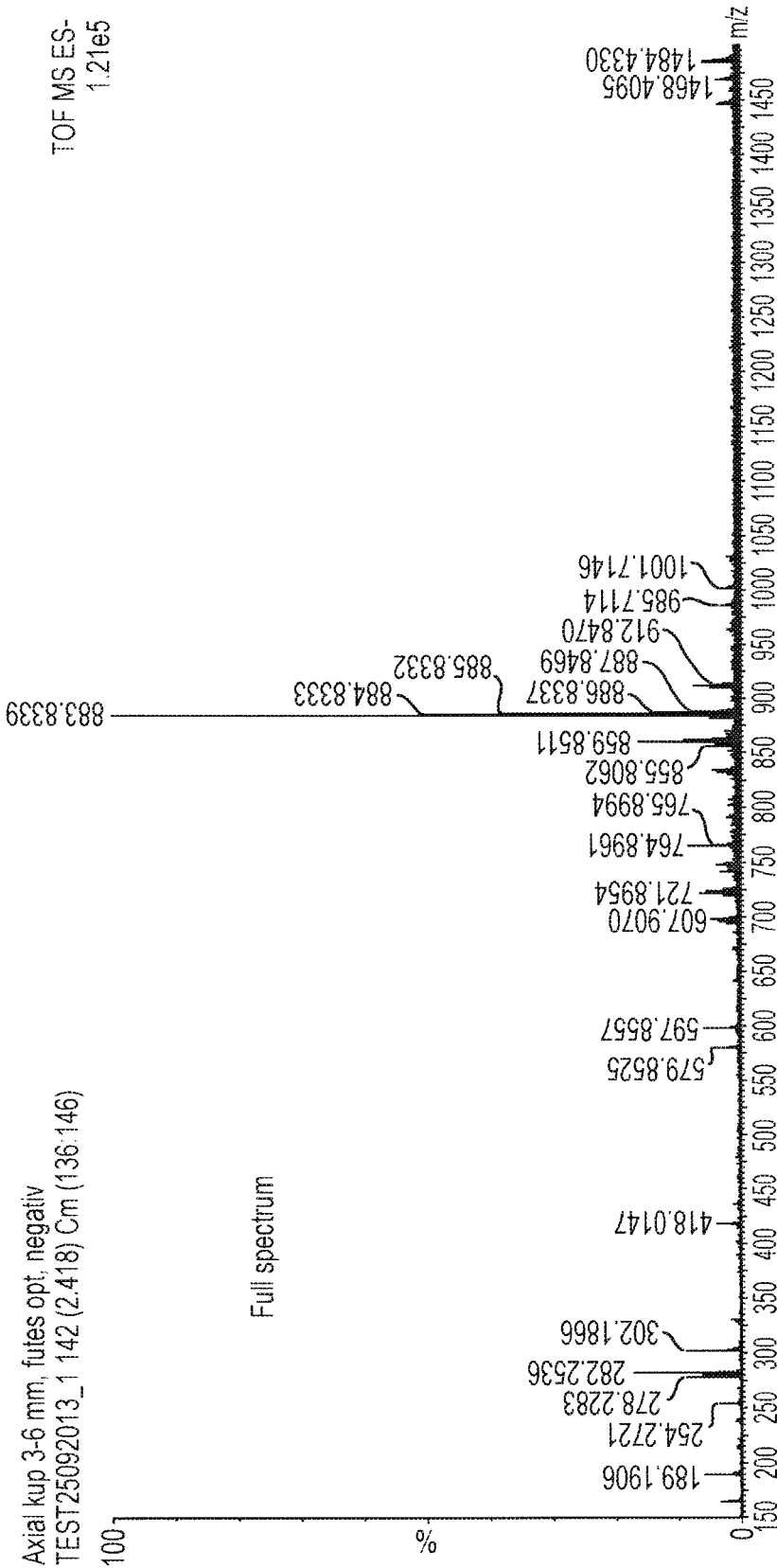

COLLISION SURFACE FOR IMPROVED IONISATION

CROSS-REFERENCE TO RELATED APPLICATION

This application is a continuation of U.S. patent application Ser. No. 15/555,845, filed Sep. 5, 2017, which is the U.S. National Stage of International Application No. PCT/GB2016/050614, filed Mar. 7, 2016, which claims priority from and the benefit of United Kingdom patent application No. 1503876.3 filed on Mar. 6, 2015, United Kingdom patent application No. 1503864.9 filed on Mar. 6, 2015, United Kingdom patent application No. 1518369.2 filed on Oct. 16, 2015, United Kingdom patent application No. 1503877.1 filed on Mar. 6, 2015, United Kingdom patent application No. 1503867.2 filed on Mar. 6, 2015, United Kingdom patent application No. 1503863.1 filed on Mar. 6, 2015, United Kingdom patent application No. 1503878.9 filed on Mar. 6, 2015, United Kingdom patent application No. 1503879.7 filed on Mar. 6, 2015 and United Kingdom patent application No. 1516003.9 filed on Sep. 9, 2015. The entire contents of these applications are incorporated herein by reference.

FIELD OF THE INVENTION

The present invention generally relates to mass and/or ion mobility spectrometry, and in particular, to apparatus for improving the ionisation of a sample. Embodiments relate to rapid evaporative ionisation mass and/or ion mobility spectrometry; mass and/or ion mobility spectrometers; separators or analysers; methods of rapid evaporative ionisation mass spectrometry ("REIMS"); methods of mass and/or ion mobility spectrometry; methods of electrosurgery and electrosurgical devices.

BACKGROUND

Rapid evaporative ionization mass spectrometry ("REIMS") is a technology which has recently been developed for the real-time identification of substrates, for example for the identification of biological tissues during surgical interventions. REIMS analysis of biological tissues has been shown to yield phospholipid profiles having high histological and histopathological specificity, similar to Matrix Assisted Laser Desorption Ionisation ("MALDI"), Secondary Ion Mass Spectrometry ("SIMS") and Desorption Electrospray Ionisation ("DESI") imaging.

Coupling of REIMS technology with handheld sampling devices has resulted in iKnife sampling technology, which can provide intra-operative tissue identification. This technology allows surgeons to resect target tissues more efficiently, such as tumours, intra-operatively by providing information that can assist a surgeon in minimizing the amount of healthy tissue removed whilst helping to resect the target tissue. iKnife sampling technology can also be used by non-surgical operators in non-surgical procedures to isolate target matter from an in vitro substrate.

In a known iKnife sampling system, a mass spectrometric signal is obtained by subjecting a substrate to alternating electric current at radiofrequency which causes localized Joule-heating and the disruption of cells along with desorption of charged and neutral particles. The resulting aerosol (e.g., "surgical smoke") is directly introduced into an atmospheric interface of an atmospheric pressure ionisation mass spectrometer for on-line mass spectrometric analysis. The aerosol contains a sufficient number of ionised molecules to allow the direct mass spectrometric fingerprinting of the biological tissues.

Post-evaporative ionisation of neutrals molecules in the sample may be used to enhance the ion yield. In this regard, electrospray and corona discharge post-ionisation methods were tested. Secondary electrospray ionisation, fused droplet electrospray ionisation and extractive electrospray ionisation have been used to increase the ion yield. These three techniques are similar in the sense that electrically charged solvent droplets are fused with aerosol particles in the gas phase and the resulting fused droplets undergo an electrospray-like ionisation process. However, these techniques suffer from the delicateness of electrospray setup, the sample carryover effects caused by DESI-like phenomena, electrospray-related restrictions on solvent type and flow rates, and patient safety considerations in human interventional environments due to the high voltages involved in these techniques.

It is also possible to enhance ionisation by facilitating the collision of the aerosol particles with collision surface in the vacuum region of the mass spectrometer. A collisional ion generator method was developed and is disclosed in WO 2013/098642 (Medimass) in which the aerosol particles enter the analyser at the atmospheric interface and are accelerated into the vacuum region of the analyser in the free jet regime. The aerosol particles accelerated by the free jet are then directed onto a collision surface causing the ion yield to be enhanced.

However, despite this enhancement, a number of problems still remain. For example, the ionisation yield for this technique remains relatively low. Also, there may be a lack of ionisation or suppression of analyte ion formation when electrosurgical diathermy is used in a coagulation mode. Also, there may be a lack of ionisation when tissue having a high triglyceride content is being dissected (e.g., in the case of breast cancer).

It is desired to provide an improved an improved apparatus and methods.

SUMMARY

From a first aspect the present invention provides apparatus for performing ambient ionisation mass spectrometry and/or ion mobility spectrometry comprising:

a substantially cylindrical, tubular, rod-shaped, coil-shaped, helical or spiral-shaped collision assembly; and a first device arranged and adapted to direct analyte, smoke, fumes, liquid, gas, surgical smoke, aerosol or vapour onto said collision assembly.

The smoke, fumes, liquid, gas, surgical smoke, aerosol or vapour comprises an analyte.

It has been found that cylindrical and tubular collision assemblies, particularly having a rounded surface, provide a relatively large analyte impact area whilst maintaining relatively high ion signals. Coil-shaped, helical or spiral-shaped collision assemblies have also been found to provide relatively high ion signals. Furthermore, these elongated collision surfaces may be relatively easily formed over, or formed by, electrically resistive heater coils and so may be heated easily, if heating is desired.

However, other shaped collision surfaces may be used. Accordingly, from another aspect the present invention provides apparatus for performing ambient ionisation mass spectrometry and/or ion mobility spectrometry comprising:

a collision assembly; and a first device arranged and adapted to direct analyte, smoke, fumes, liquid, gas, surgical smoke, aerosol or vapour onto said collision assembly.

The collision surface may be a mesh, such as a wire mesh.

The collision surface may be spherical, hemispherical, teardrop-shaped, plate-shaped, concave, dish-shaped or conical.

The collision assembly may have a first longitudinal axis and the first device may be arranged and adapted to direct the analyte, smoke, fumes, liquid, gas, surgical smoke, aerosol or vapour onto said collision assembly along a second axis which is substantially orthogonal to said first axis.

Alternatively, the collision assembly may have a first longitudinal axis and the first device may be arranged and adapted to direct the analyte, smoke, fumes, liquid, gas, surgical smoke, aerosol or vapour onto said collision assembly along said first axis.

The present invention also provides apparatus for ionising an aerosol, smoke or vapour comprising:

a hollow collision assembly having an inlet and an outlet, wherein the inner cross-sectional area of said collision assembly either: (i) is substantially constant; or (ii) reduces in a direction from said inlet to said outlet; or (iii) increases in a direction from said inlet to said outlet.

The embodiments relating to a hollow funnel-shaped collision assembly or a hollow cylindrical collision assembly have also been found to result in a high ion yield (or improved ionisation efficiency) coupled with a significant improvement in signal to noise ratio. Furthermore, these embodiments may also result in less contamination of the collision assembly and downstream ion optics by background clusters which are not of analytical interest.

The inlet may be arranged to receive said aerosol.

The aerosol may be arranged to impact upon an inner surface of said collision assembly.

The aerosol may be arranged to impact upon said inner surface so as to form or release analyte ions.

The analyte ions may be arranged to emerge from said collision assembly via said outlet.

The collision assembly may comprise a funnel-shaped collision assembly.

Alternatively, the collision assembly may comprise a tubular or cylindrical collision assembly.

The apparatus may comprise a first device arranged and adapted to direct said aerosol into said collision assembly along an axis which is substantially co-axial with a longitudinal axis of said collision assembly.

The collision assembly may be formed from a coiled structure or from a continuous tubular or conical structure.

The various apparatus described herein may comprise a heater or heater coil for heating said collision assembly.

The heater or said heater coil may be the collision assembly onto which the analyte, smoke, fumes, liquid, gas, surgical smoke, aerosol or vapour may be directed. The use of a heater coil as the collision surface has been found to have a particularly stable heat distribution.

The heater or said heater coil may be surrounded by the collision assembly or embedded within the collision assembly.

The collision assembly may comprise an aperture therein so that the heater or heater coil may be exposed by the aperture to the smoke, fumes, liquid, gas, surgical smoke, aerosol or vapour.

The apparatus may comprise one or more electrodes for supplying electrical power to said heater or said heater coil.

The apparatus may be configured to supply an electrical current to the heater or heater coil for heating the collision assembly, wherein the current is selected from the group consisting of: about $\geq 0.5$ A; $\geq$about 1 A; about $\geq 1.5$ A; about $\geq 2$ A; about $\geq 2.5$ A; about $\geq 3$ A; about $\geq 3.5$ A; about $\geq 4$ A; about $\geq 4.5$ A; and about $\geq 5$ A.

The heater or heater coil may be arranged to heat said collision assembly to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The heater or heater coil may be arranged and configured to burn off contaminants deposited on the collision assembly from the sample being analysed.

The collision assembly may be, or may comprise an outer collision surface that is: ceramic, non-ceramic, glass, glass-ceramic, quartz, metal such as steel or nickel, or metal-alloy such as iron-chromium-aluminium (FeCrAl) alloy, Kanthal, Nikrothal or Nichrome. The analyte, smoke, fumes, liquid, gas, surgical smoke, aerosol or vapour may be directed along an axis onto a region of the collision assembly having a maximum or minimum dimension orthogonal to the axis selected from the group consisting of: about $\geq 1$ mm; about $\geq 2$ mm; about $\geq 3$ mm; about $\geq 4$ mm; about $\geq 5$ mm; about $\geq 6$ mm; about $\geq 7$ mm; and about $\geq 8$ mm; and/or having a maximum or minimum dimension orthogonal to the axis selected from the group consisting of: about $\leq 8$ mm; about $\leq 7$ mm; about $\leq 6$ mm; about $\leq 5$ mm; about $\leq 4$ mm; and about $\leq 3$ mm.

The apparatus may comprise a sheath tube arranged around the collision assembly through which the smoke, fumes, liquid, gas, surgical smoke, aerosol or vapour may travel in use.

The sheath tube may extend upstream and/or downstream of the collision assembly.

The apparatus may comprise one or more voltage supplies for maintaining a potential difference between the collision assembly and the sheath tube.

The apparatus may comprise a capillary or sample tube for delivering the smoke, fumes, liquid, gas, surgical smoke, aerosol or vapour onto said collision assembly.

The exit orifice of the capillary or sample tube may be arranged a distance upstream of the collision surface of the collision assembly selected from the group consisting of: about 0 mm; about 1 mm; about 1-2 mm; about 2-3 mm; about 3-4 mm; about 4-5 mm; about 5-6 mm; about 6-7 mm; about 7-8 mm; about 8-9 mm; about 9-10 mm; and about $\geq 10$ mm. Alternatively, or additionally, the capillary or sample tube may be received in a bore and may comprise a movement limiting member attached thereto and extending radially outward from an outer surface thereof for engaging another portion of the apparatus so as to limit the extent of movement of the capillary or sample tube into the bore in order to locate the exit of the capillary or sample tube at a predetermined, fixed distance from the collision surface. For example, the movement limiting member may comprise a disc arranged around the capillary or sample tube.

The movement limiting member may be fixedly secured to the capillary or sample tube, e.g. by welding, or may be selectively movable along the capillary or sample tube so as to select the distance between the exit of the capillary or sample tube and the collision surface.

The apparatus may comprise a heater for heating the capillary or sample tube.

The heater may be configured to heat the capillary or sample tube to a temperature selected from the group consisting of: (i) about <100° C.; (ii) about 100-150° C.; (iii) about 150-200° C.; (iv) about 200-250° C.; (v) about 250-300° C.; (vi) about 300-350° C.; (vii) about >350° C.

The apparatus may comprise a first holder for supporting said collision assembly.

The first holder may be formed from a ceramic or a non-ceramic.

The one of more electrodes for supplying electrical power to said heater or heater coil may pass through said first holder.

The apparatus may comprise a main heater assembly or unit housing.

The first holder may be removably mounted to said main heater assembly or unit housing.

The main heater assembly or unit housing may comprise a bore running therethrough and a first isolation valve for selectively closing said bore; optionally wherein said first isolation valve comprises a ball valve.

The first isolation valve may be arranged and configured to open when one or more capillaries or sample tubes are inserted into said bore.

The first isolation valve may be arranged to close when said one or more capillaries or sample tubes are at least partially or fully removed from said bore.

The apparatus may comprise said one or more capillaries or sample tubes which extend or are positioned, in use, through said bore for supplying analyte, smoke, fumes, liquid, gas, surgical smoke, aerosol or vapour onto said collision assembly.

The one or more capillaries or sample tubes may extend, in use, through said first holder.

The one or more capillaries or sample tubes may have an exit which is arranged, in use, substantially adjacent said collision assembly or facing said collision assembly.

The apparatus may comprise one or more shields at least partially surrounding said collision assembly in an extended position for protecting said collision assembly.

The shield may be in the extended position, for example, as said main heater assembly is inserted within or otherwise being connected to a source housing (i.e. before complete connection).

The one or more shields may be at least partially or fully retractable from said extended position to a retracted position in which at least part of the collision assembly is not surrounded by the one or more shields.

The shield may be in the retracted position, for example, once the main heater assembly has been inserted within or otherwise connected to said source housing.

The one or more shields may be biased towards said extended position.

The apparatus may comprise a source housing.

The source housing may comprise a second isolation valve.

The main heater or removable unit housing assembly may be insertable within or connectable to said source housing and wherein, in use, said main heater assembly or removable unit housing may be then additionally rotatable from a first rotational position to a second rotational position.

The rotation of said main heater assembly or removable unit housing from said first position to said second position may be arranged and adapted to move, in use, said second isolation valve from a first operational position to a second operational position.

The first operational position of said second isolation valve may be substantially closed.

The second operational position of said second isolation valve may be substantially open.

The first device or said apparatus may comprise or form part of an ambient ion or ionisation source; or said first device or apparatus may be configured to generate aerosol, smoke or vapour from a target to be analysed and which contains ions or is subsequently ionised by an ambient ion or ionisation source or other ionisation source.

For example, the first device or apparatus may be configured to generate aerosol, smoke or vapour comprising analyte and/or analyte ions from the target and that aerosol, smoke or vapour may be collided with the collision assembly in order to form or release analyte ions.

The target may comprise native or unmodified target material.

The native or unmodified target material may be unmodified by the addition of a matrix or reagent (i.e. no matrix or reagent added).

The first device or apparatus may be arranged and adapted to generate aerosol, smoke or vapour from one or more regions of said target without said target requiring prior preparation.

The first device or apparatus may comprise or form part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

The first device or apparatus may comprise one or more electrodes and may be arranged and adapted to generate aerosol, smoke or vapour from one or more regions of said target by contacting said target with said one or more electrodes.

The one or more electrodes may comprise either: (i) a monopolar device, wherein optionally a separate return electrode is provided; (ii) a bipolar device; or (iii) a multi-phase RF device, wherein optionally at least one separate return electrode is provided.

The one or more electrodes may comprise a rapid evaporation ionization mass spectrometry ("REIMS") device.

The apparatus may comprise a device arranged and adapted to apply an AC or RF voltage to said one or more electrodes in order to generate said aerosol, smoke or vapour.

The device for applying said AC or RF voltage to said one or more electrodes may be arranged to apply one or more pulses of said AC or RF voltage to said one or more electrodes.

The application of said AC or RF voltage to said one or more electrodes may cause heat to be dissipated into said target.

The first device or apparatus may comprise a laser for irradiating said target.

The first device or apparatus may be arranged and adapted to generate aerosol from one or more regions of said target by direct evaporation or vaporisation of target material from said target by Joule heating or diathermy.

The first device or apparatus may be arranged and adapted to direct ultrasonic energy into said target.

The aerosol may comprise uncharged aqueous droplets, optionally comprising cellular material.

At least 50%, 55%, 60%, 65%, 70%, 75%, 80%, 85%, 90% or 95% of the mass or matter generated by said first device or apparatus and which forms said aerosol may be in the form of droplets.

The first device may be arranged and adapted to generate aerosol wherein the Sauter mean diameter ("SMD", d32) of said aerosol is in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating said aerosol, said aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating said aerosol, said aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating said aerosol, said aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprises biological tissue, biological matter, a bacterial colony or a fungal colony.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, soft tissue, connective tissue, peritoneal tissue, blood vessel tissue, fat tissue, ureter tissue, urethra tissue; grade I, grade II, grade III or grade IV cancerous tissue; metastatic cancerous tissue; mixed grade cancerous tissue; a sub-grade cancerous tissue; healthy or normal tissue; or cancerous or abnormal tissue.

The first device or apparatus may comprise a point of care ("POC"), diagnostic or surgical device.

Analyte or the smoke, fumes, liquid, gas, surgical smoke, aerosol or vapour may be directed onto said collision assembly so as to generate or release a plurality of analyte ions.

The present invention also provides a mass and/or ion mobility spectrometer comprising an apparatus as described hereinabove.

The mass and/or ion mobility spectrometer may comprise a spectrometer main housing or assembly and the source housing may be connected, in use, to said spectrometer main housing.

The mass and/or ion mobility spectrometer may comprise one or more: ion traps; ion mobility separation (IMS) devices (e.g., drift tube and IMS travelling wave devices); and/or mass analysers or filters. The one or more mass analysers may comprise a quadrupole mass analyser and/or Time-of-Flight (TOF) mass analyser.

The spectrometer may comprise an ion trap and/or an ion guide. Optionally, the ion guide may be configured to apply an electric field that separates ions from neutral species.

The spectrometer may comprise a device which is arranged and adapted to trap analyte ions in said ion trap and/or to guide analyte ions using said ion guide.

The spectrometer may comprise an analyser for analysing analyte ions.

The analyser may comprise: (i) a mass analyser for mass analysing said analyte ions; (ii) an ion mobility or differential ion mobility analyser; (iii) an analyser for analysing the ionic cross-sections or collision cross sections of said analyte ions; (iv) a separator for separating said analyte ions according to their ion mobility or differential ion mobility; (v) a separator for separating said analyte ions according to their ion mobility or differential ion mobility prior to mass analysing said analyte ions; or (vi) a device arranged and adapted to exclude or discard analyte ions based upon their ion mobility or differential ion mobility.

A matrix may be supplied, in use, to said analyte, aerosol, smoke, vapour or liquid whilst said analyte, aerosol, smoke, vapour or liquid is in gas phase, vapour form, aerosol form or in liquid phase. The analyte, aerosol, smoke, vapour or liquid, or at least analyte within the aerosol, smoke, vapour or liquid, may dissolve in the matrix, may be diluted by the matrix or may form clusters with the matrix.

As described above, the analyte may be diluted by the matrix or dissolved into the matrix. For example, the analyte may be in provided in the form of droplets, aerosol or liquid and may be fused or coalesced with the matrix, or dissolved into the matrix. The matrix may be in the form of droplets, solids, aerosol or liquid when in contact with the analyte. Diluting, or dissolving the analyte in the matrix, may substantially eliminate or reduce intermolecular bonding between the analyte molecules. As such, when the diluted or dissolved analyte droplet is subsequently collided with the collision assembly it fragments into smaller droplets, wherein any given smaller droplet is likely to contain fewer analyte molecules than it would if the matrix were not present. This leads to the more efficient generation of analyte ions.

It is thought that ionisation of the analyte predominantly occurs due to ionic dissociation of the analyte in the solution phase, due to interactions with counter ions present in the sample being analysed. Diluting or dissolving the analyte in the matrix reduces the concentration of the analyte in each droplet and facilitates ionic dissociation in the solution phase, thus ultimately resulting in a greater proportion of the analyte being ionised. Accordingly, any matrix that dissolves or dilutes the analyte may be used. The spectrometer may comprise a device arranged and adapted to supply matrix molecules to, and to intermix said matrix molecules with, said analyte, aerosol, smoke or vapour whilst said matrix is in a gas phase.

The spectrometer may comprise a device which is arranged and adapted to transfer the mixture from a high pressure region to a low pressure region such that said gas phase matrix cools and condenses to a liquid and wherein at least part of said aerosol, smoke or vapour dissolves in said liquid matrix so as to form dissolved analyte droplets.

The matrix may be selected from the group consisting of: (i) a solvent for said analyte, smoke, fumes, liquid, gas, surgical smoke, aerosol or vapour; (ii) an organic solvent; (iii) a volatile compound; (iv) polar or non-polar molecules; (v) water; (vi) one or more alcohols; (vii) methanol; (viii) ethanol; (ix) isopropanol; (x) acetone; (xi) acetonitrile; (xii) dimethyl sulfoxide (DMSO); (xiii) glycol; (xiv) 1-butanol; (xv) tetrahydrofuran; (xvi) ethyl acetate; (xvii) ethylene glycol; (xviii) an aldehyde; (xix) a ketone; (xx) hexane; (xxi) chloroform; and (xxii) propanol.

The matrix may initially be supplied as a solid, e.g. powder, and sublimated or melted and evaporated so as to form matrix in vapour or gas-phase that is then intermixed with the analyte. For example, a solid matrix may be mixed with the analyte. If the analyte is mixed in liquid form, the mixture may be allowed to dry, e.g., to form crystals. The mixture may then be heated to sublimate and/or evaporate the matrix and/or analyte. Examples of suitable matrices include MALDI matrices and other matrices, such as: coumarin; 9-aminoacridine; 2,5-dihydroxybenzoic acid; THAP; CHCA; and quecertin.

The matrix may be doped with one or more additives for enhancing the solvation of the analyte in the matrix or for enhancing the ionisation of the analyte.

By way of example, for analytes comprising polar lipids, low molecular weight alcohols may be used as the matrix (e.g., methanol, ethanol, isopropanol) or ketones (e.g., acetone). These matrices have been shown to enhance the ionisation of species otherwise detected in the absence of the matrix vapours at lower intensity.

A protic matrix solvent may be used, e.g., for the analysis of lipids or triglycerides. Alternatively, a non-protic or aprotic matrix solvent may be used, e.g., for the analysis of proteins.

The matrix may be doped with an acidic or basic additive. For example, the matrix may be doped with formic acid, diethylamine.

The matrix may cause derivatisation of the analyte. For example, the matrix may cause the derivatisation of cholesterol or steroids in the analyte. This may render the analyte more easily ionised.

The spectrometer may comprise a device which is arranged and adapted to accelerate analyte droplets onto said collision assembly.

The spectrometer may comprise a device arranged and adapted to maintain a pressure differential so as to accelerate analyte droplets onto said collision assembly.

After collision with the collision assembly, the matrix may be evaporated from the droplets so as to provide analyte ions that are separate from said matrix. The analyte ions may then be analysed downstream of the collision surface.

The method may comprising subjecting the analyte or analyte ions to ionisation downstream of said collision assembly. Optionally, the ionisation is performed by an ionisation source other than the use of the collision surface. The spectrometer may comprise an analyser which is arranged to analyse analyte ions resulting from said analyte, smoke, fumes, liquid, gas, surgical smoke, aerosol or vapour colliding with said collision assembly (and/or being subjected to the ionisation downstream of the collision assembly), wherein said spectrometer may further comprise an atmospheric interface adjacent a vacuum chamber, wherein analyte droplets may be accelerated onto said collision assembly by a pressure difference across said atmospheric interface.

The spectrometer may comprise a matrix introduction conduit for supplying said matrix to said aerosol, smoke, vapour or liquid.

The spectrometer may comprise an ion analyser for analysing analyte ions, wherein said ion analyser is arranged downstream of an outlet of said matrix introduction conduit.

The distance x between said outlet of said matrix introduction conduit and an inlet of said ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm; (vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about 6.0-6.5 mm; (xiv) about 6.5-7.0 mm; (xv) about 7.0-7.5 mm; (xvi) about 7.5-8.0 mm; (xvii) about 8.0-8.5 mm; (xviii) about 8.5-9.0 mm; (xix) about 9.0-9.5 mm; (xx) about 9.5-10.0 mm; (xxi) about 0.1-10 mm; (xxii) about 0.1-7.5 mm; (xxiii) about 0.1-5.1 mm; (xxiv) about 0.5-5.1 mm; and (xxv) about 0.5-5.0 mm.

The spectrometer may comprise a pump for supplying said matrix via the matrix introduction conduit at a flow rate selected from the group consisting of: (i) about 5-10 µl/min; (ii) about 10-25 µl/min; (iii) about 25-50 µl/min; (iv) about 50-100 µl/min; (v) about 100-150 µl/min; (vi) about 150-200 µl/min; (vii) about 200-250 µl/min; (viii) about 250-300 µl/min; (ix) about 300-350 µl/min; (x) about 350-400 µl/min; (xi) about 400-450 µl/min; (xii) about 450-500 µl/min; (xiii) about 500-550 µl/min; (xiv) about 550-600 µl/min; (xv) about 600-650 µl/min; (xvi) about 650-700 µl/min; (xvii) about 700-750 µl/min; (xviii) about 750-800 µl/min; (xiv) about 800-850 µl/min; (xx) about 850-900 µl/min; (xxi) about 900-950 µl/min; (xxii) about 950-1000 µl/min; (xxiii) about 50 µl/min to 1 ml/min; (xxiv) about 100-800 µl/min; (xxv) about 150-600 µl/min; and (xxvi) about 200-400 µl/min.

An outlet of said matrix introduction conduit may be opposite or coaxial with an inlet of an ion analyser.

The spectrometer may comprise a mass and/or ion mobility analyser for analysing analyte ions to obtain analyte ion data, and wherein said mass and/or ion mobility analyser is further arranged to analyse lockmass, lock mobility or calibration ions, and to calibrate said ion analyser or adjust analyte ion data based upon the data obtained from analysing said lockmass, lock mobility or calibration ions.

The first aspect of the invention also provides a method of mass and/or ion mobility spectrometry comprising:
providing a substantially cylindrical, tubular, rod-shaped, coil-shaped, helical or spiral-shaped collision assembly; and
using a first device to direct analyte, smoke, fumes, liquid, gas, surgical smoke, aerosol or vapour onto said collision assembly.

Another aspect of the invention provides a method of mass and/or ion mobility spectrometry comprising:
providing a collision assembly; and
using a first device to direct analyte, smoke, fumes, liquid, gas, surgical smoke, aerosol or vapour onto said collision assembly.

The collision assembly may have a first longitudinal axis and the first device directs the analyte, smoke, fumes, liquid, gas, surgical smoke, aerosol or vapour onto said collision assembly along a second axis which is substantially orthogonal to said first axis.

Alternatively, the collision assembly may have a first longitudinal axis and the first device directs the analyte, smoke, fumes, liquid, gas, surgical smoke, aerosol or vapour onto said collision assembly along said first axis.

Another aspect of the invention provides a method of ionising an aerosol, smoke or vapour comprising:
using a first device to direct said aerosol, smoke or vapour to impact upon an inner surface of a hollow collision assembly having an inlet and an outlet, wherein the inner cross-sectional area of said collision assembly either: (i) is substantially constant; or (ii) reduces in a direction from said inlet to said outlet; or (iii) increases in a direction from said inlet to said outlet.

The method may comprise receiving said aerosol, smoke or vapour via said inlet.

The method may comprise causing said aerosol, smoke or vapour to impact upon said inner surface so as to form analyte ions.

The method may comprise causing analyte ions to emerge from said collision assembly via said outlet.

The collision assembly may comprise a funnel-shaped collision assembly.

Alternatively, the collision assembly may comprise a tubular or cylindrical collision assembly.

The method may comprise directing said aerosol, smoke or vapour into said collision assembly along an axis which is substantially co-axial with a longitudinal axis of said collision assembly.

The collision assembly may be formed from a coiled structure or from a continuous tubular or conical structure.

The various methods described herein may comprise heating said collision assembly using a heater or heater coil.

The heater or heater coil may be the collision surface of the collision assembly.

The heater or said heater coil may be surrounded by the collision assembly or embedded within the collision assembly.

The collision assembly may comprise an aperture therein so that the heater or heater coil is exposed by the aperture to the smoke, fumes, liquid, gas, surgical smoke, aerosol or vapour.

The method may comprise supplying electrical power to said heater or said heater coil via one or more electrodes.

The method may comprise supplying an electrical current to the heater or heater coil so as to heating the collision assembly, wherein the current is selected from the group consisting of: about ≥0.5 A; ≥about 1 A; about ≥1.5 A; about ≥2 A; about ≥2.5 A; about ≥3 A; about ≥3.5 A; about ≥4 A; about ≥4.5 A; and about ≥5 A.

The method may comprise heating said collision assembly to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The heater or heater coil may burn off contaminants deposited on the collision assembly from the sample being analysed.

The collision assembly may be, or may comprise an outer collision surface that is: ceramic, non-ceramic, glass, glass-ceramic, quartz, metal such as steel or nickel, or metal-alloy such as iron-chromium-aluminium (FeCrAl) alloy.

The analyte, smoke, fumes, liquid, gas, surgical smoke, aerosol or vapour may be directed along an axis onto a region of the collision assembly having a maximum or minimum dimension orthogonal to the axis selected from the group consisting of: about ≥1 mm; about ≥2 mm; about ≥3 mm; about ≥4 mm; about ≥5 mm; about ≥6 mm; about ≥7 mm; and about ≥8 mm; and/or having a maximum or minimum dimension orthogonal to the axis selected from the group consisting of: about ≤8 mm; about ≤7 mm; about ≤6 mm; about ≤5 mm; about ≤4 mm; and about ≤3 mm.

The method may comprise providing a sheath tube arranged around the collision assembly through which the smoke, fumes, liquid, gas, surgical smoke, aerosol or vapour may travel.

The sheath tube may extend upstream and/or downstream of the collision assembly.

The method may comprise maintaining a potential difference between the collision assembly and the sheath tube.

The method may comprise providing a capillary or sample tube for delivering said the smoke, fumes, liquid, gas, surgical smoke, aerosol or vapour onto said collision assembly.

The exit orifice of the capillary or sample tube may be arranged a distance upstream of the collision surface selected from the group consisting of: about 0 mm; about ≤1 mm; about 1-2 mm; about 2-3 mm; about 3-4 mm; about 4-5 mm; about 5-6 mm; about 6-7 mm; about 7-8 mm; about 8-9 mm; about 9-10 mm; and about ≥10 mm.

The method may comprise heating the capillary or sample tube.

The heater may heat the capillary or sample tube to a temperature selected from the group consisting of: (i) about <100° C.; (ii) about 100-150° C.; (iii) about 150-200° C.; (iv) about 200-250° C.; (v) about 250-300° C.; (vi) about 300-350° C.; (vii) about >350° C.

The method may comprise using a first holder to support said collision assembly.

The method may comprise forming said first holder from a ceramic or a non-ceramic.

The method may comprise providing said one of more electrodes for supplying electrical power to said heater coil through said first holder.

The method may comprise providing a main heater or removable unit housing assembly.

The method may comprise removably mounting said first holder to said main heater assembly or removable unit housing.

The method may comprise providing a first isolation valve within a bore in said main heater assembly or removable unit housing for selectively closing said bore; optionally wherein said first isolation valve comprises a ball valve.

The method may comprise opening said first isolation valve by inserting one or more capillaries or sample tubes through said bore.

The method may comprise closing said first isolation valve by at least partially removing said one or more capillaries or sample tubes from said bore.

The method may comprise locating said one or more capillaries or sample tubes so as to extend through said bore for supplying said analyte, smoke, fumes, liquid, gas, surgical smoke, aerosol or vapour onto said collision assembly.

The method may comprise locating said one or more capillaries or sample tubes so as to extend through said first holder.

The method may comprise arranging an exit of said one or more capillaries or sample tubes substantially adjacent or facing said collision assembly.

The method may comprise providing one or more shields at least partially surrounding said collision assembly in an extended position for protecting said collision assembly.

The method may comprise at least partially or fully retracting said one or more shields from said extended position to a retracted position in which at least part of the collision assembly is not surrounded by the one or more shields; optionally wherein said one or more shields is biased towards said extended position.

The method may comprise providing a source housing.

The source housing may comprise a second isolation valve.

The method may comprise inserting said main heater assembly or removable unit housing within said source housing or otherwise connecting said main heater assembly or removable unit housing to said source housing, and rotating said main heater assembly or removable unit housing therein from a first rotational position to a second rotational position.

The step of rotating said main heater assembly or removable unit housing from said first position to said second position may move said second isolation valve from a first operational position to a second operational position.

The first operational position said second isolation valve may be substantially closed.

The second operational position said second isolation valve may be substantially open.

The method may comprise providing a spectrometer main housing or assembly, wherein said source housing is connected to said spectrometer main housing.

The method may comprise providing an ion trap and/or an ion guide; optionally wherein the ion guide applies an electric that separates ions from neutral species.

The method may comprise trapping analyte ions derived from said aerosol, smoke or vapour in said ion trap and/or guiding analyte ions using said ion guide.

The method may comprise analysing analyte ions derived from said aerosol, smoke or vapour using an analyser.

The analyser may comprise: (i) a mass analyser for mass analysing said analyte ions; (ii) an ion mobility or differential ion mobility analyser; (iii) an analyser for analysing the ionic cross-sections or collision cross sections of said analyte ions; (iv) a separator for separating said analyte ions according to their ion mobility or differential ion mobility; (v) a separator for separating said analyte ions according to their ion mobility or differential ion mobility prior to mass analysing said analyte ions; or (vi) a device arranged and adapted to exclude or discard analyte ions based upon their ion mobility or differential ion mobility.

The method may comprise supplying a matrix to said aerosol, smoke, vapour or liquid whilst said aerosol, smoke, vapour or liquid is in gas phase, vapour form, aerosol form or in liquid phase.

The method may comprise supplying matrix molecules to, and intermixing said matrix molecules with, said aerosol, smoke, vapour or liquid whilst said matrix is in a gas phase.

The method may comprise transferring the mixture from a high pressure region to a low pressure region such that said gas phase matrix cools and condenses to a liquid and wherein said at least part of said aerosol, smoke, vapour or liquid dissolves in said liquid matrix so as to form dissolved analyte droplets.

The matrix may be selected from the group consisting of: (i) a solvent for said analyte, smoke, fumes, liquid, gas, surgical smoke, aerosol or vapour; (ii) an organic solvent; (iii) a volatile compound; (iv) polar or non-polar molecules; (v) water; (vi) one or more alcohols; (vii) methanol; (viii) ethanol; (ix) isopropanol; (x) acetone; (xi) acetonitrile; (xii) dimethyl sulfoxide (DMSO); (xiii) glycol; (xiv) 1-butanol; (xv) tetrahydrofuran; (xvi) ethyl acetate; (xvii) ethylene glycol; (xviii) an aldehyde; (xix) a ketone; (xx) hexane; (xxi) chloroform; and (xxii) propanol.

The method may comprise accelerating the analyte droplets onto said collision assembly.

The method may comprise maintaining a pressure differential so as to accelerate the analyte droplets onto said collision assembly.

The method may comprise accelerating analyte droplets onto said collision assembly by a pressure difference across an atmospheric interface and analysing analyte ions resulting from said analyte droplets colliding with said collision assembly.

The method may comprise supplying the matrix via a matrix introduction conduit; and analysing said analyte ions using an ion analyser, wherein said ion analyser is arranged downstream of an outlet of the matrix introduction conduit.

The distance x between said outlet of said matrix introduction conduit and an inlet of said ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm; (vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about 6.0-6.5 mm; (xiv) about 6.5-7.0 mm; (xv) about 7.0-7.5 mm; (xvi) about 7.5-8.0 mm; (xvii) about 8.0-8.5 mm; (xviii) about 8.5-9.0 mm; (xix) about 9.0-9.5 mm; (xx) about 9.5-10.0 mm; (xxi) about 0.1-10 mm; (xxii) about 0.1-7.5 mm; (xxiii) about 0.1-5.1 mm; (xxiv) about 0.5-5.1 mm; and (xxv) about 0.5-5.0 mm.

The method may comprise supplying said matrix to said analyte via a matrix introduction conduit at a flow rate selected from the group consisting of: (i) about 50-100 μl/min; (ii) about 100-150 μl/min; (iii) about 150-200 μl/min; (iv) about 200-250 μl/min; (v) about 250-300 μl/min; (vi) about 300-350 μl/min; (vii) about 350-400 μl/min; (viii) about 400-450 μl/min; (ix) about 450-500 μl/min; (x) about 500-550 μl/min; (xi) about 550-600 μl/min; (xii) about 600-650 μl/min; (xiii) about 650-700 μl/min; (xiv) about 700-750 μl/min; (xv) about 750-800 μl/min; (xvi) about 800-850 μl/min; (xvii) about 850-900 μl/min; (xviii) about 900-950 μl/min; (xix) about 950-1000 μl/min; (xx) about 50 μl/min to 1 ml/min; (xxi) about 100-800 μl/min; (xxii) about 150-600 μl/min; and (xxiii) about 200-400 μl/min.

The method may comprise locating an outlet of the matrix introduction conduit opposite or coaxial with an inlet of the ion analyser.

The end of the matrix introduction conduit and/or the outlet end of the sample transfer conduit may taper to a smaller dimension in the downstream direction, or may comprise a Picotip.

The matrix introduction conduit and/or the sample transfer conduit may be made from a metal (e.g. stainless steel or copper), quartz or a polymer such as PEEK.

The method may comprise mass and/or ion mobility analysing analyte ions derived from said aerosol, smoke or vapour to obtain analyte ion data, analysing lockmass, lock mobility or calibration ions, and calibrating an ion analyser or adjusting analyte ion data based upon the data obtained from analysing said lockmass, lock mobility or calibration ions.

The first device may comprise or forms part of an ambient ion or ionisation source; or said first device may generate said aerosol, smoke or vapour from a target to be analysed and which contains ions or is subsequently ionised by an ambient ion or ionisation source or other ionisation source.

The target may comprise native or unmodified target material.

The native or unmodified target material may be unmodified (i.e. not modified) by the addition of a matrix or reagent.

The first device may be arranged and adapted to generate aerosol, smoke or vapour from one or more regions of said target without said target requiring prior preparation.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

The step of using said first device to generate aerosol, smoke or vapour from one or more regions of said target may further comprise contacting said target with one or more electrodes.

The one or more electrodes may comprise either: (i) a monopolar device, wherein said method optionally further comprises providing a separate return electrode; (ii) a bipolar device; or (iii) a multi-phase RF device, wherein said method optionally further comprises providing a separate return electrode or electrodes.

The one or more electrodes may comprise a rapid evaporation ionization mass spectrometry ("REIMS") device.

The method may comprise applying an AC or RF voltage to said one or more electrodes in order to generate said aerosol, smoke or vapour.

The step of applying said AC or RF voltage to said one or more electrodes may comprises applying one or more pulses of said AC or RF voltage to said one or more electrodes.

The step of applying said AC or RF voltage to said one or more electrodes may cause heat to be dissipated into said target.

The step of using said first device to generate aerosol, smoke or vapour from one or more regions of said target may comprise irradiating said target with a laser.

The first device may be arranged and adapted to generate aerosol from one or more regions of said target by direct evaporation or vaporisation of target material from said target by Joule heating or diathermy.

The step of using said first device to generate aerosol, smoke or vapour from one or more regions of said target may comprise directing ultrasonic energy into said target.

The aerosol may comprise uncharged aqueous droplets, optionally comprising cellular material.

At least 50%, 55%, 60%, 65%, 70%, 75%, 80%, 85%, 90% or 95% of the mass or matter generated by said first device and which forms said aerosol may be in the form of droplets.

The first device may be arranged and adapted to generate aerosol wherein the Sauter mean diameter ("SMD", d32) of said aerosol is in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating said aerosol, said aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating said aerosol, said aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating said aerosol, said aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise bacterial colony, a fungal colony, or biological material such as biological tissue or biological liquids, e.g., saliva, blood or pus.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, soft tissue, connective tissue, peritoneal tissue, blood vessel tissue, fat tissue, ureter tissue, urethra tissue; grade I, grade II, grade III or grade IV cancerous tissue; metastatic cancerous tissue; mixed grade cancerous tissue; a sub-grade cancerous tissue; healthy or normal tissue; or cancerous or abnormal tissue.

The first device may comprise a point of care ("POC"), diagnostic or surgical device.

The method may comprise ionising at least some of said aerosol, smoke or vapour so as to generate analyte ions.

The method may comprise directing or aspirating at least some of said aerosol, smoke or vapour into a vacuum chamber of a mass and/or ion mobility spectrometer.

The method may comprise ionising at least some said aerosol, smoke or vapour within a or said vacuum chamber of said mass and/or ion mobility spectrometer so as to generate a plurality of analyte ions.

The method may comprise causing said aerosol, smoke or vapour to impact upon the collision surface, optionally located within a vacuum chamber of said spectrometer, so as to generate the plurality of analyte ions.

The method may comprise analysing said analyte ions or ions derived from said aerosol, smoke or vapour in order to obtain spectrometric data, e.g., mass and/or ion mobility spectrometric data.

The method may comprise analysing said spectrometric data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in said target; (vi) to confirm the identity or authenticity of said target; (vii) to determine whether or not one or more impurities, illegal substances or undesired substances are present in said target; (viii) to determine whether a human or animal patient is at an increased risk of suffering an adverse outcome; (ix) to make or assist in the making a diagnosis or prognosis; and (x) to inform a surgeon, nurse, medic or robot of a medical, surgical or diagnostic outcome.

The step of analysing the spectrometric data may comprise analysing one or more sample spectra so as to classify an aerosol, smoke or vapour sample.

Analysing the one or more sample spectra so as to classify the aerosol, smoke or vapour sample may comprise unsupervised analysis of the one or more sample spectra (e.g., for dimensionality reduction) and/or supervised analysis of the one or more sample spectra (e.g., for classification).

Analysing the one or more sample spectra may comprise unsupervised analysis (e.g., for dimensionality reduction) followed by supervised analysis (e.g., for classification).

Analysing the one or more sample spectra may comprise using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; and (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

Analysing the one or more sample spectra so as to classify the aerosol, smoke or vapour sample may comprise developing a classification model or library using one or more reference sample spectra.

Analysing the one or more sample spectra so as to classify the aerosol, smoke or vapour sample may comprise performing linear discriminant analysis (LDA) (e.g., for classification) after performing principal component analysis (PCA) (e.g., for dimensionality reduction).

Analysing the one or more sample spectra so as to classify the aerosol, smoke or vapour sample may comprise performing a maximum margin criteria (MMC) process (e.g., for classification) after performing principal component analysis (PCA) (e.g., for dimensionality reduction).

Analysing the one or more sample spectra so as to classify the aerosol, smoke or vapour sample may comprise defining one or more classes within a classification model or library.

Analysing the one or more sample spectra so as to classify the aerosol, smoke or vapour sample may comprise defining one or more classes within a classification model or library manually or automatically according to one or more class or cluster criteria.

The one or more class or cluster criteria for each class may be based on one or more of: a distance between one or more pairs of reference points for reference sample spectra within a model space; a variance value between groups of reference points for reference sample spectra within a model space; and a variance value within a group of reference points for reference sample spectra within a model space.

The one or more classes may each be defined by one or more class definitions.

The one or more class definitions may comprise one or more of: a set of one or more reference points for reference sample spectra, values, boundaries, lines, planes, hyperplanes, variances, volumes, Voronoi cells, and/or positions, within a model space; and one or more positions within a class hierarchy.

Analysing the one or more sample spectra so as to classify the aerosol, smoke or vapour sample may comprise using a classification model or library to classify one or more unknown sample spectra.

Analysing the one or more sample spectra so as to classify the aerosol, smoke or vapour sample may comprise classifying one or more sample spectra manually or automatically according to one or more classification criteria.

The one or more classification criteria may comprise one or more of:

a distance between one or more projected sample points for one or more sample spectra within a model space and a set of one or more reference points for one or more reference sample spectra, values, boundaries, lines, planes, hyperplanes, volumes, Voronoi cells, or positions, within the model space being below a distance threshold or being the lowest such distance;

a position for one or more projected sample points for one or more sample spectra within a model space being one side or other of one or more reference points for one or more reference sample spectra, values, boundaries, lines, planes, hyperplanes, or positions, within the model space;

a position for one or more projected sample points for one or more sample spectra within a model space being within one or more volumes or Voronoi cells within the model space; and a probability or classification score being above a probability or classification score threshold or being the highest such probability or classification score.

The collision assembly or surface may be maintained at a first potential relative to the capillary or sample tube.

Alternatively, or additionally, the collision assembly or surface is maintained at a second potential relative to the inlet of the ion analyser.

Alternatively, or additionally, the collision assembly or surface is maintained at a third potential relative to the grounded chassis of the spectrometer.

Alternatively, or additionally, the collision assembly or surface is maintained at a fourth potential relative to the ion guide or ion trap.

Alternatively, or additionally, the inlet of the ion analyser is maintained at a fifth potential relative to the grounded chassis of the spectrometer;

Any one of, or any combination of, the first, second, third, fourth and fifth potentials may be a positive potential selected from the group consisting of: ≥2 V; 2-3 V; 3-4 V; 4-5 V; 5-10 V; 10-15; 15-20 V; 20-25 V; 25-30 V; 30-35 V; 35-40 V; 40-45 V; 45-50 V; 50-60 V; 60-70 V; 70-80 V; 80-90 V; 90-100 V; 100-120 V; 120-140 V; 140-160 V; 160-180 V; 180-200 V; 200-220 V; 220-240 V; 240-260 V; 260-280 V; 280-300 V; and ≥300V.

Alternatively, or additionally, any one of, or any combination of, the first, second, third, fourth and fifth potentials may be a negative potential selected from the group consisting of: ≥2 V; 2-3 V; 3-4 V; 4-5 V; 5-10 V; 10-15; 15-20 V; 20-25 V; 25-30 V; 30-35 V; 35-40 V; 40-45 V; 45- 50 V; 50-60 V; 60-70 V; 70-80 V; 80-90 V; 90-100 V; 100-120 V; 120-140 V; 140-160 V; 160-180 V; 180-200 V; 200-220 V; 220-240 V; 240-260 V; 260-280 V; 280-300 V; and ≥300V.

The present invention also provides a method of surgery electrosurgery comprising any one of the methods described herein, wherein the method comprises:

contacting biological tissue with a surgical or electrosurgical tool and activating said tool so as to generate said analyte, smoke, fumes, liquid, gas, surgical smoke, aerosol or vapour;

aspirating said analyte, smoke, fumes, liquid, gas, surgical smoke, aerosol or vapour;

directing said analyte, smoke, fumes, liquid, gas, surgical smoke, aerosol or vapour onto said collision assembly in order to form analyte ions; and mass and/or ion mobility analysing said analyte ions.

The present invention also provides a surgical or electrosurgical apparatus comprising an apparatus as described herein, wherein the surgical or electrosurgical apparatus comprises:

a surgical tool or electrosurgical tool comprising one or more electrodes;

a device arranged and adapted to activate said tool so as to generate said analyte, smoke, fumes, liquid, gas, surgical smoke, aerosol or vapour when said tool is in contact, in use, with biological tissue;

a device arranged and adapted to aspirate said analyte, smoke, fumes, liquid, gas, surgical smoke, aerosol or vapour; and a mass and/or ion mobility spectrometer comprising: (i) said collision assembly; (ii) said device arranged and adapted to direct said analyte, smoke, fumes, liquid, gas, surgical smoke, aerosol or vapour onto said collision assembly in order to form analyte ions; and (iii) a mass and/or ion mobility analyser for mass and/or ion mobility analysing said analyte ions.

The present invention also provides an apparatus for interfacing an analyte source with a vacuum chamber of a mass and/or ion mobility spectrometer, comprising:

a housing having a bore therethrough for receiving analyte at a first end of the bore and conveying the analyte to a second end of the bore to the vacuum chamber; and an isolation valve in the bore, wherein the isolation valve is configured to open when a capillary or sample tube is inserted through the bore into contact with the valve, and is configured to close when the capillary or tube is withdrawn from the bore.

The apparatus may comprise said capillary or sample tube.

The apparatus may comprise a collision assembly arranged at a second end of the bore for impacting said analyte or other sample from said bore thereon.

The collision assembly may be removably mounted to the housing.

The apparatus may comprise a heater for heating the collision assembly.

The housing may comprise one or more shields at least partially surrounding said collision assembly in an extended position for protecting said collision assembly.

The one or more shields may be at least partially retractable from said extended position to a retracted position in which at least part of the collision assembly is not surrounded by the one or more shields.

The one or more shields may be biased towards said extended position.

The present invention also provides a mass and/or ion mobility spectrometer comprising an apparatus as described above, wherein the bore is arranged to connect a vacuum chamber configured to at maintained at a first pressure and a region at a higher pressure, when the isolation valve is open.

The apparatus may comprise any one or combination of the features described in relation to the first aspect of the invention.

The present invention also provides an apparatus for interfacing an analyte source with a vacuum chamber of a mass and/or ion mobility spectrometer, comprising:

a housing having a bore therethrough for receiving analyte at a first end of the bore and conveying the analyte to a second end of the bore to the vacuum chamber; and a collision assembly arranged adjacent or downstream of a second end of the bore for impacting said analyte or other sample from said bore thereon, wherein the collision assembly is removably mounted to the housing.

The apparatus may comprise a heater for heating the collision assembly.

The collision assembly may be substantially cylindrical, tubular, rod-shaped, coil-shaped, helical or spiral-shaped, spherical, hemispherical, teardrop-shaped, plate-shaped, concave, dish-shaped or conical.

The housing may comprise one or more shields at least partially surrounding said collision assembly in an extended position for protecting said collision assembly.

The one or more shields may be at least partially retractable from said extended position to a retracted position in which at least part of the collision assembly is not surrounded by the one or more shields.

The one or more shields may be biased towards said extended position.

The present invention also provides a mass and/or ion mobility spectrometer comprising an apparatus as described above, wherein the housing is connected to a vacuum chamber at a second end of the bore.

The apparatus may comprise any one or combination of the features described in relation to the first aspect of the invention.

The present invention also provides an apparatus for interfacing an analyte source with a vacuum chamber of a mass and/or ion mobility spectrometer, comprising:

a housing having a bore therethrough for receiving analyte at a first end of the bore and conveying the analyte to a second end of the bore to the vacuum chamber;

a collision assembly mounted to the housing so as to be adjacent or downstream of a second end of the bore for impacting said analyte or other sample from said bore thereon; and wherein the housing comprises one or more shields configured to be movable from an extended position in which it at least partially surrounds said collision assembly and a retracted position in which at least part of the collision assembly is not surrounded by the one or more shields.

The one or more shields may be biased towards said extended position.

The present invention also provides a mass and/or ion mobility spectrometer comprising an apparatus as described above, wherein the housing is connected to a vacuum chamber at a second end of the bore.

The apparatus may comprise any one or combination of the features described in relation to the first aspect of the invention.

The present invention also provides an apparatus for interfacing an analyte source with a vacuum chamber of a mass and/or ion mobility spectrometer, comprising:

a housing having a bore therethrough for receiving analyte at a first end of the bore and conveying the analyte to a second end of the bore to the vacuum chamber; and an isolation valve for selectively closing the bore or a path in communication with the bore; wherein the isolation valve is coupled to the housing such that rotation of the housing about its longitudinal axis moves the isolation valve between an open position and a closed position.

The isolation valve may comprise a cam member configured to slide across an opening in the bore, or path in communication with the bore, as the valve is moved between the open and closed positions.

The apparatus may comprise a collision assembly arranged at a second end of the bore for impacting said analyte or other sample from said bore thereon.

The collision assembly may be removably mounted to the housing.

The apparatus may comprise a heater for heating the collision assembly.

The present invention also provides a mass and/or ion mobility spectrometer comprising an apparatus as described above, wherein the bore is arranged to connect a vacuum chamber configured to be maintained at a first pressure and a region at a higher pressure, when the isolation valve is open.

The apparatus may comprise any one or combination of the features described in relation to the first aspect of the invention.

The various embodiments herein may operate only in positive ion mode, only in negative ion mode, or in both positive and negative ion mode.

The various embodiments may not generate significant ionisation at the target. Rather, analyte in the smoke, aerosol or vapour generated at the target may be ionised downstream of the target. For example, a tool may be provided in contact with a point on the target, or directed at a point on the target, in order to generate the smoke, aerosol or vapour at that point, and substantially no ions may be generated at said point by the tool. Alternatively, it is also contemplated herein that a substantially number of ions may be generated at said target.

Apparatus for performing rapid evaporative ionisation mass spectrometry, mass and/or ion mobility spectrometers, methods of rapid evaporative ionisation mass spectrometry ("REIMS"), methods of mass and/or ion mobility spectrometry, methods of electrosurgery and electrosurgical devices are provided herein.

One aspect provides apparatus for performing rapid evaporative ionisation mass spectrometry ("REIMS"). In exemplary embodiments the apparatus includes a substantially cylindrical collision assembly having a first longitudinal axis, a heater for heating the collision assembly and a first device arranged and adapted to direct analyte, smoke, fumes, liquid, gas, surgical smoke, aerosol or vapour onto the heated collision assembly along a second axis which is substantially orthogonal to the first axis.

A known collisional ion generator REIMS technique as disclosed in WO 2013/098642 (Medimass) involves generating a sample of aerosol droplets that are comprised of aqueous droplets covered with polar lipids. The aqueous droplets are accelerated by the free jet expansion in the atmospheric inlet of a mass spectrometer such that the high velocity droplets impact onto a collision surface or other gaseous particles, producing gaseous ions of the polar lipid molecules. However, the ionisation yield of this technique is relatively low.

It has been recognised that the ion yield in the conventional method is relatively low due to the poor conversion rate of the droplets into individual molecular species mostly caused by the strong intermolecular bonds between the analyte molecules.

The arrangement according to an exemplary embodiment includes a cylindrical collision surface which is aligned substantially orthogonally to the direction of impact of aerosol or analyte droplets has been found to be particularly advantageous in terms of resulting in a high ion yield.

In exemplary embodiments the collision assembly includes a ceramic cylinder or a non-ceramic cylinder.

The collision assembly may further include a heater or a heater coil.

The heater or heater coil may be located within the collision assembly.

The apparatus may further include one or more electrodes for supplying electrical power to the heater or heater coil.

The heater or heater coil may be arranged to heat the collision assembly to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.;

(viii) about 700-800° C.; (ix) about 800-900° C.; (x) about 900-1000° C.; (xi) about 1000-1100° C.; and (xii) about >1100° C.

The apparatus may further include a first holder for supporting the collision assembly.

The first holder may be formed from a ceramic or a non-ceramic.

The one of more electrodes for supplying electrical power to the heater or heater coil may pass through the first holder.

The apparatus in exemplary embodiments further includes a main heater assembly.

The first holder may be removably mounted to the main heater assembly.

The main heater assembly may further include a first isolation valve.

The first isolation valve may be arranged to open when one or more capillaries or sample tubes are positioned within the main heater assembly.

The first isolation valve may be arranged to close when one or more capillaries or sample tubes are at least partially or fully removed from the main heater assembly.

The apparatus may further include one or more capillaries or sample tubes which extend or are positioned, in use, through the main heater assembly.

The one or more capillaries or sample tubes may extend, in use, through the first holder.

The one or more capillaries or sample tubes may have an exit which is arranged, in use, substantially adjacent the collision assembly.

According to an exemplary embodiment the apparatus may further include one or more shields for protecting the collision assembly when the main heater assembly is inserted within or otherwise connected to a source housing.

The one or more shields may be arranged to at least partially or fully retract as the main heater assembly is inserted within or otherwise connected to the source housing.

The apparatus may further include a source housing.

The source housing may further include a second isolation valve.

According to an exemplary embodiment the main heater assembly is insertable within or connectable to the source housing and wherein, in use, the main heater assembly is additionally rotatable from a first rotational position to a second rotational position.

The rotation of the main heater assembly from the first position to the second position may be arranged and adapted to move, in use, the second isolation valve from a first operational position to a second operational position.

In the first operational position the second isolation valve is substantially closed.

In the second operational position the second isolation valve is substantially open.

Another aspect provides a mass and/or ion mobility spectrometer comprising apparatus as described above.

The spectrometer may further include a main housing or assembly and wherein the source housing is connected, in use, to the main housing.

The spectrometer may further include an ion trap and/or an ion guide.

The spectrometer may further include a device which is arranged and adapted to trap analyte ions in the ion trap and/or to guide analyte ions using the ion guide.

According to an exemplary embodiment the spectrometer further includes an analyser for analysing analyte ions.

The analyser may comprise: (i) a mass analyser for mass analysing the analyte ions; (ii) an ion mobility or differential ion mobility analyser; (iii) an analyser for analysing the ionic cross-sections or collision cross sections of the analyte ions; (iv) a separator for separating the analyte ions according to their ion mobility or differential ion mobility; (v) a separator for separating the analyte ions according to their ion mobility or differential ion mobility prior to mass analysing the analyte ions; or (vi) a device arranged and adapted to exclude or discard analyte ions based upon their ion mobility or differential ion mobility.

A matrix may be supplied, in use, to the analyte whilst the analyte is in gas phase, vapour form, aerosol form or in liquid phase.

The spectrometer may further include a device arranged and adapted to supply matrix molecules to, and to intermix the matrix molecules with, the analyte whilst the matrix is in a gas phase.

The spectrometer may further include a device which is arranged and adapted to transfer the mixture of the analyte and the matrix from a high pressure region to a low pressure region such that the gas phase matrix cools and condenses to a liquid and wherein the analyte dissolves in the liquid matrix so as to form dissolved analyte droplets.

The matrix may be selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The spectrometer may further include a device which is arranged and adapted to accelerate analyte droplets onto the collision assembly.

The spectrometer may further include a device arranged and adapted to maintain a pressure differential so as to accelerate analyte droplets onto the collision assembly.

The spectrometer may further include an analyser which is arranged to analyse analyte ions resulting from the analyte, smoke, fumes, liquid, gas, surgical smoke, aerosol or vapour colliding with the collision assembly, wherein the spectrometer further includes an atmospheric interface adjacent a vacuum chamber, wherein analyte droplets are accelerated onto the collision assembly by a pressure difference across the atmospheric interface.

The spectrometer may further include a matrix introduction conduit for supplying the matrix to the analyte.

The spectrometer may further include an ion analyser for analysing the analyte ions, wherein the ion analyser is arranged downstream of an outlet of the matrix introduction conduit.

The distance x between the outlet of the matrix introduction conduit and an inlet of the ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm; (vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about 6.0-6.5 mm; (xiv) about 6.5-7.0 mm; (xv) about 7.0-7.5 mm; (xvi) about 7.5-8.0 mm; (xvii) about 8.0-8.5 mm; (xviii) about 8.5-9.0 mm; (xix) about 9.0-9.5 mm; (xx) about 9.5-10.0 mm; (xxi) about 0.1-10 mm; (xxii) about 0.1-7.5 mm; (xxiii) about 0.1-5.1 mm; (xxiv) about 0.5-5.1 mm; and (xxv) about 0.5-5.0 mm.

The spectrometer may further comprise a pump for supplying the matrix to the analyte via a matrix introduction conduit at a flow rate selected from the group consisting of: (i) about 50-100 µl/min; (ii) about 100-150 µl/min; (iii) about 150-200 µl/min; (iv) about 200-250 µl/min; (v) about 250-300 µl/min; (vi) about 300-350 µl/min; (vii) about 350-400 µl/min; (viii) about 400-450 µl/min; (ix) about 450-500 µl/min; (x) about 500-550 µl/min; (xi) about 550-600 µl/min; (xii) about 600-650 µl/min; (xiii) about 650-700 µl/min; (xiv) about 700-750 µl/min; (xv) about 750-800 µl/min; (xvi) about 800-850 µl/min; (xvii) about 850-900 µl/min; (xviii) about 900-950 µl/min; (xix) about 950-1000 µl/min; (xx) about 50 µl/min to 1 ml/min; (xxi) about 100-800 µl/min; (xxii) about 150-600 µl/min; and (xxiii) about 200-400 µl/min.

An outlet of the matrix introduction conduit may be located opposite or coaxial with an inlet of an ion analyser.

The spectrometer may further include a mass and/or ion mobility analyser for analysing the analyte ions to obtain analyte ion data, and wherein the analyser is further arranged to analyse lockmass, lock mobility or calibration ions, and to calibrate the ion analyser or adjust analyte ion data based upon the data obtained from analysing the lockmass, lock mobility or calibration ions.

Another aspect provides a method of Rapid Evaporative Ionisation Mass Spectrometry ("REIMS"). In exemplary embodiments the method includes providing a substantially cylindrical collision assembly having a first longitudinal axis; heating the collision assembly; and directing analyte, smoke, fumes, liquid, gas, surgical smoke, aerosol or vapour onto the heated collision assembly along a second axis which is substantially orthogonal to the first axis.

The collision assembly may include a ceramic cylinder or a non-ceramic cylinder.

The collision assembly may further include a heater or a heater coil.

The method may further include locating the heater or heater coil within the collision assembly.

The method may further include supplying electrical power to the heater or heater coil via one or more electrodes.

The method may further include heating the collision assembly to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The method may further include using a first holder to support the collision assembly.

The first holder may be formed from a ceramic or a non-ceramic.

The method may further include passing one of more electrodes for supplying electrical power to the heater coil pass through the first holder.

The method may further include providing a main heater assembly.

The method may further include removably mounting the first holder to the main heater assembly.

The method may further include providing a first isolation valve within the main heater assembly.

The method may further include opening the first isolation valve when one or more capillaries or sample tubes are passed through the main heater assembly.

The method may further include closing the first isolation valve when the one or more capillaries or sample tubes are at least partially or fully removed from the main heater assembly.

The method may further include locating one or more capillaries or sample tubes so as to extend through the main heater assembly.

The method may further include locating the one or more capillaries or sample tubes so as to extend through the first holder.

The method may further include arranging an exit of the one or more capillaries or sample tubes substantially adjacent the collision assembly.

The method may further include providing one or more shields for protecting the collision assembly when the main heater assembly is inserted within or otherwise connected to a source housing.

The method may further include at least partially or fully retracting the one or more shields as the main heater assembly is inserted within or otherwise connected to the source housing.

The method may further include providing a source housing.

The source housing may further include a second isolation valve.

The method may further include inserting the main heater assembly within the source housing or otherwise connecting the main heater assembly to the source housing, and rotating the main heater assembly from a first rotational position to a second rotational position.

The step of rotating the main heater assembly from the first position to the second position may move the second isolation valve from a first operational position to a second operational position.

In the first operational position the second isolation valve is substantially closed.

In the second operational position the second isolation valve is substantially open.

The method may further include providing a main housing or assembly, wherein the source housing is connected to the main housing.

The method may further include providing an ion trap and/or an ion guide.

The method may further include trapping analyte ions in the ion trap and/or guiding analyte ions using the ion guide.

The method may further include analysing the analyte ions using an analyser.

The analyser may comprise: (i) a mass analyser for mass analysing the analyte ions; (ii) an ion mobility or differential ion mobility analyser; (iii) an analyser for analysing the ionic cross-sections or collision cross sections of the analyte ions; (iv) a separator for separating the analyte ions according to their ion mobility or differential ion mobility; (v) a separator for separating the analyte ions according to their ion mobility or differential ion mobility prior to mass analysing the analyte ions; or (vi) a device arranged and adapted to exclude or discard analyte ions based upon their ion mobility or differential ion mobility.

The method may further include supplying a matrix to the analyte whilst the analyte is in gas phase, vapour form, aerosol form or in liquid phase.

The method may further include supplying matrix molecules to, and intermixing the matrix molecules with, the analyte whilst the matrix is in a gas phase.

The method may further include transferring the mixture of the analyte and the matrix from a high pressure region to a low pressure region such that the gas phase matrix cools and condenses to a liquid and wherein the analyte dissolves in the liquid matrix so as to form dissolved analyte droplets.

The matrix may be selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The method may further include accelerating analyte droplets onto the collision assembly.

The method may further include maintaining a pressure differential so as to accelerate analyte droplets onto the collision assembly.

The method may further include analysing analyte ions resulting from the analyte, smoke, fumes, liquid, gas, surgical smoke, aerosol or vapour colliding with the collision assembly, and accelerating analyte droplets onto the collision assembly by a pressure difference across an atmospheric interface.

The method may further include supplying a matrix to the analyte.

The method may further include analysing the analyte ions using an ion analyser, wherein the ion analyser is arranged downstream of an outlet of a matrix introduction conduit.

The distance x between the outlet of the matrix introduction conduit and an inlet of the ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm; (vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about 6.0-6.5 mm; (xiv) about 6.5-7.0 mm; (xv) about 7.0-7.5 mm; (xvi) about 7.5-8.0 mm; (xvii) about 8.0-8.5 mm; (xviii) about 8.5-9.0 mm; (xix) about 9.0-9.5 mm; (xx) about 9.5-10.0 mm; (xxi) about 0.1-10 mm; (xxii) about 0.1-7.5 mm; (xxiii) about 0.1-5.1 mm; (xxiv) about 0.5-5.1 mm; and (xxv) about 0.5-5.0 mm.

The method may further comprise supplying the matrix to the analyte via a matrix introduction conduit at a flow rate selected from the group consisting of: (i) about 50-100 μl/min; (ii) about 100-150 μl/min; (iii) about 150-200 μl/min; (iv) about 200-250 μl/min; (v) about 250-300 μl/min; (vi) about 300-350 μl/min; (vii) about 350-400 μl/min; (viii) about 400-450 μl/min; (ix) about 450-500 μl/min; (x) about 500-550 μl/min; (xi) about 550-600 μl/min; (xii) about 600-650 μl/min; (xiii) about 650-700 μl/min; (xiv) about 700-750 μl/min; (xv) about 750-800 μl/min; (xvi) about 800-850 μl/min; (xvii) about 850-900 μl/min; (xviii) about 900-950 μl/min; (xix) about 950-1000 μl/min; (xx) about 50 μl/min to 1 ml/min; (xxi) about 100-800 μl/min; (xxii) about 150-600 μl/min; and (xxiii) about 200-400 μl/min.

The method may further include locating an outlet of a matrix introduction conduit opposite or coaxial with an inlet of an ion analyser.

The method may further include mass and/or ion mobility analysing the analyte ions to obtain analyte ion data, analysing lockmass, lock mobility or calibration ions, and calibrating an ion analyser or adjusting analyte ion data based upon the data obtained from analysing the lockmass, lock mobility or calibration ions.

A further aspect provides a method of electrosurgery. In exemplary embodiments the method includes contacting biological tissue with a rapid evaporative ionisation mass spectrometry ("REIMS") electrosurgical tool and activating the electrosurgical tool so as to generate analyte, smoke, fumes, liquid, gas, surgical smoke, aerosol or vapour; aspirating the analyte, smoke, fumes, liquid, gas, surgical smoke, aerosol or vapour; providing a substantially cylindrical collision assembly having a first longitudinal axis; heating the collision assembly; directing the analyte, smoke, fumes, liquid, gas, surgical smoke, aerosol or vapour onto the heated collision assembly along a second axis which is substantially orthogonal to the first axis in order to form analyte ions; and mass and/or ion mobility analysing the analyte ions.

A further aspect provides an electrosurgical apparatus. In exemplary embodiments the apparatus includes a rapid evaporative ionisation mass spectrometry ("REIMS") electrosurgical tool comprising one or more electrodes; a device arranged and adapted to activate the electrosurgical tool when the electrosurgical tool is in contact, in use, with biological tissue so as to generate analyte, smoke, fumes, liquid, gas, surgical smoke, aerosol or vapour; a device arranged and adapted to aspirate the analyte, smoke, fumes, liquid, gas, surgical smoke, aerosol or vapour; and a mass and/or ion mobility spectrometer comprising: (i) a substantially cylindrical collision assembly having a first longitudinal axis; (ii) a heater for heating the collision assembly; (iii) a first device arranged and adapted to direct the analyte, smoke, fumes, liquid, gas, surgical smoke, aerosol or vapour onto said heated collision assembly along a second axis which is substantially orthogonal to said first axis in order to form analyte ions; and (iv) a mass and/or ion mobility analyser for mass and/or ion mobility analysing said analyte ions.

It has also been found that dissolving analyte in a matrix substantially eliminates the intermolecular bonding between the analyte molecules resulting in improved performance. When the dissolved analyte is subsequently collided with a heated (cylindrical) collision surface so as to fragment into droplets, any given droplet is likely to contain fewer analyte molecules than it would if the matrix were not present.

The approach according to the exemplary embodiment therefore leads to the more efficient generation of ions when the matrix in each droplet is evaporated.

The step of colliding dissolved analyte droplets with the (cylindrical) collision surface may cause the step of evaporating the matrix from the analyte by converting kinetic energy of the analyte and matrix into heat.

The step of colliding analyte droplets may cause the smaller dissolved analyte droplets to be generated, at least some of which have only a single analyte molecule therein. This enhances the ionisation process.

The analyte may, for example, include a polar lipid and the vapour or aerosol may include aqueous droplets covered with the polar lipids.

The analyte may include triglycerides.

The analyte to which the matrix is supplied may include ionised analyte molecules.

The method may further include the step of generating the gas phase analyte, vapour analyte, aerosol, or liquid from a sample to be analysed.

The gas phase analyte, vapour analyte or aerosol may be generated by heating the sample containing the analyte e.g. by diathermic evaporation of the sample.

The method may either be part of a surgical method or a non-surgical method. For example, the method may be a surgical method in which the sample may be human or animal tissue containing the analyte. The sample may be subjected to electrosurgical diathermic evaporation, or other forms of rapid evaporation, in order to form the gas phase analyte, vapour analyte or aerosol. By way of example only, the device and method may be used for the identification of human tissues in breast cancer surgery. By analysing the analyte ions it is possible to determine whether or not the tissues are cancerous.

Alternatively, the method may include a non-surgical method. For example, human or animal tissue that is not part of the human or animal body (i.e. previously excised, deposited or removed) may be analysed, or samples or biological tissues other than human or animal tissues may be analysed. Again, by analysing the analyte ions it is possible to determine the properties or constituents of the sample, such as whether or not they contain cancerous tissues.

The disclosed methods may be used in other non-surgical methods, such as country of origin identification, pharmaceutical testing, food safety testing (e.g. dairy), cosmetics testing, military applications, air pollution testing, post-mortem analysis, microbe identification (e.g. bacteria) and automated sampling.

The various methods disclosed above may be used to analyse non-biological samples and compounds.

The analyte that is formed from the sample may be partially charged and/or may have a relatively high organic content.

The method may further include evaporating the matrix from the analyte in second smaller dissolved analyte droplets so as to provide analyte ions that are substantially separate from the matrix.

The step of evaporating the matrix from the analyte may result in charge transfer to or from the analyte so as to ionise the analyte to form analyte ions.

After the step of evaporating the matrix from the analyte, the method may further include trapping analyte ions in an ion trap and/or guiding analyte ions using an ion guide.

The matrix may initially be supplied as a solid e.g. powder and sublimated or melted and evaporated so as to form matrix in vapour or gas-phase that is intermixed with the analyte.

Alternatively, the matrix may be supplied to, and intermixed with, the analyte as a liquid, aerosol or vapour. If the analyte and/or matrix is in liquid form then the mixture of analyte and matrix may need to be subsequently converted into the first dissolved analyte droplets e.g. by spraying.

The dielectric constant of the matrix may be sufficiently high such that the solvation of the analyte involves ionic dissociation resulting in solvated ions of the analyte present in the condensed phase. In these cases, the impact on the collision surface is more likely to produce solvated ions in the gas phase, which may eventually yield ions formed by deprotonation (in a negative ion mode, i.e. $[M-H]^-$), ions formed by protonation (in a positive ion mode, i.e. $[M+H]^+$), and/or molecular ions.

Isopropanol has been found to be a particularly advantageous matrix to use e.g., for lipid species.

By way of example, for analytes comprising polar lipids, the matrix may be or may include, low molecular weight alcohols (e.g. methanol, ethanol, isopropanol) or ketones (e.g. acetone). These matrices have been shown to enhance the ionisation of all or certain species otherwise detected in the absence of the matrix vapours at lower intensity.

The mixture of analyte and matrix may be a homogeneous or heterogeneous mixture.

Voltages may be applied to the ion trap or ion guide so as to trap or guide the ions respectively. The ions may then be delivered from the ion trap or ion guide to an ion analyser for analyzing the mass and/or ion mobility of the ions.

The ions may be separated according to ion mobility prior to being mass analysed. Ions may then be excluded or discarded based upon their ion mobility.

Any one of the above mentioned ranges may be combined with any one of the ranges in the list of ranges for distance x.

The inlet of the ion analyser may include an aperture or orifice that separates a vacuum chamber of the ion analyser from a higher pressure region upstream of the ion analyser. For example, the inlet may be an atmospheric pressure interface.

In the alternative, the matrix introduction conduit may deliver matrix directly into a sample transfer conduit that performs the step of providing the analyte.

Alternatively, a sample transfer conduit may be provided that performs the step of providing the analyte, and the outlet of the matrix introduction conduit may be provided at a location about the circumference of sample transfer conduit. A gas flow may be arranged so as to sweep the matrix from the outlet to the inlet of the ion analyser that analyses the ions.

The device for evaporating the sample may comprise an electrosurgical tool such as a diathermic device.

The device may have an end, point or region for inserting onto a sample to evaporate the sample and wherein the analyte inlet is adjacent the end, point or region.

The apparatus may include a source of the matrix compound for supplying the matrix compound to the conduit.

The accelerating means may include a vacuum pump for creating a pressure differential between a first region and a second region for accelerating the first dissolved analyte droplets between the two regions and onto the collision surface.

The apparatus may include a mass and/or ion mobility spectrometer having an atmospheric interface arranged between the first and second regions, wherein the second region may include a vacuum chamber that is connected to a vacuum pump and which houses the collision surface.

The apparatus may include an ion trap or ion guide for trapping or guiding the analyte ions.

The ion analyser may include a mass and analyser or spectrometer and/or ion mobility analyser or spectrometer.

The apparatus may be arranged and configured to perform any one of the methods described herein.

The mixing region may be provided upstream of the inlet to the ion analyser, or the mixing region may be provided at least in part downstream of the ion analyser.

The inlet of the ion analyser may include an aperture or orifice that separates a vacuum chamber of the ion analyser from a higher pressure region upstream of the ion analyser. For example, the inlet may include an atmospheric pressure interface.

The matrix introduction conduit may deliver matrix directly into a sample transfer conduit that performs the step of providing the analyte.

Alternatively, a sample transfer conduit may be provided that performs the step of providing the analyte and the outlet of the matrix introduction conduit may be provided at a location about the circumference of sample transfer conduit. A gas flow may be arranged so as to sweep the matrix from the outlet to the inlet of the ion analyser that analyses the ions.

The apparatus may include a source of the lockmass, lock mobility or calibration compound or ions.

The lockmass, lock mobility or calibration compound/ions may be introduced into the matrix introduction conduit, the analyte introduction conduit or may be supplied in a separate conduit.

Aerosol particles containing the analyte (or gas phase analyte molecules) may be introduced into a mass and/or ion mobility spectrometer together with a volatile matrix compound, which may include an organic solvent. The volatile matrix compound may be introduced to the analyte as a solid (e.g. powder), liquid, aerosol or vapour. The mixture of analyte and matrix may be drawn into the spectrometer by a pressure differential across the inlet to the spectrometer. The lower pressure inside the spectrometer results in the gas that entrains the analyte and matrix expanding, causing a temperature drop in the free jet region. This causes gaseous or vapourised analyte and/or matrix to condense such that the analyte dissolves in the matrix. The role of the matrix compound may be to produce aerosol particles containing the matrix in excess of the analyte molecules and incorporating the analyte molecules in solvated form. The solvation substantially eliminates the intermolecular secondary binding forces between the analyte molecules, since each dissolved analyte molecule is fully surrounded by the matrix molecules. The separation of analyte molecules in condensed phase increases the probability that when the aerosol particles impact upon the collision surface they will form clusters that each contain only a single analyte molecule. The matrix molecule may or may not have a high dielectric constant and/or a high vapour pressure.

BRIEF DESCRIPTION OF THE DRAWINGS

Various embodiments of the present invention will now be described, by way of example only, and with reference to the accompanying drawings in which:

FIG. 1 illustrates a method of rapid evaporative ionisation mass spectrometry ("REIMS") wherein an RF voltage is applied to bipolar forceps resulting in the generation of an aerosol or surgical plume which is captured through an irrigation port of the bipolar forceps and is then transferred to a mass and/or ion mobility spectrometer for ionisation and mass and/or ion mobility analysis;

FIG. 2 shows an embodiment in which the analyte and matrix may be provided in the gas or vapour phase;

FIG. 3 shows another embodiment in which the analyte and matrix may be provided in the liquid phase;

FIG. 4A shows a mass spectrum obtained without the use of a matrix and FIG. 4B shows a mass spectrum obtained using a matrix;

FIG. 5A shows an embodiment of a mass spectrometer interface comprising a Venturi device for introducing analyte aerosol and matrix into a mass spectrometer, FIG. 5B shows an expanded view of FIG. 5B, and FIG. 5C shows a close up of the sampling device in the interface;

FIGS. 6A and 6B show different views of an embodiment comprising a removable collision surface assembly;

FIG. 7A shows a cross section of assembly shown in FIGS. 6A-6B, and FIG. 7B shows expanded view of a portion of the cross section in FIG. 7A;

FIG. 8A shows the apparatus of FIGS. 6A-6B with the retractable shields in an extended position and FIG. 8B shows the retractable shields in a retracted position;

FIG. 9A shows a collision surface assembly and FIG. 9B shows a cross sectional view of the collision surface assembly;

FIG. 10 shows the collision surface assembly and associated ceramic holder;

FIG. 11A shows a REIMS source assembly with a rotatable isolation valve in the closed position and FIG. 11B shows the assembly with the vacuum isolation valve in the open position;

FIG. 12A-12E show views of components of the isolation valve;

FIG. 13A shows an exploded view of the REIMS source assembly including a CAM valve seal, FIG. 13B shows a perspective view of the seal, FIG. 13C shows a side cross-sectional view of the seal and FIG. 13D shows a magnified view of part of the seal in FIG. 13C;

FIG. 14 shows a main heater assembly, REIMS source housing and main assembly of a mass spectrometer according to an embodiment;

FIG. 15 shows a further embodiment wherein a funnel-shaped collision assembly is provided and wherein an aerosol is arranged to impact upon an inner surface of the collision assembly in order to form analyte ions;

FIG. 16 shows another embodiment wherein a hollow cylindrical collision assembly is provided and wherein an aerosol is arranged to impact upon an inner surface of the collision assembly in order to form analyte ions;

FIG. 17A shows an arrangement wherein the collision surface is spherical and FIG. 17B shows an embodiment wherein the collision surface is coil-shaped;

FIG. 18A shows a mass spectrum obtained using a collision surface that is not heated and FIG. 18B shows a mass spectrum obtained using a heated collision surface;

FIG. 19A shows the ion signal intensity obtained as a function of the maximum diameter of the collision surface for Leu Enk in negative ion mode, and FIG. 19B shows the ion signal intensity obtained for Leu Enk in positive ion mode;

FIG. 20A shows the ion signal intensity obtained for lipids in negative ion mode, and FIG. 20B shows the ion signal intensity obtained for lipids in positive ion mode;

FIG. 21 shows a mass spectrum obtained using a non-heated spherical collision surface;

FIG. 22 shows a mass spectrum obtained using a non-heated cylindrical collision surface;

FIG. 23 shows a mass spectrum obtained using a heated, Kathal® coil-shaped collision surface;

FIG. 24 shows a mass spectrum obtained using a quartz cylinder collision surface heated by a coil arranged within the cylinder;

FIG. 25 shows a mass spectrum obtained using a glass-ceramic MACOR® cylinder collision surface heated by a coil arranged within the cylinder;

FIG. 26A shows a mass spectrum obtained using a ceramic collision surface heated by a heater coil embedded therein, and FIG. 26B shows the mass spectrum of FIG. 26A within the mass range of 600-900;

FIG. 27A shows a mass spectrum obtained using a heated nickel coil-shaped collision surface, and FIG. 27B shows the mass spectrum of FIG. 27A within the mass range of 600-900;

FIG. 28A shows the ion signal intensity detected for different distances between the exit of a sample transfer capillary and a kathal coil collision surface, FIG. 28B shows the mass spectra at a distance of 3 mm and FIG. 28C shows the mass spectra at a distance of 5 mm;

FIG. 29A shows the mass spectrum obtained using a cone as the collision surface and FIG. 29B shows the mass spectrum obtained when the conical surface tapers outwards to a cylindrical section;

FIGS. 30A and 30B show mass spectra obtained using disc shaped collision members;

FIG. 31A shows the mass spectrum obtained using a collision member that is hemispherical with the planar surface of the hemisphere facing upstream, FIG. 31B shows the mass spectrum obtained using a collision member that is hemispherical with the planar surface of the hemisphere facing downstream, and FIG. 31C shows the mass spectrum obtained using a collision member that has a planar upstream surface and a conical downstream surface;

FIG. 32A shows the mass spectrum obtained using a collision assembly having an outer diameter of 5 mm, FIG. 32B shows the mass spectrum obtained using a collision assembly having an outer diameter of 3.5 mm, and FIG. 32C shows the mass spectrum obtained using a collision assembly having an outer diameter of 2 mm;

FIG. 33A shows the mass spectrum obtained using spherical collision assemblies of different diameters, and FIG. 33B shows the total ion current as a function of the outer diameter of the spherical collision surface;

FIGS. 36A-36F show spectra obtained whilst maintaining the sample delivery capillary at different temperatures;

FIG. 37B-37D shows detailed spectra for some of these distances;

Figure 38A:
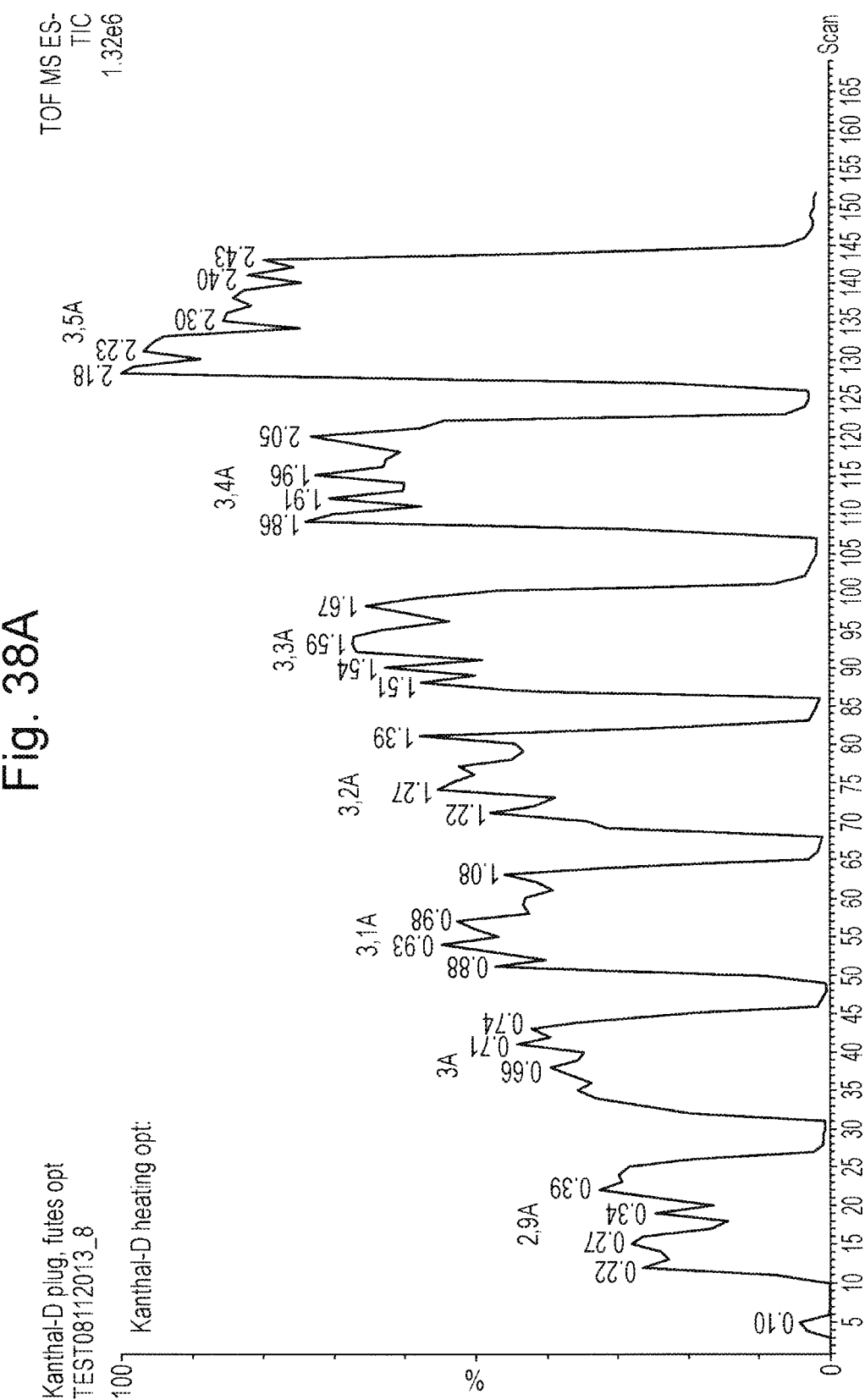
Figure 38B:
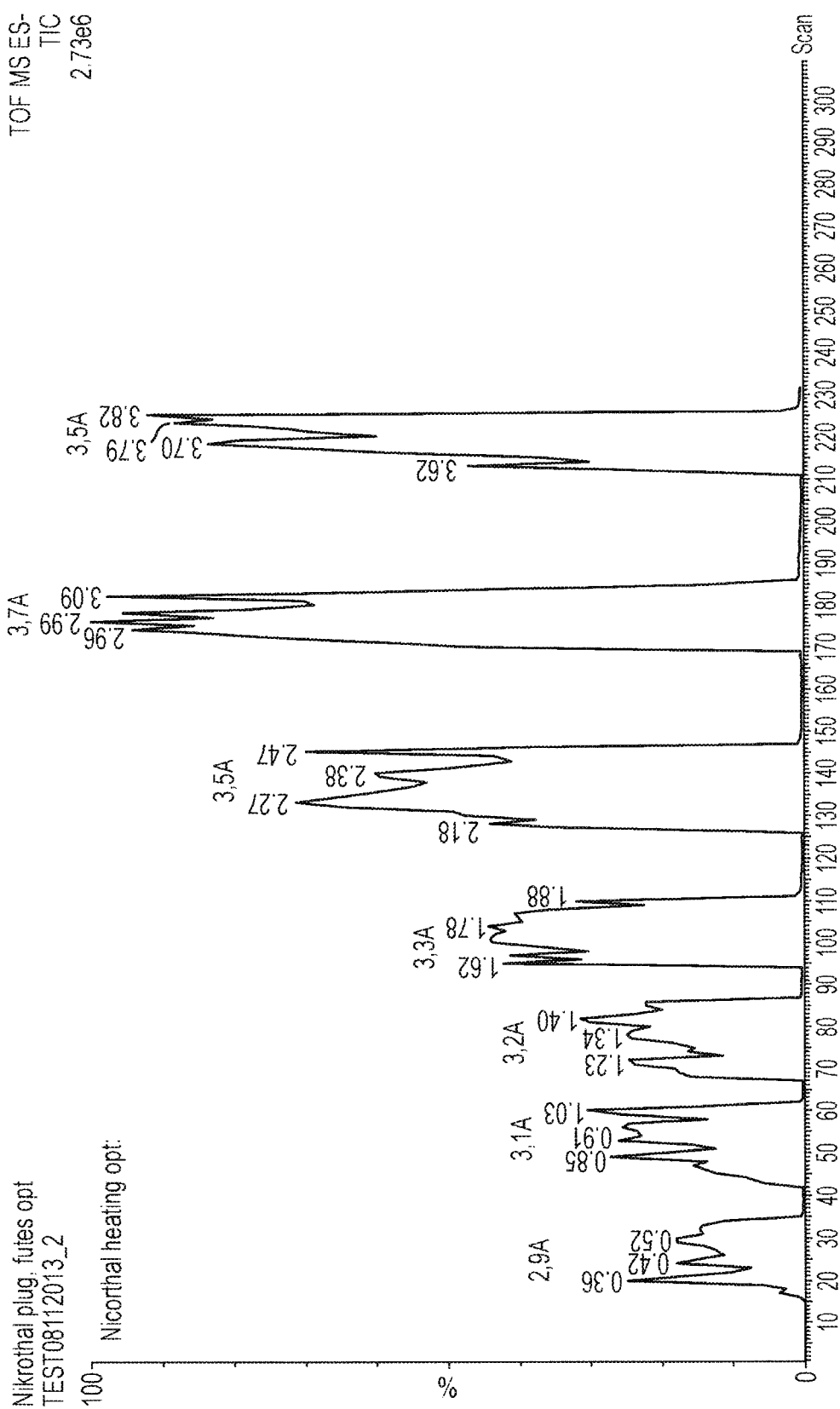
Figure 39:
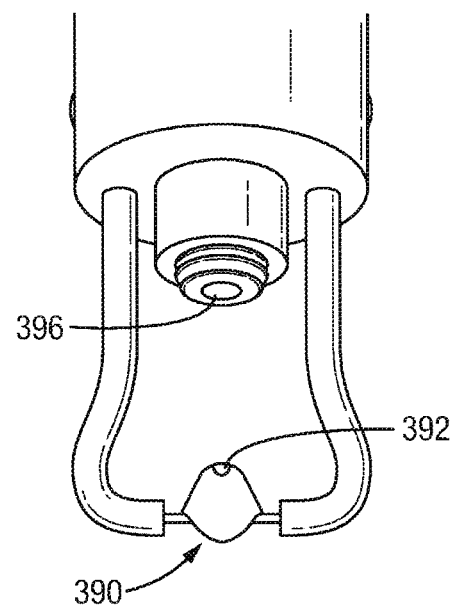
Figure 40A:
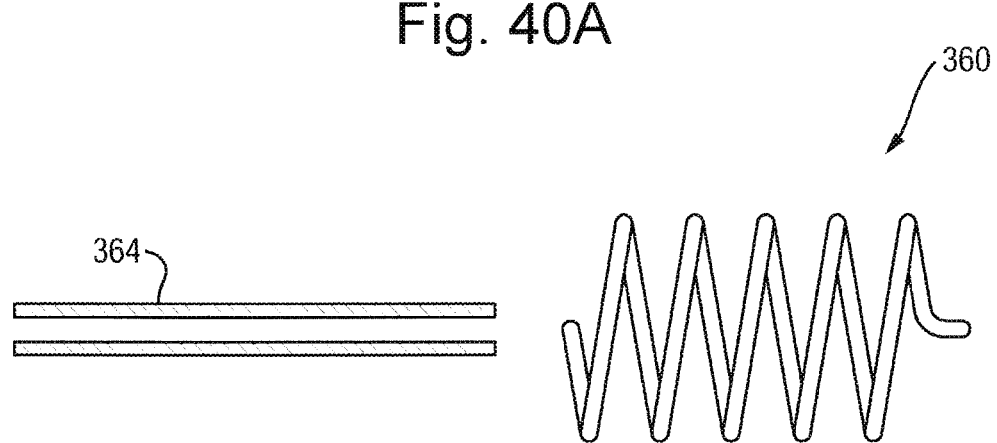
Figure 40B:
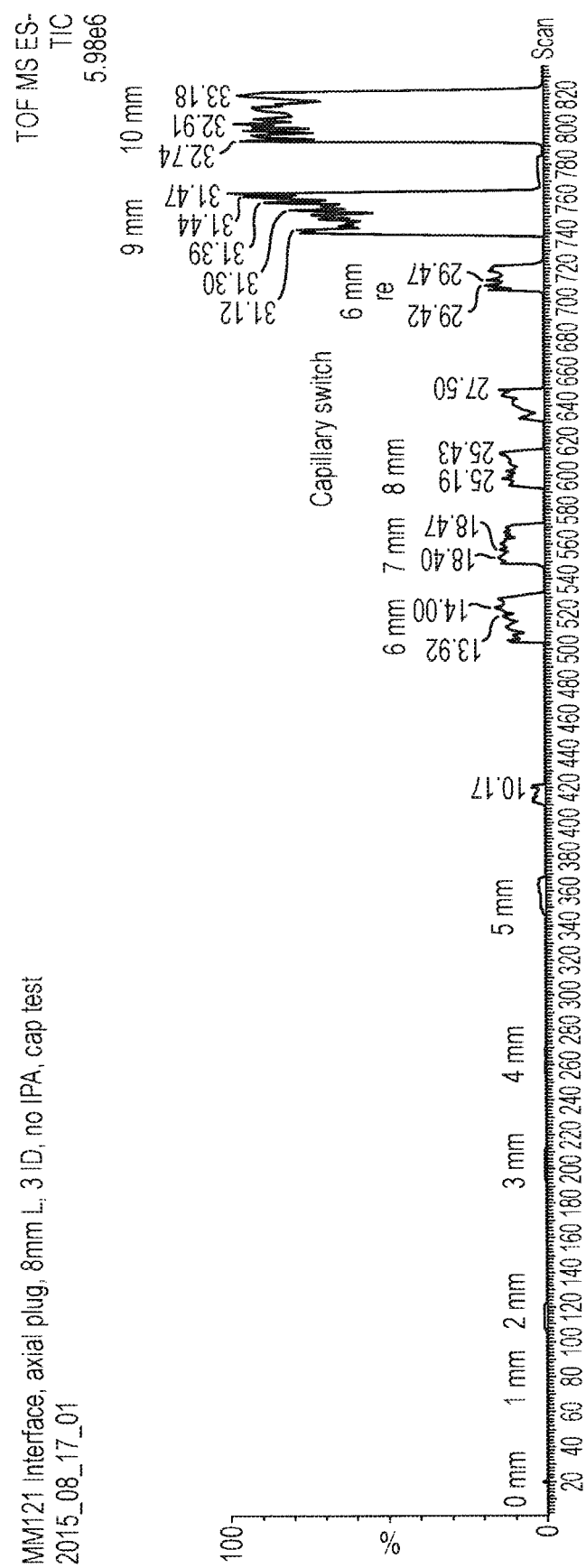
Figure 40C:
Figure 40D:
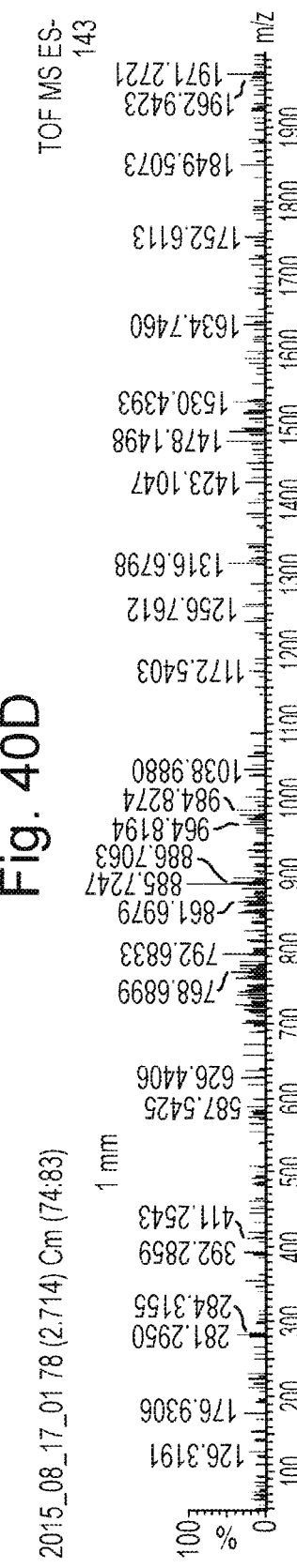
Figure 40E:
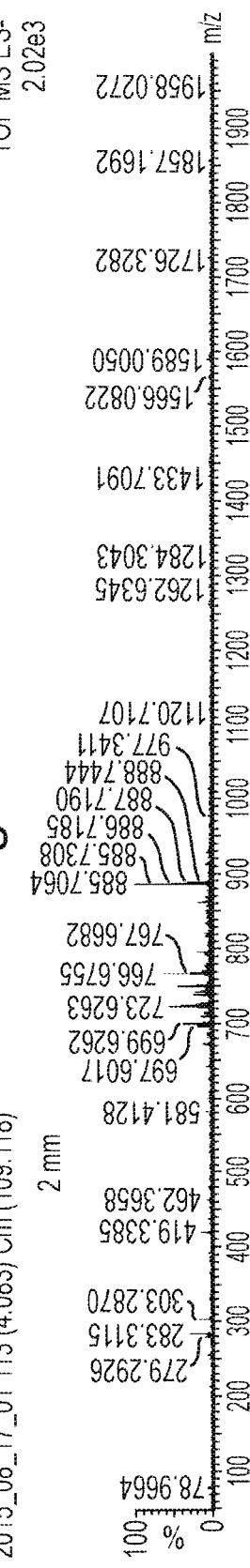
Figure 40F:
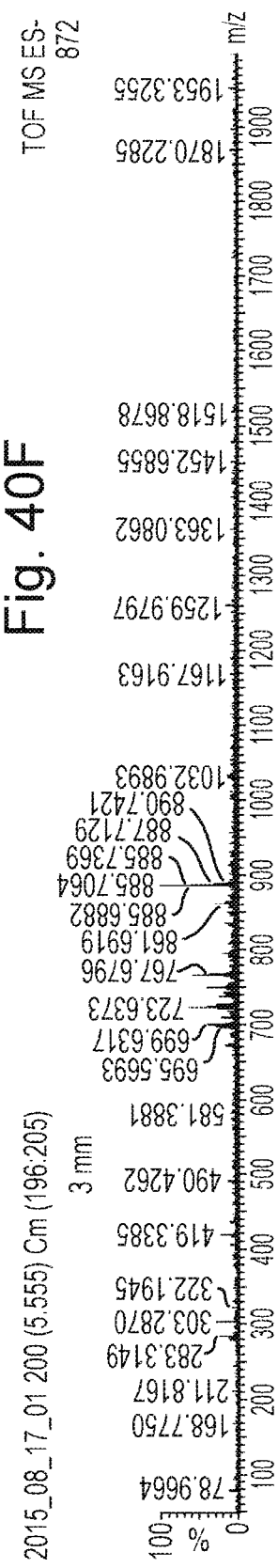
Figure 40G:
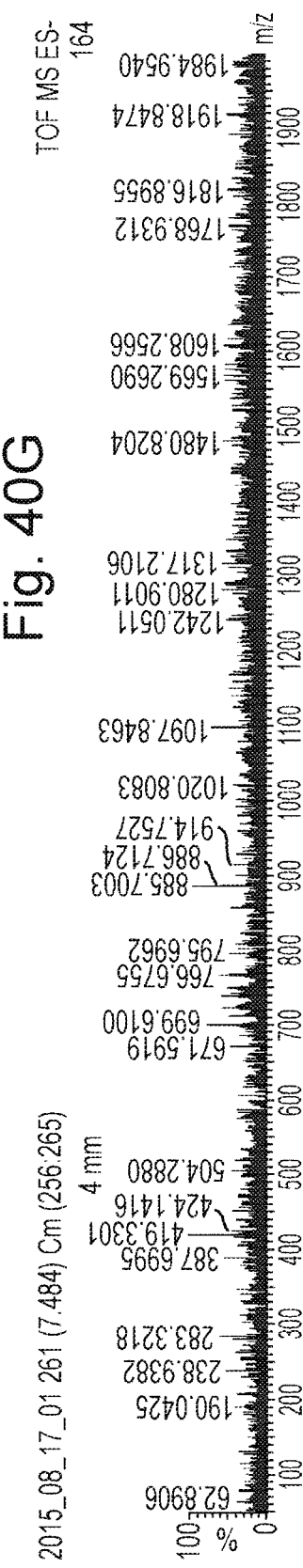
Figure 40H:
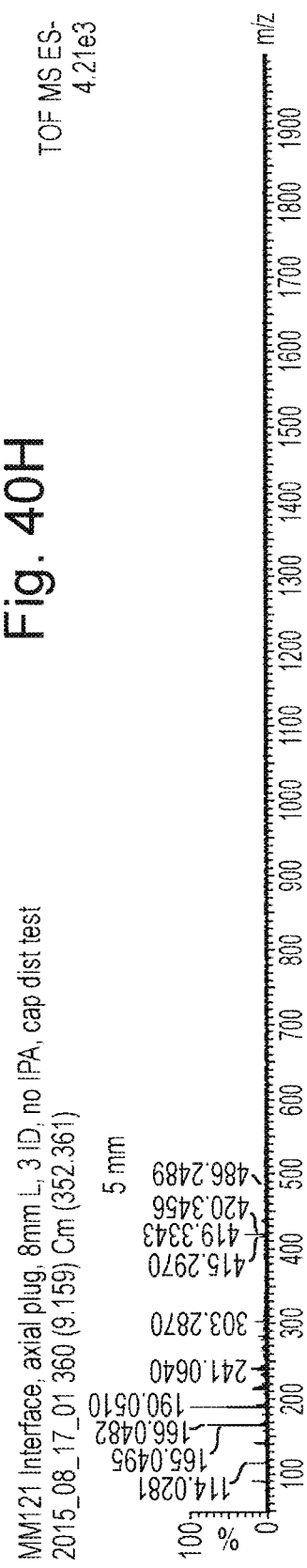
Figure 41A:
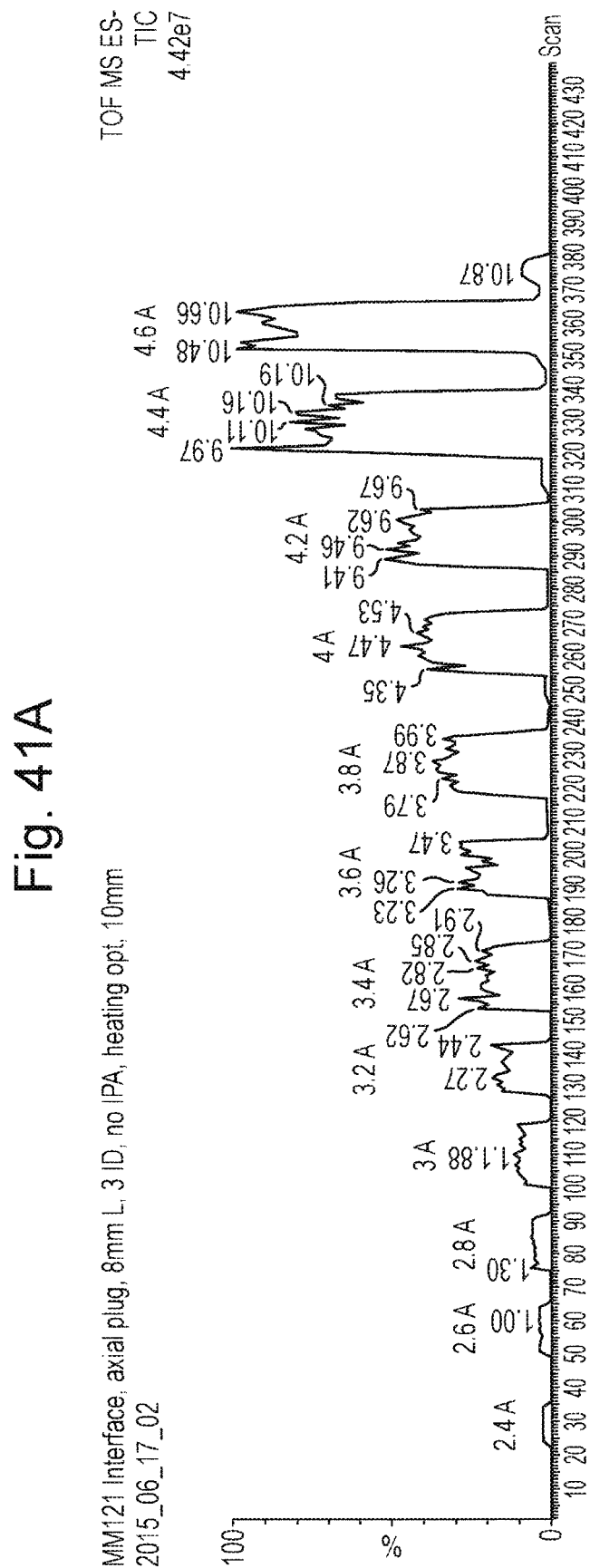
Figure 41E:
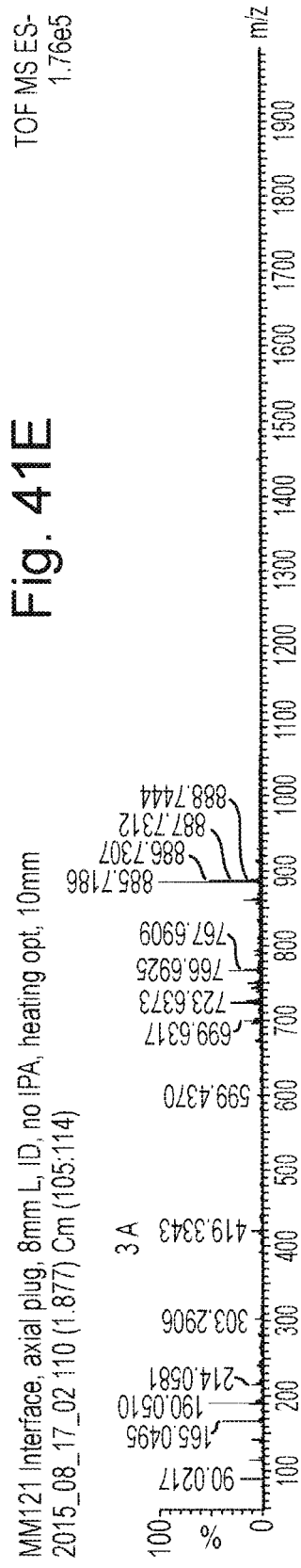
Figure 41F:
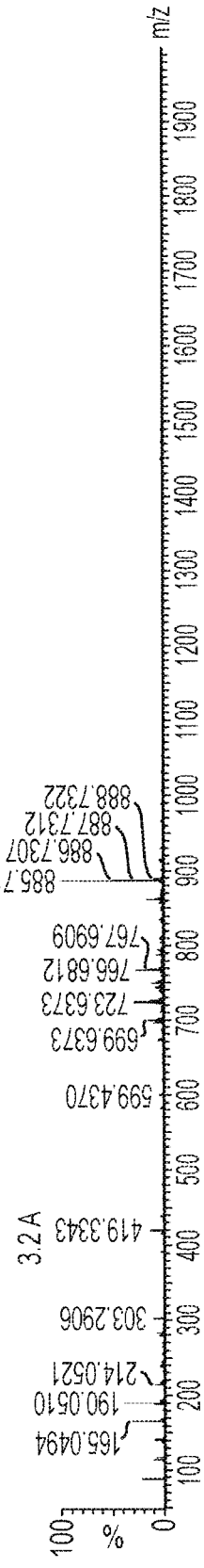
Figure 41G:
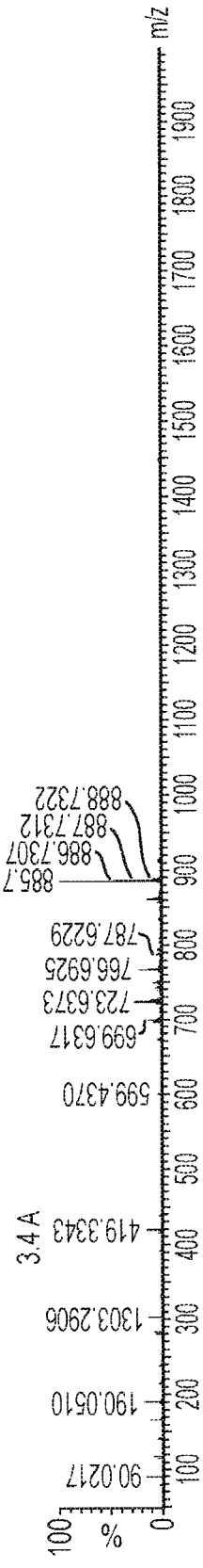
Figure 41K:
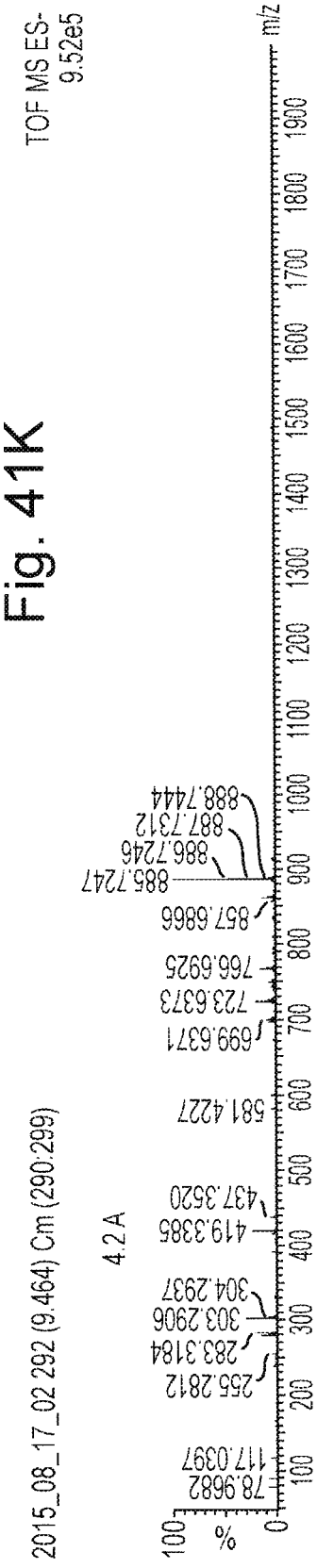
Figure 41L:
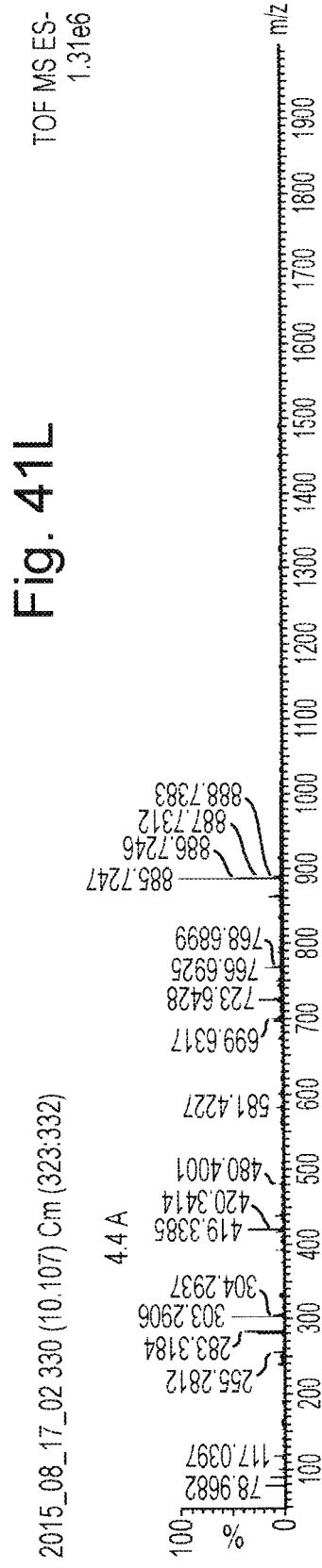
Figure 41M:
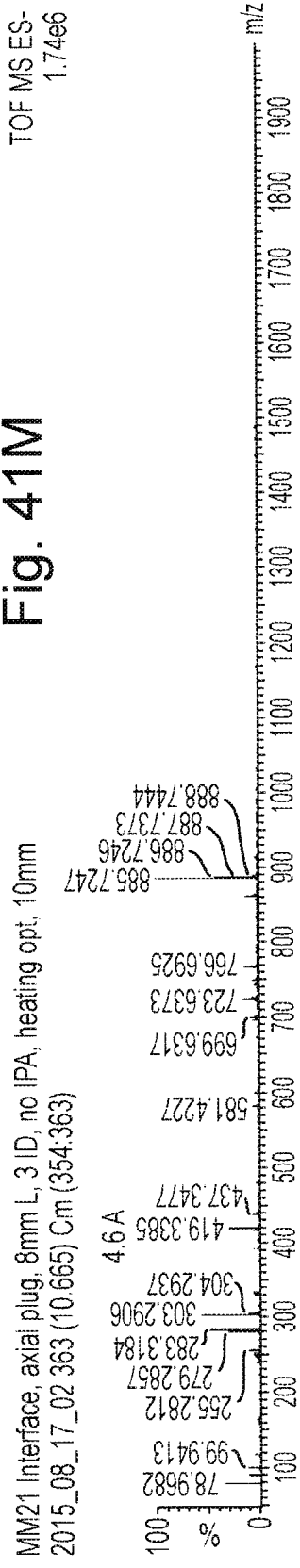
Figure 42A:
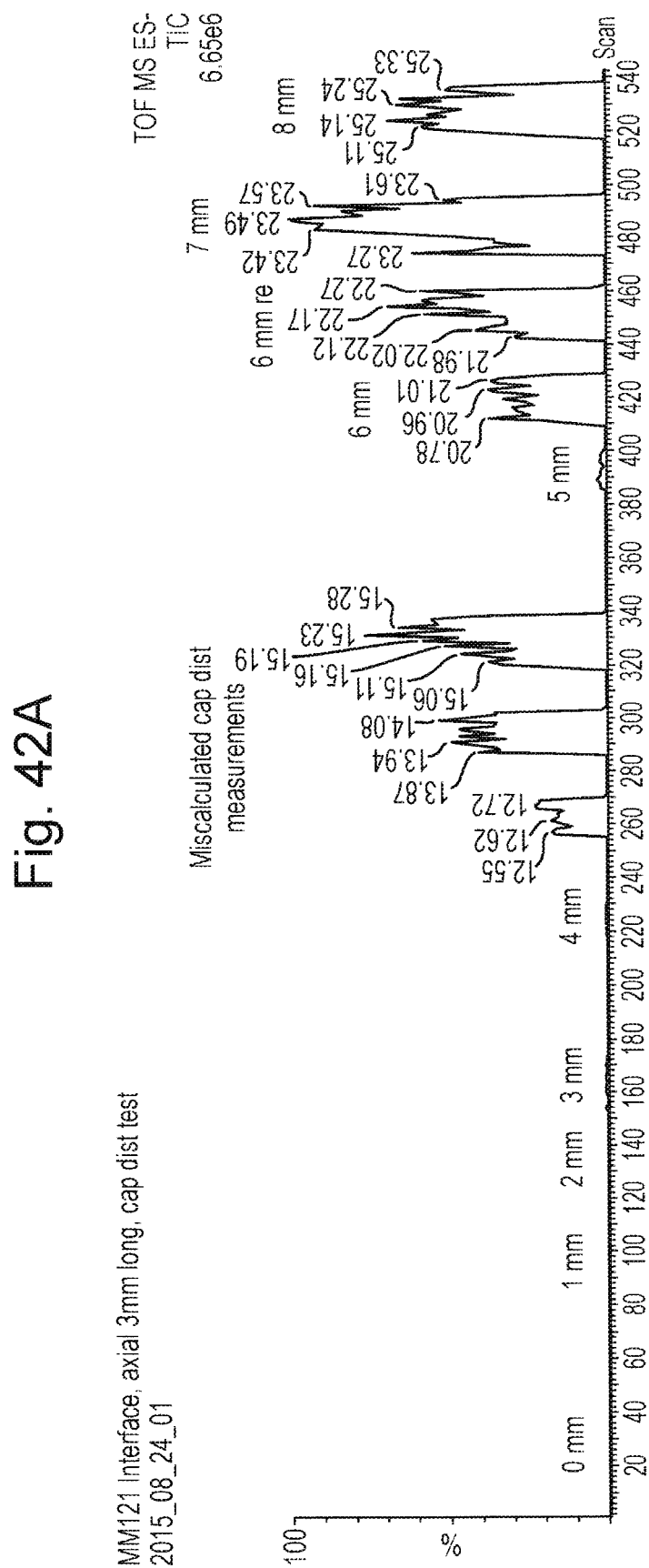
Figure 42B:
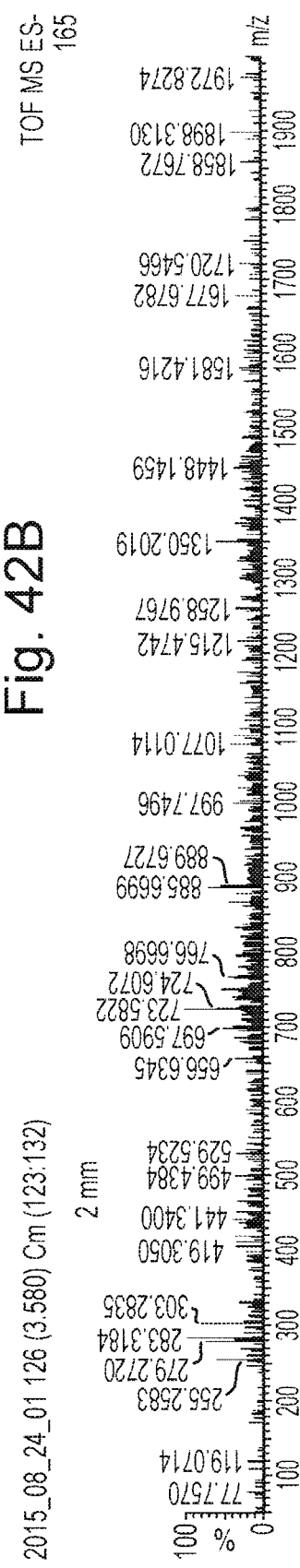
Figure 42C:
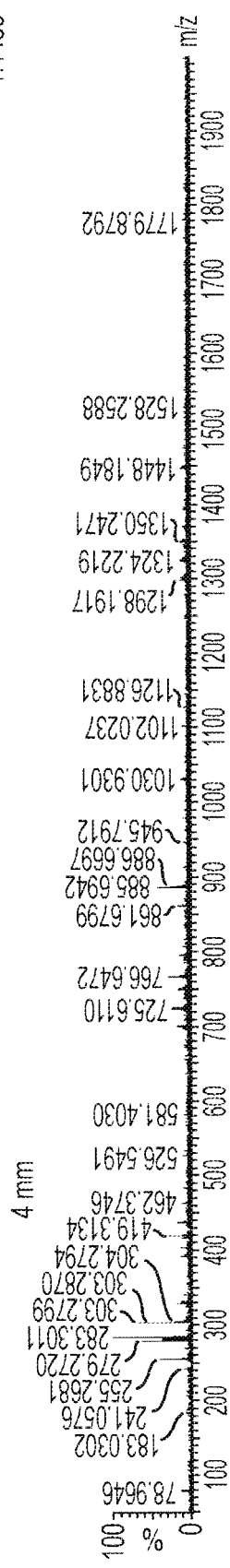
Figure 42D:
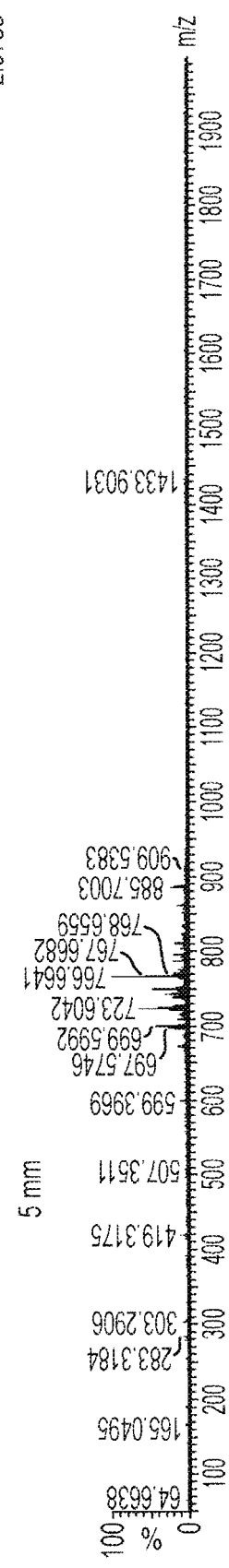
Figure 42E:
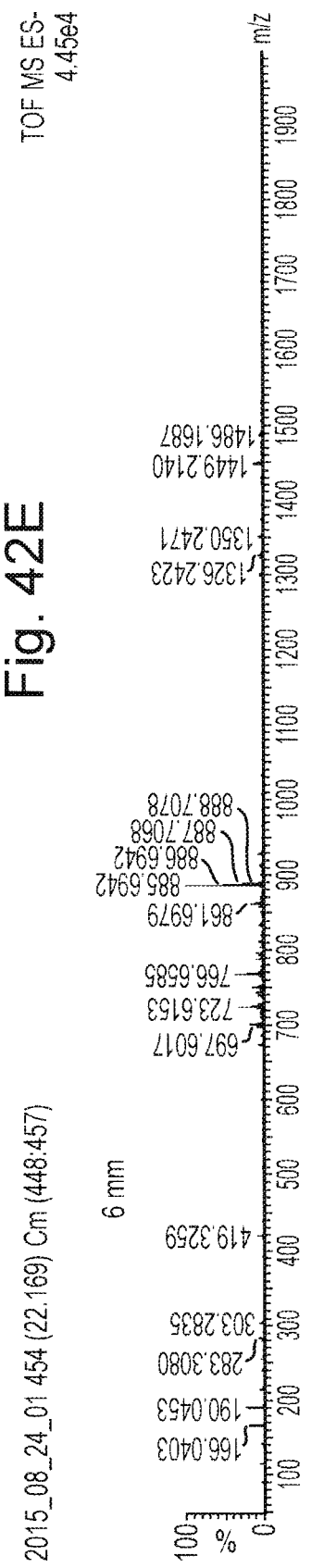
Figure 42F:
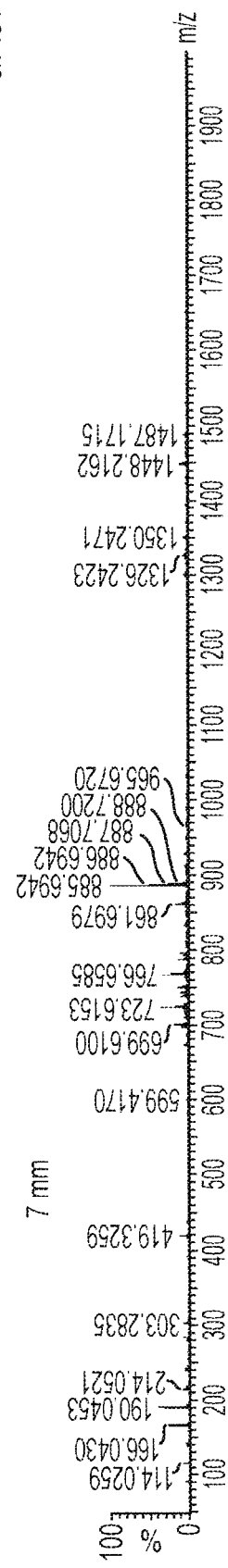
Figure 42G:
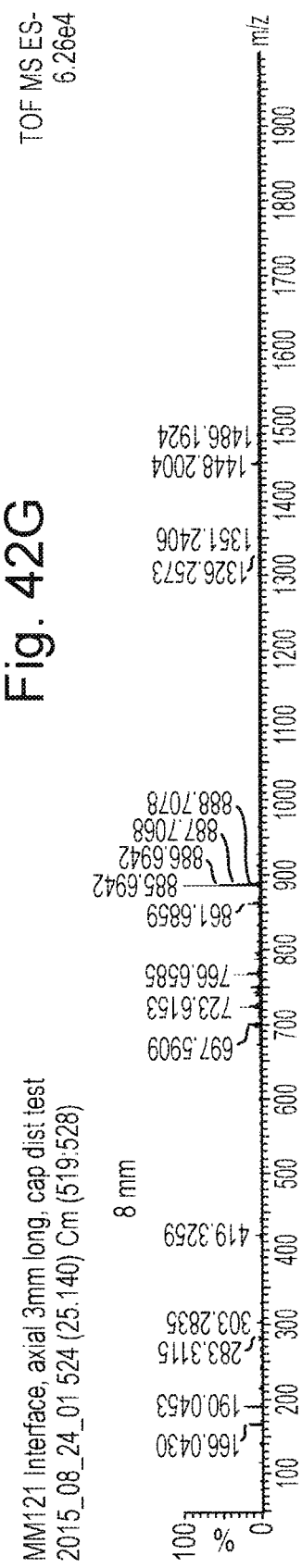
Figure 42H:
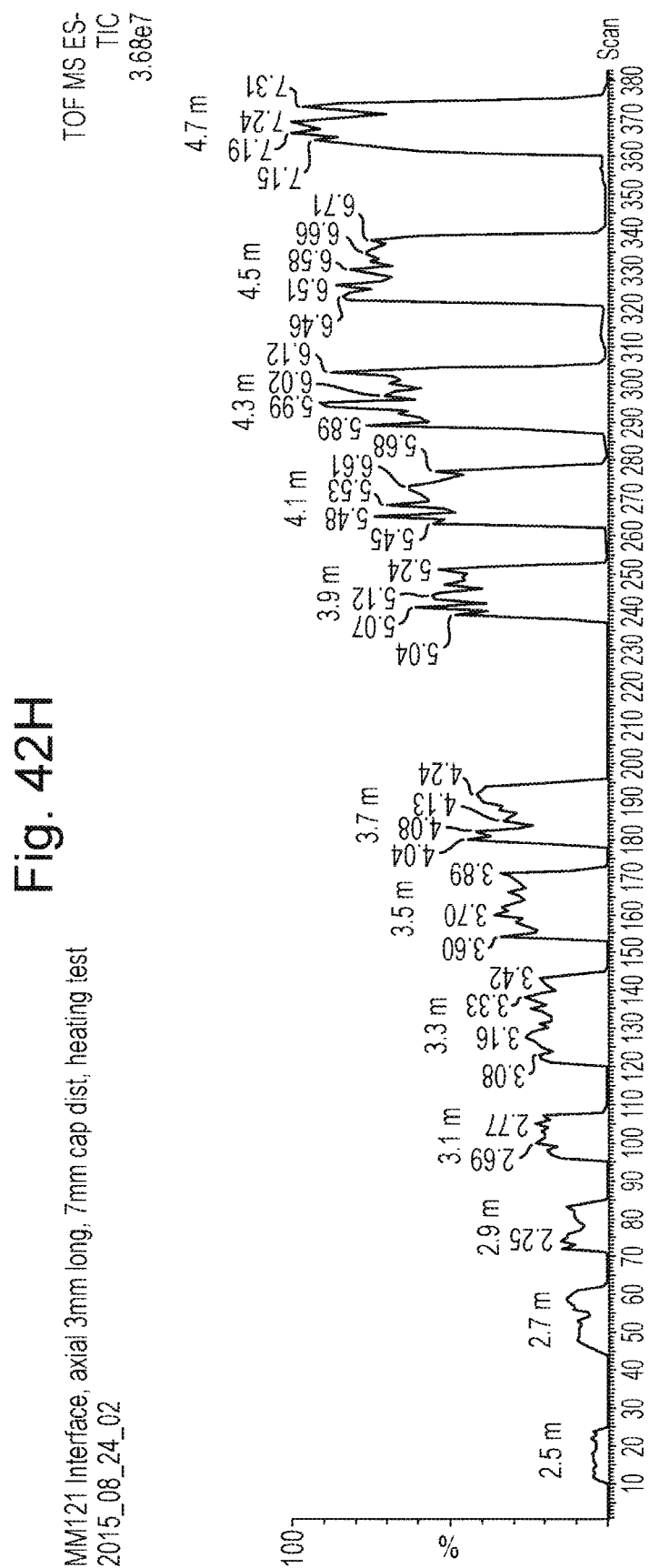
Figure 42I:
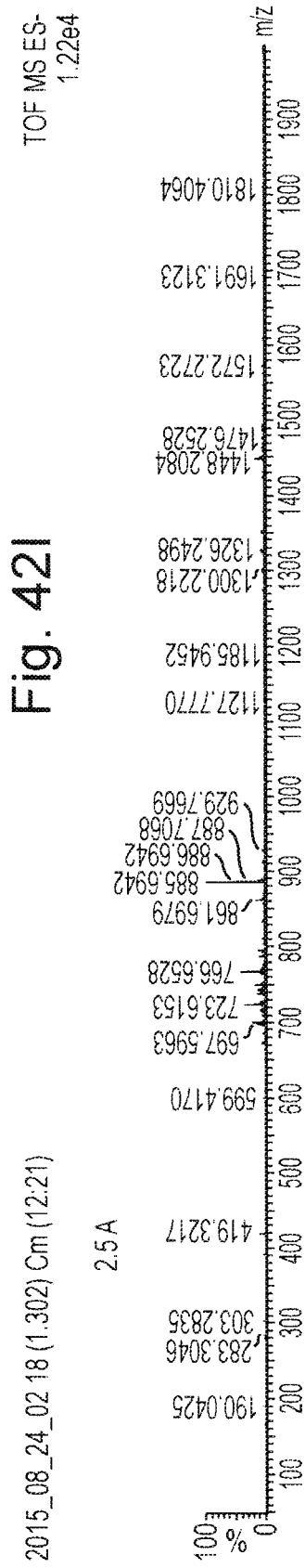
Figure 42J:
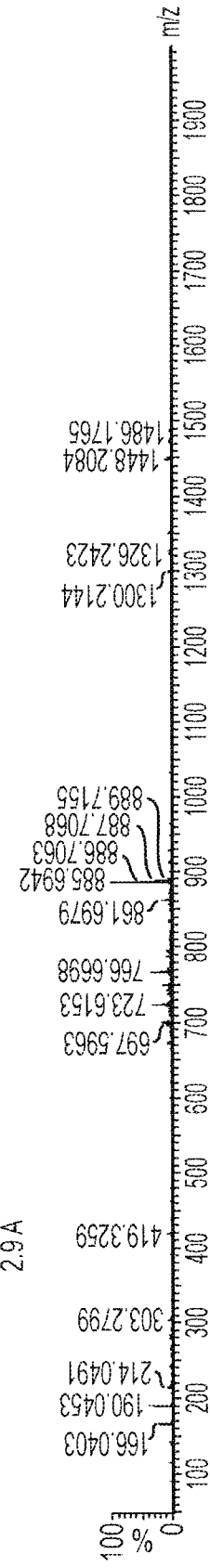
Figure 42K:
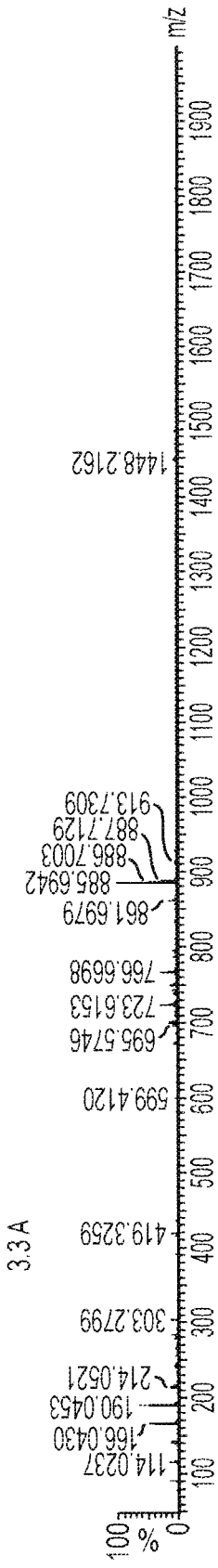
Figure 42L:
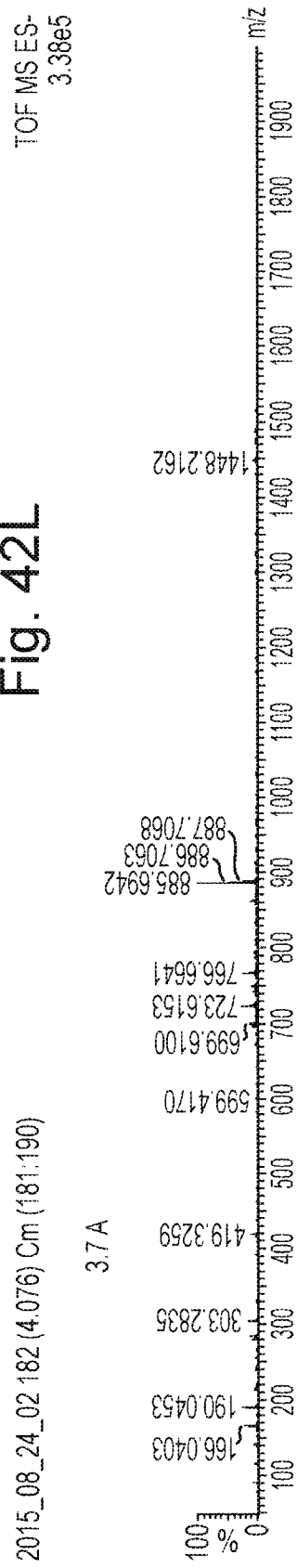
Figure 42M:
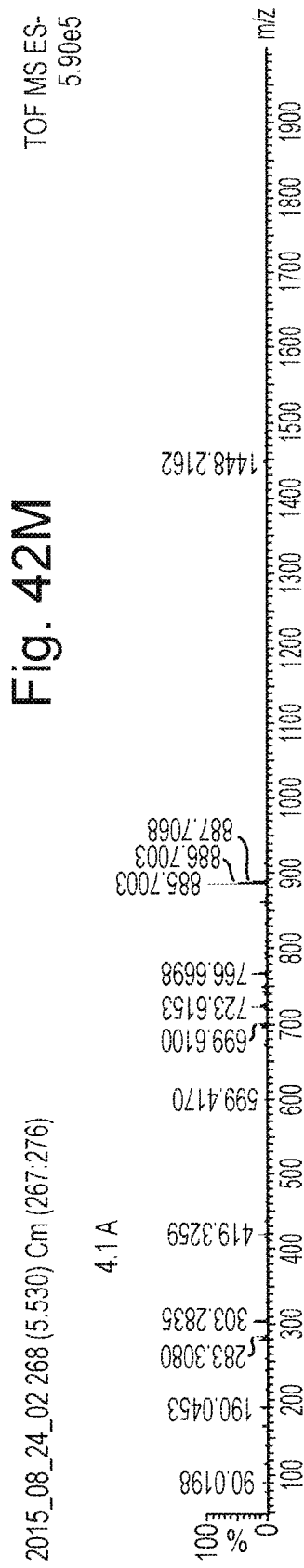
Figure 42N:
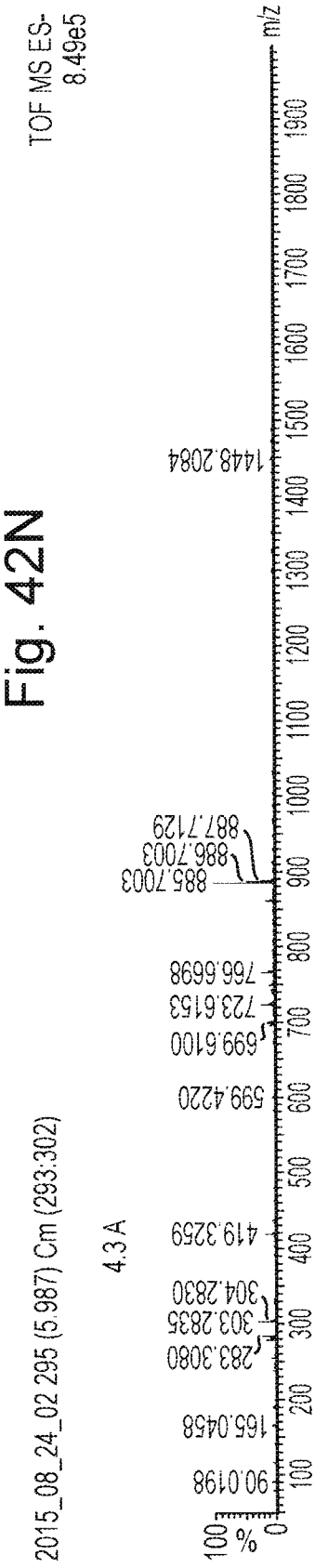
Figure 42O:
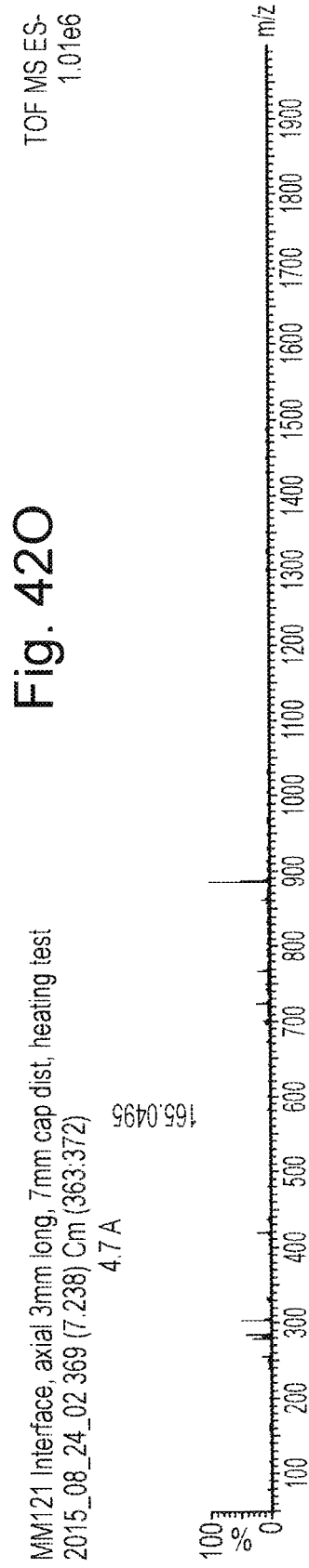
Figure 43A:
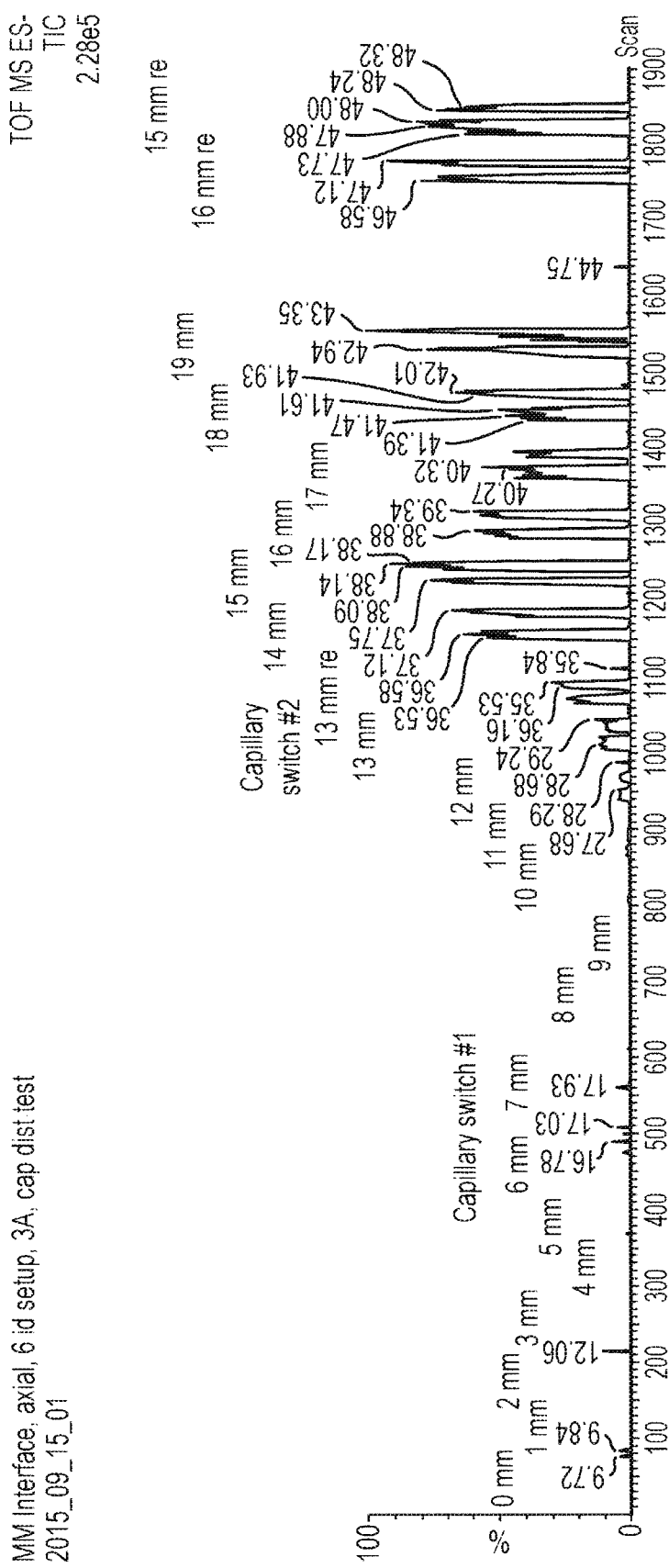
Figure 43G:
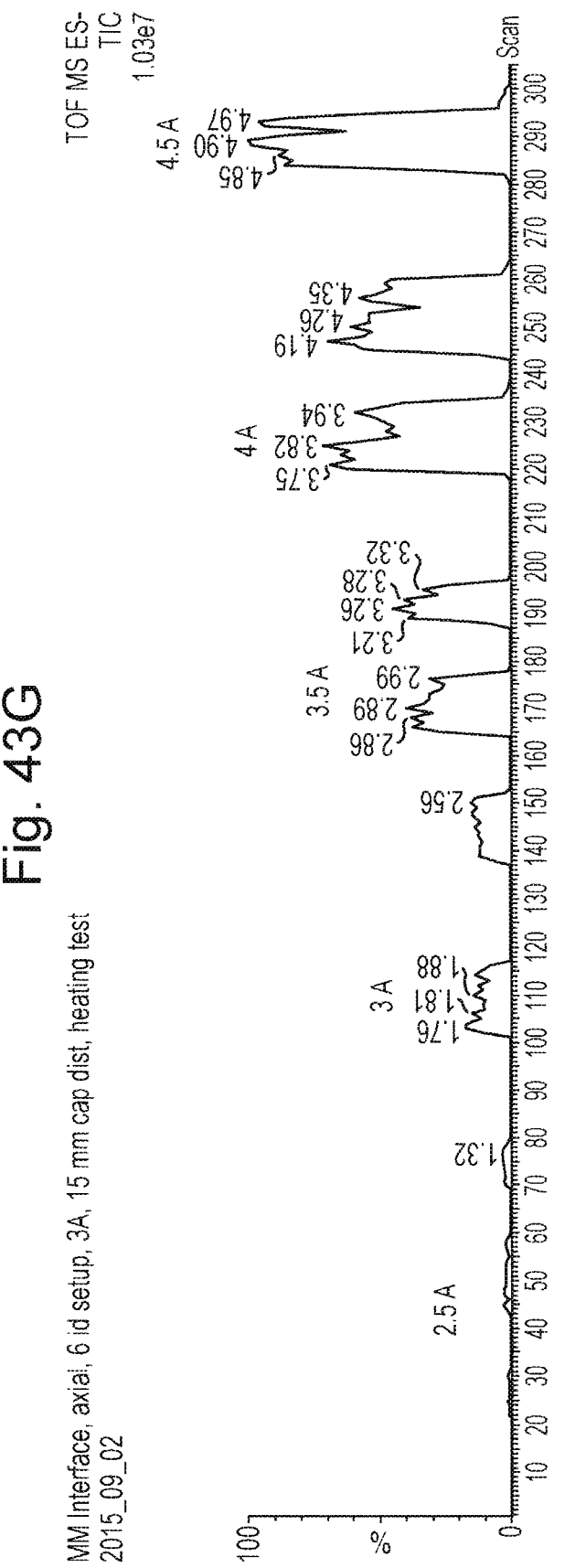
Figure 43K:
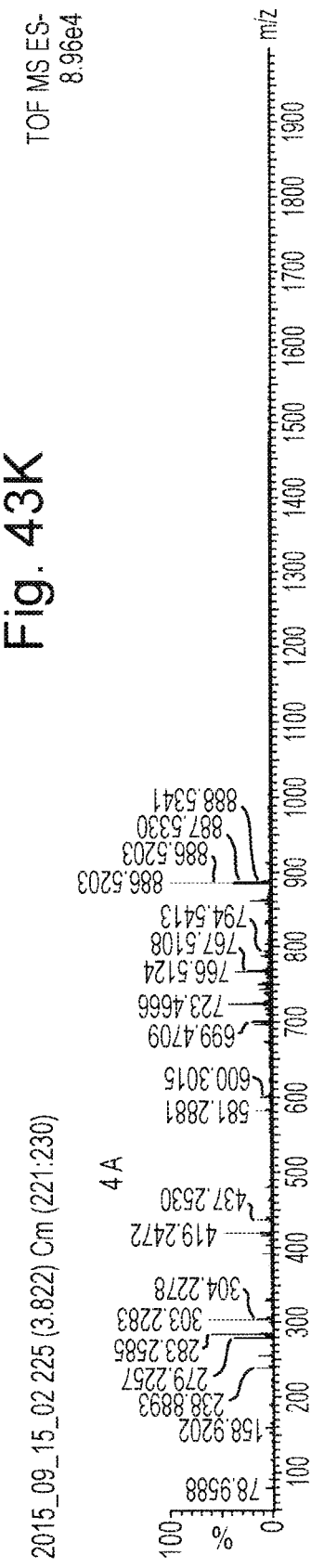
Figure 43L:
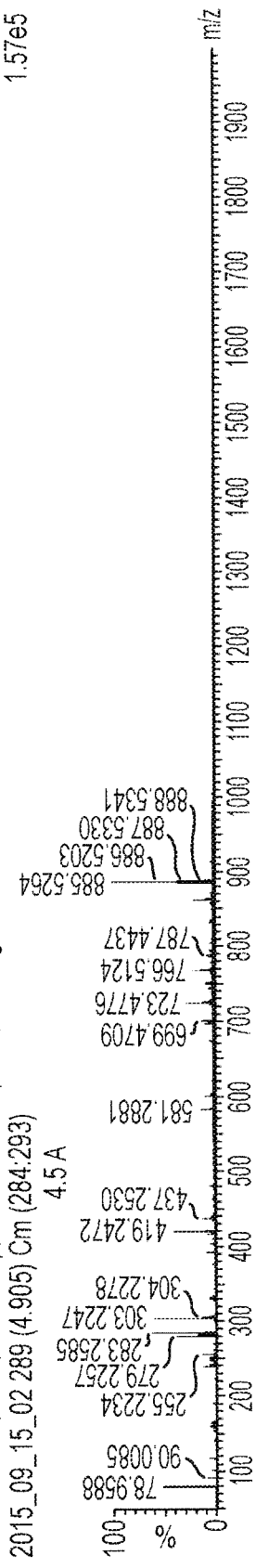
Figure 44A:
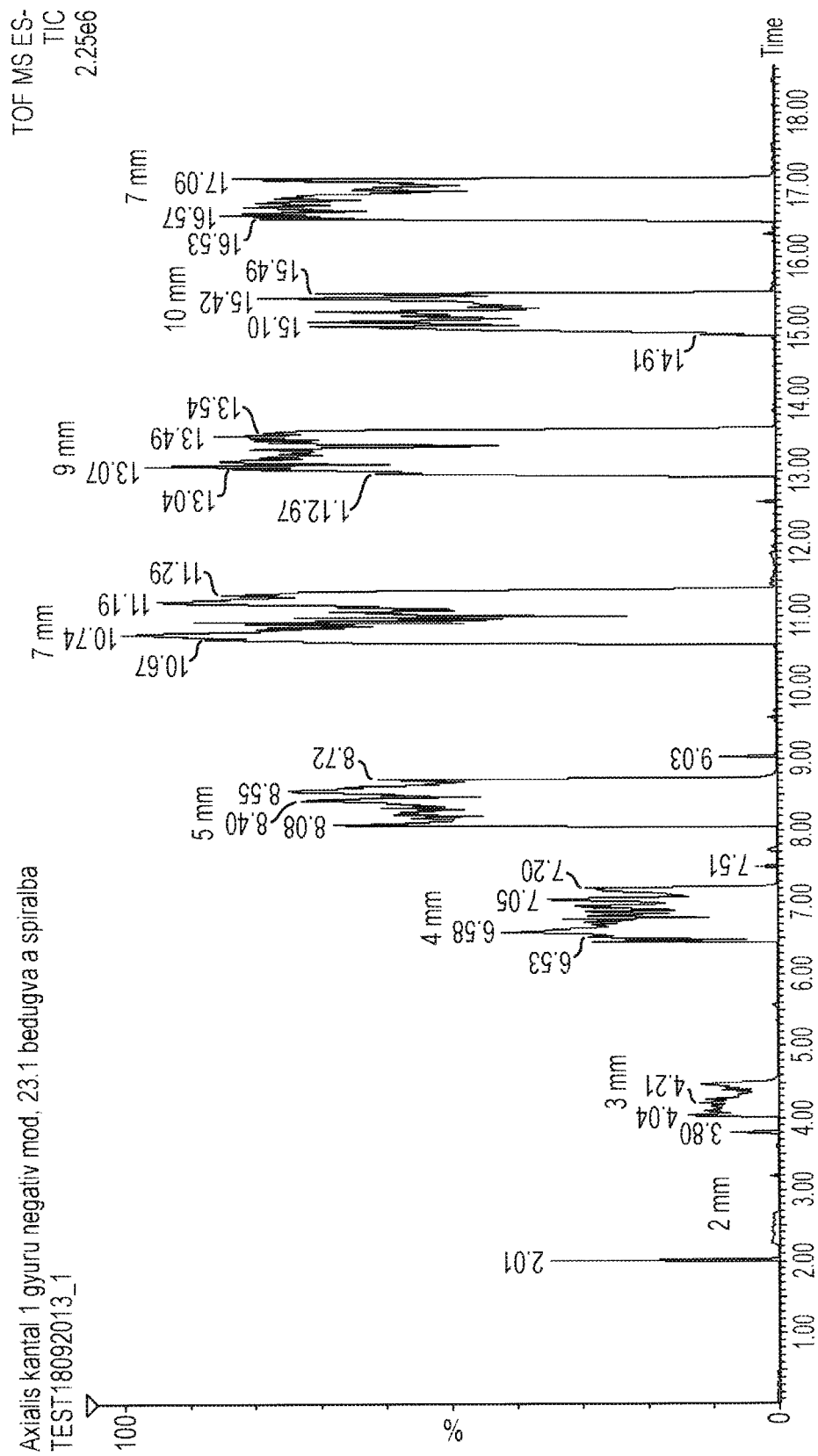
Figure 44D:
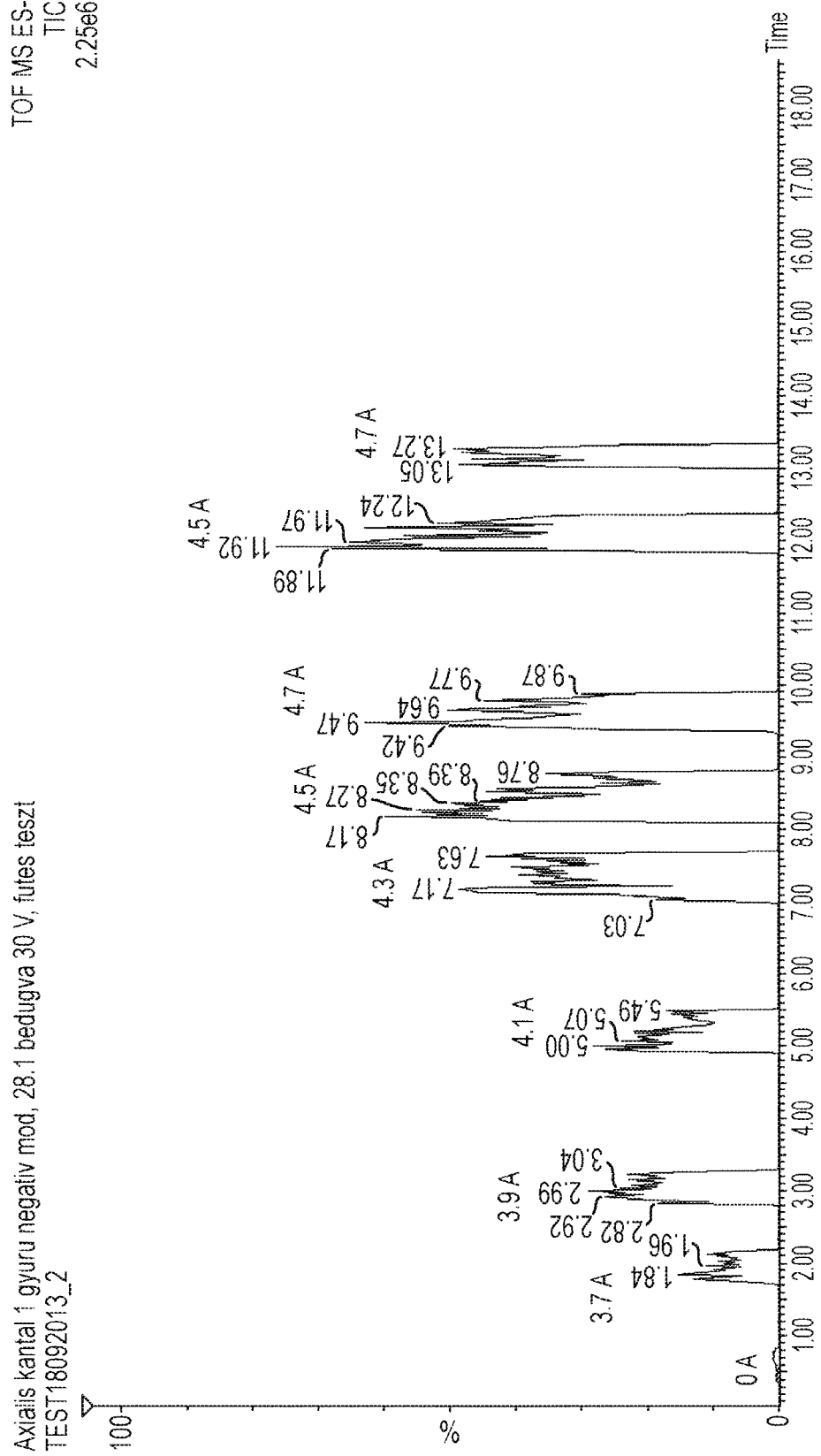
Figure 45A:
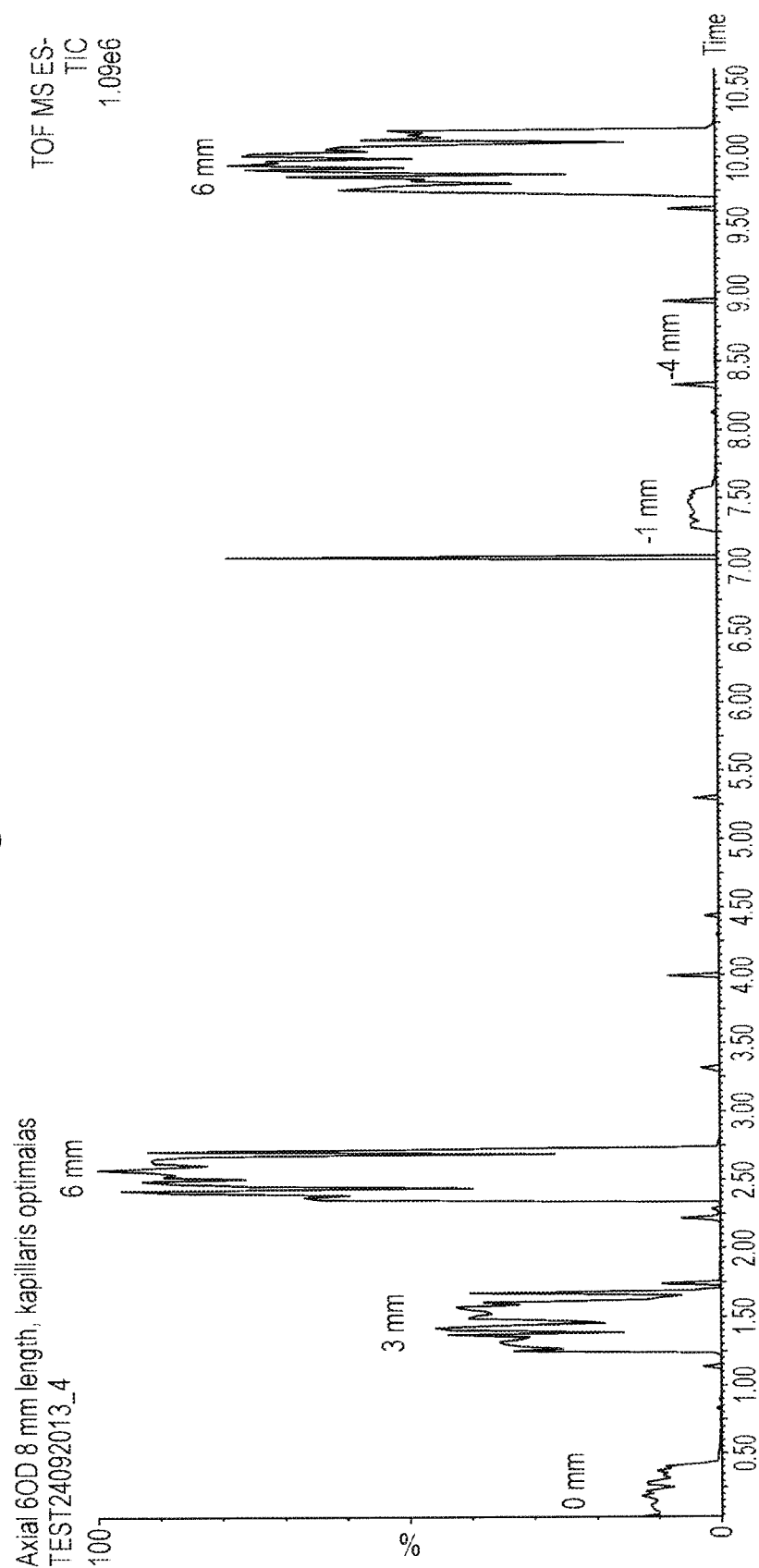
Figure 45B:
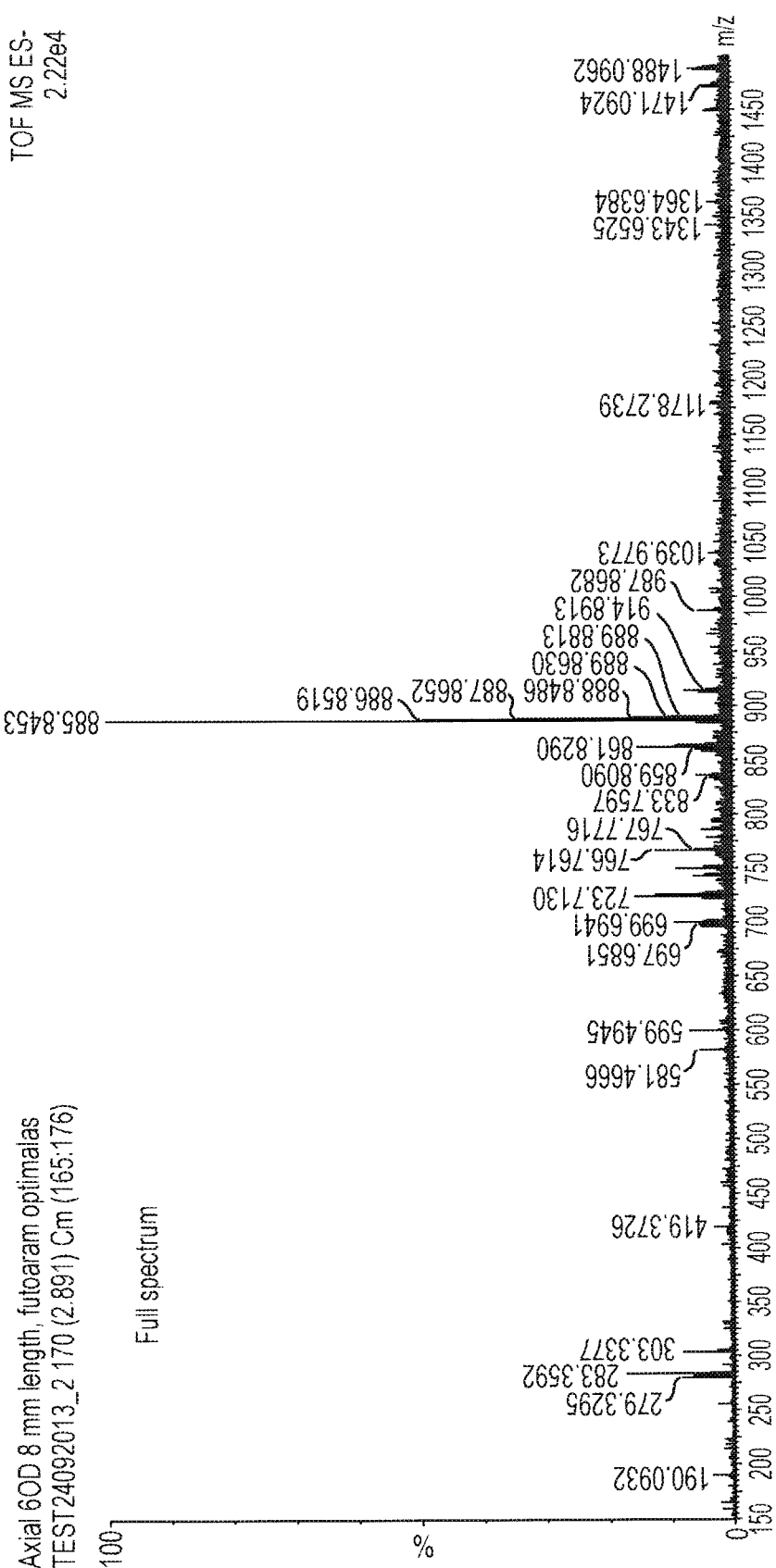
Figure 45D:
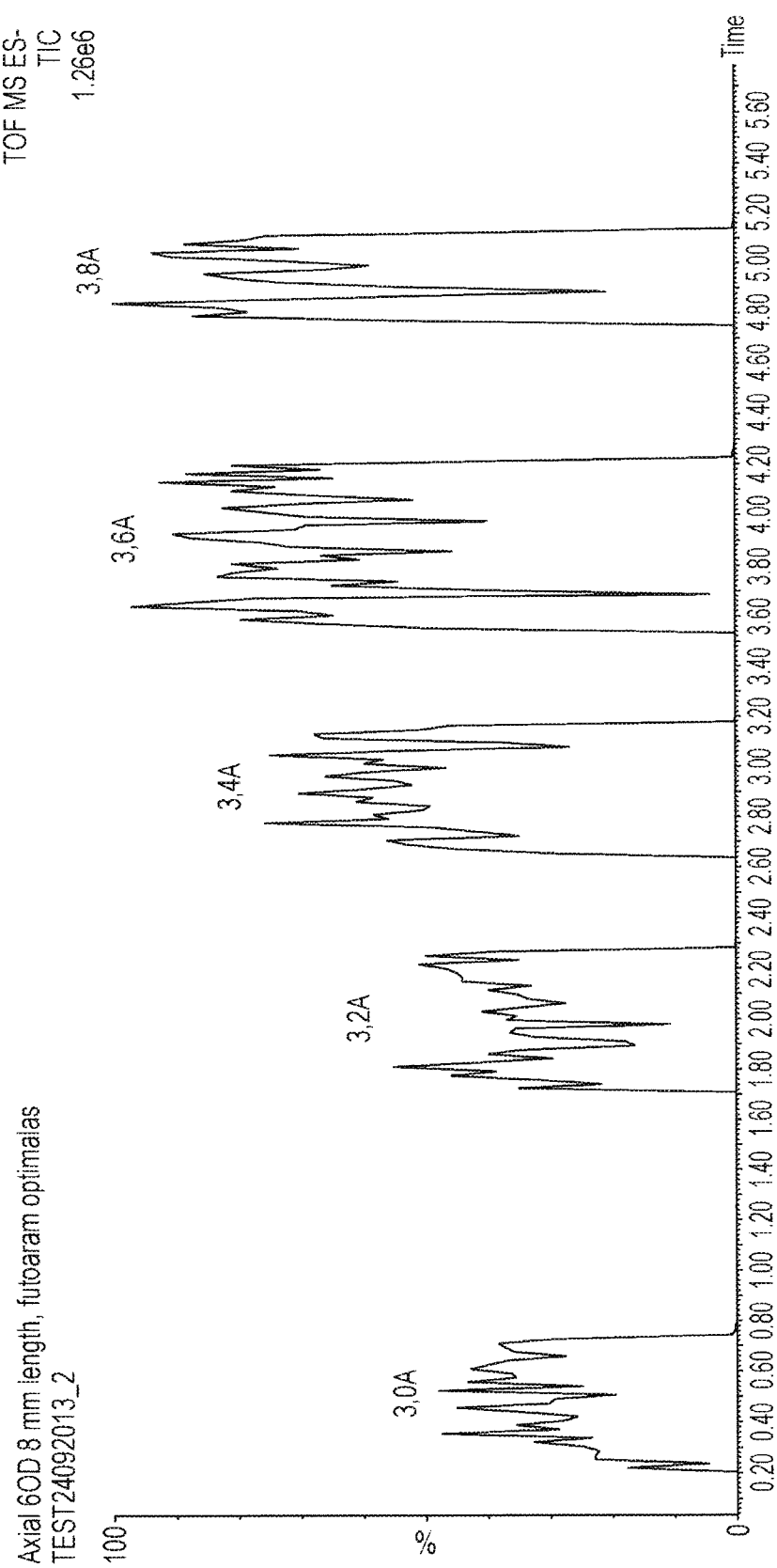
Figure 46A:
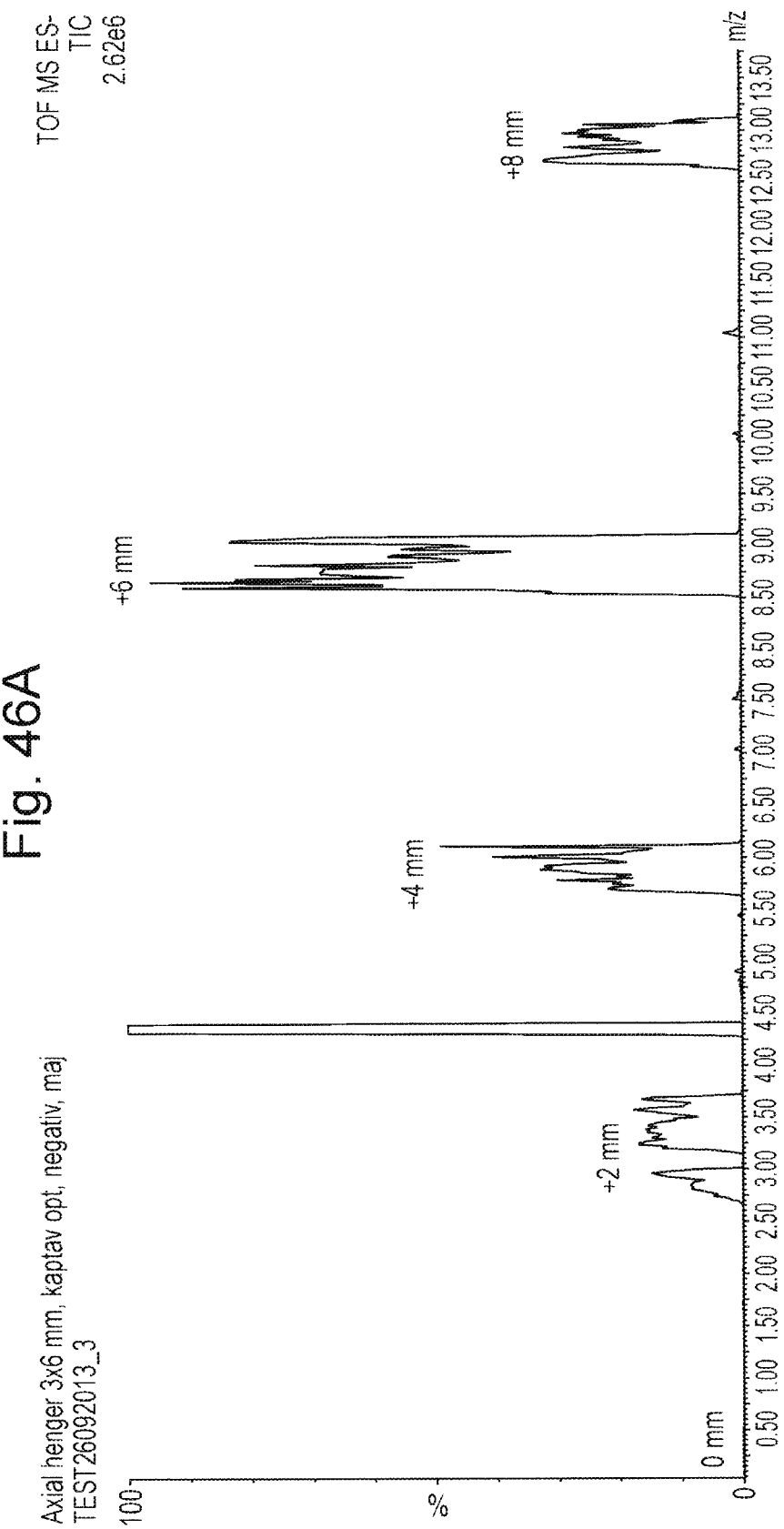
Figure 46B:
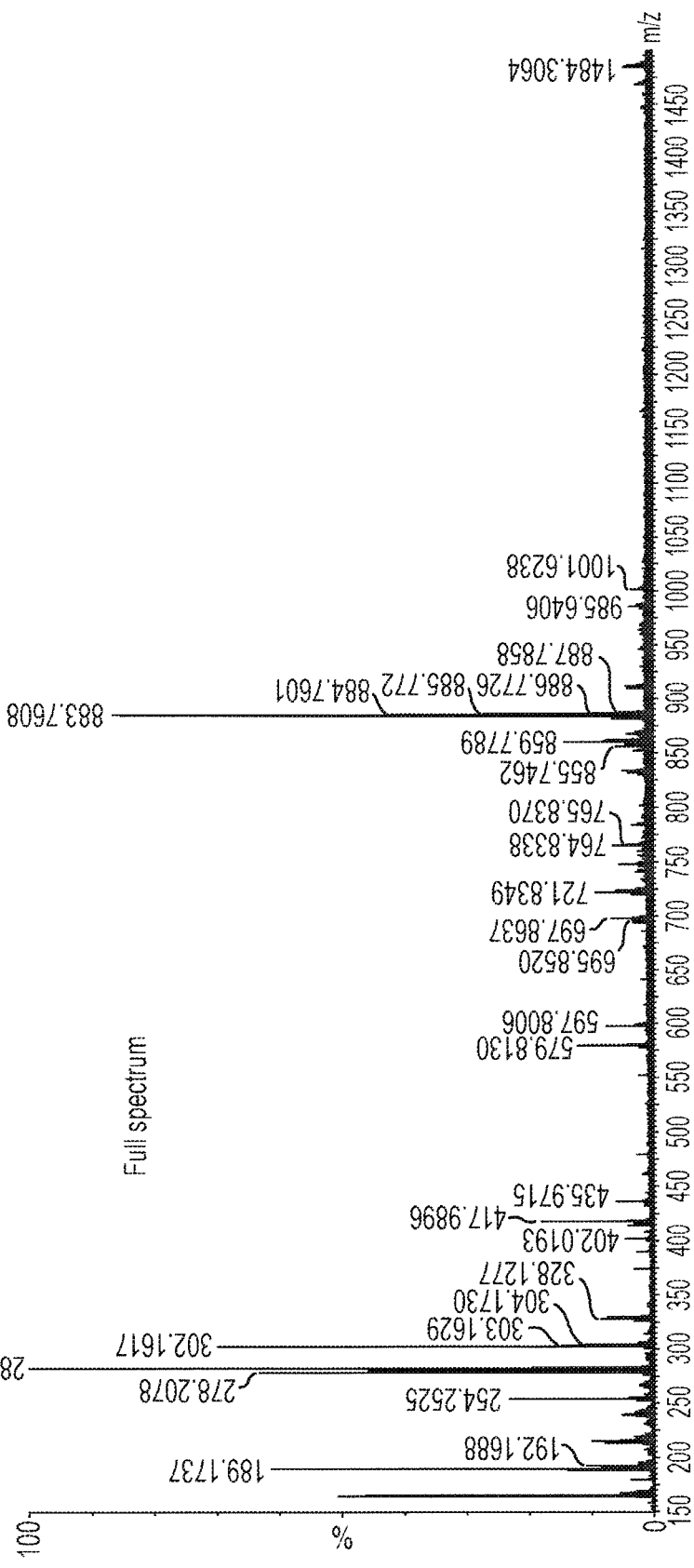
Figure 46C:
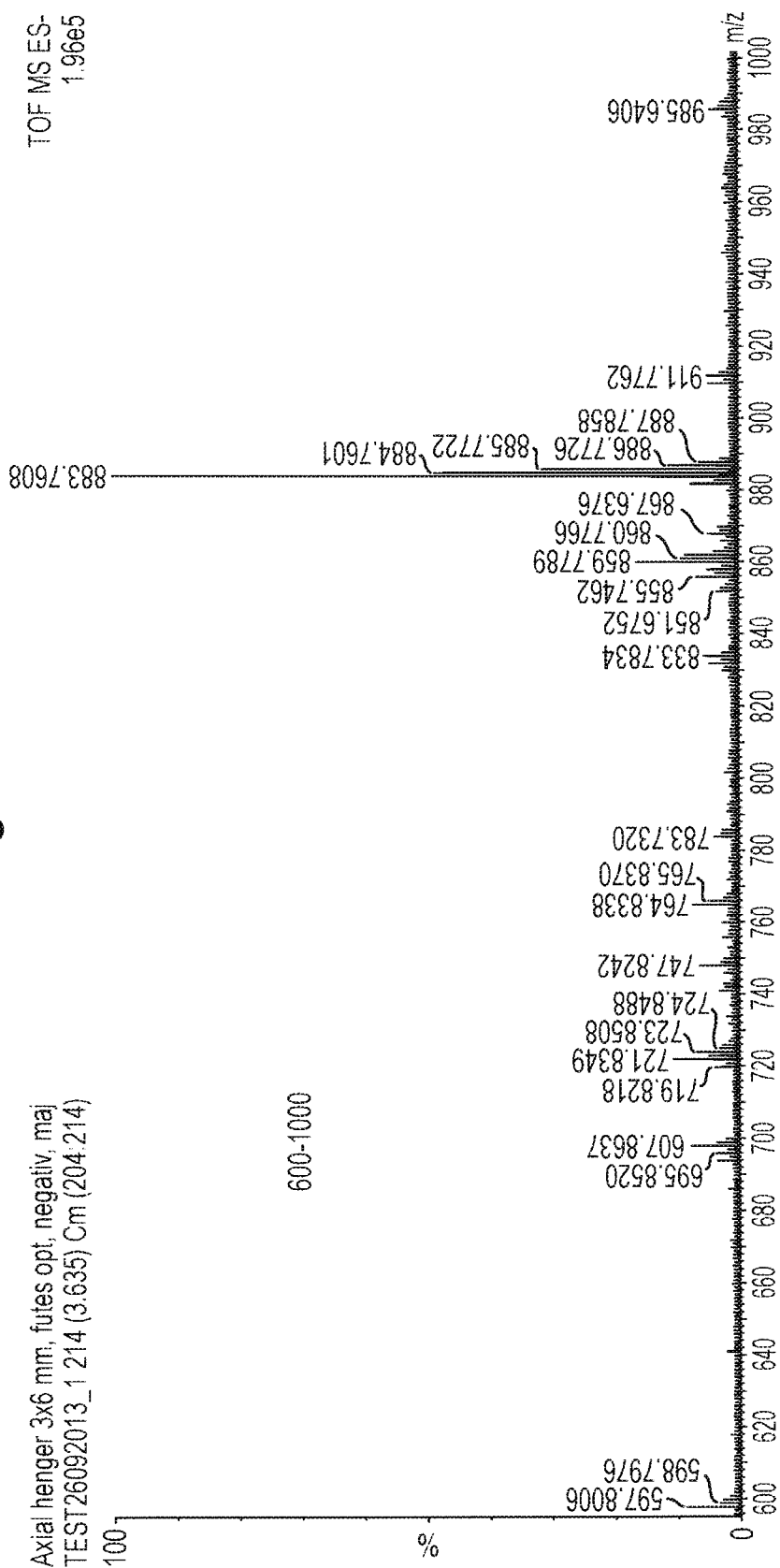
Figure 46D:
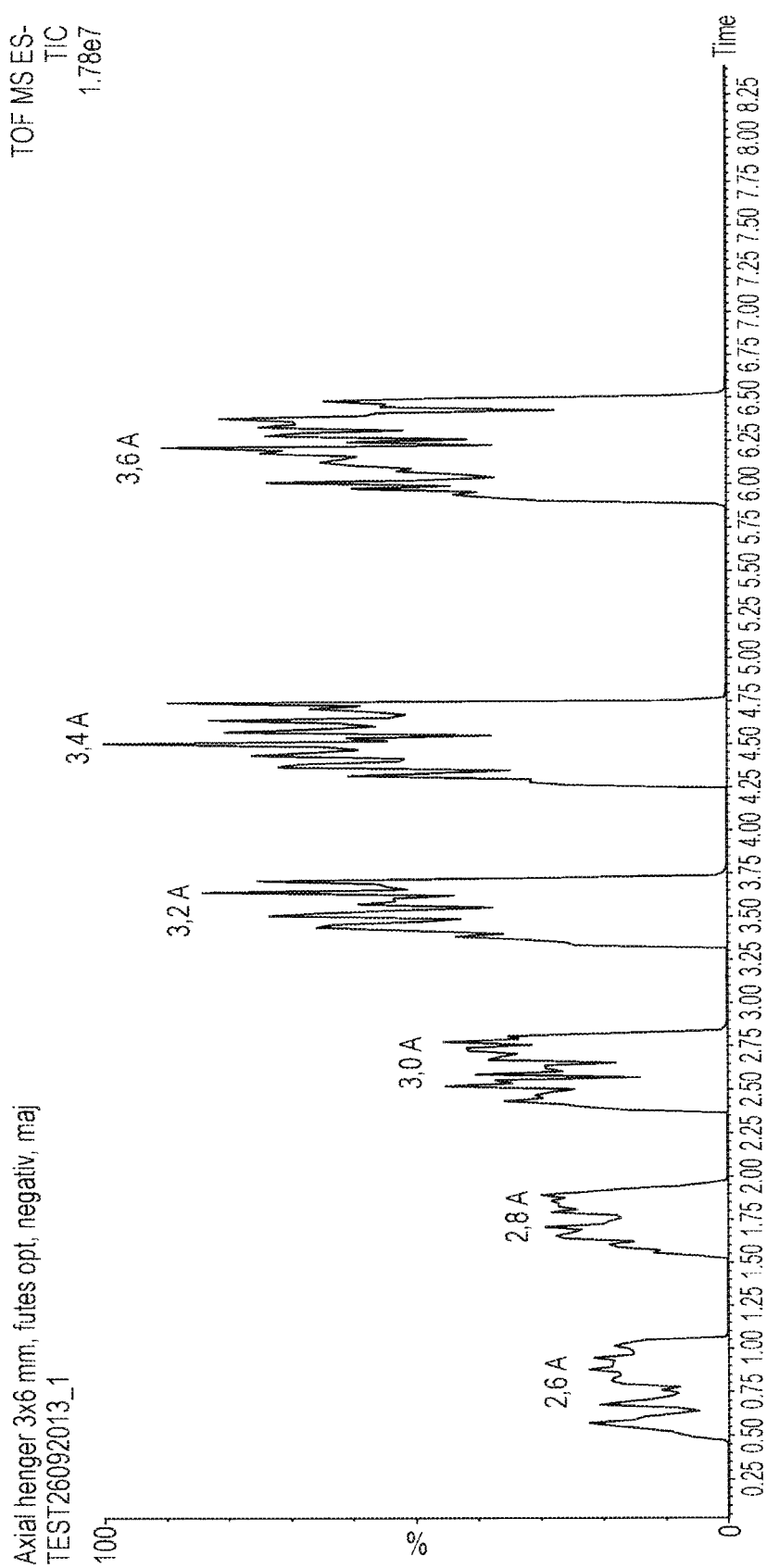
Figure 47A:
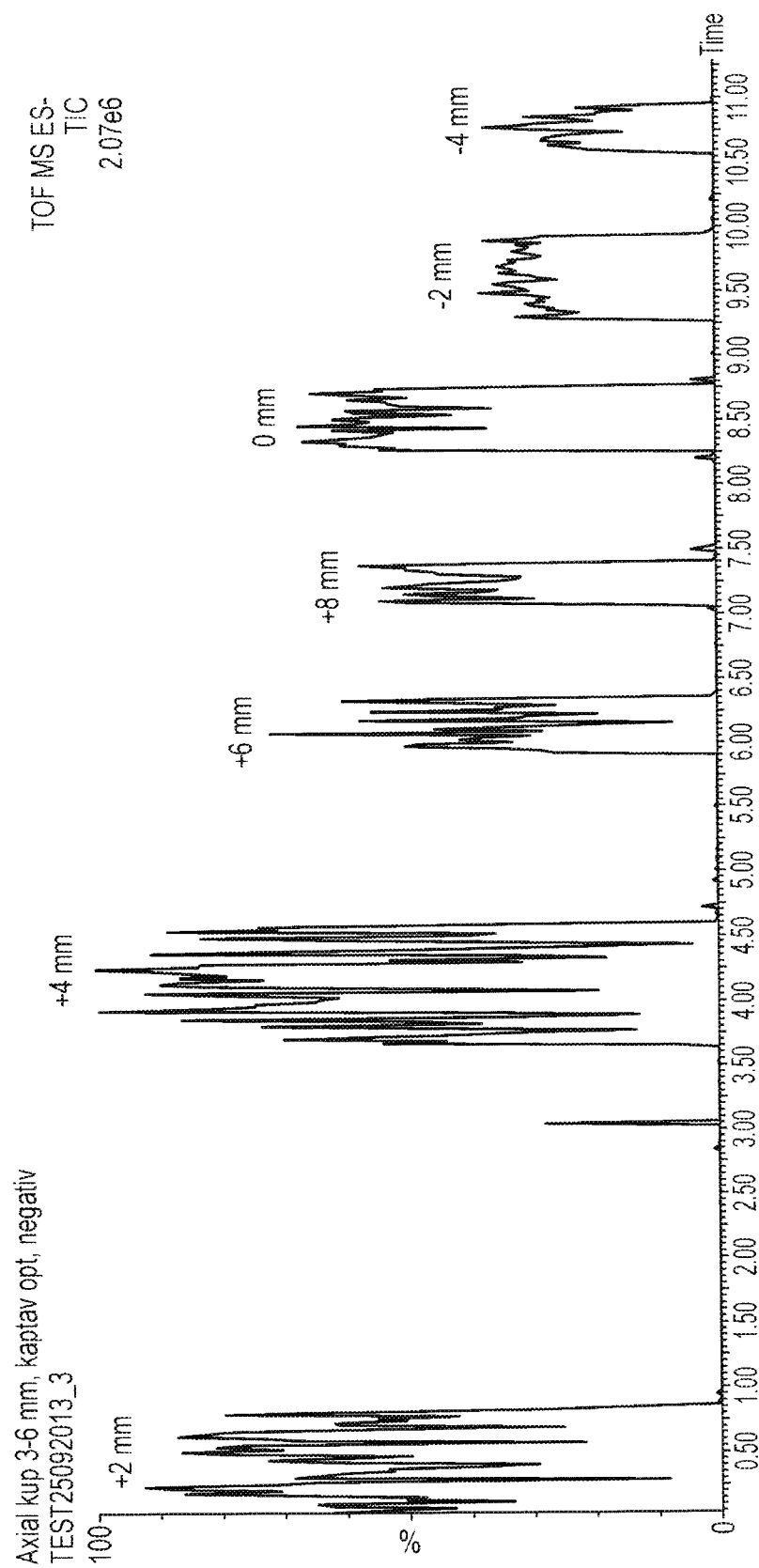
Figure 47C:
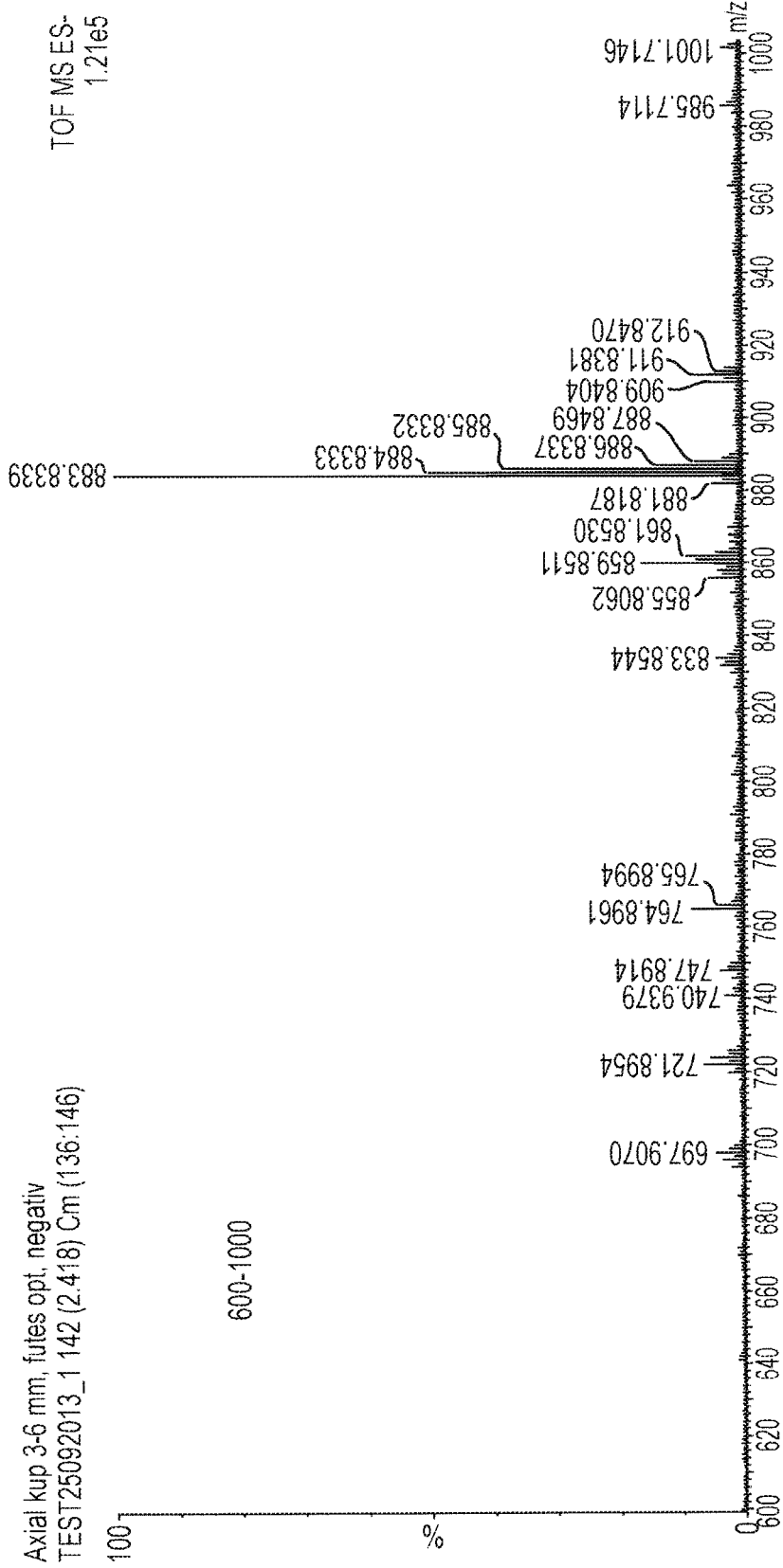
Figure 47D:
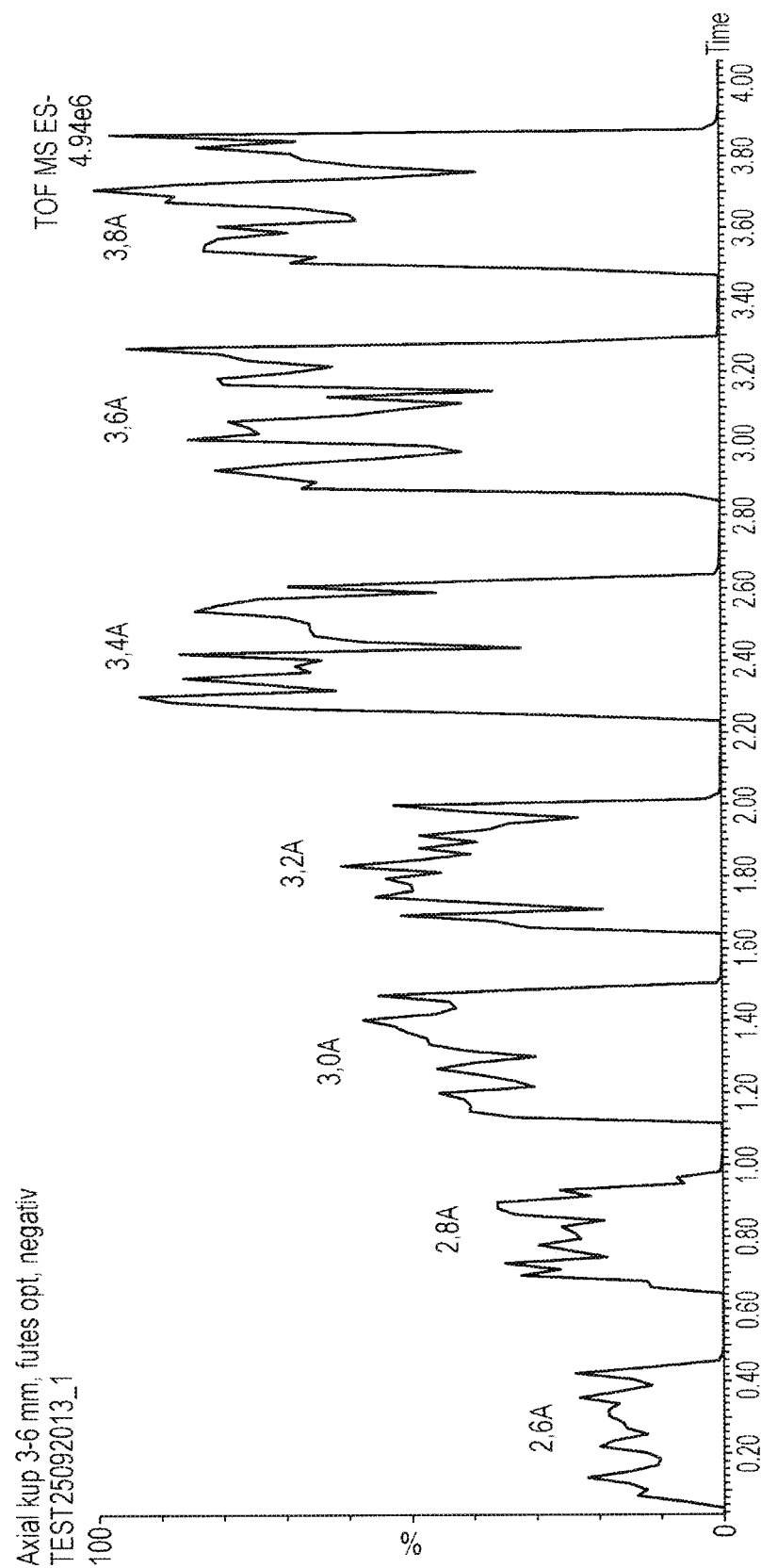
Figure 48:
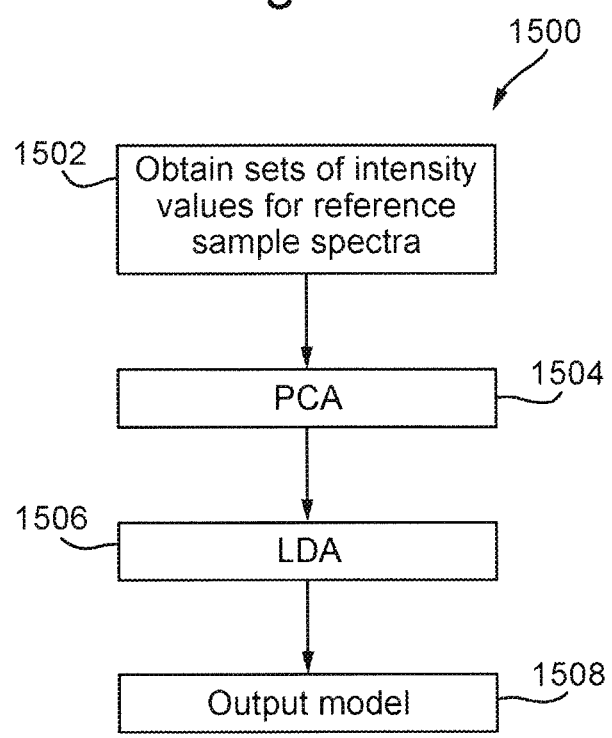
Figure 49:
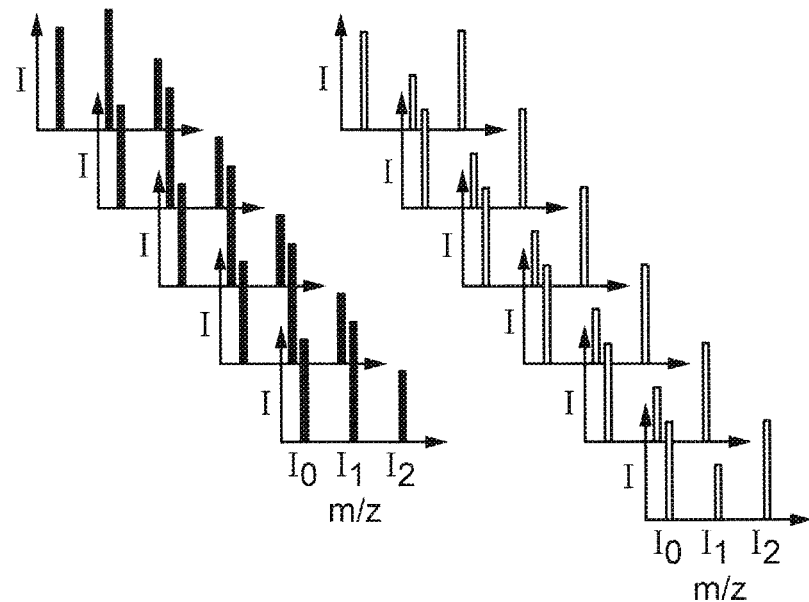
Figure 50:
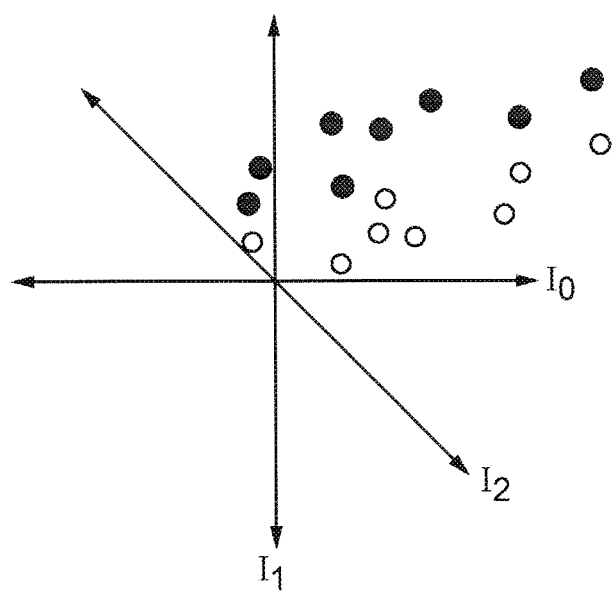
Figure 51:
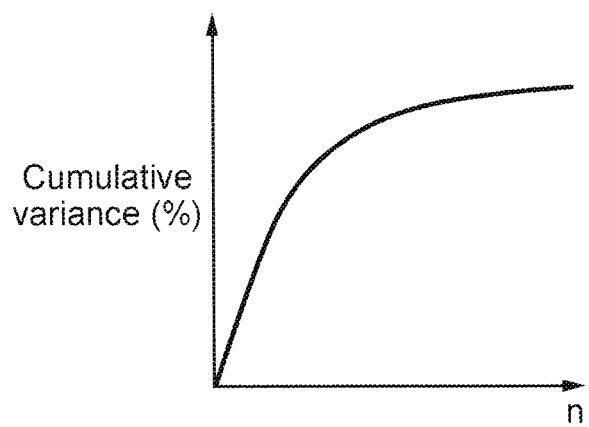
Figure 52:
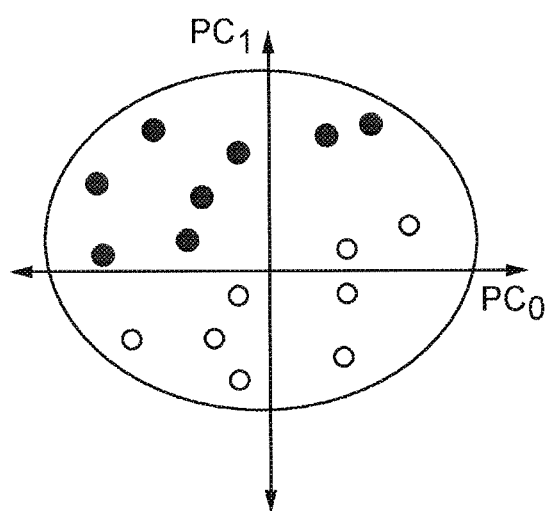
Figure 53:
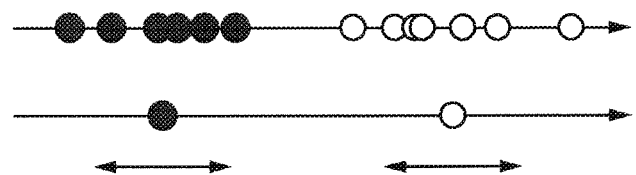

FIG. 38A shows the ion signals detected when analysing a sample using a Kathal-D coil collision surface whilst various different currents are used to heat the coil, FIG. 38B shows the ion signals detected when analysing a sample using a NiCrothal coil collision surface whilst different currents are used to heat the coil, and FIG. 38C shows the ion signals detected when analysing a sample using another coil collision surface whilst various different currents are used to heat the coil;

FIG. 39 shows another embodiment wherein the collision assembly comprises a Kathal coil coated in a substantially spherical ball having an aperture therein;

FIG. 40A shows another embodiment wherein the collision surface is the inner surface of a coil, FIG. 40B shows the ion signal measured using the collision assembly of FIG. 40A for various different locations of the sample capillary exit relative to the coil; and FIGS. 40C-40M show detailed spectra obtained using the collision assembly of FIG. 40A for the various different locations of the sample capillary exit relative to the coil;

FIG. 41A shows the total ion current obtained using the embodiment of FIG. 40A for different heater coil currents, and FIGS. 41B-41M show the spectra obtained at each coil current in FIG. 41A;

FIG. 42A shows the ion signal measured using another collision coil for various different locations of the sample capillary exit relative to the coil, FIGS. 42B-42G show detailed spectra obtained using the collision assembly for the various different locations, FIG. 42H shows the total ion current obtained for different heater coil currents, and FIGS. 42I-42O show the spectra obtained at each coil current in FIG. 42H;

FIG. 43A shows the ion signal measured using another collision coil for various different locations of the sample capillary exit relative to the coil, FIGS. 43B-43F show detailed spectra obtained for the various different locations, FIG. 43G shows the total ion current obtained for different heater coil currents, and FIGS. 43H-43L show the spectra obtained at each coil current in FIG. 43H;

FIG. 44A shows the ion signal measured using a tubular collision surface arranged coaxially with the sample capillary exit axis for various different locations of the capillary exit relative to the collision surface, FIGS. 44B and 44C show detailed spectra over different mass ranges using the collision assembly, and FIG. 44D shows the total ion current obtained for different heater coil currents;

FIG. 45A shows the ion signal measured using another tubular collision surface arranged coaxially with the sample capillary exit axis for various different locations of the capillary exit relative to the collision surface, FIG. 45B shows a full spectrum obtained using the collision assembly, FIG. 45C shows a detailed portion of the spectrum in FIG. 45B, and FIG. 45D shows the total ion current obtained for different heater coil currents;

FIG. 46A shows the ion signal measured using another tubular collision surface arranged coaxially with the capillary exit axis for various different locations of the sample capillary exit relative to the collision surface, FIG. 46B shows a full spectrum obtained using the collision assembly, FIG. 46C shows a detailed portion of the spectrum in FIG. 46B, and FIG. 46D shows the total ion current obtained for different heater coil currents;

FIG. 47A shows the ion signal measured using a conical collision surface arranged coaxially with the sample capillary exit axis for various different locations of the capillary exit relative to the collision surface, FIG. 47B shows a full spectrum obtained using the collision assembly, FIG. 47C shows a detailed portion of the spectrum in FIG. 47B, and FIG. 47D shows the total ion current obtained for different heater coil currents;

FIG. 48 shows a method of analysis that comprises building a classification model according to various embodiments;

FIG. 49 shows a set of reference sample spectra obtained from two classes of known reference samples;

FIG. 50 shows a multivariate space having three dimensions defined by intensity axes, wherein the multivariate space comprises plural reference points, each reference point corresponding to a set of three peak intensity values derived from a reference sample spectrum;

FIG. 51 shows a general relationship between cumulative variance and number of components of a PCA model;

FIG. 52 shows a PCA space having two dimensions defined by principal component axes, wherein the PCA space comprises plural transformed reference points or scores, each transformed reference point or score corresponding to a reference point of FIG. 50;

FIG. 53 shows a PCA-LDA space having a single dimension or axis, wherein the LDA is performed based on the PCA space of FIG. 52, the PCA-LDA space comprising plural further transformed reference points or class scores, each further transformed reference point or class score corresponding to a transformed reference point or score of FIG. 52.

Figure 54:
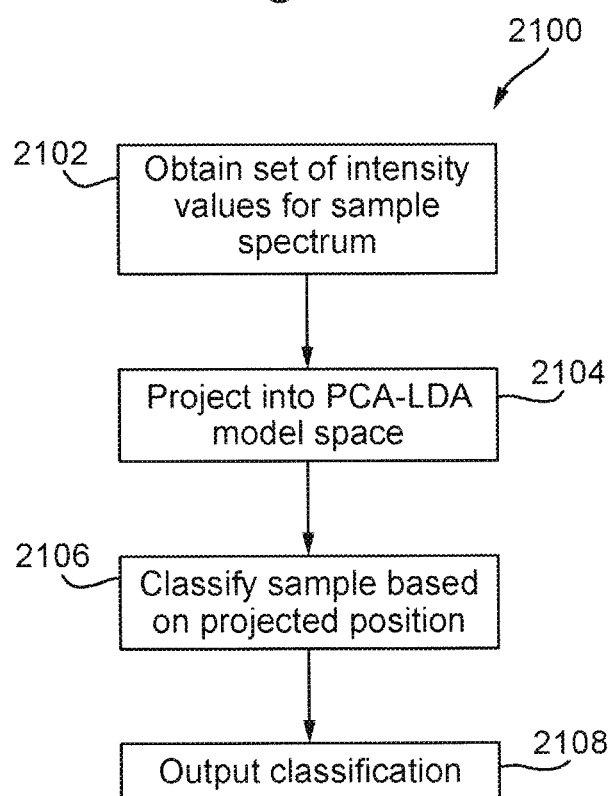
Figure 55:
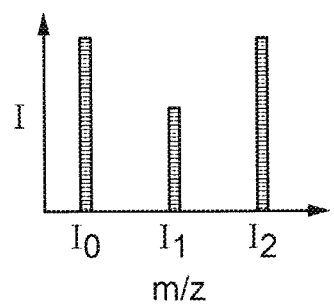
Figure 56:
Figure 57:
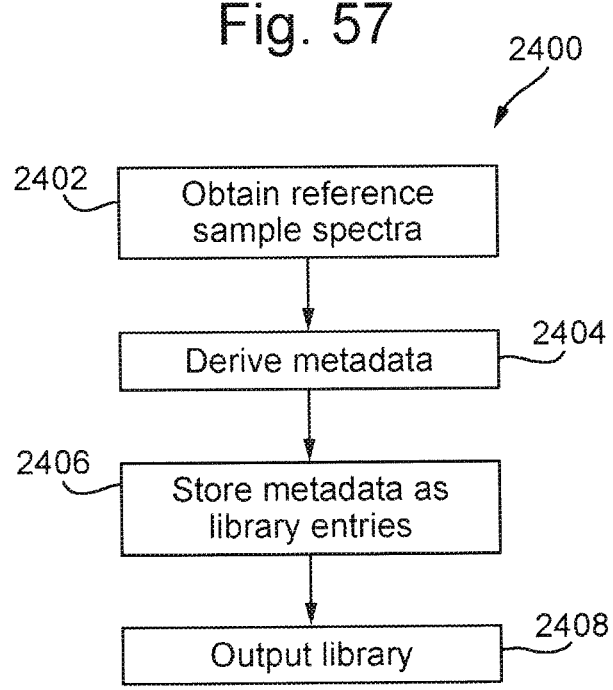
Figure 58:
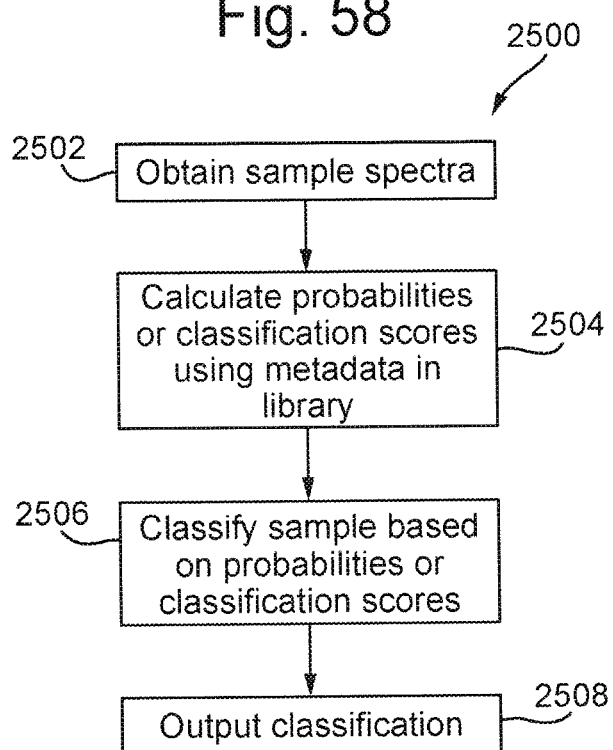

FIG. 54 shows a method of analysis that comprises using a classification model according to various embodiments;

FIG. 55 shows a sample spectrum obtained from an unknown sample;

FIG. 56 shows the PCA-LDA space of FIG. 53, wherein the PCA-LDA space further comprises a PCA-LDA projected sample point derived from the peak intensity values of the sample spectrum of FIG. 55;

FIG. 57 shows a method of analysis that comprises building a classification library according to various embodiments; and FIG. 58 shows a method of analysis that comprises using a classification library according to various embodiments.

DETAILED DESCRIPTION

Various embodiments will now be described in more detail below which in general relate to generating an aerosol, surgical smoke or vapour from one or more regions of a target (e.g., in vivo tissue) using an ambient ionisation ion source.

The aerosol, surgical smoke or vapour is then aspirated into a vacuum chamber of a mass and/or ion mobility spectrometer and is caused to impact upon a collision surface causing the aerosol, smoke or vapour to be ionised by impact ionisation which results in the generation of analyte ions.

The resulting analyte ions (or fragment or product ions derived from the analyte ions) are then mass and/or ion mobility analysed and the resulting mass and/or ion mobility spectrometric data may then be subjected to multivariate analysis in order to determine one or more properties of the target in real time.

For example, the multivariate analysis may enable a determination to be made as to whether or not a portion of tissue which is currently being resected is cancerous or not.

Ambient Ionisation Ion Sources

According to various embodiments a device is used to generate an aerosol, smoke or vapour from one or more regions of a target (e.g., in vivo tissue). The device may comprise an ambient ionisation ion source which is characterised by the ability to generate analyte aerosol, smoke or vapour, e.g., from a native or unmodified target. The aerosol, smoke or vapour may then be mixed with a matrix and aspirated into a vacuum chamber of a mass and/or ion mobility spectrometer. The mixture may be caused to impact upon a collision surface causing the aerosol, smoke or vapour to be ionised by impact ionisation which results in the generation of analyte ions. The resulting analyte ions (or fragment or product ions derived from the analyte ions) may then be mass and/or ion mobility analysed and the resulting mass and/or ion mobility spectrometric data may be subjected to multivariate analysis or other mathematical treatment in order to determine one or more properties of the target, e.g., in real time. For example, the multivariate analysis may enable a determination to be made as to whether or not a portion of tissue which is currently being resected is cancerous or not.

It will be apparent that the requirement to add a matrix or a reagent directly to a sample prevents the ability to perform in vivo analysis of tissue and also, more generally, prevents the ability to provide a rapid simple analysis of target material.

In contrast, therefore, ambient ionisation techniques are particularly advantageous since firstly they do not require the addition of a matrix or a reagent (and hence are suitable for the analysis of in vivo tissue) and since secondly they enable a rapid simple analysis of target material to be performed. For example, other types of ionisation ion sources such as Matrix Assisted Laser Desorption Ionisation ("MALDI") ion sources require a matrix or reagent to be added to the sample prior to ionisation.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular advantage of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
| --- | --- |
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Airflow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |

| Acronym | Ionisation technique |
| --- | --- |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a CO2 laser having a wavelength of 10.6 µm may be used to generate the aerosol, smoke or vapour.

The laser ionisation ion source may emit radiation at a wavelength that is not close to the high absorption coefficient of water, i.e. at a wavelength that is non-resonant with water. Such lasers may still generate the smoke, aerosol or vapour from the target for analysis, although may cause less damage to the target than a laser wavelength that is resonant with water. For example, the non-resonant laser may only ablate the surface layer(s) of the target.

According to other embodiments the ambient ionisation ion source may comprise an ultrasonic ablation ion source, or a hybrid electrosurgical-ultrasonic ablation source, that generates a liquid sample which is then aspirated as an aerosol. The ultrasonic ablation ion source may comprise a focused or unfocussed ultrasound.

According to an embodiment the first device for generating aerosol, smoke or vapour from one or more regions of a target may comprise a tool which utilises an RF voltage, such as a continuous RF waveform. According to other embodiments a radiofrequency tissue dissection system may be used which is arranged to supply pulsed plasma RF energy to a tool. The tool may comprise, for example, a Plasma Blade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode. According to an embodiment the first device comprises a surgical water/saline jet device such as a resection device, a hybrid of such device with any of the other devices herein, an electrosurgery argon plasma coagulation device, a hybrid argon plasma coagulation and water/saline jet device.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

Rapid Evaporative Ionisation Mass Spectrometry ("REIMS")

Figure 1:
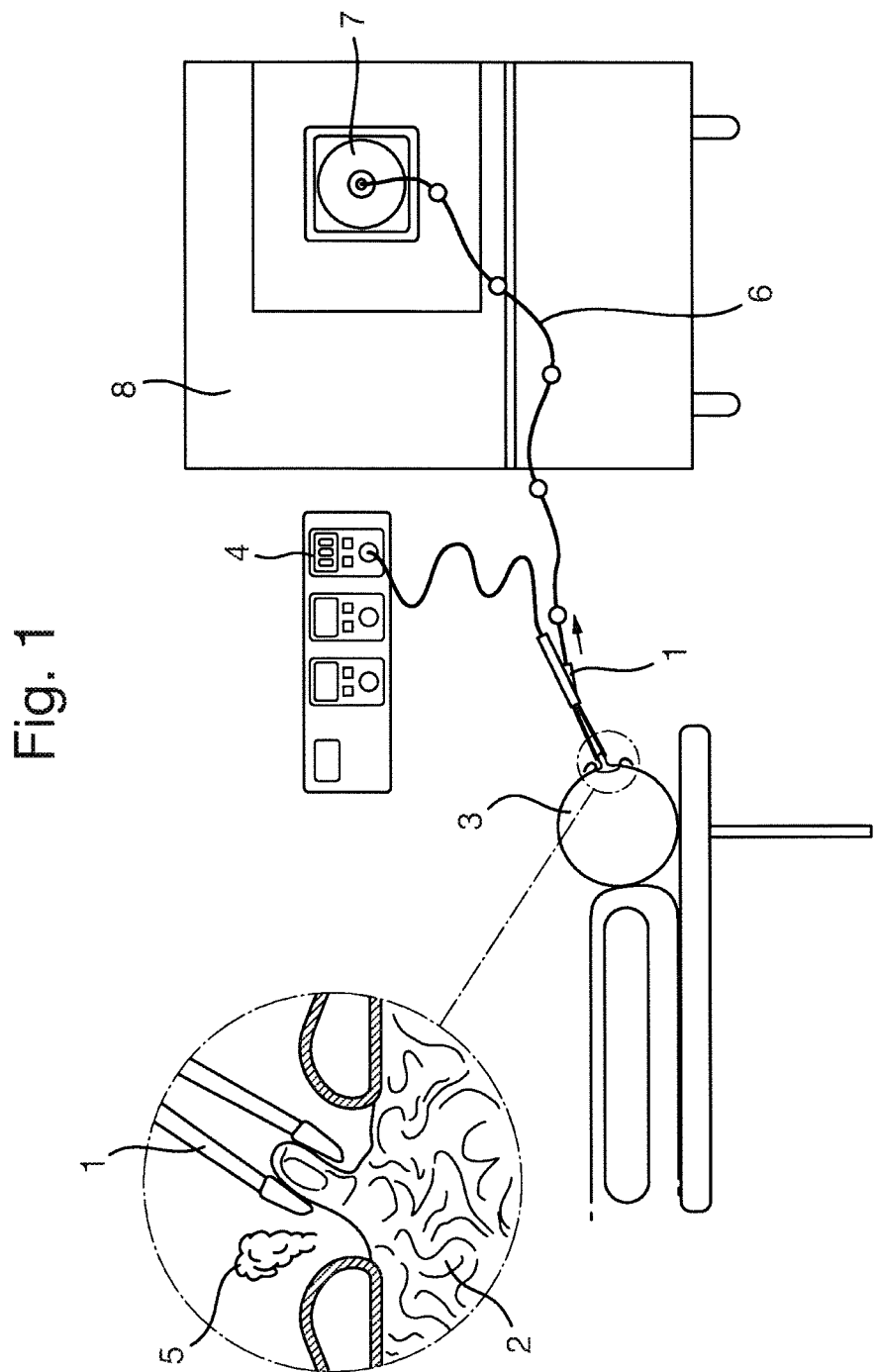

FIG. 1 illustrates a method of rapid evaporative ionisation mass spectrometry ("REIMS") wherein bipolar forceps 1 may be brought into contact with in vivo tissue 2 of a patient 3. In the example shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of a mass spectrometer 8.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass spectrometer 8. According to one embodiment the collision surface may be heated. The aerosol is caused to ionise upon impacting the collision surface resulting in the generation of analyte ions. The ionisation efficiency of generating the analyte ions may be improved by the addition of the organic solvent.

However, the addition of an organic solvent is not essential.

Analyte ions which are generated by causing the aerosol, smoke or vapour 5 to impact upon the collision surface are then passed through subsequent stages of the mass spectrometer and are subjected to mass analysis in a mass analyser. The mass analyser may, for example, comprise a quadrupole mass analyser or a Time of Flight mass analyser.

Figure 2:
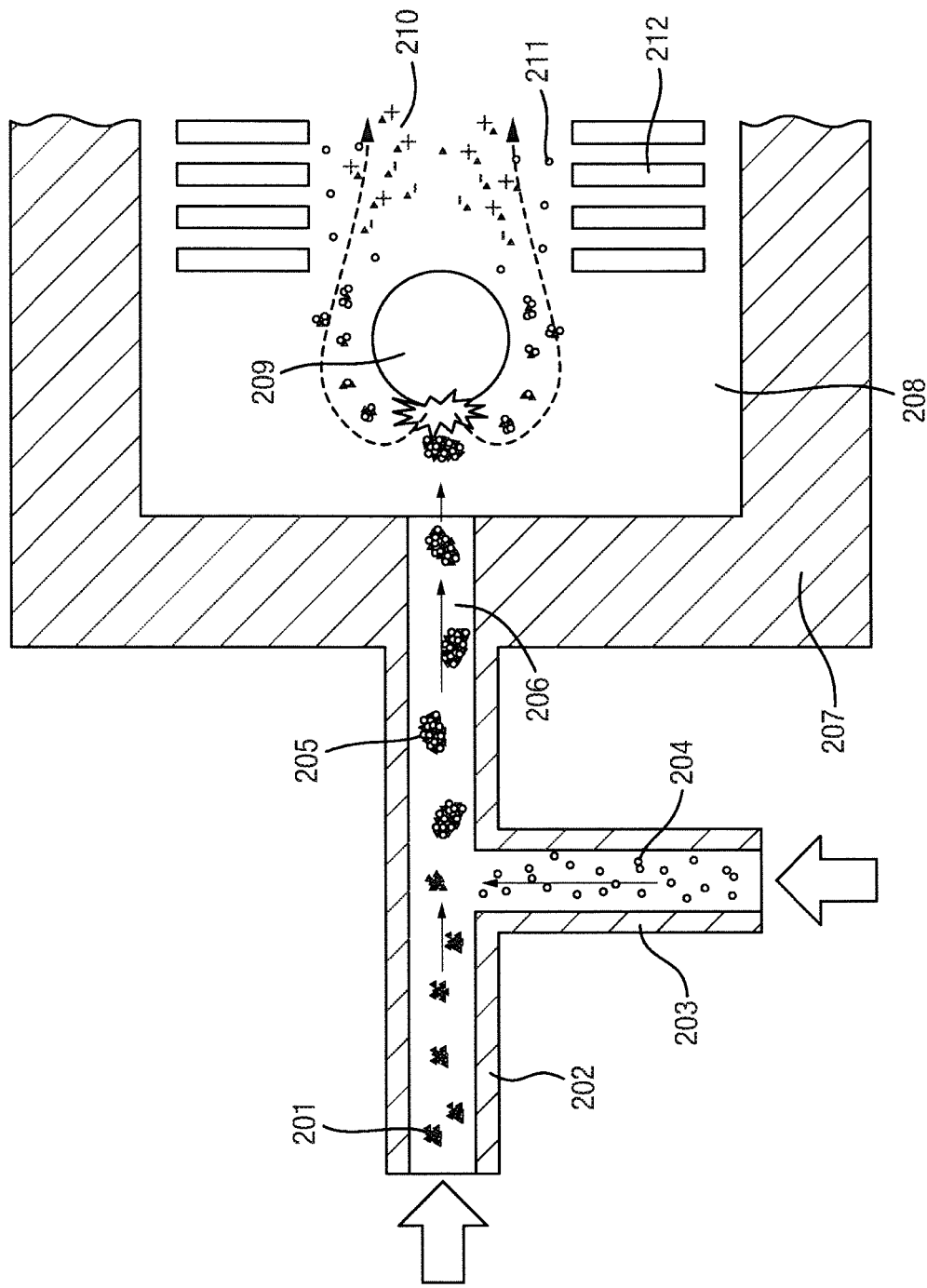

FIG. 2 shows a schematic of an embodiment, e.g., that may be used to analyse the aerosol, surgical smoke or vapour generated from the target. The device may comprise an ion analyser or mass spectrometer 207 having an inlet 206, a vacuum region 208, a solid collision surface 209 and ion optics 212 such as a Stepwave® ion guide arranged within the vacuum region 208. The device also may include a sample transfer tube 202 and a matrix introduction conduit 203. The sample transfer tube 202 has an inlet for receiving the aerosol sample 201 (which may correspond to the surgical smoke, vapour or aerosol described in relation to FIG. 1) from a sample being investigated and an outlet that is connected to the inlet 206 of the ion analyser 207. The matrix introduction conduit 203 has an inlet for receiving a matrix compound and an outlet that intersects with the sample transfer tube 202 so as to allow the matrix 204 to be intermixed with the aerosol sample 201 in the sample transfer tube 202.

A method of operating the device of FIG. 2 will now be described. A sample, such as a biological sample, is subjected to the REIMS technique. For example, a diathermic device may be used to evaporate biological tissue from the sample so as to form an aerosol, e.g., as described above in relation to FIG. 1. The aerosol particles 201 are then introduced into the inlet of the sample transfer tube 202. A matrix compound 204 is introduced into the inlet of the matrix introduction conduit 203. The aerosol particles 201 and matrix compound 204 are drawn towards the inlet 206 of the ion analyser 207 by a pressure differential caused by the vacuum chamber 208 being at a lower pressure than the inlets to the tubes 202, 203. The aerosol particles 201 may encounter the molecules of matrix compound 204 in, and downstream of, the region that the sample transfer tube 202 intersects with the matrix introduction conduit 203. The aerosol particles 201 intermix with the matrix 204 so as to form aerosol particles containing matrix molecules 205, in which both the molecular constituents of the aerosol sample 201 and the matrix compound 204 are present. The matrix molecules 204 may be in excess compared to the molecular constituents of aerosol sample 201.

The particles 205 may exit the sample transfer tube 202 and pass into the inlet 206 of the ion analyser 207. The particles 205 then enter into the decreased pressure region 208 and gain substantial linear velocity due to the adiabatic expansion of gas entering the vacuum region 208 from the sample transfer tube 202 and due to the associated free jet formation. The accelerated particles 205 may impact on a solid collision surface 209, where the impact event fragments the particles 205, leading to the eventual formation of gas phase ions 210 of the molecular constituents of the aerosol sample 201 and the formation of matrix molecules 211. The solid collision surface 209 may be controlled and maintained at a temperature that is substantially higher than the ambient temperature.

The matrix 204 includes a solvent for the analyte 201, such that the analyte 201 dissolves by the matrix 204, thereby eliminating intermolecular bonding between the analyte molecules 201. As such, when the dissolved analyte 205 is then collided with the collision surface 209, the dissolved analyte 205 will fragment into droplets and any given droplet is likely to contain fewer analyte molecules than it would if the matrix were not present. This in turn leads to a more efficient generation of analyte ions 210 when the matrix in each droplet is evaporated. The matrix may include an organic solvent and/or a volatile compound. The matrix may include polar molecules, water, one or more alcohols, methanol, ethanol, isopropanol, acetone or acetonitrile. Isopropanol is of particular interest.

The matrix molecules 211 may freely diffuse into the vacuum. In contrast, the gas phase ions 210 of the molecular constituents of the aerosol sample 201 may be transferred by the ion optics 212 to an analysis region (not shown) of the ion analyser 207. The ions 210 may be guided to the analysis region by applying voltages to the ion optics 212. The ions may then be analysed by the ion analyser 207, which may comprise a mass spectrometer or an ion mobility spectrometer, or a combination of the two. As a result of the analysis, chemical information about the sample 201 may be obtained.

Figure 3:
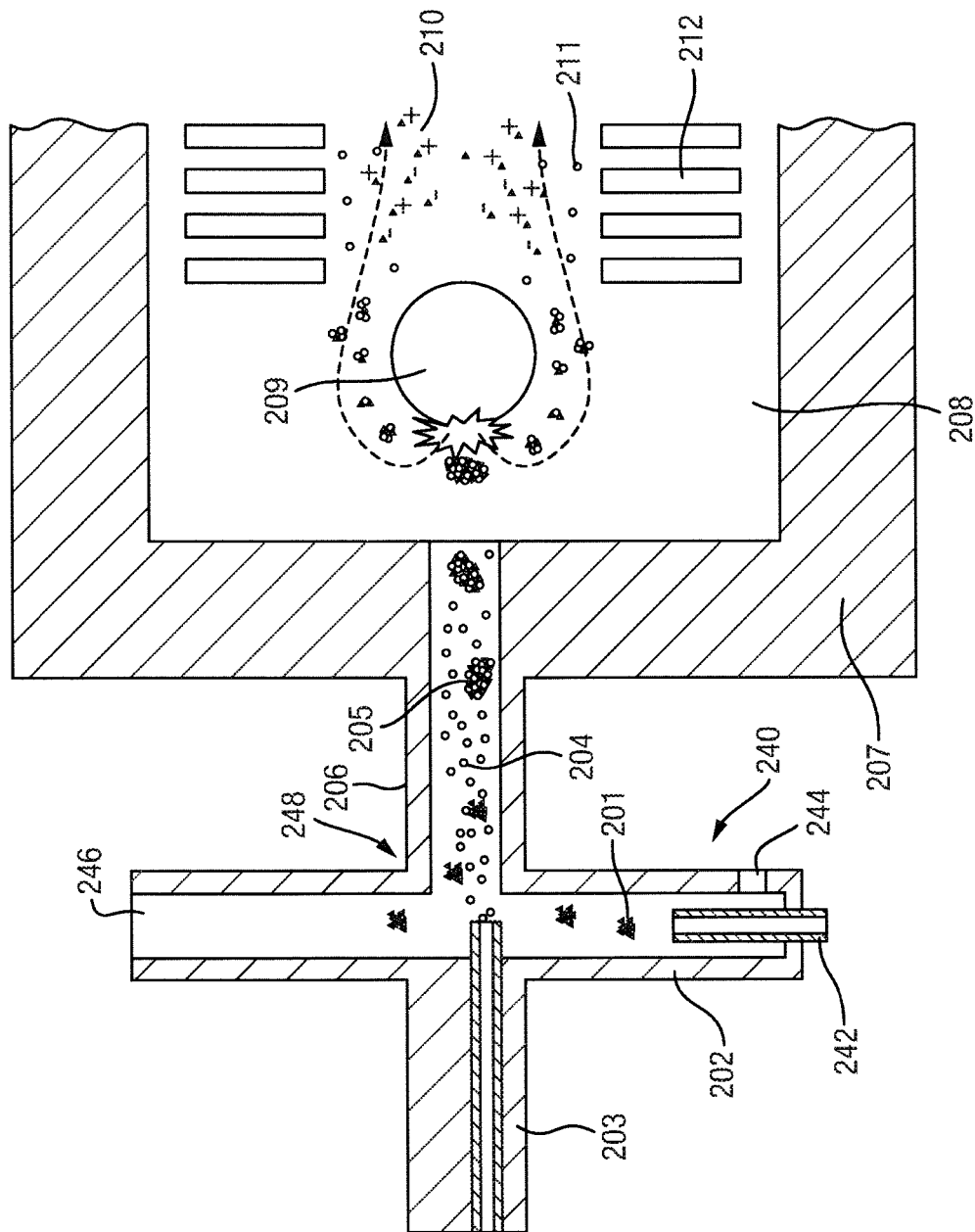

Although FIG. 2 shows the sample transfer tube 202 coaxial with the inlet 206, it is contemplated that alternatively the matrix introduction conduit 203 may be coaxial with the inlet 206 and that the sample transfer tube 202 may be orthogonal to the inlet 206. FIG. 3 shows a schematic of an embodiment that is substantially similar to that shown and described in relation to FIG. 2, except that the sample 201 is delivered by a fluid/liquid transfer pump or a Venturi pump 240 and the matrix 204 may be delivered in liquid form. This allows the matrix compound 204 to be mixed into the aerosol 201 as a vapour, or as a liquid, prior to introduction into the ion analyser 207.

The Venturi pump 240 may comprise an inlet tube 242 that may be connected to a device or probe (e.g., a REIMS device or probe as described herein) and may be configured to transport aerosol particles or liquid from a sample (e.g., biologic tissue) to the Venturi pump 240.

The Venturi pump may comprise a gas inlet 244 that may be arranged and adapted to introduce a gas (e.g., nitrogen or standard medical air) into the flow path of the aerosol particles 201 or liquid being transported into the Venturi pump 240 by the inlet tube 242. The Venturi pump 240 may therefore facilitate the aspiration of aerosol particles 201 or other gaseous sample containing the analyte. The Venturi pump also comprises an exhaust 246 for exhausting the Venturi gas from the system such that it is not directed into the vacuum chamber 208 of the spectrometer 207.

The Venturi pump 240 may comprise a sample transfer portion or capillary 202 that may be arranged and adapted to direct the sample and gas mixture produced by the Venturi pump 240 towards a junction 248. A matrix introduction conduit 203 is arranged and adapted to introduce matrix or a matrix compound 204 into the junction 248 and direct the flow of the matrix compound 204 towards an inlet tube 206.

The aerosol particles 201 and the matrix 204 may intermix at the junction 248 and the resulting aerosol particles 205 may be carried into the inlet tube 206 by the suction from the vacuum chamber 208. The larger aerosol particles 201 may be too heavy to be carried into the inlet tube 206 and may travel past the junction 248 and leave the apparatus via the exhaust 246.

Whilst shown as contiguous in FIG. 3, the sample transfer portion 202 may be a separate component from the junction 248 and inlet tube 206. The junction 248 may comprise a connector or connecting portion (not shown) for connecting to a separate sample transfer portion 202. The connection between the junction 248 and the sample transfer portion 206 may be fluidly sealed and/or may comprise a ring clamp.

As described hereinabove, an important aspect is the formation of molecular clusters 205 containing the original analyte aerosol constituents 201 and the matrix compound 204, followed by the surface-induced dissociation of these clusters 205.

Figure 4A:
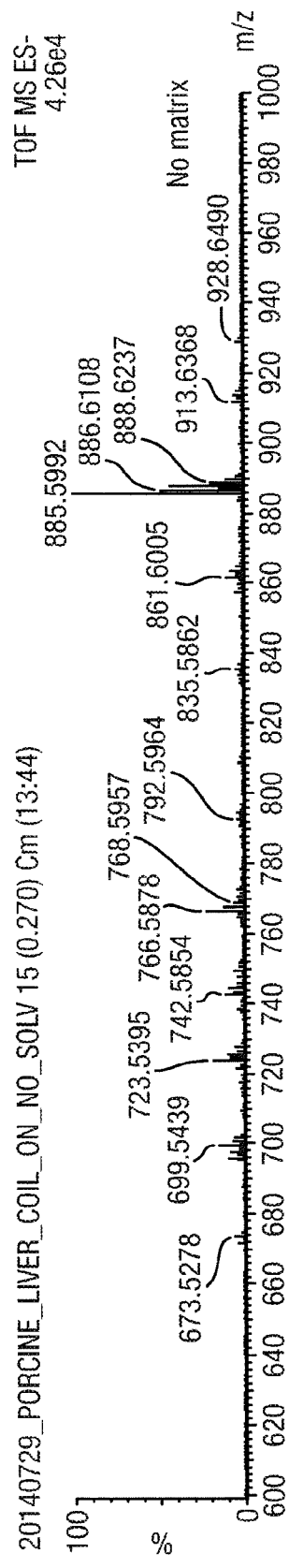
Figure 4B:
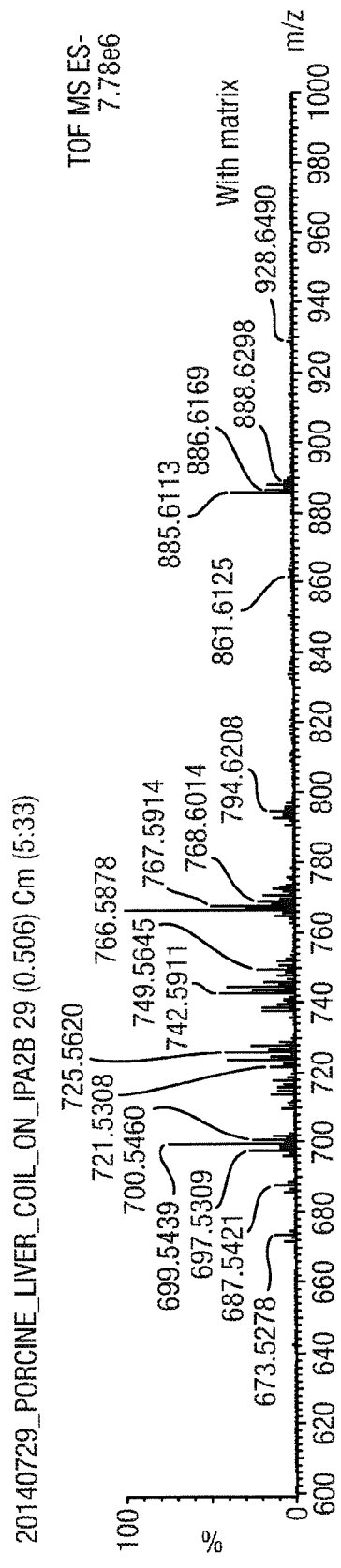

The benefit of using a matrix can be seen from FIG. 4A and FIG. 4B.

FIG. 4A shows a mass spectrum obtained by subjecting a sample to a REIMS technique in which an aerosol was generated from a target, the aerosol was collided with a heated collision surface and the resulting ions generated therefrom were mass analysed. The mass spectrum in FIG. 4B was obtained by subjecting the same sample to the same analysis technique except that the aerosol was mixed with a matrix (isopropanol) before being collided with the collision surface and then mass analysed. It can be seen from the two mass spectra in FIGS. 4A and 4B that the use of a matrix substantially increases the intensity of ions detected.

Figure 5A:
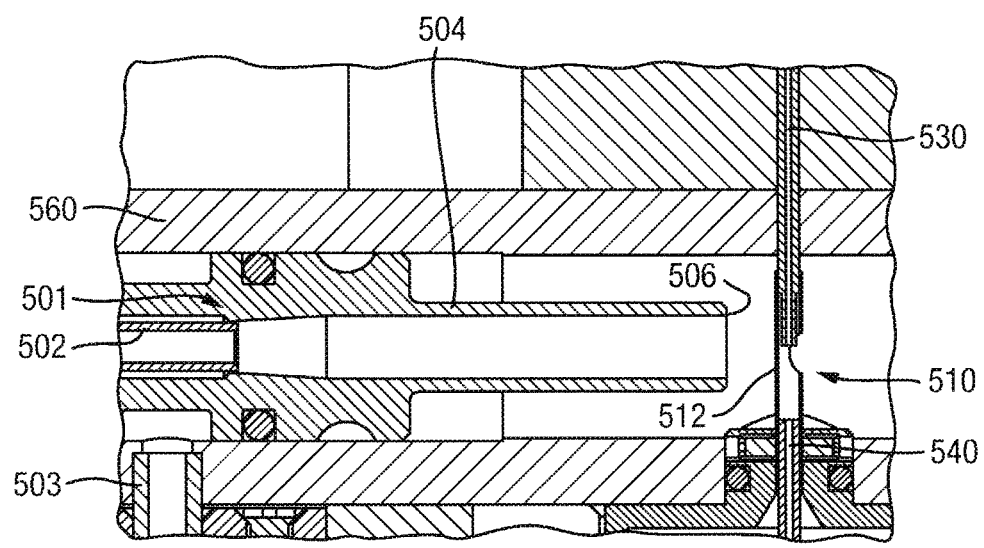

FIG. 5A shows another embodiment of a mass spectrometer interface for introducing the analyte aerosol and matrix into the mass spectrometer. The instrument comprises a Venturi pump 501. The Venturi pump 501 comprises a tube 502 that may be connected to a device or probe (e.g., a REIMS device or probe as described herein) and may be configured to transport aerosol particles from a sample (e.g., biologic tissue) to the Venturi pump 501. The Venturi pump 501 may comprise a gas inlet 503 that may be arranged and adapted to introduce a gas (e.g., a Venturi gas) into the flow path of the aerosol particles being transported into the Venturi pump 501 by the tube 502. The Venturi pump 501 may comprise an elongated sample transfer tube 504 that may be arranged and adapted to transfer the sample and gas mixture from the tube 502 onto a sampling device 510 via an outlet end 506 of the sample transfer tube 504.

The sampling device 510 may broadly comprise a hollow tube or whistle 512, a matrix introduction conduit 530 and an inlet tube 540. The matrix introduction conduit 530 may be arranged and adapted to introduce a matrix in liquid or gas form through a channel 534 (FIG. 5B) within the matrix introduction conduit 530. Matrix leaves the matrix introduction conduit 530 through an end 534 disposed or located within the whistle 512 and it may be nebulised by a gas that is being drawn into the inlet tube 540. The quality of nebulisation of the matrix may be controlled and affected by the dimensions and/or relative distances between the various parts of the sampling device 510, as described in more detail below.

The inlet tube 540 leads to an inlet of a ion analyser or mass spectrometer and may be arranged and adapted such that a mixture of sample, gas and matrix passes through an end 542 of the inlet tube 540 disposed or located within the whistle 512 and through a passage 544 to be transferred into a ion analyser or mass spectrometer. In these arrangement the collision surface 209 is arranged downstream of the inlet tube 540.

Figure 5B:
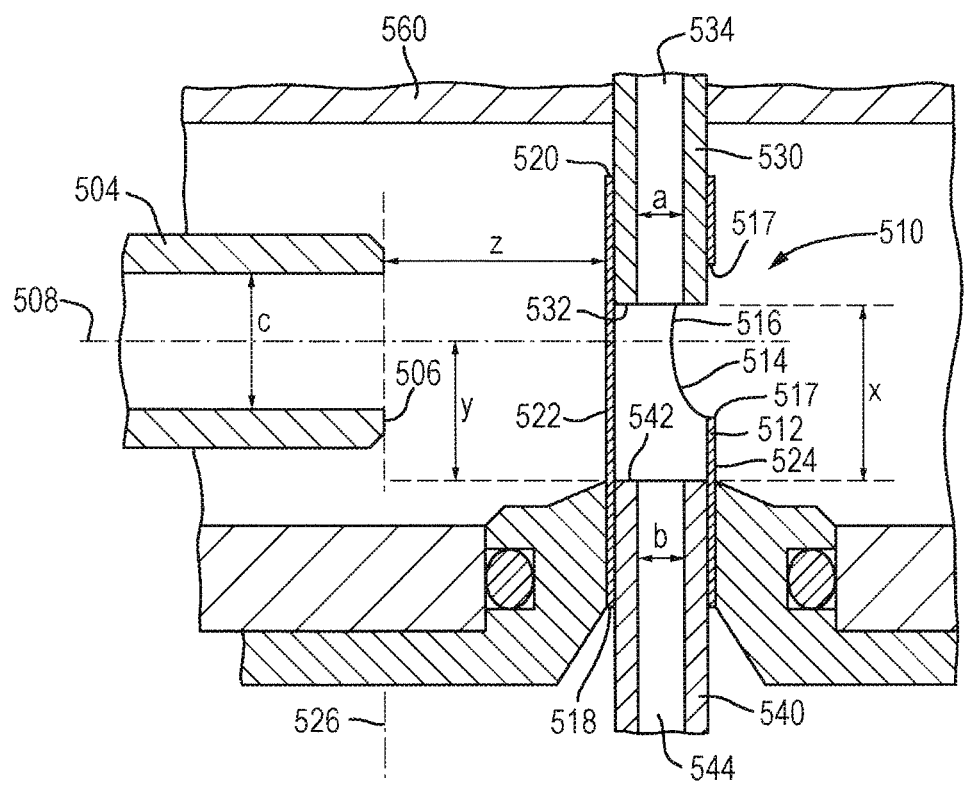
Figure 5C:
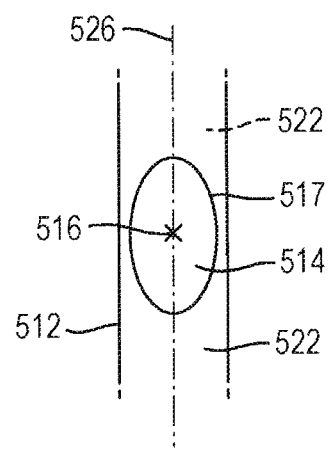

FIG. 5C shows a close-up view of the sampling device 510 (without the matrix introduction conduit 530 therein).

The whistle 12 may be provided in the form of a hollow tube optionally having a first side 522 that may be arranged so as to face the outlet end 506 of the sample transfer tube 504, and a second, opposite side 524 optionally facing away from the outlet end 506 of the sample transfer tube 504.

The whistle 512 may comprise a first end 518 that may be located concentrically around the inlet tube 540 and may be in sealing engagement therewith. The whistle may comprise a second end 520 that may be located concentrically around the matrix introduction conduit 530 and may be in sealing engagement therewith.

A void, aperture or cut-out 514 may be provided on the second side 524 of the whistle 512, and the cut-out 514 may form an inlet such that the sample and gas mixture flowing past the whistle 512 from the outlet end 506 of the sample transfer tube 504 may transfer into the interior of the whistle 512.

The mixture of sample and gas exiting the outlet end 506 of the sample transfer tube 504 may impact on the first side 522 of the whistle 512, and then travel around the outside surface and into the cut-out 514. Once the sample and gas mixture is in the interior of the whistle, it may mix with the nebulised matrix emerging from the matrix introduction conduit 530 before the mixture of sample, gas and matrix is optionally transferred into the inlet tube 540 through the end 542 of the inlet tube 540. The mixture of sample, gas and matrix may then be transferred via the passage 544 to an ion analyser or mass spectrometer.

Positioning the cut-out 514 on the second side 524 of the whistle 512 means that the initial impact of the sample and gas mixture is on a surface that is not directly exposed to the vacuum of the mass spectrometer. In various embodiments, therefore, the sampling device 510 is arranged and adapted such that the initial impact of the sample and gas mixture is on a surface that is not directly exposed to the vacuum of the mass spectrometer.

The cut-out 514 may have a substantially semi-circular profile when the whistle 512 is viewed in cross-section (as shown, for example, in FIGS. 5A and 5B). This will mean that the edge 517 of the cut-out 514 is oval when viewed from a direction facing the second side 524 of the whistle 512 (see FIG. 5C). Alternatively, the cut-out 514 may have a different shape profile when the whistle 512 is viewed in cross-section, for example a square, triangular or irregular shaped profile. The edge 517 of the cut-out 514 may also be square, triangular or irregular when then whistle 512 is viewed from a direction facing the second side 524 of the whistle 512 (see FIG. 5C).

The position and orientation of the whistle 512 can affect the quantity and quality of sample that is transferred into the mass spectrometer. The cut-out 514 may comprise a centre point 516 which may be in line with a longitudinal centreline 508 of the sample transfer tube 504. FIG. 5C shows a view of the second side 524 of the whistle 512 (the whistle 512 is shown in isolation in FIG. 5C), and the centre point 516 can be seen as the centre point of the oval.

The whistle 512 may be oriented such that longitudinal axis 526 of the whistle lies coincident with an axis of symmetry of the cut-out 514. The centre point 516 may lie on the longitudinal axis 526 of the whistle 512 and/or an axis of symmetry of the cut-out. The axis of symmetry of the cut-out may comprise the longitudinal axis of symmetry, wherein the longitudinal direction may be defined as the direction along the longitudinal axis 526.

The position of the various parts of the sampling device 510 can also affect the quantity and quality of sample that is transferred into the mass spectrometer.

Now referring to FIG. 5B, a distance x is defined as the distance (e.g., the shortest distance) between the end 532 of the matrix introduction conduit 530 and the end 542 of the inlet tube 540.

A distance y is defined as the distance (e.g., the shortest distance) between the centre point 516 of the cut-out 514 and the end 542 of the inlet tube 540.

A distance z is defined as the distance (e.g., the shortest distance) between the outlet end 506 of the sample transfer tube 504 and the whistle 512 (e.g., the first side 522 of the whistle 512).

The diameter a of the matrix introduction conduit 530 can affect the quality of the spectra and the intensity of the spectral peaks detected by the mass spectrometer, and can also affect the nebulisation of the matrix (if delivered in a liquid state) as it leaves the end of the matrix introduction conduit 530.

The diameter b of the inlet tube 540, and the diameter c of the sample transfer tube 504 can also affect the quantity the spectra and the intensity of the spectral peaks detected by the mass spectrometer. The diameter b of the inlet tube 540 may be tuned to provide the maximum flow therethrough that is acceptable for the pumping system in the downstream vacuum chamber.

The diameters a, b and c may correspond to the diameters at the end 532 of the matrix introduction conduit 530, the end 542 of the inlet tube and the outlet end 506 of the sample transfer tube 504, respectively.

Any or all of the diameters a, b and c may be greater than, less than or substantially equal to 0.005 mm, 0.010 mm, 0.025 mm, 0.050 mm, 0.075 mm, 0.1 mm, 0.2 mm, 0.4 mm, 0.6 mm, 0.8 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm or 5 mm.

Any or all of the diameters/distances a, b, c, x, y and z may be changed to optimise the quantity and quality of sample that is transferred into the mass spectrometer and/or the quality of the spectra obtained by the mass spectrometer.

The end 532 of the matrix introduction conduit 530 and/or the end 542 of the inlet tube and/or the outlet end 506 of the sample transfer tube 504 may taper to a smaller dimension in the downstream direction. Aspects of the disclosure may extend to methods of optimising the sampling device 510, comprising identifying one or more parameters associated with the sampling device and/or mass spectrometer (for example ion abundance, ion signal intensity or mass spectrometer response) and changing one or more of the distances a, b, c, x, y and z until the one or more parameters are optimised, maximised or minimised.

The Venturi pump 501 may be for introducing aerosol particles into the sample transfer tube 504. The sampling device 510 may be provided for sampling the aerosol. The matrix introduction conduit 530 may be arranged to introduce a matrix (such as isopropanol) into the sampling device 510 and the inlet tube 540 may be arranged to direct a mixture of aerosol particles and matrix onwards to an ion analyser or mass spectrometer.

The Venturi pump 501 may facilitate the aspiration of aerosol or other gaseous sample containing the analyte and may be driven by nitrogen or standard medical air. Aerosol sampling may be arranged to occur orthogonally to the outlet end 506 of the Venturi pump 501 as shown from FIGS. 5A and 5B. The outlet 532 of the matrix introduction conduit 530 may be spaced apart from the inlet tube 540 to the ion analyser or mass spectrometer by the distance x. The distance x can be modified as required to achieve an optimum ion intensity in the range to be analysed, e.g., phospholipids.

Altering the value of the distance x can change the velocity of the gas being drawn into the inlet tube 540 and can have an effect upon the nebulisation conditions. If the nebulisation conditions are less favourable then the matrix droplets may not be of the correct size for interacting with the analyte aerosol and/or may not fragment efficiently when the aerosol collides with the collision surface.

Although the matrix has been described in FIG. 5 as being introduced opposite the inlet to the ion analyser and downstream of the sample transfer tube, it may alternatively be introduced into the sample transfer tube.

Alternatively, the matrix may be introduced coaxially with the inlet to the ion analyser.

Alternatively, the matrix may be introduced at a location around the circumference of the transfer tube and may be swept towards and into the inlet to the ion analyser by a gas flow.

Calibration, lockmass or lock mobility compounds may be used in the various techniques described herein for calibrating the ion analyser or providing a reference mass to the ion analyser. The calibration, lockmass or lock mobility compound may be introduced via the matrix introduction conduit, via the sample transfer tube, or in another location.

The inlet or sampling tube and collision surface or assembly 209, 215 may be mounted in a housing that may be removed from the housing of the mass analyser or REIMS source, as will be described further below.

Figure 6A:
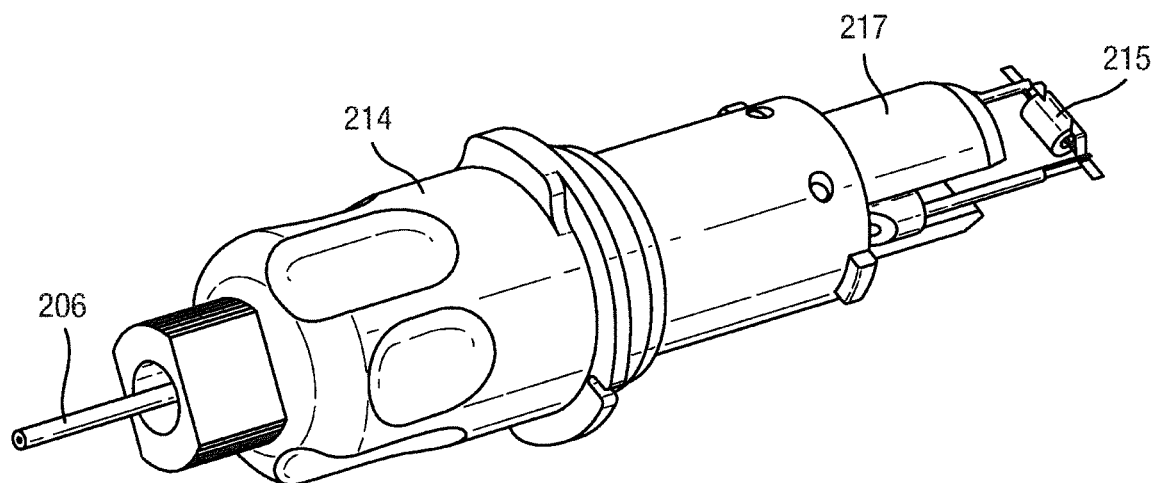
Figure 6B:
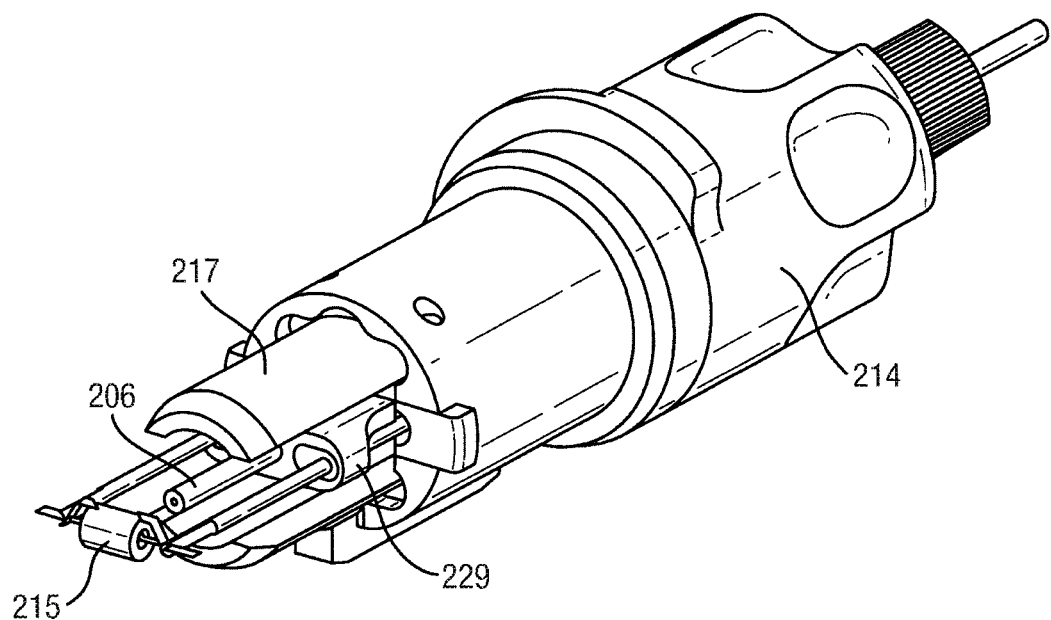

FIGS. 6A and 6B show schematic 3D views from different angles of an embodiment comprising a removable heated collision surface assembly 215 and a capillary or sampling tube 206. The whole unit is self-contained and may be removed from the housing of a mass spectrometer or from a REIMS source housing without using tools and without breaking vacuum. The unit comprises a main body 214 that receives the sampling tube 206 at one end thereof and has the collision surface or assembly 215 arranged at the other end. The unit housing 214 may be formed from PEEK and may comprise a main heater assembly. The sampling tube 206 may correspond to the inlet 206 to the mass analyser 207 and the collision surface assembly 215 may comprise the collision surface 209 described in relation to FIGS. 2 and 3. The sampling tube 206 runs through the unit to a region adjacent to the collision surface assembly 215 for delivering the aerosol to the collision surface 209. Retractable shields 217 may be provided for shielding and protecting the collision surface assembly 215 when the unit is removed from the mass spectrometer or REIMS source. The shields 217 are shown in the retracted position, i.e., in the position they are in when the unit is inserted into the mass spectrometer or REIMS source. However, when the unit is removed the shields may automatically extend so as to surround and protect the collision surface assembly 215. The shields 217 may be metal and will be described in more detail further below. FIG. 6B shows more detail of the collision surface assembly 215, which may be mounted in the unit by an assembly comprising a ceramic holder 229. This will be described in more detail further below.

The capillary or sample tube 206 may be removed from the unit housing 214 simply by pulling it out from the housing 214. The collision surface assembly 215 may be also removable from the unit housing 214 and may be replaced quickly without the use of tools. The structure that allows these functions will now be described.

Figure 7A:
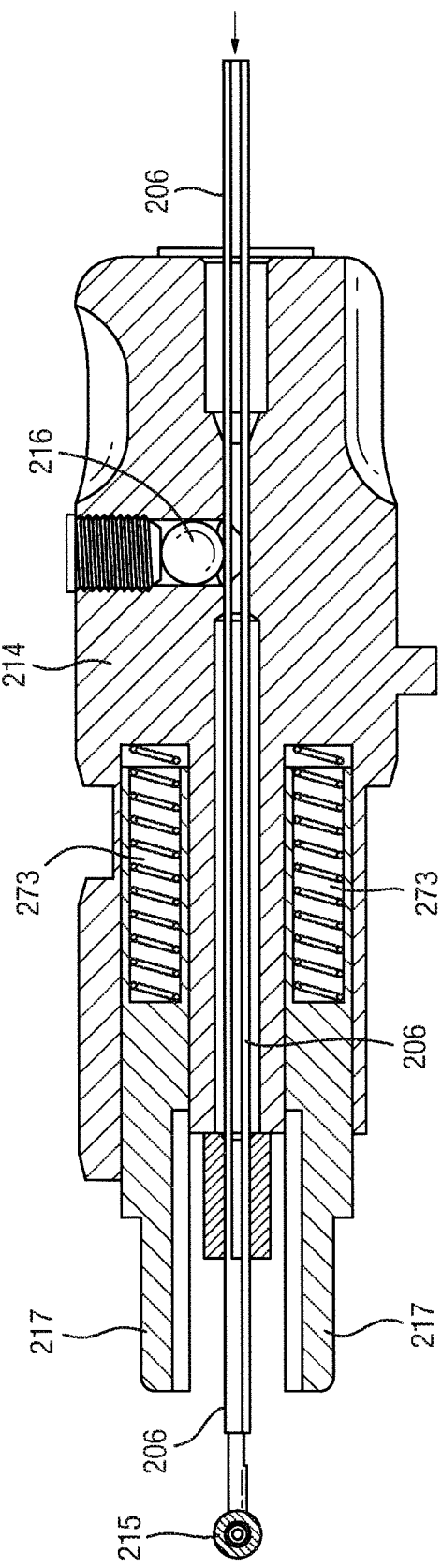
Figure 7B:
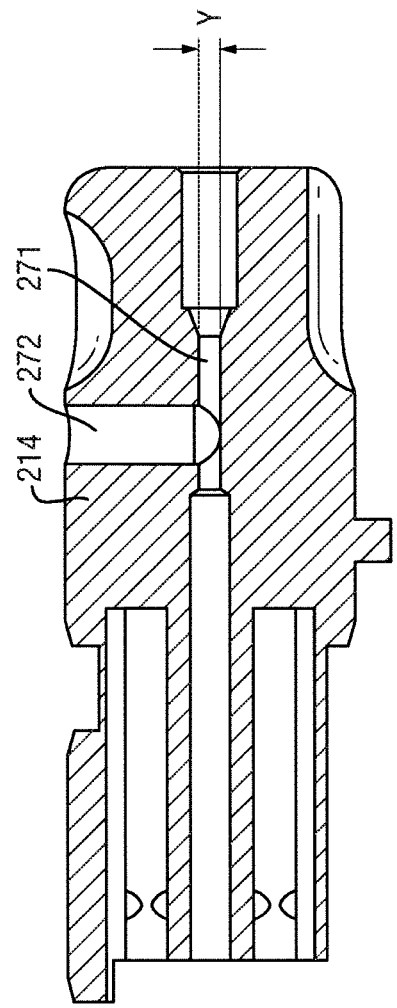

FIGS. 7A and 7B shows a cross sectional view through the removable unit shown in FIG. 6B. The unit housing 214 comprises a bore 271 along its central axis so that the inlet capillary 206 may be inserted into a first end of the unit housing 214, pass through the unit housing 214 and out of the second opposite end of the unit housing 214 so that the exit end of the inlet capillary 206 is arranged adjacent to the collision surface assembly 215. A part of the bore 271 at the first end of the unit housing 214 may be configured to secure the capillary 206 in a fixed location. For example, the part of the bore 271 at the first end may be configured to engage with a screw threaded connector (not shown) on the capillary 206 so as to hold the capillary 206 in an axially fixed location.

It is desired to seal the bore 271 when the capillary 206 is not located within the unit housing 214. For example, the unit may be connected to a mass analyser 207 or mass spectrometer 102 such that the second end of the unit that comprises the collision surface assembly 215 is in a vacuum region of the analyser or spectrometer and the first end of the unit that receives the capillary 206 is in a higher pressure region. In such an arrangement, removal of the capillary 206 from the unit housing 214 may cause an undesirable flow of gas through the unit housing 214 and into the vacuum region of the spectrometer. The unit may therefore have a (first) vacuum isolation mechanism which may automatically operate when the capillary or sample tube 206 is removed. The vacuum isolation mechanism may comprise a ball valve. The ball valve may comprise an isolation ball 216 and may be arranged and configured such that the isolation ball 216 moves into the bore 271 through the unit housing 214 when the capillary 206 is not in the bore 271 so as to seal the bore 271 closed to isolate the vacuum chamber of the mass spectrometer from the external atmosphere. The isolation ball 216 may be provided in a conduit or recess 272 that is interconnected with the bore 271 and the ball 216 may be biased so as to move into the bore 271 by gravity, a spring or some other mechanism. Alternatively, or additionally, the ball 216 may be biased into the bore 271 by suction from the vacuum pressure of the mass spectrometer.

When a capillary or sample tube 206 is inserted into the unit the valve may be automatically opened. For example, the isolation valve may be configured such that insertion of the capillary or sample tube 206 pushes or otherwise displaces the isolation ball 216, opening the bore 271 and allowing the capillary or sample tube 206 to be further pushed home into the correct position.

FIG. 7B shows a cross sectional view though the unit housing 214 without the capillary or sample tube 206, shield 217, collision assembly 215 and vacuum isolation mechanism comprising the ball 216. The dimension Y of the bore 271 in the unit housing 214 may be substantially similar to the outer diameter of the capillary or sample tube 206 such that once the capillary or sample tube 206 is inserted into the housing 214 then minimal or substantially zero gas leakage will occur.

As described above, and shown in FIG. 7A, the collision surface assembly 215 may be protected by retractable shields 217. The retractable shields 217 may be mounted to the unit housing 214 by a biasing mechanism 273, such as one or more spring, that bias the shields 217 to the extended position surrounding and protecting the relatively fragile support mechanism and associated electrical wires for the collision surface assembly 215, which will be described in more detail below. When the unit is initially engaged with the main housing of the mass analyser or spectrometer or is inserted into a REIMS source assembly (not shown), the retractable shields 217 are automatically forced to fully retract to the positions shown in FIG. 7A, thereby exposing the collision surface assembly 215.

Figure 8A:
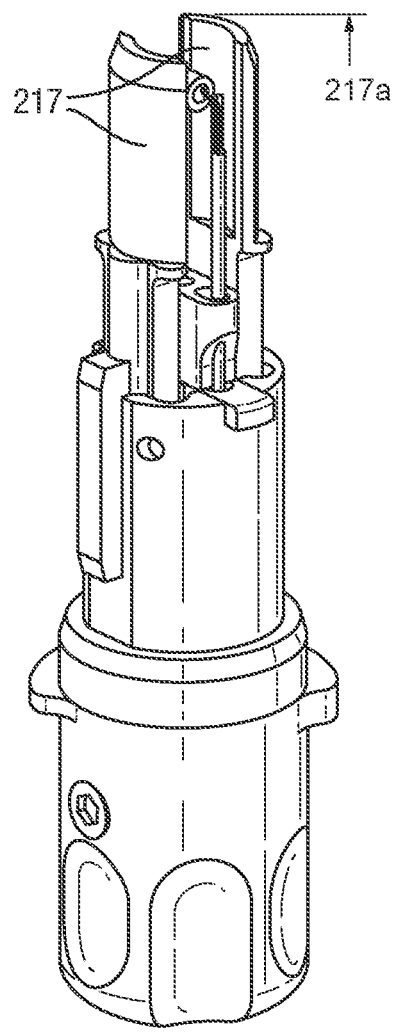
Figure 8B:
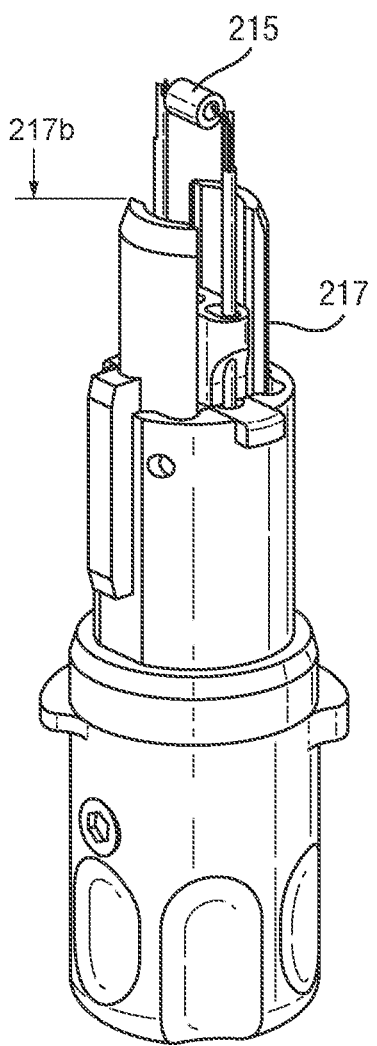

FIGS. 8A and 8B show the removable unit of FIGS. 6A, 6B, 7A and 7B, with the shields 217 in the extended position 217a and retracted position 217b respectively. In FIG. 8A the shields 217 are extended so as to fully protect the collision surface or collision assembly 215. In FIG. 8B the shields 217 are fully retracted, e.g., once the unit has been inserted into the REIMS source assembly.

FIGS. 9A and 9B show a perspective view and a cross sectional view of the collision assembly 215. The collision assembly 215 comprises a heated impact surface 209 that may be formed from an alumina (ceramic) cylinder 226. The cylinder 226 may be mounted around a heater coil 227 for heating the cylinder 226 and collision surface in use. Electrical power may be supplied to the heater coil 227 via two electrodes 228 so as to cause the coil 227 to generate heat. The coil 227 may be formed of a material such as Kanthal® and may be supplied with a power in the order of approximately 10 W. The collision surface may be heated to a temperature in the range of 700-1100° C. during operation.

FIG. 10 shows a schematic of the collision assembly 215 that may be removed from the unit housing 214. The assembly comprises the heated impact surface cylinder 226, coil assembly 227, electrodes 228, two conductor tubes and a holder 229 for adding mechanical stability to the assembly. The holder 229 allows for easy replacement of burnt out or contaminated collision surfaces. The holder may be ceramic.

As described above, the removable unit comprising the collision assembly 215 may be inserted or removed from the housing of the mass analyser or spectrometer or REIMS source.

Figure 11A:
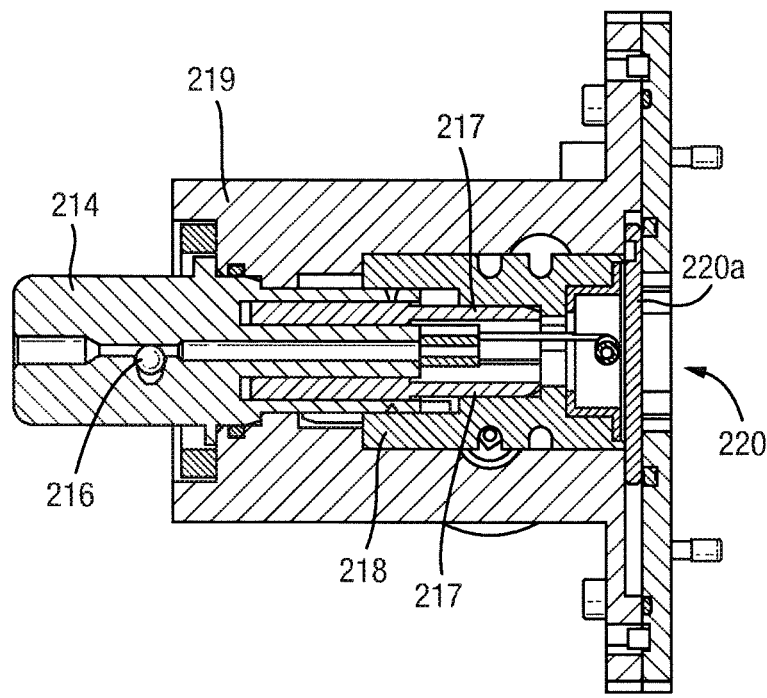
Figure 11B:
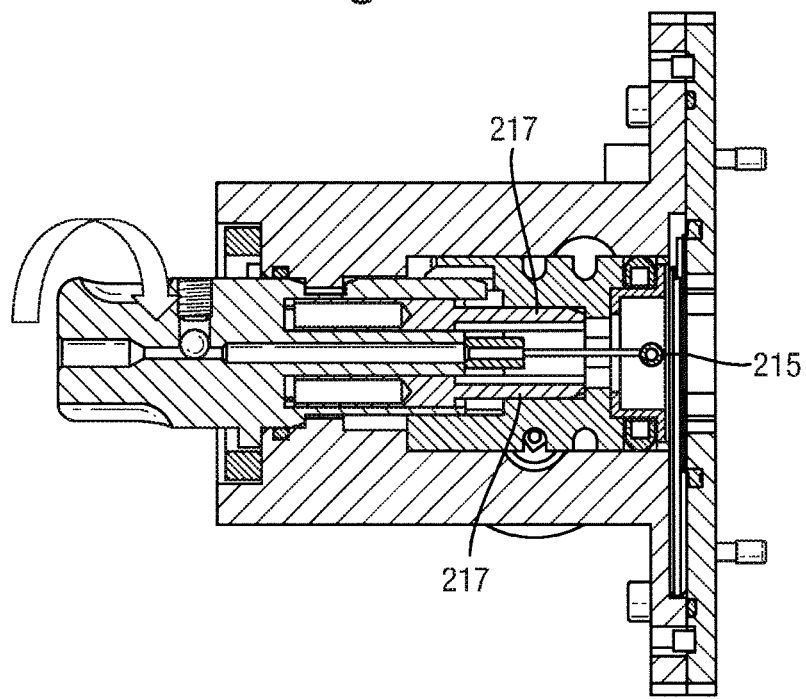

FIGS. 11A and 11B show sectional views of the unit comprising the unit housing 214 and the collision assembly 215 when connected to the REIMS source housing 219. The REIMS source housing 219 comprises an axial conduit therethrough. A first end of the axial conduit is open, for receiving the removable unit. A (second) isolation valve 220 is arranged at the second end of the conduit for selectively blocking gas flow through the conduit. FIG. 11A shows the instrument when the isolation valve 220 is closed, whereas FIG. 11B shows the instrument when the isolation valve 220 is open. The REIMS source housing 219 also comprises an isolation valve actuation barrel 218 arranged within the conduit and connected to the isolation valve 220 for activating the valve 220.

In use, the removable unit housing 214 is inserted into the conduit of the REIMS source housing 219 such that the collision surface assembly 215 is arranged adjacent the isolation valve 220. During insertion of the removable unit, the shields 217 retract so as to expose the collision surface assembly 215. Although not shown, the inlet capillary 206 is inserted into the bore 271 in the removable unit so as to displace the isolation ball 216 and extended until its exit orifice is adjacent the collision surface assembly 215. During insertion of the removable unit into the REIMS source housing 219, the unit housing 214 interconnects with the isolation valve actuation barrel 218.

FIG. 11A shows the instrument in a standby configuration. In this mode the vacuum of the mass spectrometer is isolated from atmosphere via the isolation valve 220, which comprises a cam 220a closed across the conduit in the REIMS source housing 219. The interconnection between the removable unit housing 214 and the actuation barrel 218, and the interconnection between the actuation barrel 218 and the valve cam 220a, are configured such that rotation of the removable unit about its longitudinal axis opens the valve 220. Rotation of the removable unit housing 214 may rotate the actuation barrel 218 about the longitudinal axis, which may rotate the cam 220a about the longitudinal axis so as to unblock the conduit. For example, the removable unit may be rotated by 270° in order to open the valve 220.

Figure 12A:
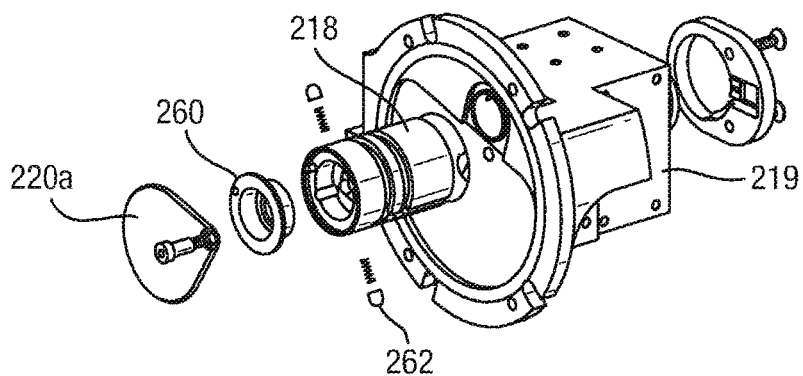
Figure 12B:
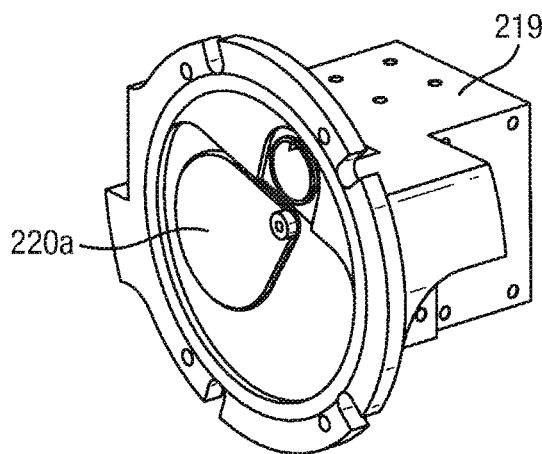
Figure 12D:
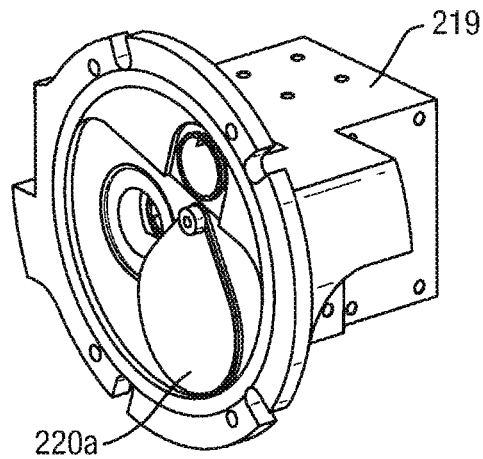
Figure 12C:
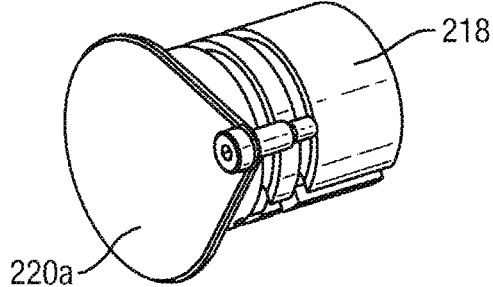
Figure 12E:
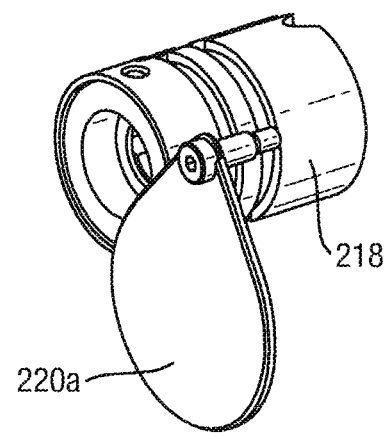

FIGS. 12A-12E show perspective views of the REIMS source housing 219 and valve 220. FIG. 12A shows an exploded view of the components of the isolation valve 220 and the REIMS source housing 219. More specifically, FIG. 12A shows the actuation barrel 218 for the isolation valve 220 during insertion into the REIMS source housing 219, and shows the cam 220a of the isolation valve 220 prior to attachment. A heat shield 260 made from, for example, stainless steel may be provided between the cam 220a and the isolation valve 220. Electrical contacts 262 may be provided in contact with the heat shield 260 to ensure that the heat shield 260 remains at the same electrical potential as the housing 219. The electrical contacts 262 may be provided in the actuation barrel 218 (which is electrically connected to the housing 219) and may be biased into contact with the heat shield 260, e.g., by springs. FIG. 12B shows the REIMS source housing 219 after the insertion of the isolation valve and shows the cam 220a in the closed position so as to close the conduit through the REIMS source housing 219, i.e., in the standby mode. FIG. 12C shows the position of the actuation barrel 218 and cam 220a in the standby mode. FIG. 12D shows the REIMS source housing 219 after the insertion of the isolation valve and shows the cam 220a in the open position so as to open the conduit through the REIMS source housing 219, i.e., in the operative mode. FIG. 12E shows the position of the actuation barrel 218 and cam 220a in the operative mode.

Figure 13A:
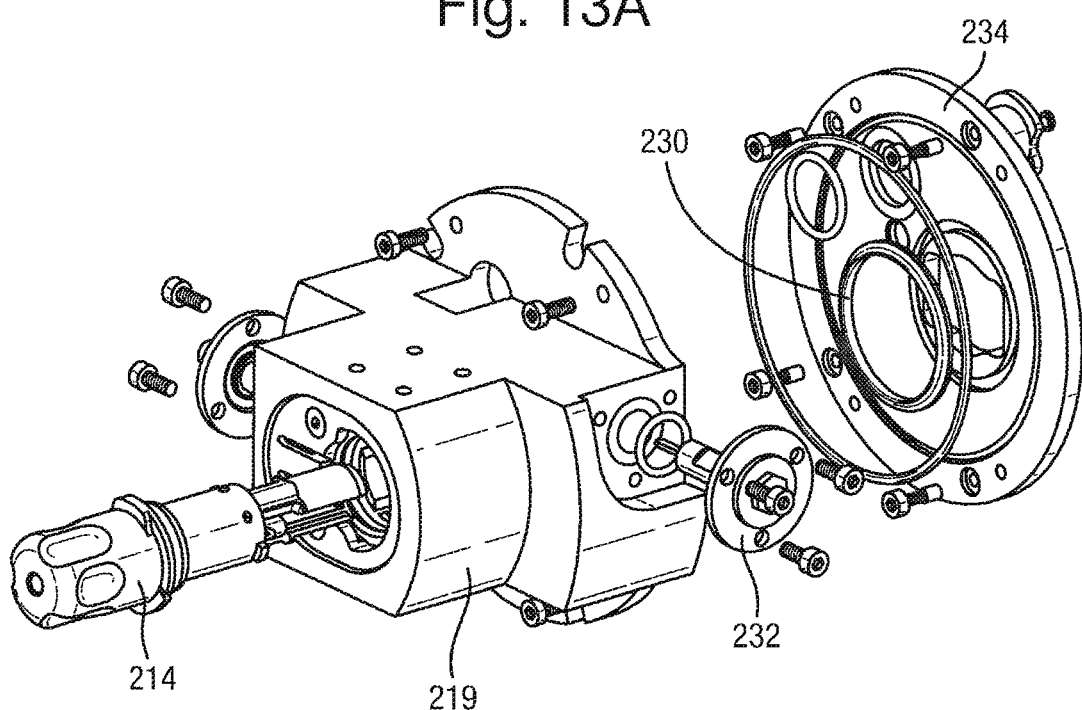
Figure 13B:
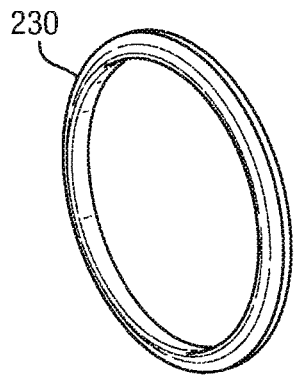
Figure 13C:
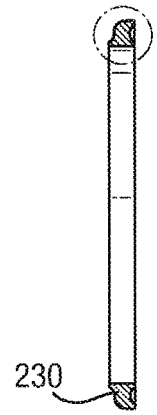
Figure 13D:
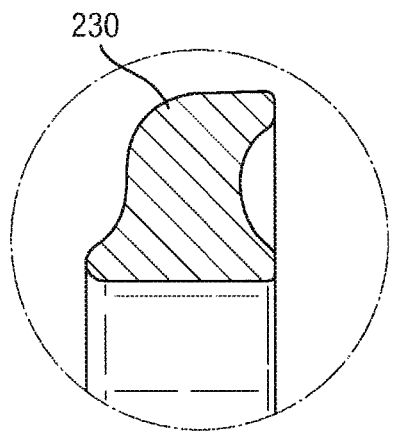

FIG. 13A-13D show a cam seal 230 that may be used to seal the cam 220a of the isolation valve 220. More specifically, FIG. 13A shows an exploded view of the apparatus, prior to insertion of the removable unit housing 214 into the REIMS source housing 219. The electrical feed-through 232 heating the collision surface 209 is also shown. The cam seal 230 is arranged between the cam 220a on the REIMS source housing 219 and a connector plate 234 and serves to provide a seal around the conduit opening in the REIMS source housing 219 when the cam 220a is open and closed. FIGS. 13B and 13C show perspective and side cross-sectional views of the seal 230. FIG. 13D shows a magnified view of part of the seal 230 in FIG. 13C. The profile of the seal 230 allows compression to occur due to the forces applied by the isolation valve 220 and the vacuum system without having to include additional fixings. The specific profile of the valve seal 230 as shown in FIG. 13D allows the same O-ring groove to be used as would be the case for a standard O-ring allowing the seal to remain captive. The surface of the seal 230 that contacts the REIMS source housing 219 curves away from the housing 219 when moving in a direction that is radially outward from the axis through the conduit. This allows the cam 220a to slide over the seal 230 without significant frictional force that might otherwise result in damage or displacement of the seal 230. This is not possible using a standard O-ring.

Figure 14:
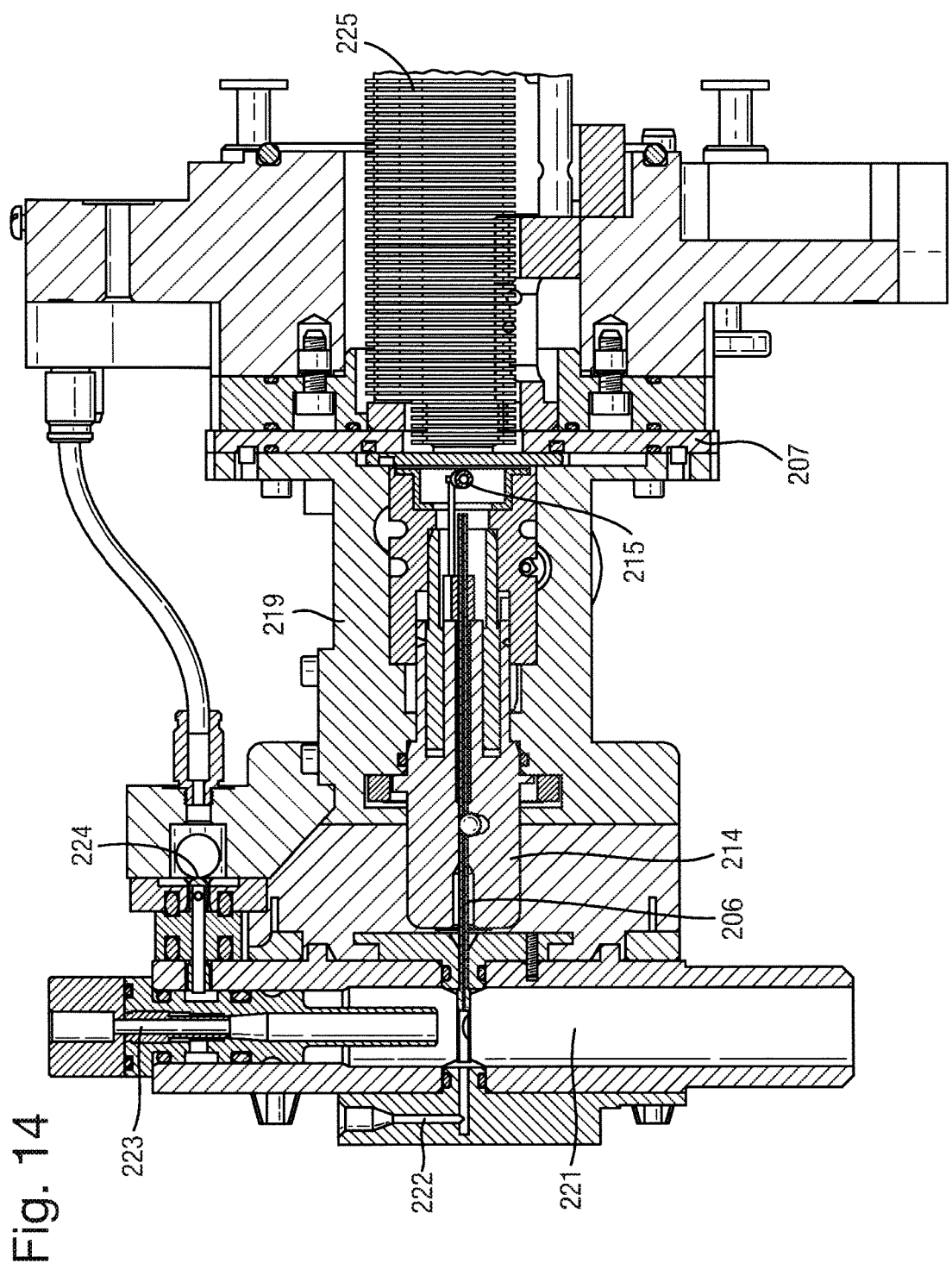

FIG. 14 shows the REIMS source housing 219 and removable unit comprising housing 214 of FIG. 11A and FIG. 11B with the capillary 206 inserted in the bore 271 of the removable unit. The REIMS source housing 219 is connected to the mass analyser 207 via the isolation valve 220. The inlet end of the capillary 206 receives analyte and matrix from the venturi pump 223, which is the same arrangement as shown and described in relation to FIGS. 5A-5D. The instrument may be operated in a manner as described hereinabove, for example, in relation to FIGS. 2, 3 and 5.

As described above, the mixture of analyte sample and matrix may be transferred from through the inlet capillary 206 and may emerge from the inlet capillary 206 and impact upon the collision surface 215. The collision surface 215 may be heated, for example, by an inductive heater. A further heater may be provided to heat the mixture of sample and matrix as it travels along the inlet tube 206. This heater may be an inductive heater and may comprise a conductive metal (e.g., tungsten) wrapped around the inlet tube 206.

The mixed composition of analyte and matrix may be arranged to be ionised by impacting the collision surface 215. This step may be arranged to perform kinetic ionisation and also secondary chemical ionisation. As described above, the mixture may be heated and it may be heated to the extent that thermal ionisation also occurs. The resulting analyte ions may then be passed into the ion guide 225. The ion guide 225 may be arranged to separate analyte ions from neutral flux or background gas in a known manner, e.g., by manipulating the ions using electric fields.

The various embodiments provide an apparatus and associated method for the chemical analysis of aerosols and gaseous samples containing analytes using mass spectrometry or other gas-phase ion analysis modalities. The method starts with the introduction of an aerosol or other gaseous sample 201 containing the analyte into an enclosed space, where the sample is mixed with a low molecular weight matrix compound 204. This homogeneous or heterogeneous mixture is then introduced into the atmospheric interface of a mass spectrometer or ion mobility spectrometer via inlet 206. On the introduction of the mixture into the low pressure regime of the analytical instrument, aerosol particles containing molecular constituents of the sample and the matrix compound are formed, which are accelerated by the free jet expansion. The mixed composition aerosol particles 205 are subsequently dissociated via collisions a solid collision surface 209, 215. The dissociation events produce neutral and charged species, including the molecular ions of the chemical constituents of the sample 210. The ions 210 may be separated from the neutral species by using electric fields, e.g., by using an ion guide 212, 225 such as a Stepwave® ion guide so as to guide ions 210 a different path to the neutral species. The molecular ions 210 are then subjected to mass or mobility analysis. This provides a simple solution for the analysis of molecular constituents of aerosols in an on-line fashion without the application of high voltages or lasers.

The method and device disclosed above provides a solution for the on-line mass spectrometric and ion mobility spectrometric analysis of gas phase or aerosol-type samples.

According to various further embodiments the matrix compound may be mixed into the sample aerosol as a vapour or as a liquid at any point prior to introduction of the sample into the ion analyser device.

Although a particular solid collision surface geometry for performing the surface induced dissociation of the clusters has been described above, it will be appreciated that other geometries can be implemented (provided that the clusters impact the collision surface at sufficiently high velocity to induce dissociation).

Figure 15:
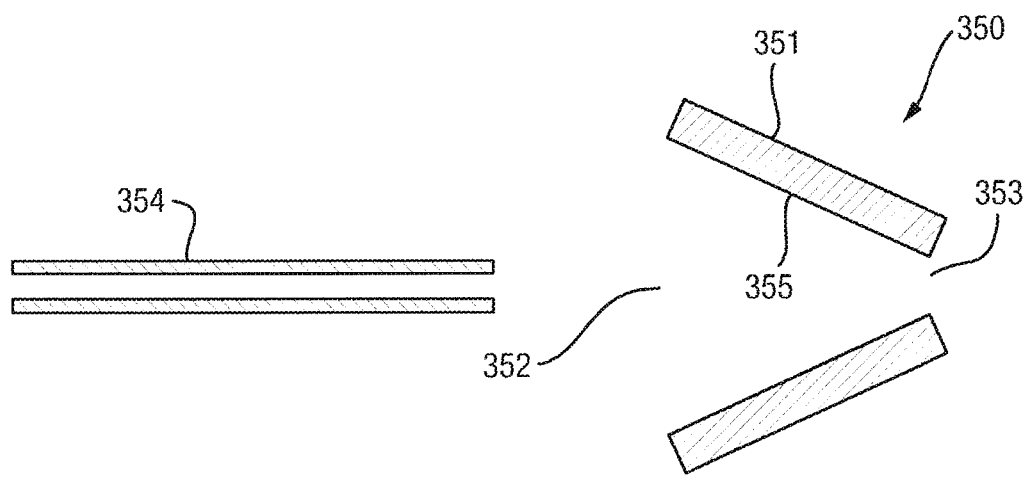

FIG. 15 shows a simplified schematic of an embodiment wherein the collision surface or assembly 209, 215 is replaced by a hollow collision assembly 350. The capillary 206 is represented by capillary 354. The hollow collision assembly 350 may comprise a funnel-shaped assembly 351 having a relatively large inlet 352 and a relatively small outlet 353. The funnel-shaped collision assembly 350 progressively tapers or reduces in internal diameter along the axis of the assembly in a direction from the inlet end 352 towards the outlet end 353, i.e., in a direction of flow of aerosol particles and resulting analyte ions.

Aerosol particles or molecules may according to an embodiment be arranged to emerge from the exit of a capillary 354 or other aerosol introduction tube such that the aerosol particles or molecules are then directed towards the inlet 352 of the collision assembly 350 so that at least some of the aerosol then impacts upon the edge and/or inner surface 355 of the collision assembly 350. Aerosol which impacts upon the edge and/or inner surface 355 of the collision assembly 350 may be caused to be ionised upon impact, thereby generating analyte ions. The resulting analyte ions are then arranged to emerge from the outlet 353 of the collision assembly 350, e.g., by gas flow. This embodiment may lead to a reduction in undesired or non-analyte clusters being ionised and hence in a reduction in unwanted background ions being generated. In particular, relatively large mass background clusters may remain on axis as they enter and pass through the hollow collision assembly 350, thereby avoiding impact upon the edge or inner surface 355 of the collision assembly 350. As a result, large mass background clusters may not impact upon the edge or inner surface 355 of the collision assembly 350 and hence may not be ionised by impacting the edge or inner surface 355 of the collision assembly 350.

Un-ionised or neutral (unwanted) background clusters which emerge from the outlet 353 of the collision assembly 350 (without having impacted upon the edge or inner surface 355 of the collision assembly 350) can then effectively be separated from charged analyte ions of interest by using electric fields. For example, un-ionised or neutral (unwanted) background clusters which emerge from the outlet 353 of the collision assembly 350 (without having impacted upon the edge or inner surface 355 of the collision assembly 350) may be separated from charged analyte ions of interest by passing both the analyte ions and the undesired neutral background clusters through a StepWave® ion guide 212, 225 (e.g., as shown in FIG. 14). As discussed above, a StepWave® ion guide comprises an ion guide formed of conjoined ring electrodes. Neutral particles or molecules (such as unwanted background clusters) and analyte ions may both be received in a first portion of the ion guide. The ring electrodes in the first portion of the ion guide may be arranged to have a relatively large internal diameter. Transient DC voltages or potentials may be applied to the electrodes which has the effect of urging the analyte ions along the length of the ion guide. A constant radial DC voltage gradient may be maintained across a subsequent portion of the ion guide, e.g., across a central section of the ion guide. The constant radial DC voltage gradient has the effect of directing analyte ions from the one portion of the ion guide into another portion of the ion guide. For example, the analyte ions may be directed into a second portion of the ion guide wherein the conjoined ring electrodes may have a relatively small diameter. It will be appreciated that the radial DC voltage gradient has no effect upon the neutral (unwanted) particles or molecules. As a result, unwanted neutral background clusters will continue straight through the ion guide and can be exhausted via a pump. At the same time, analyte ions can be confined radially within the second portion of the ion guide. If the ring electrodes of the second portion are arranged to have a relatively small diameter then the analyte ions can then confined in a narrow diameter beam aiding subsequent onwardly transmission e.g., through a differential pumping aperture or into an ion guide having a relatively narrow acceptance angle. Ultimately, the analyte ions or fragment, product or daughter ions derived from the analyte ions can be mass analysed by a mass analyser 207 arranged downstream of the StepWave® ion guide.

The embodiment shown and described above in relation to FIG. 15 has multiple benefits including improving the signal to noise. Furthermore, utilization of a hollow collision assembly 350 has been found to result in an improved ionisation efficiency of the aerosol.

Another benefit of the embodiment shown and described above with reference to FIG. 15 is that the hollow collision assembly 350 suffers from less contamination due to the impact of undesired particles or molecules upon the collision assembly 350. As a result, the collision assembly 350 requires less frequent cleaning or other maintenance. Furthermore, reducing the impact of unwanted particles or molecules upon the collision assembly 350 and the use of a StepWave® ion guide downstream of the collision assembly 350 to direct undesired background clusters to an exhaust results in a significant reduction in the contamination of ion-optics such as ion guides, quadrupole mass filters, ion traps, ion mobility spectrometry devices and differential pumping apertures which are located downstream of the collision assembly 350 and/or the StepWave® ion guide.

The collision assembly may be heated, e.g., by an electrically resistive heater coil wrapped around the assembly 351. A strong ion signal may be obtained by using a heater coil current of $\geq 2.5$ A, optionally $\geq 3$ A, and optionally $\geq 4$ A. A strong ion signal may be obtained by arranging the assembly 351 2-3 mm from the exit of the capillary 354.

Figure 16:
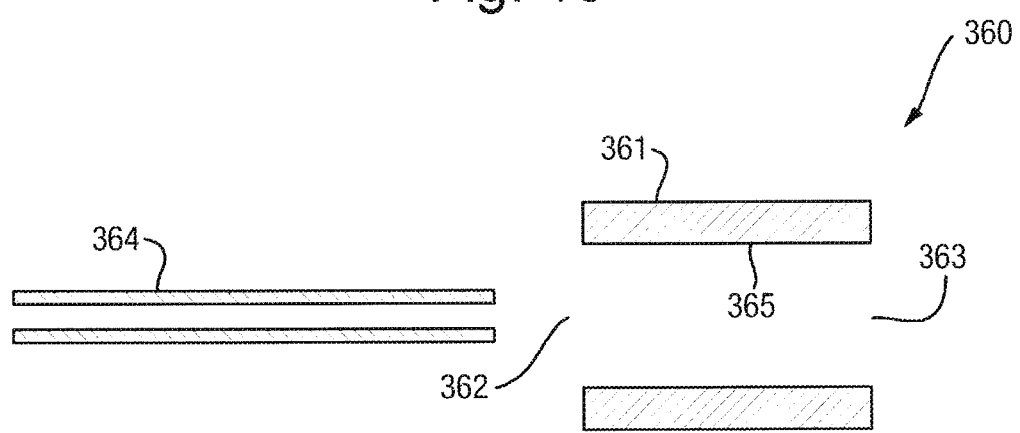

According to another embodiment the funnel-shaped collision assembly 351 shown in FIG. 15 may be replaced with a hollow cylindrical collision assembly 361 as shown in FIG. 16. According to this embodiment the internal diameter of the collision assembly 360 remains essentially constant along the longitudinal length of the collision assembly 360. The hollow cylindrical collision assembly has an inlet 362 and an outlet 363. Aerosol particles or molecules may be arranged to emerge from the exit of a capillary 364 or other aerosol introduction tube such that the aerosol particles or molecules are then directed towards the inlet 362 of the collision assembly 360. Aerosol is arranged to impact upon the edge and/or an inner surface 365 of the collision assembly 361. This embodiment has also been found to exhibit the same benefits as that of a hollow funnel-shaped collision assembly 351, namely improved ionisation efficiency, improved signal to noise and reduced contamination of ion-optics.

The collision assembly 361 may be heated, e.g., by an electrically resistive heater coil wrapped around the assembly 361. The ion signal was found to be optimised using a heater coil current of ≥3.5 A, optionally ≥4 A, and optionally ≥5 A. The optimal ion signal may be obtained by arranging the assembly 351 3-4 mm from the exit of the capillary 354.

It is apparent, therefore, that both a hollow funnel-shaped collision assembly 351 and a hollow cylindrical collision assembly 361 are particularly beneficial and represent a significant improvement over the known arrangements disclosed in WO 2013/098642 (Medimass).

Although the collision surface has been described as being spherical, cylindrical or funnel shaped, other configurations are also contemplated.

Figure 17A:
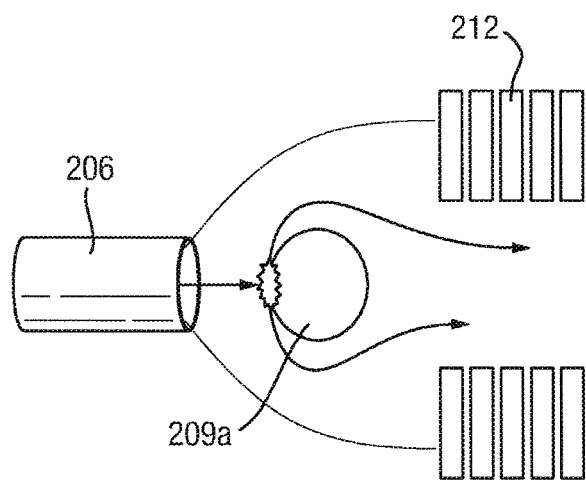
Figure 17B:
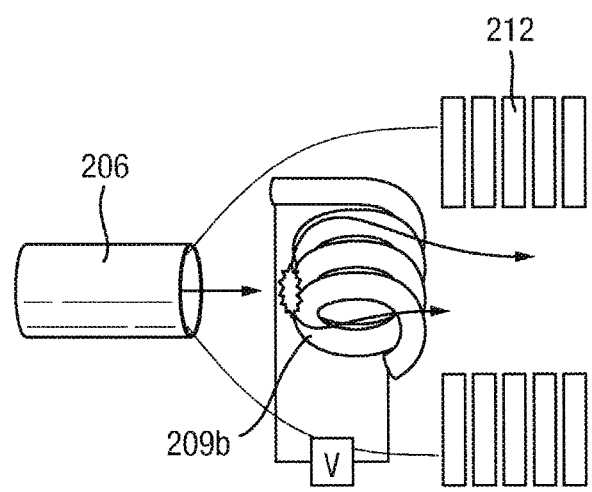

FIGS. 17A and 17B show schematics of example configurations of the collision surface that may be. FIG. 17A corresponds to the collision surface 209 shown in FIGS. 2 and 3. For example, the collision surface 209 may be a spherical, stainless-steel collision surface 209a and may be mounted approximately 6 mm from the end of the inlet capillary 206 into the analyser 207. FIG. 17B shows a collision surface 209 according to an embodiment that may be used, in the form of a coil-shaped collision surface 209b. Ions may be transferred by the ion optics 212 to an analysis region (not shown) of the ion analyser 207. As discussed above, the ion optics 212 may comprise a Stepwave® ion guide.

It has been recognised that the REIMS mechanism may lead to substantially equal generation of positively and negatively charged ions, which may subsequently form relatively large molecular clusters of neutral electrical charge. These neutral clusters are not manipulated well by electric fields within the analyser or spectrometer and hence may be eliminated, e.g., by the instrument ion optics 212. The collision surface 209,215 described herein serves to break up the molecular clusters 205, releasing the ions so that they may be guided by the electrical fields within the analyser or spectrometer. However, it has also been recognised that the provision of the collision surface 209,215 may induce cross-contamination between measurements of different samples. For example, certain bacterial metabolites were found to induce relatively strong memory effects after only a small number of repetitive measurements, e.g., certain sphingolipids produced by *Bacteroides* spp. or lipopolypeptides such as surfactin and lichenysin produced by certain *Bacillus* spp. This cross-contamination could be mitigated by cleaning the atmospheric pressure interface before each analysis. However, this is undesirable, particularly in automated instruments. In order to avoid contamination of the collision surface 209,215 the surface may be heated, e.g., to several hundred degrees Celsius. For example, heating the collision surface 209, 215 may cause carbonaceous deposits on the collision surface 209 to react with oxygen introduced through the inlet capillary 206. The carbonaceous deposits will then be converted to $CO_2$ gas, which can leave the collision surface 209, 215 and hence not contaminate the instrument during subsequent analyses. The coil-shaped collision surface 209b of FIG. 17B provides a particularly reproducible heat distribution.

The collision element or surface 209, 215 may be constructed from a material that may be heated by passing an electric current through it, e.g., by applying voltage V in FIG. 17B, enabling it to be easily heated during analysis. For example, the collision surface 209, 215 may be manufactured out of a heat-resistant iron-chromium-aluminium (Fe-CrAl) alloy such as kanthal. Using such a heated collision surface 209, 215 significantly reduces memory effects and thus the frequency of instrument cleaning may be greatly reduced. For example, thousands of database entries are able to be recorded without any memory effects and even prolonged exposure to lipopolypeptides did not result in any observed carry-over.

Spherical, coil-shaped or other shaped collision surfaces may be used. For example, a cylindrical or tubular collision surface may be used, which may be heated e.g., from inside the cylinder or tube. The cylindrical or tubular structure may comprise or be formed from quartz, ceramic, glass, glass-ceramic (e.g., MACOR®).

The spectral profile obtained using the heated collision surface 209, 215 may, in some cases, be different to the spectral profile obtained using the collision surface 209, 215 unheated, for example, as shown in FIGS. 18A and 18B.

FIGS. 18A and 18B show the spectral profiles resulting from the analysis of *Bacteroides fagilis* using a non-heated collision surface and a heated collision surface, respectively. This indicates that not all spectral constituents are thermally stable enough to be analysed using this type of heated surface technique. For example, the effect of the heated surface seems to be especially strong on phosphatidic acid (which is common in, e.g., fungi such as *C. albicans*) and sphingolipid species (which is common in e.g., *Bacteroidetes phylum*), while it has less effect on the spectral appearance observed for phosphatidylglycerol and phosphatidylethanolamines (which are, e.g., the main phospholipid species in Proteus mirabilis).

As described above, the introduction of a matrix compound 204, such as isopropyl alcohol (IPA), upstream of the collision surface 209, 215 has been found to improve analyte ionisation and sensitivity of the instrument. It has also been found that the introduction of the matrix compound 204 may restore spectral features that would otherwise be missing by using a heated collision surface rather than a non-heated collision surface. For example, FIGS. 18A and 18B demonstrate that the use of a heated collision surface was found to eliminate spectral features such as ceramides in *Bacteroides fragilis*. The introduction of isopropanol into the sampled aerosol 201 before introduction into the mass analyser 207 or spectrometer was found to restore these spectral features and generate a mass spectral fingerprint similar to that of an atmospheric pressure interface with a non-heated collision surface. Furthermore, the addition of the matrix 204 (e.g., isopropanol) to the sample aerosol 201 led to similar or higher signal intensities as compared to direct aerosol introduction, and thus enables the use of a Venturi pump 213 for aerosol transport.

Although the collision surface 209, 215 has been described in the context of various shapes, other shapes are also contemplated. For example, the collision surface may be conical. Experimental data has been collected for collision surfaces of various maximum diameters.

Figure 19A:
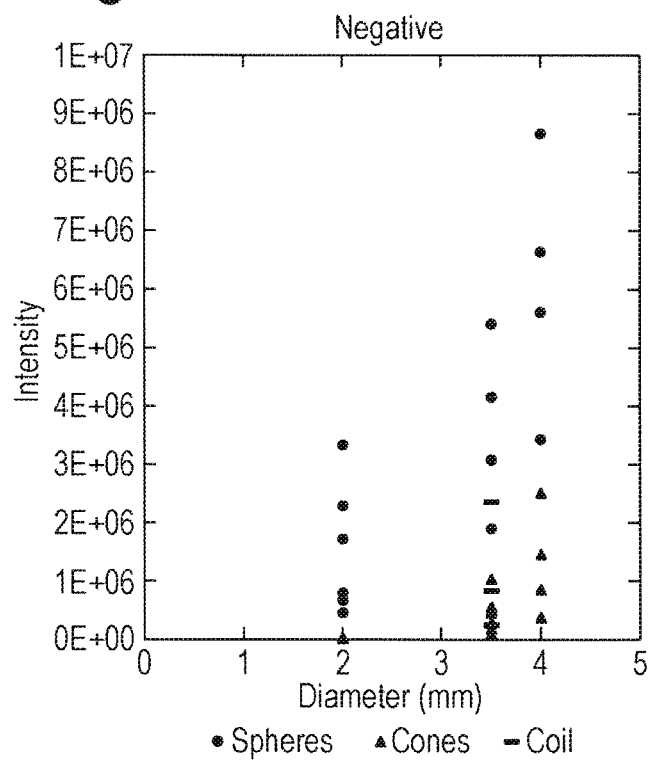
Figure 19B:
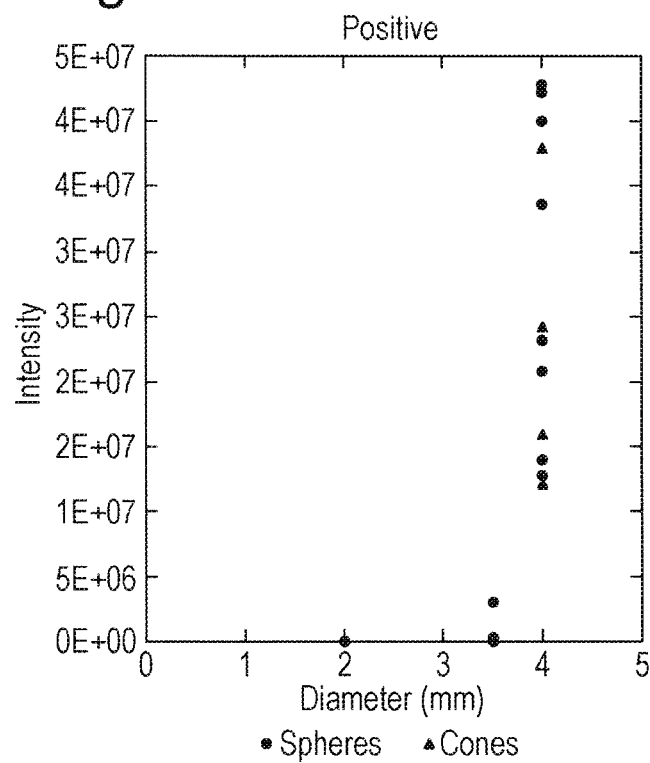
Figure 20A:
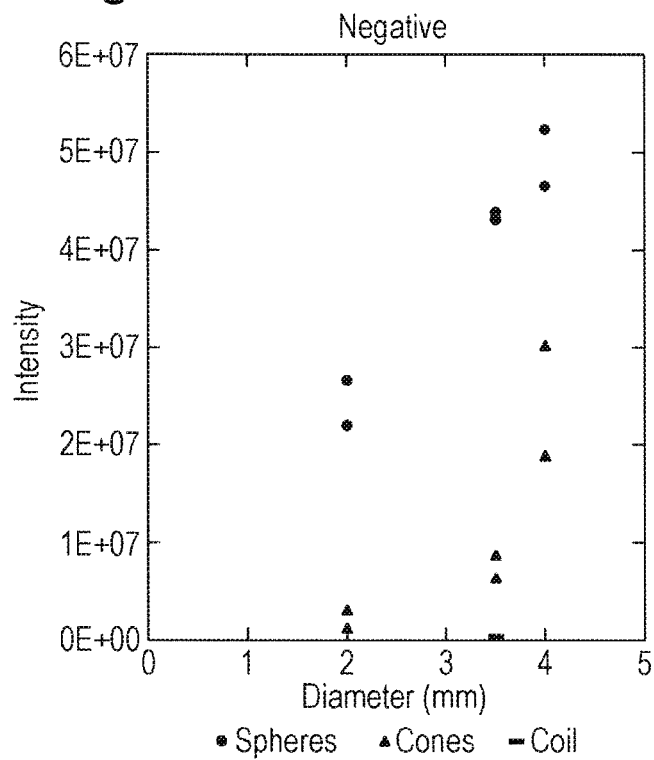
Figure 20B:
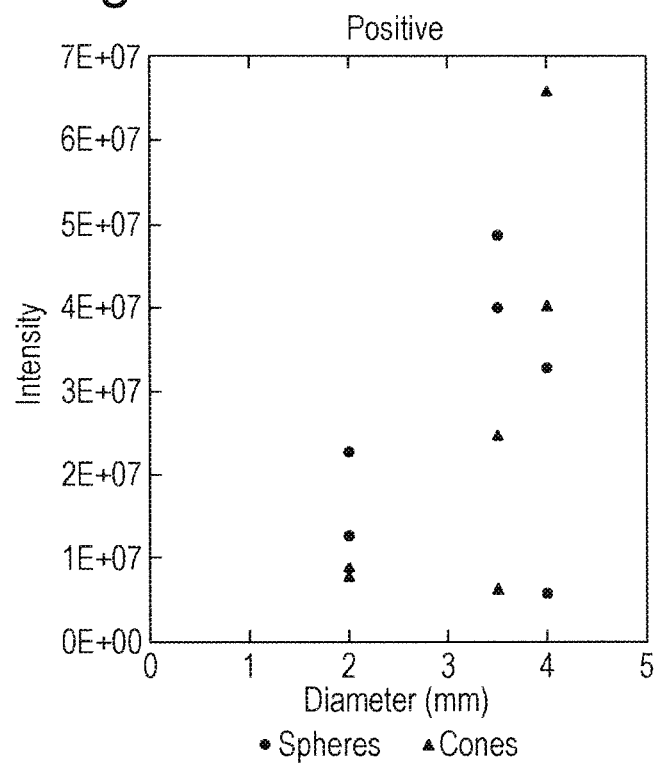

FIGS. 19A-19B and 20A-20B show the intensity of the ion signal obtained as a function of the maximum diameter of the collision surface 209, 215 for spherical, conical and coil-shaped collision surfaces. The data was obtained by vapourising a mixture of Leucine Enkephalin (25 ng/µl in 3:1 IPA:water) and lipids PC14:0 and PG14:0 (25 ng/µl in 3:1 IPA:water) in an ultrasonic nebuliser, and then introducing the nebulised material into a mass spectrometer comprising the collision surface 209,215. The peak intensities monitored were: Leu Enk [M–H]– having a mass to charge ratio of 554, Leu Enk [M+H]+ having a mass to charge ratio of 556, PG14:0 [M–H]– having a mass to charge ratio of 665, and PC14:0 [M+Na]+ having a mass to charge ratio of 701. FIGS. 19A and 19B show data collected for Leu Enk, for collision surfaces 209, 215 of different shapes and different diameters, in negative ion mode and positive ion mode, respectively. FIGS. 20A and 20B show data collected for lipids, for collision surfaces 209, 215 of different shapes and different diameters, in negative ion mode and positive ion mode, respectively.

In general, the signal intensity increases with increasing diameter of the collision surface 209,215. When the coil was heated the intensity dropped for both the Leu Enk and the lipid mix, in contrast to tissue analysis for which the intensity is greater when the coil is heated.

Figure 21:
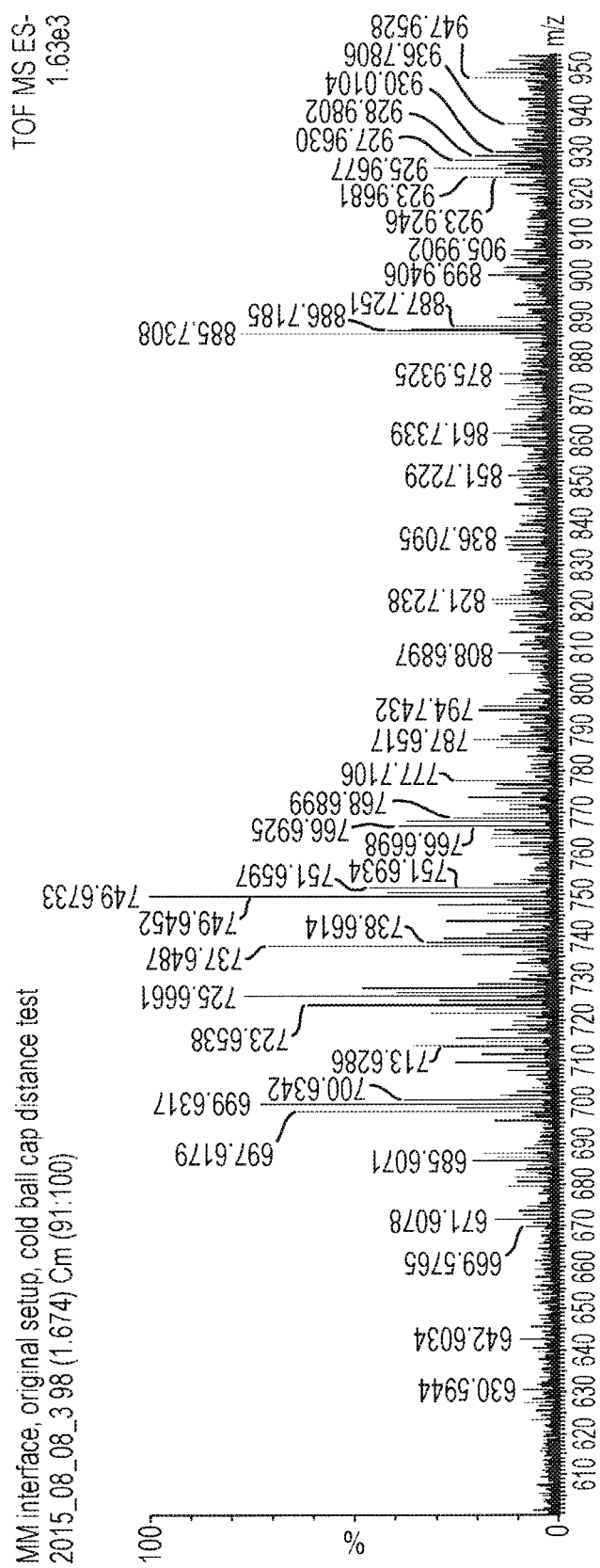

FIG. 21 shows a mass spectrum obtained using a non-heated spherical collision surface. The collision surface had a diameter of 3.5 mm and was arranged 2 mm from the capillary outlet 206.

Figure 22:
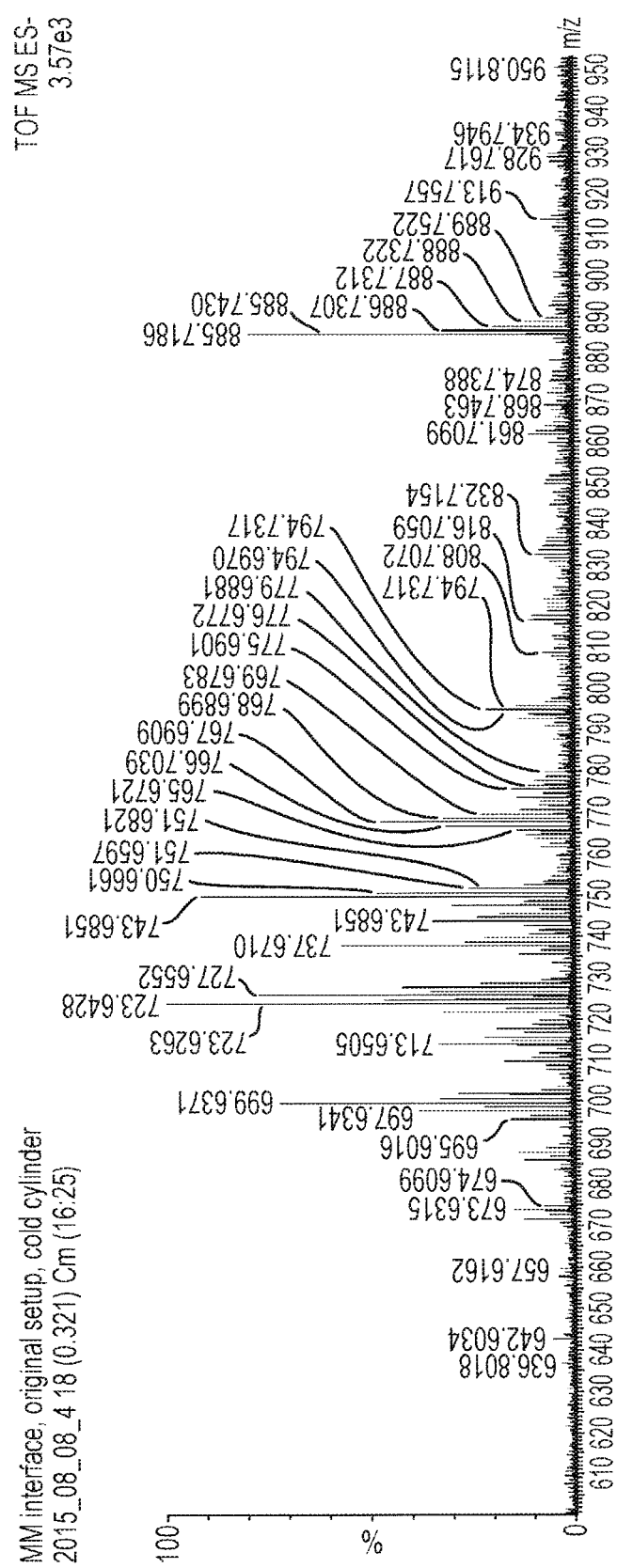

FIG. 22 shows a mass spectrum obtained using a non-heated cylindrical collision surface. The collision surface had a diameter of 3.5 mm and was arranged 2 mm from the capillary outlet 206.

Figure 23:
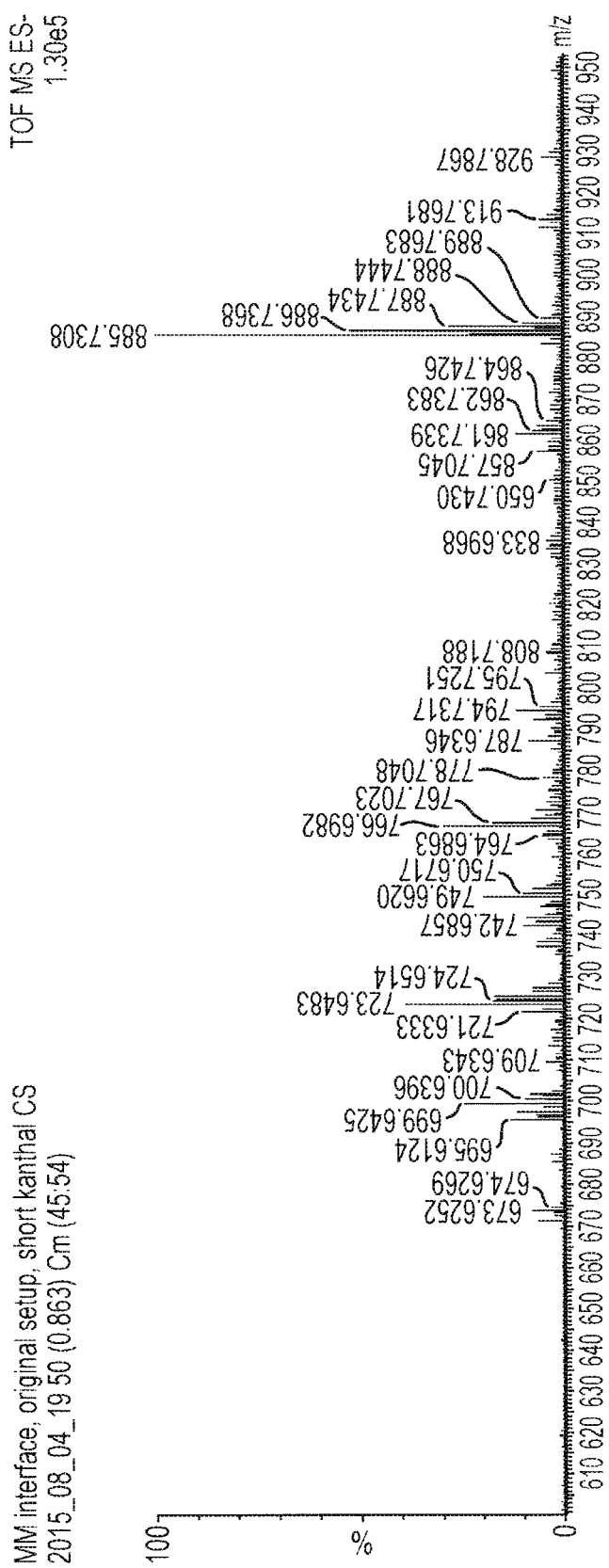

FIG. 23 shows a mass spectrum obtained using a heated, Kathal® coil-shaped collision surface. The coil was heated by a current of 2.9 A and using a 40 V offset. This coil configuration was particularly useful for avoiding contamination of the collision surface during sample analysis.

Figure 24:
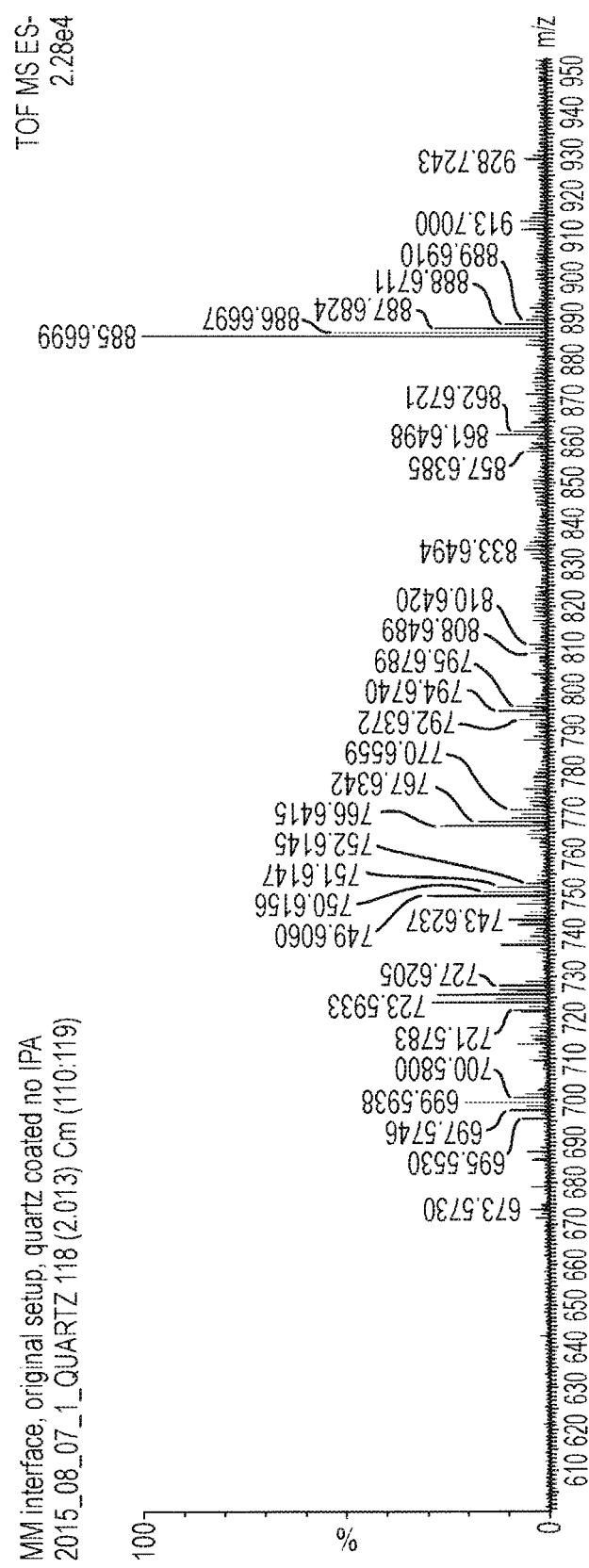

FIG. 24 shows a mass spectrum obtained using a quartz cylinder collision surface heated by a coil arranged within the cylinder. The coil was heated by a current of 2.9 A. This configuration produced good spectral results with relatively low contamination of the collision surface (a black contamination spot was observed), although the spectrum is lower magnitude than when the exposed coil was used as the collision surface.

Figure 25:
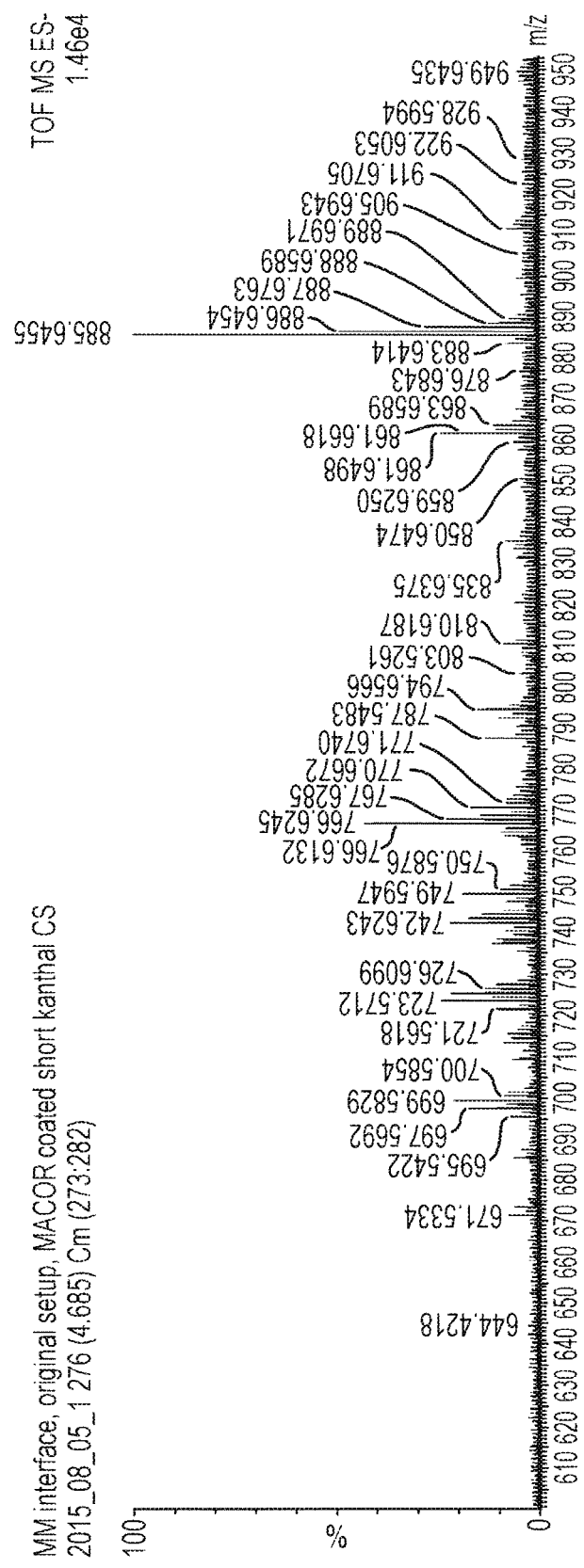

FIG. 25 shows a mass spectrum obtained using a glass-ceramic MACOR® cylinder collision surface heated by a coil arranged within the cylinder. The coil was heated by a current of 1.2 A. This configuration resulted in higher contamination than the quartz collision surface, and the spectrum is of lower magnitude than when the exposed coil was used as the collision surface.

Figure 26A:
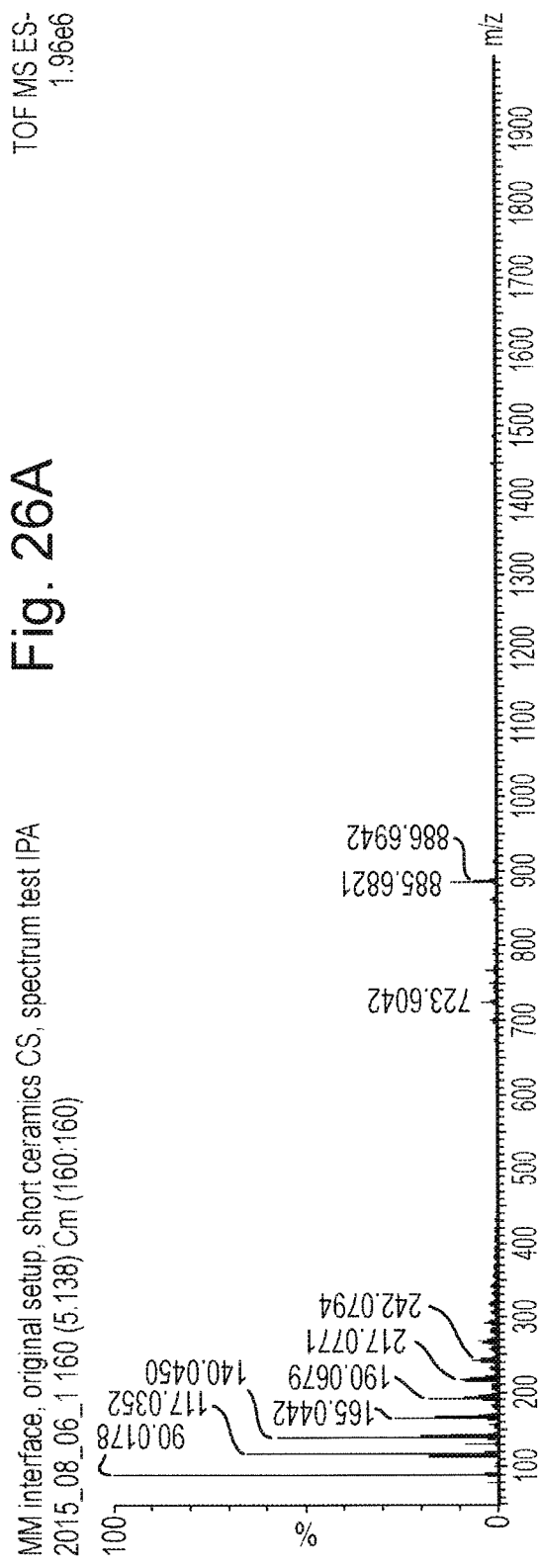
Figure 26B:
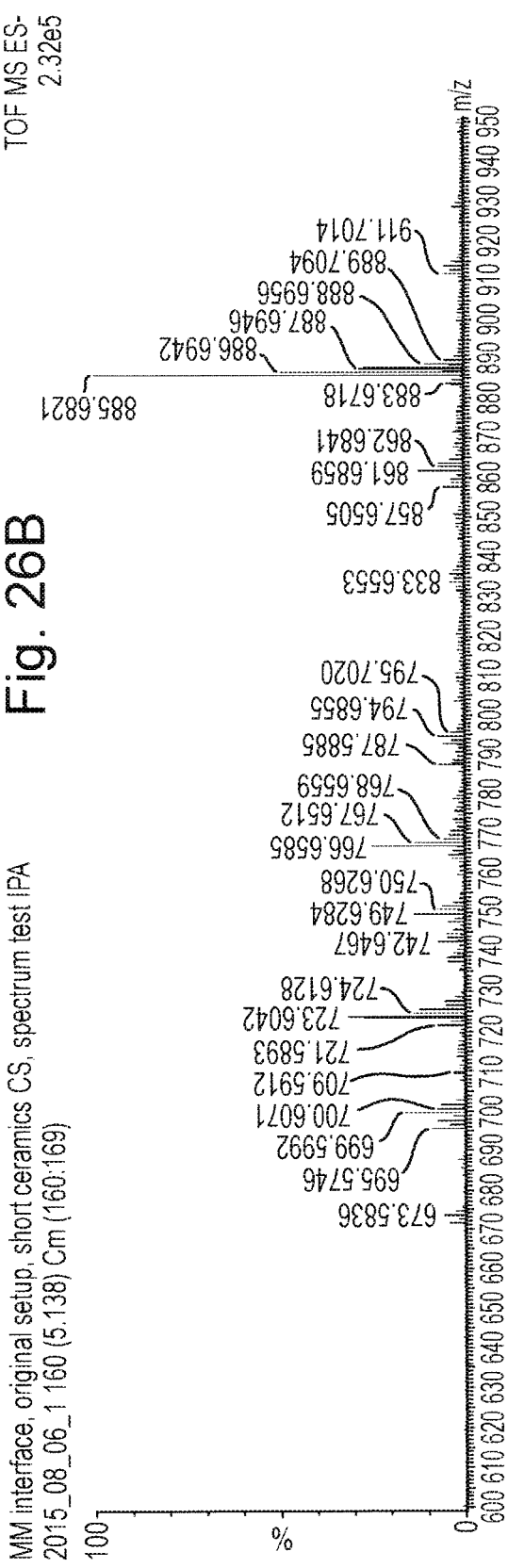

FIG. 26A shows a mass spectrum obtained using a ceramic collision surface heated by a heater coil embedded therein. The coil was heated by a current of 2.9 A. This configuration produced particularly strong intensities at lower masses and resulted in substantially no contamination of the collision surface. FIG. 26B shows the mass spectrum of FIG. 26A within the mass range of 600-900.

FIG. 27A shows a mass spectrum obtained using a heated nickel coil-shaped collision surface. The coil was heated by a current of 2.25 A and using a 40 V offset. This coil configuration acquired a greenish colour during use and produced a spectrum with more noise than the Kanthal® coil. FIG. 27B shows the mass spectrum of FIG. 27A within the mass range of 600-900.

Figure 28A:
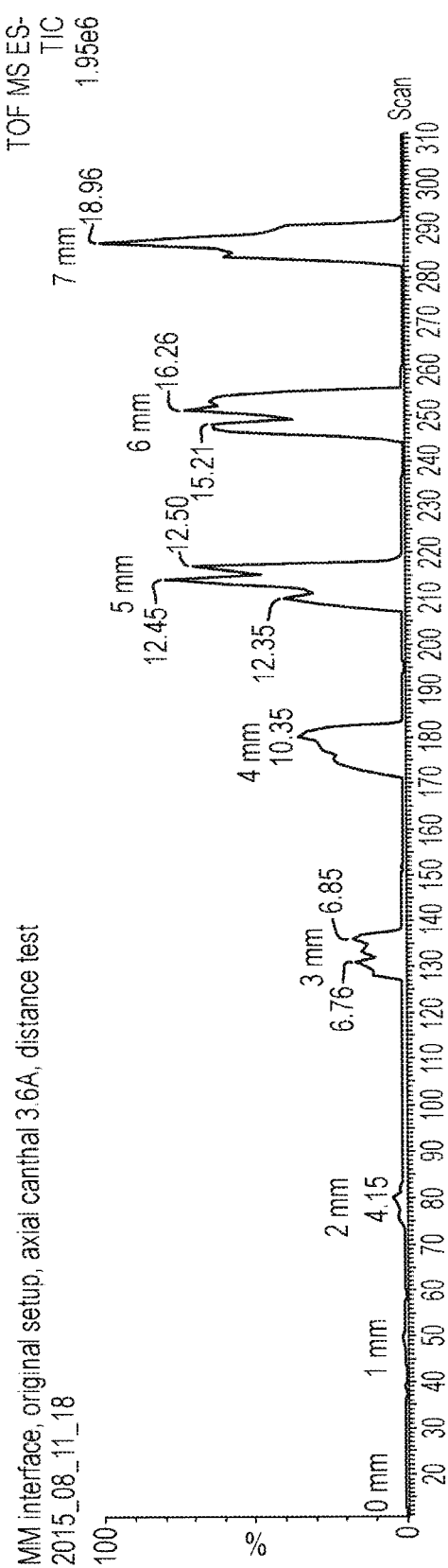
Figure 28B:
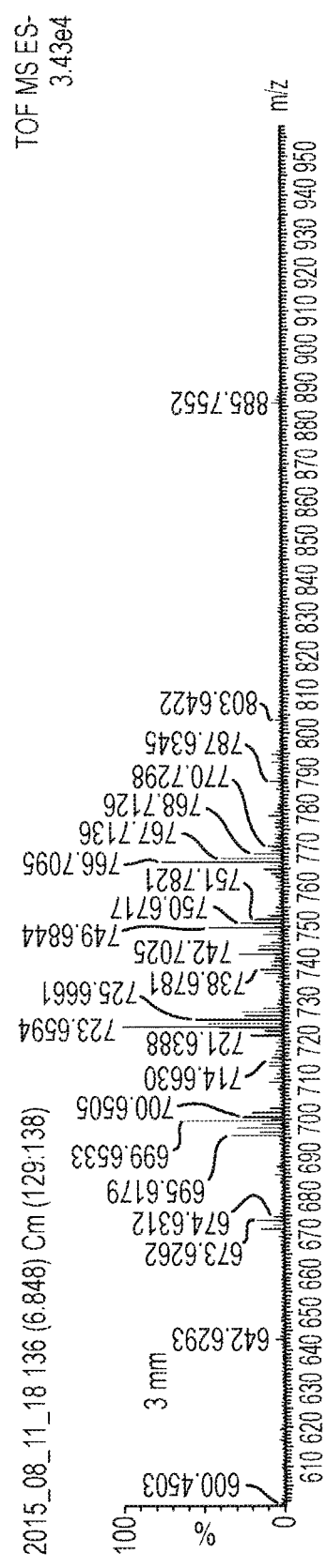
Figure 28C:
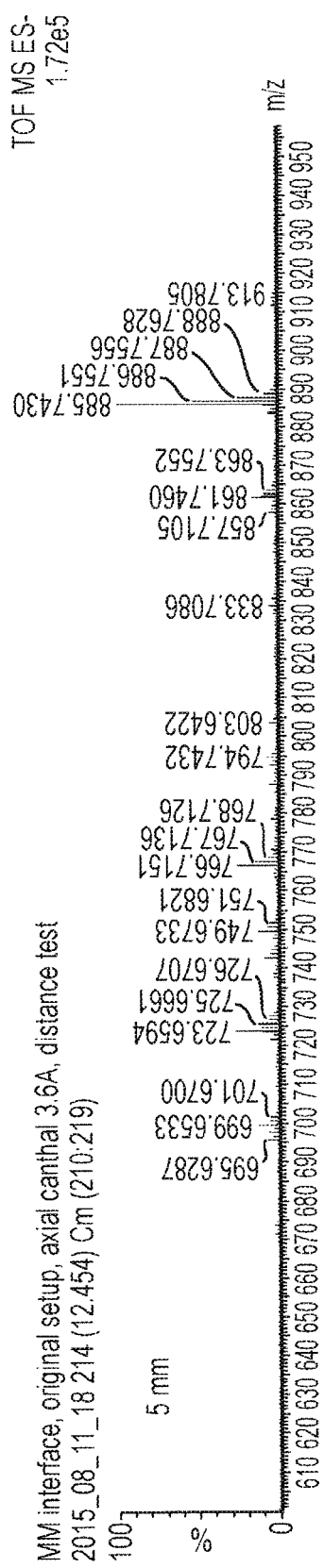

FIG. 28A shows the ion signal intensity detected for different distances between the exit of the capillary 206 and the kathal coil collision surface 209. The coil was heated by a current of 3.6 A and using a 40 V offset. No contamination of the coil was observed after the analyses. FIG. 28B shows the mass spectra at a distance of 3 mm and FIG. 28C shows the mass spectra at a distance of 5 mm. It was observed that spectra begin to appear when the distance is increased to around 3 mm and that peeks begin to appear when the distance is increased to around 5 mm.

Different collision surface geometries were examined in order to optimise the sensitivity of the instrument and the spectrum. The analyses were performed on porcine liver using REIMS analysis. The apparatus comprised a stainless steel capillary for conveying the sample aerosol to the collision surface. The capillary had a length of 49.65 mm, an inner diameter of 0.02 inches (0.05 cm) and an outer diameter of 1.16 inches (2.9 cm). The collision surface was positioned 2 mm from the end of the capillary. Four types of collision surfaces were tested: conical, planar, cylindrical and spherical.

Figure 29A:
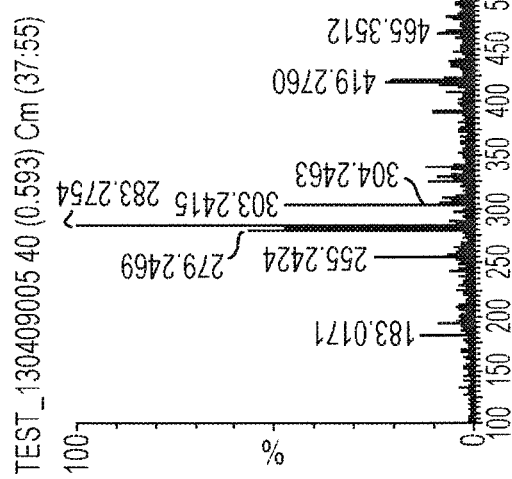
Figure 29B:
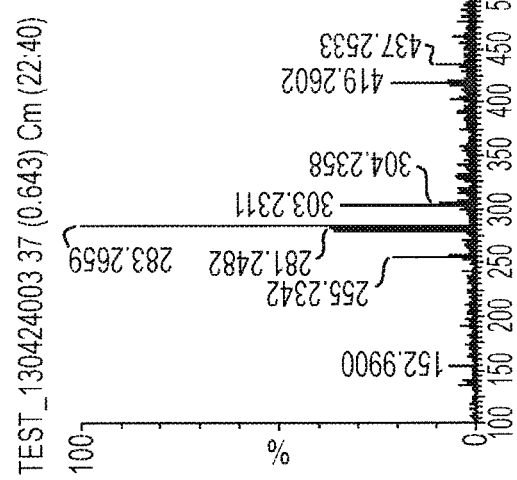

Conical collision surfaces were examined in which the apex of the cone was located towards the capillary outlet and such that the conical surface tapered to a greater diameter in a direction downstream of the capillary. FIG. 29A shows the mass spectrum obtained using a cone as the collision surface and FIG. 29B shows the mass spectrum obtained when the conical surface tapers outwards to a cylindrical section of length 6.9 mm and diameter 3.5 mm. The conical collision surfaces generate relatively high fragmentation of the gas molecules, in this example, resulting in a mass spectra with the exclusive presence of fatty acids.

A number of planar collision surfaces were examined.

FIGS. 30A and 30B show mass spectra obtained using disc shaped collision members, i.e. members wherein the upstream and downstream sides are planar. The collision member used to obtain the spectrum of FIG. 30A had a diameter of 5 mm and the collision member used to obtain the spectrum of FIG. 30B had a diameter of 3 mm. The total ion current observed for each of these collision surfaces was relatively low (~7.5E4 counts) and so was the sensitivity for ions in the mass spectrum.

Collision assemblies were also examined having a planar surface facing upstream towards the outlet of the capillary and non-planar downstream surfaces.

FIG. 31A shows the mass spectrum obtained using a collision member that is hemispherical, with the planar surface of the hemisphere facing towards the capillary exit. The hemisphere had a diameter of 3.5 mm. FIG. 31B shows the mass spectrum obtained using a collision member that has a planar upstream surface facing towards the capillary exit and a hemispherical downstream surface that is spaced apart from the upstream surface by a cylindrical section. The hemispherical surface had a diameter of 3.5 mm and the cylindrical section had a length of 7 mm. FIG. 31C shows the mass spectrum obtained using a collision member that has a planar upstream surface facing towards the capillary exit and a conical downstream surface that is spaced apart from the upstream surface by a cylindrical section (7 mm in length and 3.5 mm in diameter). The conical portion of the reduces in diameter in the downstream direction. These geometries also resulted in relatively low total ion currents (<7E4 counts) and relatively poor sensitivity.

Cylindrical collision assemblies were also examined having the longitudinal axis of the cylinder perpendicular to the axis through the exit of the capillary. Cylindrical collision assemblies of different outer diameters were examined. The cylinders each had a length of 8.7 mm and were arranged 2 mm downstream of the capillary exit, although only the central part of the cylinder participated in the collision of the gas molecules as it was the only part that showed deposition after venting the instrument.

FIG. 32A shows the mass spectrum obtained using a collision assembly having an outer diameter of 5 mm, FIG. 32B shows the mass spectrum obtained using a collision assembly having an outer diameter of 3.5 mm, and FIG. 32C shows the mass spectrum obtained using a collision assembly having an outer diameter of 2 mm. The averaged total ion current for the three collision surfaces over two replicates were 2.6E5 for the cylinder having a diameter of 2 mm, 2.8E5 for the cylinder having a diameter of 3.5 mm, and 7.5E4 for the cylinder having a diameter of 5 mm. These cylindrical collision assemblies showed better results than the planar surfaces with an order of magnitude higher.

Figure 33A:
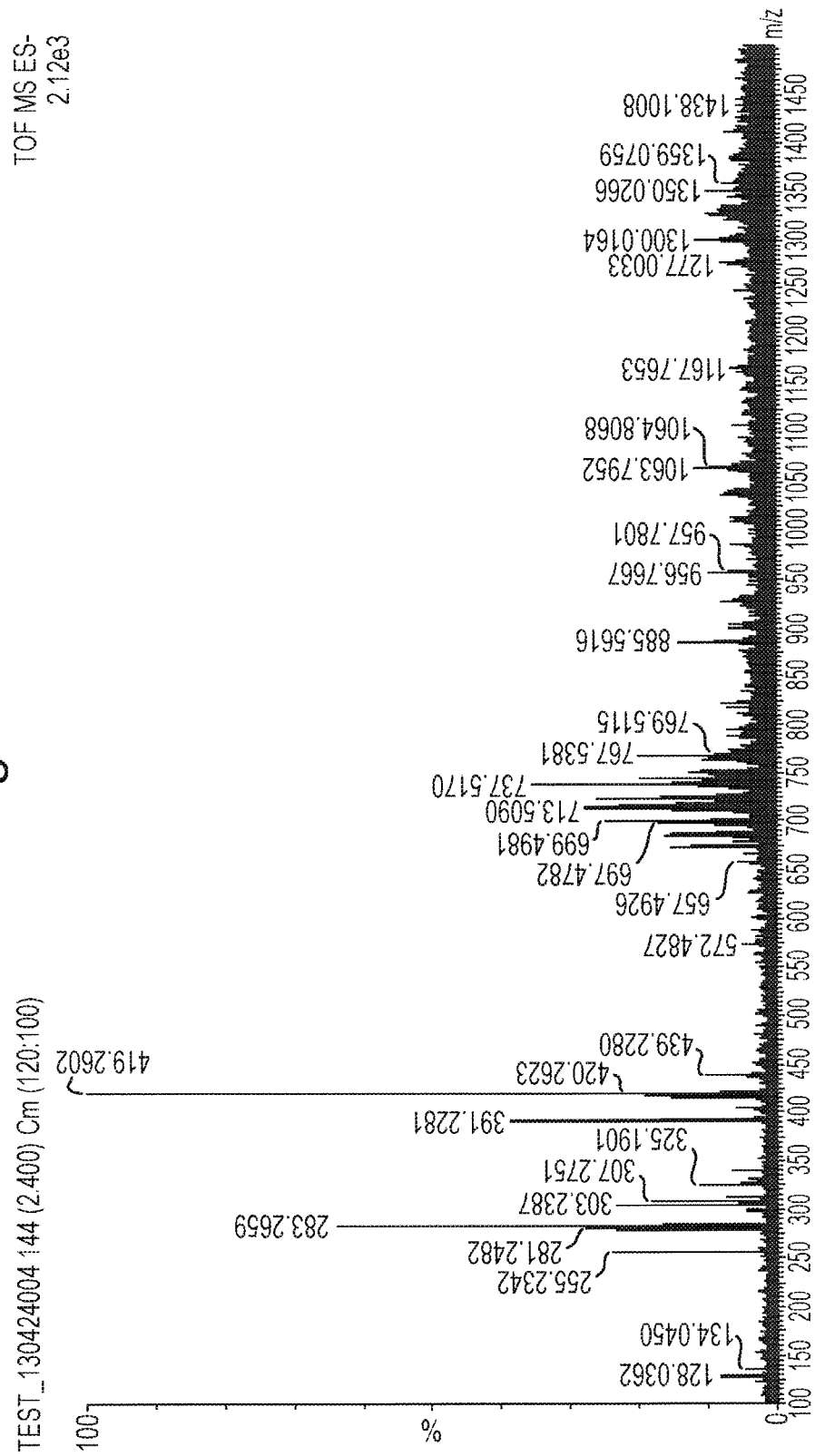
Figure 33B:
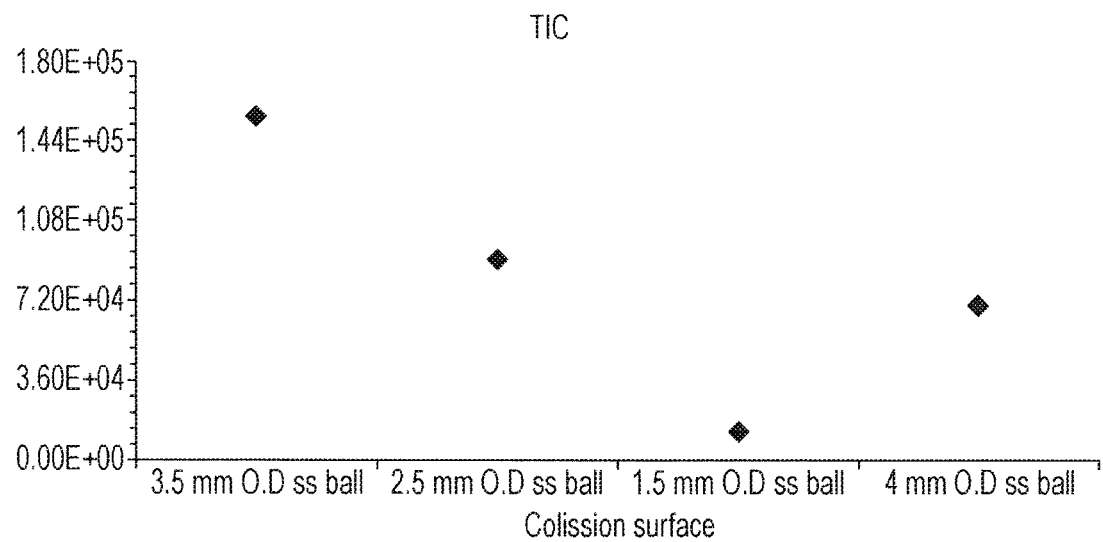

Spherical collision assemblies having different outer diameters were examined. The spheres were each arranged 2 mm downstream of the capillary exit. The spherical collision assemblies had outer diameters of 1.5 mm, 2.5 mm, 3.5 mm and 4 mm. The four spherical collision surfaces showed the same mass spectrum, as shown in FIG. 33A, but differed in intensity. FIG. 33B shows the total ion current as a function of the outer diameter of the spherical collision surface.

A hemispherical collision assembly was also examined in which the curved surface was directed towards the capillary exit and the planar surface faced away from the capillary exit. This configuration resulted in a relatively low total ion current and a poor mass spectrum.

It has been found that rounded collision surfaces, such as cylinders and spheres, provide good collision surfaces. Spherical collision surfaces having a diameter of around 3.5 mm have been found to provide high total ion currents and good mass spectra.

Figure 34A:
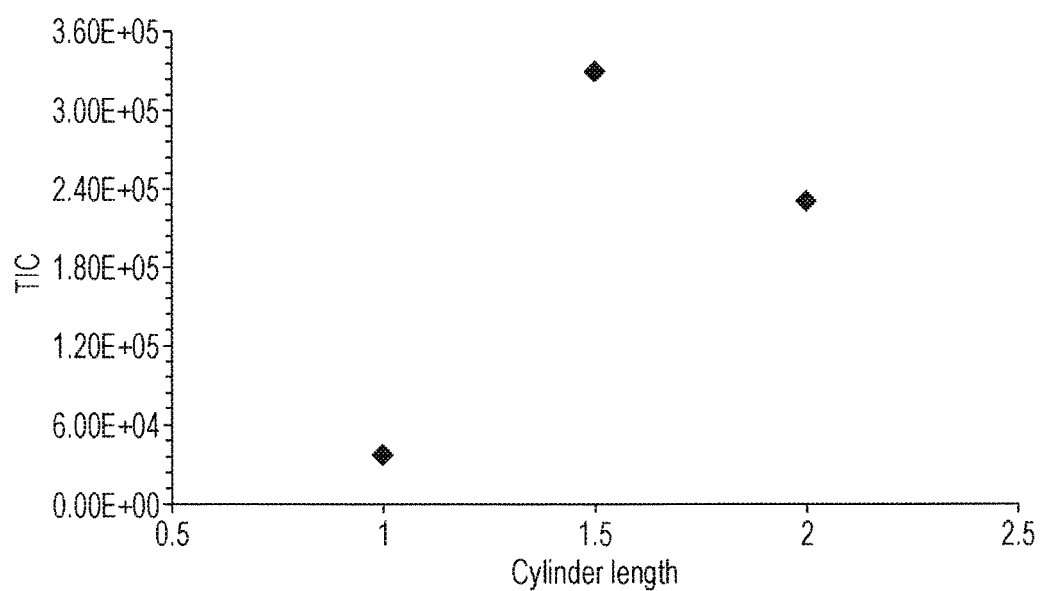
FIG. 34A shows the effect on the total ion current resulting from arranging a cylindrical sheath tube around the collision assembly.
Figure 34B:
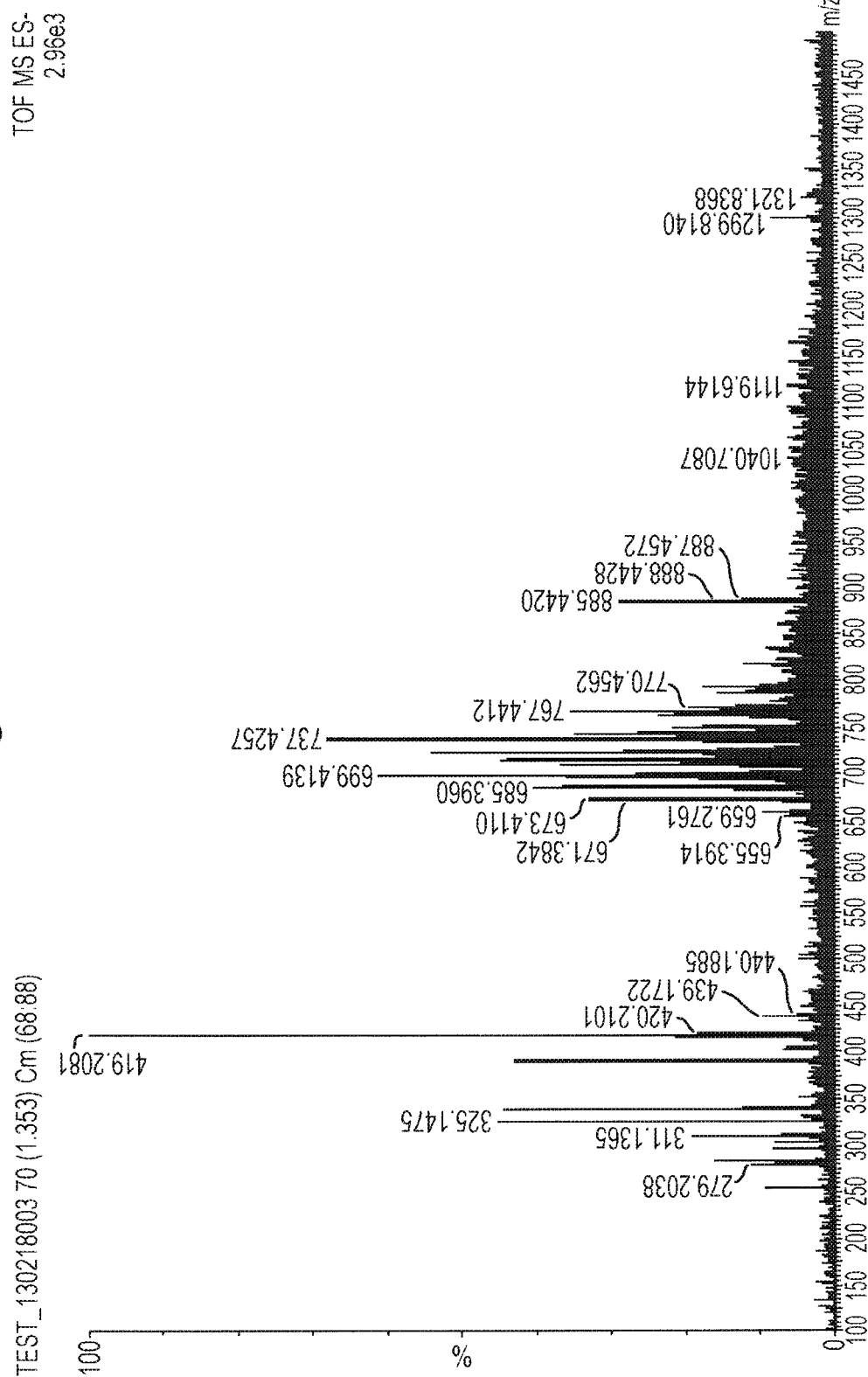
FIG. 34B shows a mass spectrum obtained using this configuration.

A sheath tube may be arranged circumferentially around the collision surface, e.g., in order modify the kinetics around the collision surface and the total ion current and mass spectrum. Various configurations of sheath tube were investigated, including cylindrical tubes having different lengths, e.g., 1 cm, 1.5 cm and 2 cm. These tubes were arranged around a spherical collision surface having a diameter of 3.5 mm and arranged 2 mm the capillary end. The effect on the total ion current of cylindrical sheath tubes having different lengths is shown in FIG. 34A. It can be seen from this that the optimum shield length in this example is 1.5 cm for the analysis of porcine liver. FIG. 34B shows a mass spectrum obtained using the configuration having the 1.5 cm sheath tube. The absence of dimers in the mass spectrum, due to the use of the sheath tube, is notable. The absence of dimmers in the mass spectrum for approximately 10 minutes was observed, making this set up useful for the analysis of animal tissue using REIMS.

It has also been found that cleaning the venturi pump and inlet capillary flushing with methanol helps reduce the presence of dimers in the mass spectra.

Figure 35A:
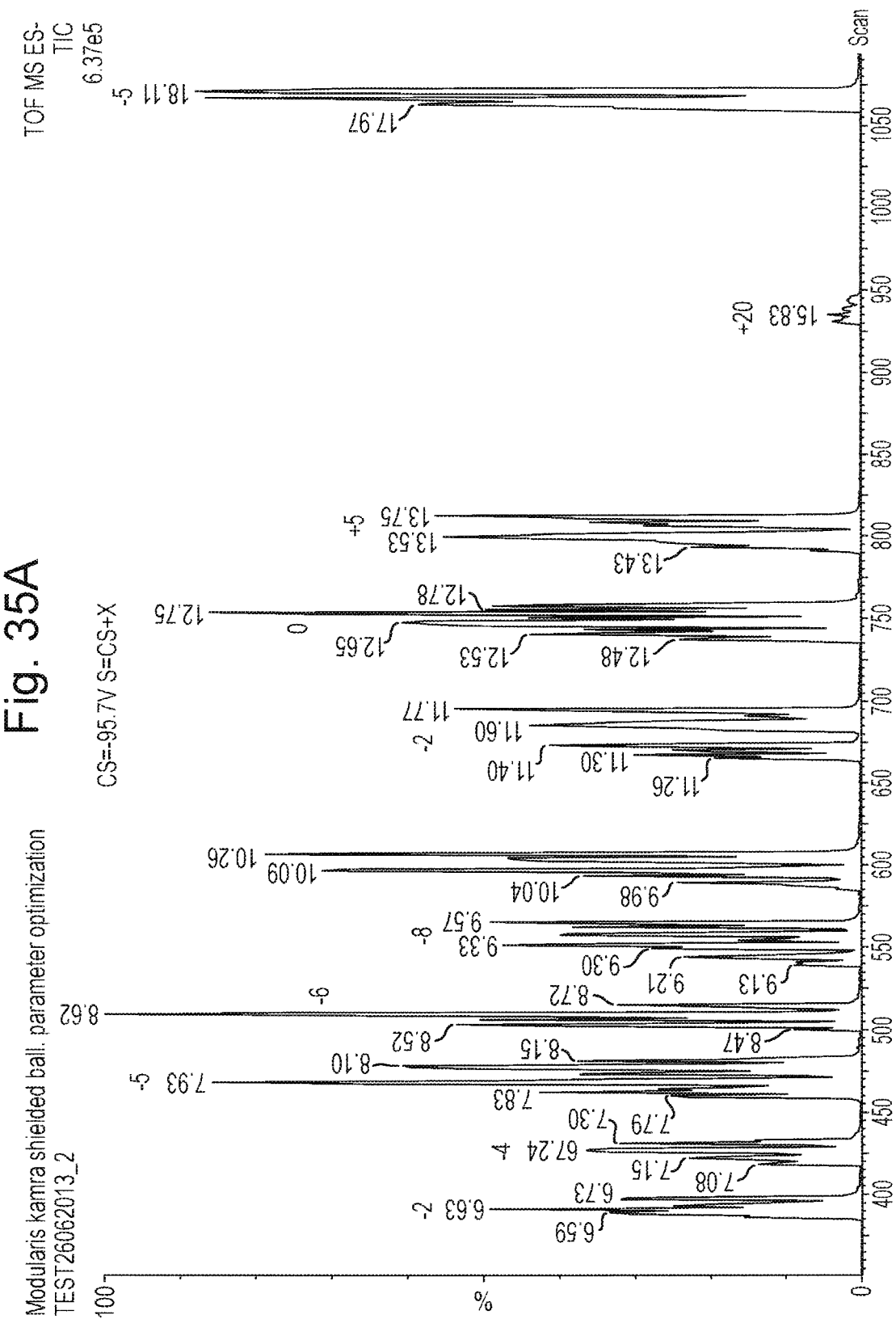
FIG. 35A shows the effect of different relative voltages between the collision surface and the sheath tube.

A voltage difference may be maintained between the collision surface and the sheath tube in order to improve the mass spectra. FIG. 35A shows the effect of different relative voltages between the collision surface and the sheath tube. The spectra were obtained using a spherical collision surface of 3.5 mm diameter arranged 2 mm downstream of the capillary outlet. The distance between the spherical surface and the sheath was 2 mm.

Figure 35B:
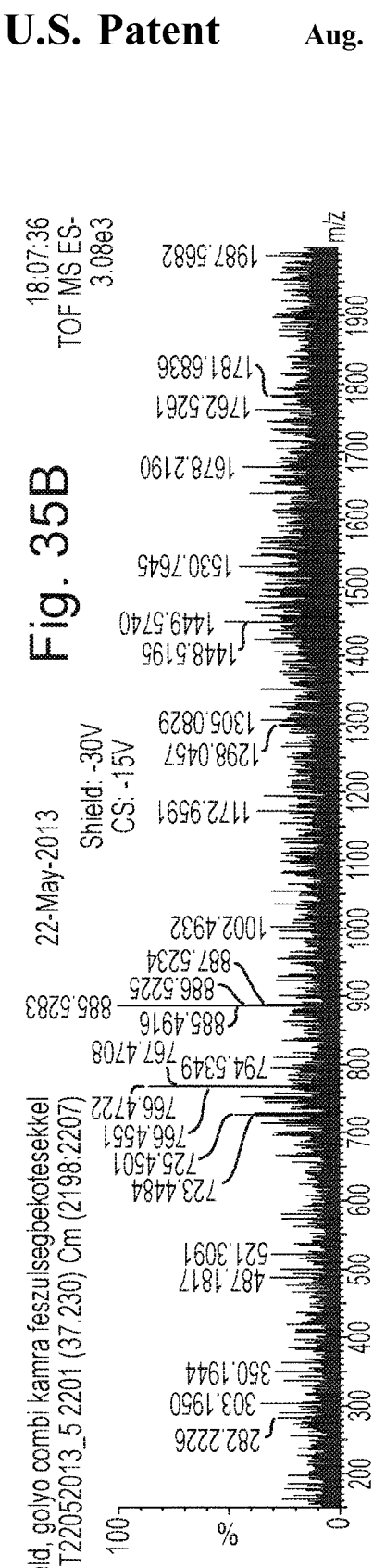
FIGS. 35B-35D show detailed spectra obtained at different voltages differences between the collision surface and sheath tube.
Figure 35C:
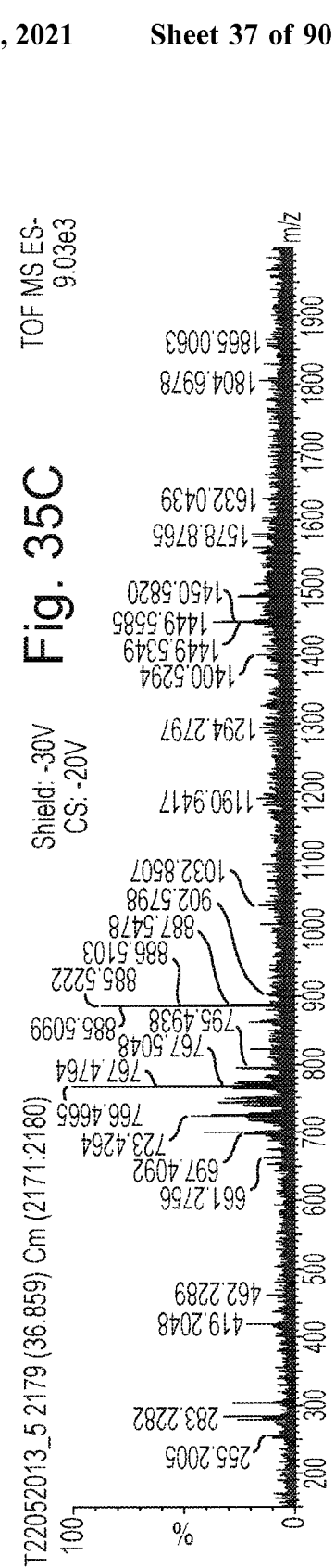
Figure 35D:
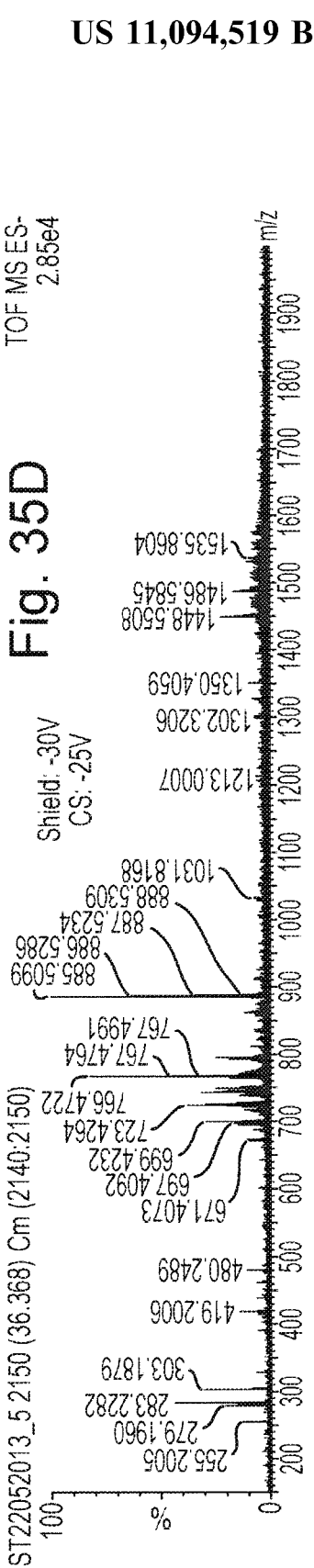
Figure 36A:
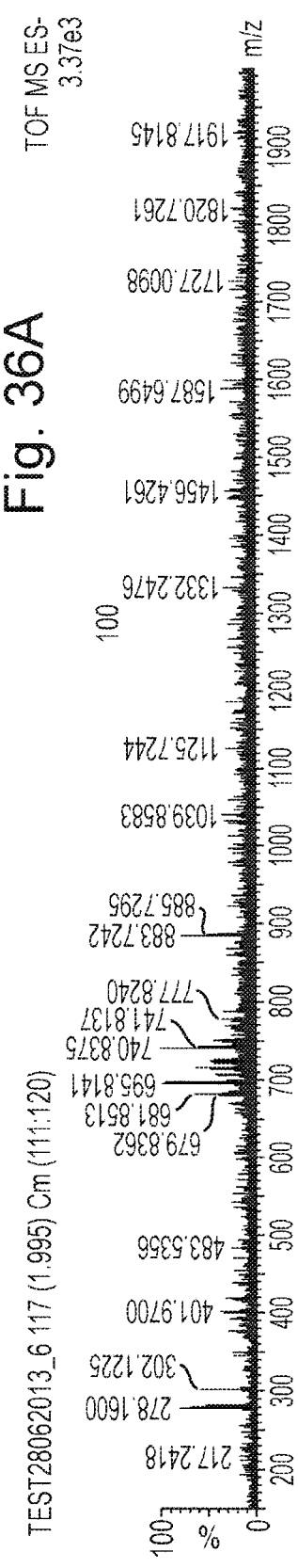
Figure 36B:
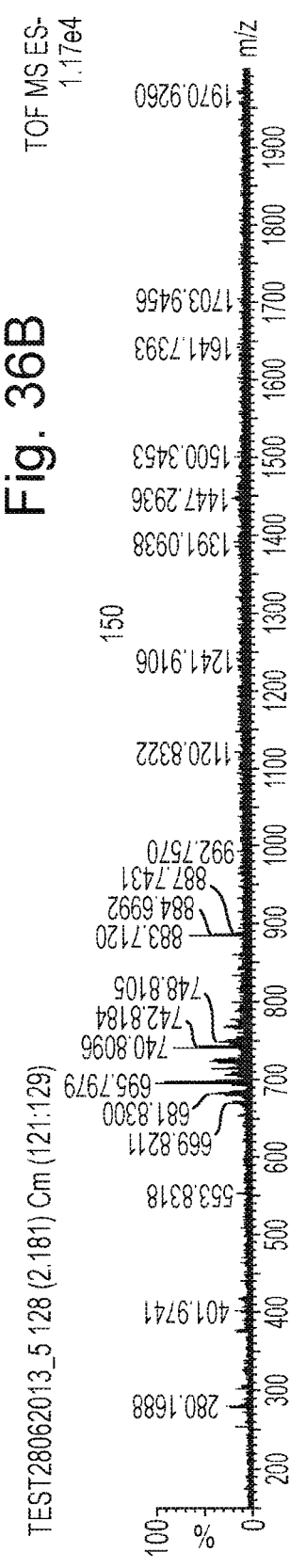
Figure 36C:
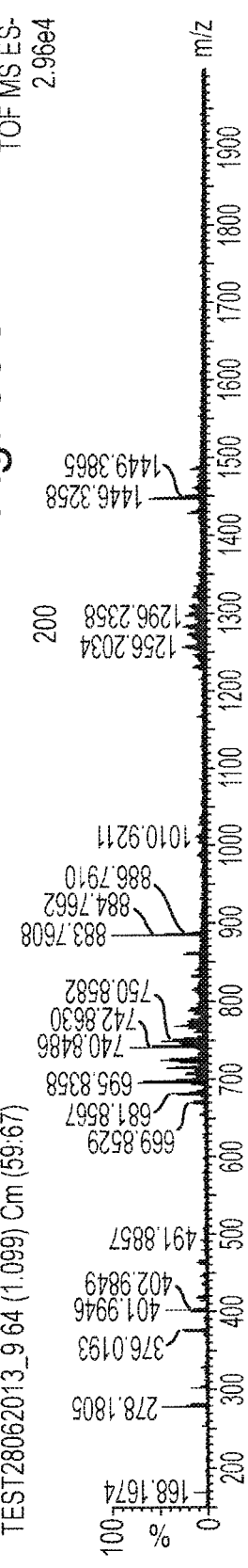

FIGS. 35B-35D show detailed spectra obtained at different voltages differences between the collision surface and sheath tube. FIG. 35B shows a spectrum obtained with the sheath tube maintained at −30 V and the collision surface maintained at −15 V. FIG. 35C shows a spectrum obtained with the sheath tube maintained at −30 V and the collision surface maintained at −20 V. FIG. 35D shows a spectrum obtained with the sheath tube maintained at −30 V and the collision surface maintained at −25 V. It has been found that maintaining the collision surface at a voltage around 5 V higher than the sheath tube provides improved spectra.

The capillary tube that delivers sample to the collision surface may be heated. This may improve the ion intensities detected, particularly when the collision surface is not heated. FIGS. 36A-36F show spectra obtained whilst maintaining the capillary at 100° C., 150° C., 200° C., 250° C., 300° C., and 350° C., respectively. It was found that a capillary temperature of around 200° C. provides the optimum signal together with an acceptable amount of problems associated with capillary blockage. When the collision surface is heated it may not be necessary, or even desired, to heat the capillary tube.

Figure 37A:
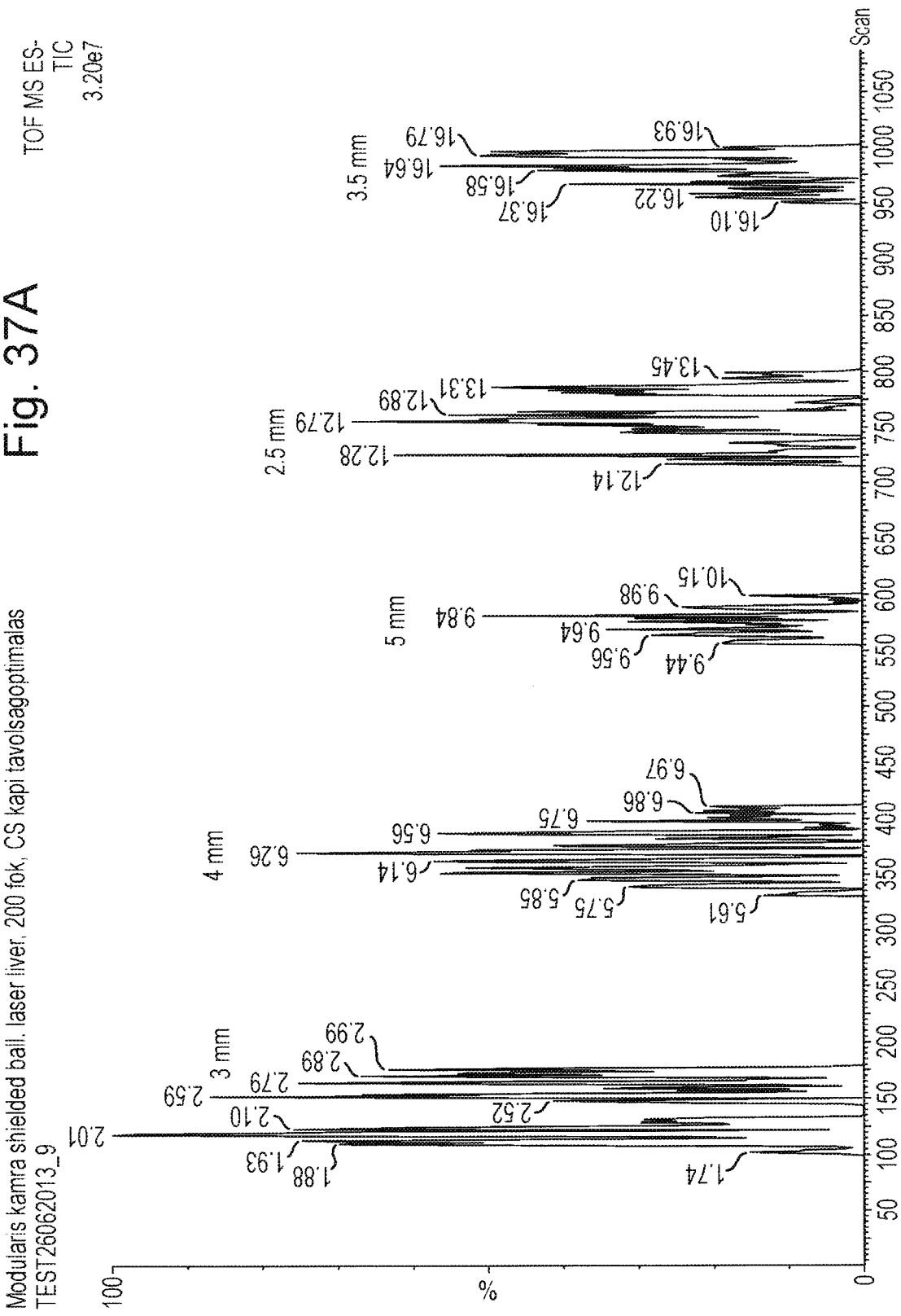
FIG. 37A shows spectra obtained with different distances between the sample capillary exit and the collision surface.
Figure 37D:
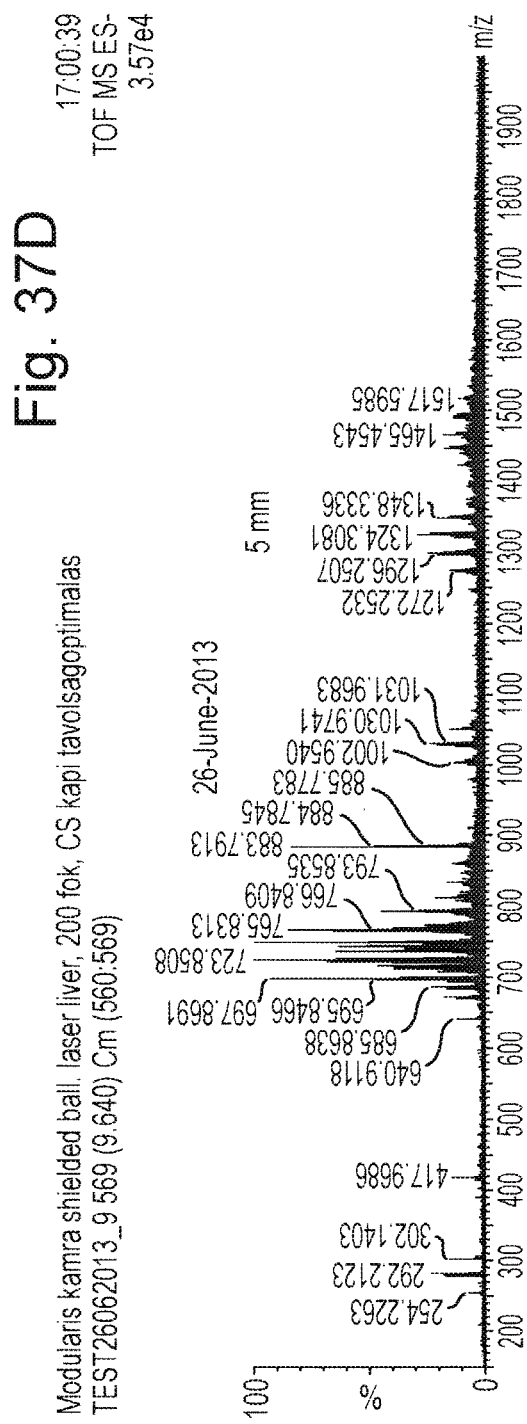

The distance between the capillary exit and the collision surface was also investigated. FIG. 37A shows spectra obtained with distances between the capillary exit and collision surface of 2.5 mm, 3 mm, 3.5 mm, 4 mm and 5 mm (for a capillary maintained at a temperature of 200° C.). FIG. 37B-37D shows more detailed spectra for the distances of 3 mm, 4 mm and 5 mm respectively. The results indicate that the optimum distance between the capillary exit and collision surface is between 2 mm and 3 mm, particularly for unheated collision surfaces.

As described, the collision surface may be a coil, or a coil may be used in the collision assembly to heat the collision surface. The coil may be made from a material that is electrically resistive, so that it is heated as an electrical current is passed through the coil. Example materials for the coil are kanthal, kathal-D, Nickel and NiCrothal.

FIG. 38A shows the ion signals detected when analysing a sample using a Kathal-D coil collision surface whilst various different currents between 2.9 A and 3.5 A are used to heat the coil. It can be seen that the optimum heating current is around 3.5 A. FIG. 38B shows the ion signals detected when analysing a sample using a NiCrothal coil collision surface whilst various different currents between 2.9 A and 3.5 A are used to heat the coil. It can be seen that the optimum heating current is around 3.5 A. FIG. 38C shows the ion signals detected when analysing a sample using another coil collision surface whilst various different currents between 3.8 A and 4.4 A are used to heat the coil. It can be seen that the optimum heating current is around 4.2 A.

FIG. 39 shows another embodiment, wherein the collision assembly comprises a Kathal coil coated in a substantially spherical ball 390. The spherical ball coating 390 may be glass, ceramic or one of the other coil coatings described herein. The ion signal was optimised using a heating current of ≥5 A, optionally ≥5.5 A (2.3V), through the coil. This current is higher than that of a naked coil. However, this embodiment produced spectra that were relatively more intense than the naked coil. Also, the collision assembly of this embodiment produced a low signal to noise ratio, e.g., 0.1%. The coating may have an aperture 392 therein to expose the coil. The aperture 392, and therefore the exposed coil, may face the exit of the capillary 396 for delivering the sample to the collision surface.

FIG. 40A shows another embodiment that is similar to that shown in FIG. 16, except that the hollow collision assembly 361 is formed by a coil. Aerosol particles or molecules may be arranged to emerge from the exit of a capillary or other aerosol introduction tube such that the aerosol particles or molecules are then directed towards the inlet of the coiled collision assembly. Aerosol is arranged to impact upon an inner surface of the coiled collision assembly. The coil may an electrically resistive wire and may be heated by passing an electric current through the coil.

FIG. 40B shows the ion signal measured using the collision assembly of FIG. 40A for various different locations of the capillary exit relative to the coil. The distance is measured relative to the exit end of the coil and in a direction upstream. In this example, the coil is 8 mm long and hence the exit end of the capillary is arranged within the coil at distances less than 8 mm. The internal radius of the coil is 3 mm. At distances greater than 8 mm the exit end of the capillary is located upstream of the coil entrance. As can be seen, signals of higher intensity were obtained when the exit end of the capillary was spaced upstream of the coil. In this example, the coil was heated using an electrical current of 3 A.

FIGS. 40C-40M show detailed spectra obtained using the collision assembly of FIG. 40A for the various different locations of the capillary exit relative to the coil. FIGS. 40C-40M show spectra obtained using a capillary exit located a distance upstream from the exit end of the coil of 0 mm, 1 mm, 2 mm, 3 mm, 4 mm, 5 mm, 6 mm, 7 mm, 8 mm, 9 mm and 10 mm respectively. As can be seen, the optimum spectra were obtained at distances of 9-10 mm, i.e. with the capillary exit spaced 1-2 mm upstream of the coil.

In this example, the coil was heated using an electrical current of 3 A. However, other currents may be used to heat the coil.

FIG. 41A shows the total ion current obtained using the embodiment of FIG. 40A, when the capillary exit was located 2 mm upstream of the coil, for different heater coil currents. As shown in FIG. 41A, twelve different heater coil currents between 2.4 A and 4.6 A were tested. The total ion current increases substantially linearly in response to increasing the heating current through the coil. The total ion current response continued to increase with increasing current beyond 4.6 A. This is in contrast to the use of a coil collision surface that has its axis orthogonal to the capillary exit axis, in which the total ion current did not continue to improve beyond a certain point when the heating current was increased.

The coaxial arrangement of the capillary exit and the collision coil shown in FIG. 40A may provide enhanced ionisation, e.g., over a collision coil having its longitudinal axis orthogonal to the capillary exit. For example, in the arrangement shown in FIG. 40A the aerosol from the capillary may collide with several coil edges inside the coil and, if the coil is heated, there may be longer thermal impact while the aerosol particles are inside the heated coil. In contrast, when the longitudinal axis of the coil is arranged orthogonal to the axis through the capillary exit, these effects may not be present. Rather, after a singular collision with the collision surface the particles may gradually move further from the coil, which may limit the effectiveness of liberating ionised molecules from the droplet/aerosol particles using the impact and thermal effect. However, as described above, a matrix may be used to overcome this, as the matrix itself allows a more effective liberation of ions from droplets.

FIGS. 41B-41M show the spectra obtained at each coil current in FIG. 41A. The spectra show a steady increase in intensity and signal to noise ratio with increasing coil current. As described above, a matrix may be used to assist in ionisation. The use of a matrix has been found to decrease the dependency for the ion signal on the heating current used.

Coils of other lengths and internal radii may also be used.

FIG. 42A shows the ion signal measured using a collision coil having a length of 4 mm and an internal diameter of 3 mm, for various different locations of the capillary exit relative to the coil. The distance is measured relative to the exit end of the coil and in a direction upstream. In this example, the exit end of the capillary is arranged within the coil at distances less than 4 mm. At distances greater than 4 mm the exit end of the capillary is located upstream of the coil entrance. As can be seen, ion signals where obtained when the exit end of the capillary was spaced upstream of the coil. In this example, the ion signals began to rise rapidly at distances of 6 mm and above, i.e. when the exit of the capillary is located 2 mm or more upstream of the coil.

FIGS. 42B-42G show detailed spectra obtained using the collision assembly for the various different locations of the capillary exit relative to the coil. FIGS. 42B-42G show spectra obtained using a capillary exit located a distance upstream from the exit end of the coil of 2 mm, 4 mm, 5 mm, 6 mm, 7 mm and 8 mm respectively. As can be seen, the signal to noise ratio increases with increasing distance.

In this example, the coil was heated using an electrical current of 2.9 A. However, other currents may be used to heat the coil.

FIG. 42H shows the total ion current obtained when the capillary exit was located 3 mm upstream of the coil, for different heater coil currents. As shown in FIG. 42H, seven different heater coil currents between 2.5 A and 4.7 A were tested. The total ion current increases in substantially linearly in response to increasing the heating current through the coil.

FIGS. 42I-42O show the spectra obtained at each coil current in FIG. 42H. The spectra of FIGS. 42I-42O correspond to the coil currents of 2.5 A, 2.9 A, 3.3 A, 3.7 A, 4.1 A, 4.3 A and 4.7 A respectively. The spectra show a steady increase in intensity and signal to noise ratio with increasing coil current.

FIG. 43A shows the ion signal measured using a collision coil having a length of 8 mm and an internal diameter of 6 mm, for various different locations of the capillary exit relative to the coil. The distance is measured relative to the exit end of the coil and in a direction upstream. In this example, the exit end of the capillary is arranged within the coil at distances less than 8 mm. At distances greater than 8 mm the exit end of the capillary is located upstream of the coil entrance. As can be seen, better ion signals where obtained when the exit end of the capillary was spaced upstream of the coil. In this example, the ion signals were optimal at distances of 14 mm and above, i.e. when the exit of the capillary is located 6 mm or more upstream of the coil.

FIGS. 43B-43F show detailed spectra obtained using the collision assembly for the various different locations of the capillary exit relative to the coil. FIGS. 43B-43F show spectra obtained using a capillary exit located a distance upstream from the exit end of the coil of 9 mm, 11 mm, 13 mm, 17 mm and 19 mm. As can be seen, the best spectrum was obtained at 13 mm, i.e. with the capillary exit 5 mm upstream of the coil.

In this example, the coil was heated using an electrical current of 3 A. However, other currents may be used to heat the coil.

FIG. 43G shows the total ion current obtained when the capillary exit was located 7 mm upstream of the coil, for different heater coil currents. As shown in FIG. 43G, five different heater coil currents between 2.5 A and 4.5 A were tested. The total ion current increases in substantially linearly in response to increasing the heating current through the coil.

FIGS. 43H-43L show the spectra obtained at each coil current in FIG. 43G. The spectra show a steady increase in intensity and signal to noise ratio with increasing coil current.

It was found that arranging the longitudinal axis of the coil substantially parallel with the exit axis of the capillary provides better spectra with higher temperature coils than arranging the coil axis orthogonal to the capillary exit axis. In particular, these arrangements may provide a magnitude higher intensity at higher temperatures. The optimal signals were obtained when the capillary exit was spaced upstream of the coil entrance, e.g., 2-3 mm. Arranging the coil axis substantially parallel to the capillary exit axis also seemed to reduce contamination of the instrument, e.g., to reduce contamination of the downstream Stepwave ion guide.

FIG. 44A shows the ion signal measured using a tubular collision surface arranged coaxially with the capillary exit axis and having a length of 1 mm and an internal diameter of 3 mm, for various different locations of the capillary exit relative to the collision surface. In this example, the ion signals were optimal when the capillary exit was spaced from the collision surface by a distance of 7 mm.

FIGS. 44B and 44C show detailed spectra over different mass ranges obtained when analyzing porcine liver using the collision assembly described in relation to FIG. 44A, when the capillary exit is located 7 mm upstream of the collision surface entrance.

FIG. 44D shows the total ion current obtained when the capillary exit was located 7 mm upstream of the collision surface entrance, for different heater coil currents. As shown in FIG. 44D, nine different heater coil currents between 0 A and 4.7 A were tested. The total ion current is optimal at around 4.5 A.

FIG. 45A shows the ion signal measured using a tubular collision surface arranged coaxially with the capillary exit axis and having a length of 8 mm and an internal diameter of 6 mm, for various different locations of the capillary exit relative to the collision surface. In this example, the ion signals were optimal when the capillary exit was spaced from the collision surface by a distance of 6 mm. The set up was similar to that used in FIG. 43, except with a different atmospheric interface.

FIG. 45B shows a full spectrum obtained when analyzing porcine liver using the collision assembly described in relation to FIG. 45A when the capillary exit is located 6 mm upstream of the collision surface entrance and using a coil heater current of 3.4 A.

FIG. 45C shows a detailed portion of the spectrum in FIG. 45B.

FIG. 45D shows the total ion current obtained when the capillary exit was located 5 mm upstream of the collision surface entrance, for different heater coil currents. As shown in FIG. 45D, five different heater coil currents between 3 A and 3.8 A were tested. The total ion current is optimal at around 3.4 A.

FIG. 46A shows the ion signal measured using a tubular collision surface arranged coaxially with the capillary exit axis and having a length of 8 mm and an internal diameter of 3 mm, for various different locations of the capillary exit relative to the collision surface. In this example, the ion signals were optimal when the capillary exit was spaced from the collision surface by a distance of 6 mm. The set up was similar to that used in FIG. 40, except with a different atmospheric interface.

FIG. 46B shows a full spectrum obtained using the collision assembly described in relation to FIG. 46A when the capillary exit is located 6 mm upstream of the collision surface entrance and using a coil heater current of 3.2 A.

FIG. 46C shows a detailed portion of the spectrum in FIG. 46B.

FIG. 46D shows the total ion current obtained when the capillary exit was located 5 mm upstream of the collision surface entrance, for different heater coil currents. As shown in FIG. 46D, six different heater coil currents between 2.6 A and 3.6 A were tested. The total ion current is optimal at around 3.4 A.

FIG. 47A shows the ion signal measured using a conical collision surface arranged coaxially with the capillary exit axis and having a length of 8 mm, for various different locations of the capillary exit relative to the collision surface. The conical collision surface had an internal diameter that tapered from 6 mm at the entrance end to 3 mm at the exit end. In this example, the ion signals were found to be optimal when the capillary exit was arranged at the entrance to the collision surface (i.e. at 0 mm).

FIG. 47B shows a full spectrum obtained by analysing porcine liver using the collision assembly of FIG. 47A using a coil heater current of 3.4 A.

FIG. 47C shows a detailed portion of the spectrum in FIG. 47B.

FIG. 47D shows the total ion current obtained for different heater coil currents. As shown in FIG. 47D, seven different heater coil currents between 2.6 A and 3.8 A were tested. The total ion current is optimal at around 3.4 A.

The embodiments provide an apparatus and associated method for the chemical analysis of aerosols and gaseous samples containing analytes using mass and/or ion mobility spectrometry or other gas-phase ion analysis modalities. The method starts with the introduction of an aerosol or other gaseous sample 201 containing the analyte into an enclosed space, where the sample 201 is mixed with a low molecular weight matrix compound 204. This homogeneous or heterogeneous mixture is then introduced into the atmospheric interface of a mass and/or ion mobility spectrometer 102 via inlet 206. On the introduction of the mixture into the low pressure regime of the analytical instrument, aerosol particles containing molecular constituents of the sample and the matrix compound are formed, which are accelerated by the free jet expansion. The mixed composition aerosol particles 205 are subsequently dissociated via collisions with solid collision surfaces 209. The dissociation events produce neutral and charged species, including the molecular ions 210 of the chemical constituents of the sample. The ions 210 may be separated from the neutral species by using electric fields, e.g., by using an ion guide 212, such as a Stepwave® ion guide so as to guide ions 210 on a different path to the neutral species. The molecular ions 210 are then subjected to mass and/or mobility analysis. This provides a simple solution for the analysis of molecular constituents of aerosols in an on-line fashion without the application of high voltages or lasers.

The method and device provides a solution for the on-line mass and/or ion mobility spectrometric analysis of gas phase or aerosol-type samples.

According to various further embodiments the matrix compound 204 may be mixed into the sample aerosol 201 as a vapour or as a liquid at any point prior to introduction of the sample into the ion analyser device 207.

Although the embodiments described above relate to a particular solid collision surface geometry for performing the surface induced dissociation of the clusters, it will be appreciated that other geometries can be implemented (provided that the clusters impact the collision surface 209 at sufficiently high velocity to induce dissociation).

Analysing Sample Spectra A list of analysis techniques which are intended to fall within the scope of the present invention are given in the following table:

Analysis Techniques
Univariate Analysis
Multivariate Analysis
Principal Component Analysis (PCA)
Linear Discriminant Analysis (LDA)
Maximum Margin Criteria (MMC)
Library Based Analysis
Soft Independent Modelling Of Class Analogy (SIMCA)
Factor Analysis (FA)
Recursive Partitioning (Decision Trees)
Random Forests
Independent Component Analysis (ICA)
Partial Least Squares Discriminant Analysis (PLS-DA)
Orthogonal (Partial Least Squares) Projections To Latent Structures (OPLS)
OPLS Discriminant Analysis (OPLS-DA)
Support Vector Machines (SVM)
(Artificial) Neural Networks
Multilayer Perceptron
Radial Basis Function (RBF) Networks
Bayesian Analysis
Cluster Analysis
Kernelized Methods
Subspace Discriminant Analysis
K-Nearest Neighbours (KNN)
Quadratic Discriminant Analysis (QDA)
Probabilistic Principal Component Analysis (PPCA)
Non negative matrix factorisation
K-means factorisation
Fuzzy c-means factorisation
Discriminant Analysis (DA)

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

FIG. 48 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

FIG. 49 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

FIG. 50 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

FIG. 51 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \quad (1)$$

FIG. 52 shows the resultant PCA space for the reference sample spectra of FIGS. 49 and 50. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 49 and therefore to a reference point of FIG. 50.

As is shown in FIG. 52, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \quad (2)$$

where the matrix Z contains the scores transformed into the LDA space.

FIG. 53 shows a PCA-LDA space having a single dimension or axis, wherein the LDA is performed in the PCA space of FIG. 52. As is shown in FIG. 53, the LDA space comprises plural further transformed reference points or PCA-LDA scores, with each further transformed reference point corresponding to a transformed reference point or PCA score of FIG. 52.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \quad (3)$$

where $V_g$ are the class covariance matrices in the PCA space.

The transformed class average position $z_g$ for class g may be given by $$s_g U = z_g \quad (4)$$

where $s_g$ is the class average position in the PCA space.

Multivariate Analysis—Using a Model for Classification

By way of example, a method of using a classification model to classify an aerosol, smoke or vapour sample will now be described.

FIG. 54 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

FIG. 55 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (5)$$

Then, a transformed PCA-LDA vector $z_x$ for the sample spectrum can be obtained as follows:

$$s_x U = z_x \quad (6)$$

FIG. 56 again shows the PCA-LDA space of FIG. 53. However, the PCA-LDA space of FIG. 56 further comprises the projected sample point, corresponding to the transformed PCA-LDA vector $z_x$, derived from the peak intensity values of the sample spectrum of FIG. 55.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \quad (8)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

FIG. 57 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \middle/ \log \frac{M_{max}}{M_{min}} \right\rfloor$$

where $N_{chan}$ is a selected value and [x] denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}=1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2} \Gamma(C)}{\sqrt{\pi} \Gamma(C-1/2)} \frac{1}{\left(C + \frac{(y_i - \mu_i)^2}{D_i^2}\right)^C}$$

where $1/2 \leq C < \infty$ and where $\Gamma(C)$ is the gamma function.

The above equation is a generalised Cauchy distribution which reduces to a standard Cauchy distribution for C=1 and becomes a Gaussian (normal) distribution as $C \to \infty$. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_j^2)^{3/2}}$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library-Based Analysis—Using a Library for Classification

By way of example, a method of using a classification library to classify an aerosol, smoke or vapour sample will now be described.

FIG. 58 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y | \mu, D) = \prod_{i=1}^{N_{chan}} Pr(y_i | \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class is given by:

$$Pr(s | y) = \frac{L_s^{(1/F)}}{\Sigma_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue.

Various surgical, therapeutic, medical treatment and diagnostic methods are contemplated.

However, other embodiments are contemplated which relate to non-surgical and non-therapeutic methods of mass and/or ion mobility spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

The mass and/or ion mobility spectrometer described herein may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

Although the present invention has been described with reference to preferred embodiments, it will be understood by those skilled in the art that various changes in form and detail may be made without departing from the scope of the invention as set forth in the accompanying claims.

The invention claimed is:

1. An apparatus for interfacing an analyte source with a vacuum chamber of a mass and/or ion mobility spectrometer, comprising:
    a housing having a bore therethrough for receiving an analyte at a first end of the bore and conveying the analyte to a second end of the bore to the vacuum chamber;
    a collision assembly arranged adjacent or downstream of a second end of the bore for impacting said analyte or other sample from said bore thereon, wherein the collision assembly is removably mounted to the housing; and
at least one of:
(i) a first isolation valve in the bore, wherein the first isolation valve is configured to open when a capillary or sample tube is inserted through the bore into contact with the first isolation valve, and is configured to close when the capillary or sample tube is withdrawn from the bore; and
(ii) a second isolation valve for selectively closing either the bore or a path in communication with the bore, wherein the second isolation valve is coupled to the housing such that rotation of the housing about its longitudinal axis moves the second isolation valve between an open position and a closed position.

2. The apparatus as claimed in claim 1, wherein the first isolation valve is a ball valve comprising an isolation ball that is configured to move into the bore through the housing when neither a capillary nor a sample tube is inside the bore so as to seal the bore closed to isolate the vacuum chamber from the first end of the bore.

3. The apparatus as claimed in claim 2, wherein the isolation ball is biased to move into the bore by at least one of: gravity; a spring; or suction from the pressure of the vacuum chamber.

4. The apparatus as claimed in claim 1, wherein the second isolation valve comprises a cam member configured to, as the second isolation valve is moved between the open and closed positions, slide across an opening in either the bore or path in communication with the bore.

5. An apparatus for interfacing an analyte source with a vacuum chamber of a mass and/or ion mobility spectrometer, comprising:
    a housing having a bore therethrough for receiving an analyte at a first end of the bore and conveying the analyte to a second end of the bore to the vacuum chamber; and
    a collision assembly arranged adjacent or downstream of a second end of the bore for impacting said analyte or other sample from said bore thereon, wherein the collision assembly is removably mounted to the housing, and wherein the housing comprises one or more shields at least partially surrounding said collision assembly in an extended position for protecting said collision assembly.

6. The apparatus as claimed in claim 5, wherein said one or more shields is at least partially retractable from said extended position to a retracted position in which at least part of the collision assembly is not surrounded by the one or more shields.

7. The apparatus as claimed in claim 6, wherein said one or more shields is biased towards said extended position.

8. The apparatus as claimed in claim 1, comprising the first isolation valve and the second isolation valve.

9. A method of interfacing an analyte source with a vacuum chamber of a mass and/or ion mobility spectrometer comprising:
    providing an apparatus for interfacing an analyte source with a vacuum chamber of a mass and/or ion mobility spectrometer, the apparatus comprising:
        a housing having a bore therethrough for receiving an analyte at a first end of the bore and conveying the analyte to a second end of the bore to the vacuum chamber; and
        a collision assembly arranged adjacent or downstream of a second end of the bore for impacting said analyte or other sample from said bore thereon, wherein the collision assembly is removably mounted to the housing;
    and the method further comprising:
    connecting the housing at the second end of the bore to the vacuum chamber of the mass and/or ion mobility spectrometer while maintaining a vacuum in the vacuum chamber.

10. The method of claim 9, wherein connecting the housing at the second end of the bore to the vacuum chamber comprises connecting the vacuum chamber with a region that is at a higher pressure than the vacuum chamber.

11. The method of claim 9, further comprising inserting a capillary or sample tube through the bore of the housing.

12. The method of claim 11, further comprising supplying analyte, smoke, fumes, liquid, gas, surgical smoke, aerosol or vapour through the capillary or sample tube and onto the collision assembly.

13. The method of claim 11, wherein:
    inserting the capillary or sample tube through the bore of the housing comprises opening a first isolation valve in the bore; and
    connecting the housing at the second end of the bore to the vacuum chamber of the mass and/or ion mobility spectrometer comprises rotating the housing from a first position to a second position to open a second isolation valve.

14. The method of claim 9, further comprising retracting one or more shields at least partially surrounding said collision assembly from an extended position for protecting said collision assembly.

15. A mass and/or ion mobility spectrometer, comprising:
a vacuum chamber;
a housing removably connected to the spectrometer, the housing having a bore therethrough for conveying an analyte into the vacuum chamber, the bore having a first end for receiving the analyte and a second end connected to the vacuum chamber; and
a collision assembly arranged adjacent or downstream of the second end of the bore for impacting said analyte or other sample from said bore thereon, wherein the collision assembly is removably mounted to the housing such that the collision assembly is removable from the spectrometer by disconnecting the housing from the spectrometer.

16. The mass and/or ion mobility spectrometer of claim 15, further comprising a capillary or sample tube removably inserted through the bore of the housing.

17. The mass and/or ion mobility spectrometer of claim 15, further comprising at least one of:
a first isolation valve in the bore, wherein the first isolation valve is configured to open when a capillary or sample tube is inserted through the bore into contact with the valve, and is configured to close when the capillary or tube is withdrawn from the bore; and
a second isolation valve for selectively closing the bore or a path in communication with the bore, wherein the second isolation valve is coupled to the housing such that rotation of the housing about its longitudinal axis moves the second isolation valve between an open position and a closed position.

18. The mass and/or ion mobility spectrometer of claim 15, wherein the housing comprises one or more shields configured to be movable from an extended position in which the one or more shields at least partially surround said collision assembly and a retracted position in which at least part of the collision assembly is not surrounded by the one or more shields.

* * * * *